(12) United States Patent
Vedrine et al.

(10) Patent No.: US 10,765,811 B2
(45) Date of Patent: Sep. 8, 2020

(54) VERSATILE SYRINGE PLATFORM

(71) Applicant: Genentech, Inc., South San Francisco, CA (US)

(72) Inventors: Lionel Vedrine, Palo Alto, CA (US); Steven N. Roe, San Mateo, CA (US); Mukund Patel, San Jose, CA (US)

(73) Assignee: Genentech, Inc., South San Francisco, CA (US)

( * ) Notice: Subject to any disclaimer, the term of this patent is extended or adjusted under 35 U.S.C. 154(b) by 573 days.

(21) Appl. No.: 14/962,554

(22) Filed: Dec. 8, 2015

(65) Prior Publication Data

US 2016/0325047 A1     Nov. 10, 2016

Related U.S. Application Data

(60) Provisional application No. 62/088,844, filed on Dec. 8, 2014.

(51) Int. Cl.
    *A61M 5/315*      (2006.01)
    *A61M 5/24*      (2006.01)
    (Continued)

(52) U.S. Cl.
    CPC ....... *A61M 5/31513* (2013.01); *A61F 9/0017* (2013.01); *A61M 5/24* (2013.01);
    (Continued)

(58) Field of Classification Search
    CPC .......... A61M 5/31513; A61M 5/31528; A61M 5/2459; A61M 5/3137; A61M 5/3145;
    (Continued)

(56) References Cited

U.S. PATENT DOCUMENTS 1,644,173 A * 10/1927 Carr .......................... F16N 3/12
                                                             222/390
2,457,859 A * 1/1949 Austin .............. A61M 5/31595
                                                             604/210
(Continued)

FOREIGN PATENT DOCUMENTS

EP        0718002 A2     6/1996
EP        0676969 B1     1/1999
(Continued)

OTHER PUBLICATIONS

International Search Report for International Patent Application No. PCT/US2015/064464, dated Jul. 11, 2016.
(Continued)

*Primary Examiner* — Jenna Zhang
(74) *Attorney, Agent, or Firm* — Weiss & Arons LLP

(57) ABSTRACT

Apparatus and methods for medicament delivery. The apparatus may include, and the methods may involve, a delivery device for delivering a target amount of the medicament from a distal end of the device. The device may include a rod for moving a plunger that discharges the medicament from the distal end. The device may avoid or reduce deformation of the plunger during the discharge. The plunger motion may be stopped by detent that interacts with the rod. The apparatus and the methods may provide an operator indication of progress of stages of operation. The device may feature triggers corresponding to stages of medicament displacement from the device, such as pre-delivery stages, including priming.

98 Claims, 60 Drawing Sheets

(51) Int. Cl.
*A61F 9/00* (2006.01)
*A61M 5/31* (2006.01)
*A61M 5/32* (2006.01)
*A61M 5/36* (2006.01)
*A61M 5/28* (2006.01)
*A61M 5/20* (2006.01)
*B29C 45/16* (2006.01)
*B29L 31/00* (2006.01)

(52) U.S. Cl.
CPC ........ *A61M 5/2448* (2013.01); *A61M 5/2459* (2013.01); *A61M 5/3137* (2013.01); *A61M 5/3145* (2013.01); *A61M 5/3146* (2013.01); *A61M 5/3157* (2013.01); *A61M 5/31505* (2013.01); *A61M 5/31528* (2013.01); *A61M 5/31573* (2013.01); *A61M 5/31581* (2013.01); *A61M 5/31586* (2013.01); *A61M 5/31596* (2013.01); *A61M 5/3202* (2013.01); *A61M 5/3298* (2013.01); *A61M 5/36* (2013.01); *A61M 5/2033* (2013.01); *A61M 5/284* (2013.01); *A61M 2005/2451* (2013.01); *A61M 2005/31508* (2013.01); *A61M 2205/581* (2013.01); *A61M 2205/582* (2013.01); *A61M 2205/583* (2013.01); *A61M 2207/00* (2013.01); *B29C 45/16* (2013.01); *B29L 2031/7544* (2013.01)

(58) Field of Classification Search
CPC ............ A61M 5/3146; A61M 5/31505; A61M 5/3298; A61M 5/2448; A61M 5/31581; A61M 5/31596; A61M 5/3202; A61M 5/36; A61M 5/24; A61M 5/31573; A61M 5/31586; A61M 5/2033; A61M 2005/2451; A61M 2005/31508; A61M 2205/582; A61M 2205/583; A61M 2205/581; A61M 2207/00; A61F 9/0017; B29L 2031/7544; B29C 45/16
See application file for complete search history.

(56) References Cited

U.S. PATENT DOCUMENTS

| | | | | |
|---|---|---|---|---|
| 2,660,342 A * | 11/1953 | Ruf | .................... | A61M 5/31551 222/309 |
| 2,745,575 A * | 5/1956 | Spencer | .................... | B41L 27/10 222/327 |
| 2,756,747 A * | 7/1956 | Axelrad | ............ | A61M 5/31513 604/219 |
| 2,874,877 A * | 2/1959 | Spencer | .................... | B41F 31/02 222/162 |
| 3,162,217 A * | 12/1964 | Poli, Jr. | .................... | A61M 5/24 141/27 |
| 3,791,560 A | 2/1974 | Harris, Sr. | | |
| 3,915,651 A | 10/1975 | Nishi | | |
| 4,269,331 A * | 5/1981 | Watson | ................ | A47G 19/183 222/390 |
| 4,367,739 A * | 1/1983 | LeVeen | ................. | A61M 5/486 604/224 |
| 4,467,620 A * | 8/1984 | Bradley | .................... | F16N 3/06 222/380 |
| 4,641,766 A | 2/1987 | Vlasich | | |
| 4,710,178 A | 12/1987 | Leonard et al. | | |
| 4,710,179 A * | 12/1987 | Haber | ................ | A61M 5/31595 604/211 |
| 4,810,249 A * | 3/1989 | Haber | ................ | A61M 5/31555 222/390 |
| 4,883,472 A | 11/1989 | Michel | | |
| 4,952,205 A | 8/1990 | Mauerer et al. | | |
| 5,114,406 A * | 5/1992 | Gabriel | ............... | A61M 5/2033 604/134 |
| 5,472,022 A * | 12/1995 | Michel | .................. | A61J 1/2096 141/1 |
| 5,603,701 A | 2/1997 | Fischer | | |
| 5,716,338 A | 2/1998 | Hjertman et al. | | |
| 5,728,075 A | 3/1998 | Levander | | |
| 5,788,670 A | 8/1998 | Reinhard et al. | | |
| 5,935,101 A | 8/1999 | Kato et al. | | |
| 5,988,452 A | 11/1999 | Dent et al. | | |
| 6,004,297 A | 12/1999 | Steenfeldt-Jensen et al. | | |
| 6,004,298 A | 12/1999 | Levander | | |
| 6,019,750 A | 2/2000 | Fowles et al. | | |
| 6,063,057 A | 5/2000 | Choh | | |
| 6,102,895 A | 8/2000 | Cortella et al. | | |
| 6,235,004 B1 | 5/2001 | Steenfeldt-Jensen et al. | | |
| 6,254,579 B1 | 7/2001 | Cogger et al. | | |
| 6,263,778 B1 * | 7/2001 | Brass | .................... | F01B 15/007 222/390 |
| 6,290,679 B1 | 9/2001 | Hostettler et al. | | |
| 6,293,433 B1 | 9/2001 | Joulia | | |
| 6,352,522 B1 | 3/2002 | Kim et al. | | |
| 6,391,414 B1 | 5/2002 | Hjertman et al. | | |
| 6,454,745 B1 | 9/2002 | Donnan et al. | | |
| 6,485,470 B2 | 11/2002 | Hostettler et al. | | |
| 6,491,667 B1 | 12/2002 | Keane et al. | | |
| RE38,067 E | 4/2003 | Gueret | | |
| 6,554,161 B2 | 4/2003 | Main | | |
| 6,562,006 B1 * | 5/2003 | Hjertman | .......... | A61M 5/31553 604/208 |
| 6,562,008 B1 | 5/2003 | Reilly et al. | | |
| 6,579,269 B1 | 6/2003 | Kleyman | | |
| 6,609,533 B2 | 8/2003 | Sundararajan | | |
| 6,634,076 B2 | 10/2003 | Hjertman et al. | | |
| 6,641,566 B2 | 11/2003 | Douglas et al. | | |
| 6,656,150 B2 | 12/2003 | Hill et al. | | |
| 6,689,101 B2 | 2/2004 | Hjertman et al. | | |
| 6,712,794 B2 | 3/2004 | Kust et al. | | |
| 6,719,728 B2 | 4/2004 | Mason et al. | | |
| 6,740,062 B2 | 5/2004 | Hjertman | | |
| 6,793,646 B1 | 9/2004 | Giambattista et al. | | |
| 6,807,797 B2 | 10/2004 | Forsberg et al. | | |
| 6,945,961 B2 | 9/2005 | Miller et al. | | |
| 6,972,006 B2 | 12/2005 | Ferguson | | |
| 7,018,365 B2 | 3/2006 | Strauss et al. | | |
| 7,033,337 B2 | 4/2006 | Hjertman | | |
| 7,104,971 B2 | 9/2006 | Hjertman | | |
| 7,112,187 B2 * | 9/2006 | Karlsson | .................. | A61M 5/20 604/187 |
| 7,311,692 B2 | 12/2007 | Kato et al. | | |
| RE40,428 E | 7/2008 | Keane et al. | | |
| 7,392,735 B2 * | 7/2008 | Brass | ................. | B05C 17/0133 222/390 |
| 7,396,347 B2 | 7/2008 | Hjertman et al. | | |
| 7,473,241 B2 | 1/2009 | Hjertman et al. | | |
| 7,556,614 B2 | 7/2009 | Griffiths et al. | | |
| 7,645,267 B2 | 1/2010 | Vetter et al. | | |
| 7,699,811 B2 | 4/2010 | Hasegawa | | |
| 7,708,719 B2 | 5/2010 | Wilmot et al. | | |
| 7,740,607 B2 * | 6/2010 | Willis | ..................... | A61M 5/30 604/68 |
| 7,879,002 B2 | 2/2011 | Jessop | | |
| 7,967,010 B2 | 6/2011 | Vedrine et al. | | |
| 7,967,772 B2 | 6/2011 | McKenzie et al. | | |
| 8,092,421 B2 | 1/2012 | Seiferlein et al. | | |
| 8,128,604 B2 | 3/2012 | Yeandel et al. | | |
| 8,172,824 B2 | 5/2012 | Pfeifer et al. | | |
| 8,221,382 B2 | 7/2012 | Moy et al. | | |
| RE43,834 E | 11/2012 | Steenfeldt-Jensen et al. | | |
| 8,469,923 B2 | 6/2013 | Vedrine et al. | | |
| 8,486,007 B2 | 7/2013 | Marshall et al. | | |
| 8,517,992 B2 | 8/2013 | Jones | | |
| 8,529,521 B2 | 9/2013 | Erickson et al. | | |
| 8,556,865 B2 | 10/2013 | Krulevitch et al. | | |
| 8,568,367 B2 | 10/2013 | Griffiths et al. | | |
| 8,613,731 B2 | 12/2013 | Hansen et al. | | |
| 8,627,983 B2 | 1/2014 | White | | |
| 8,715,248 B2 | 5/2014 | McKinnon | | |
| 8,814,002 B2 | 8/2014 | Pires et al. | | |
| 8,834,158 B2 * | 9/2014 | Leiner | .................... | A61C 5/062 222/390 |

(56) References Cited

U.S. PATENT DOCUMENTS

| | | | |
|---|---|---|---|
| 9,095,658 B2* | 8/2015 | Wieselblad | A61M 5/31551 |
| 9,494,264 B2* | 11/2016 | Avery | A61J 1/16 |
| 2002/0010431 A1* | 1/2002 | Dixon | A61B 17/8822 604/221 |
| 2005/0261634 A1* | 11/2005 | Karlsson | A61M 5/2033 604/197 |
| 2006/0131344 A1* | 6/2006 | Brass | B05C 17/0133 222/390 |
| 2008/0071226 A1* | 3/2008 | Moser | A61M 5/3156 604/207 |
| 2009/0054850 A1* | 2/2009 | Moser | A61M 5/31535 604/208 |
| 2010/0036320 A1* | 2/2010 | Cox | A61M 5/31541 604/135 |
| 2011/0125088 A1* | 5/2011 | Dixon | A61B 17/8822 604/82 |
| 2012/0244493 A1* | 9/2012 | Leiner | B65D 83/0011 433/90 |
| 2013/0043282 A1* | 2/2013 | Niklasson | A61M 5/3137 222/390 |
| 2013/0296796 A1* | 11/2013 | Hourmand | A61M 5/326 604/197 |
| 2014/0249482 A1* | 9/2014 | Wieselblad | A61M 5/31511 604/211 |
| 2015/0080811 A1* | 3/2015 | Wieselblad | A61M 5/3155 604/207 |
| 2015/0290397 A1* | 10/2015 | Wieselblad | A61M 5/31551 604/211 |
| 2015/0359978 A1* | 12/2015 | Egerstrom | A61M 15/0065 128/200.14 |
| 2016/0325047 A1* | 11/2016 | Vedrine | A61M 5/24 |

FOREIGN PATENT DOCUMENTS

| | | |
|---|---|---|
| EP | 0856324 A3 | 9/1999 |
| EP | 1003581 B1 | 11/2000 |
| EP | 0679103 B1 | 1/2001 |
| EP | 0947209 B1 | 8/2003 |
| EP | 0965002 B1 | 1/2004 |
| EP | 1185322 B1 | 12/2005 |
| EP | 1324790 B1 | 12/2005 |
| EP | 2043708 B1 | 12/2010 |
| EP | 2308529 A3 | 4/2011 |
| EP | 2468335 A1 | 6/2012 |
| EP | 2237819 B1 | 9/2013 |
| WO | WO03017854 A1 | 3/2003 |
| WO | WO2013058698 A1 | 4/2013 |
| WO | WO-2014111371 A1 * | 7/2014 ......... A61M 5/3146 |
| WO | WO2014111371 A1 | 7/2014 |

OTHER PUBLICATIONS

Official Action in Japanese Patent Application No. 2017-530306, dated Oct. 29, 2019.

* cited by examiner

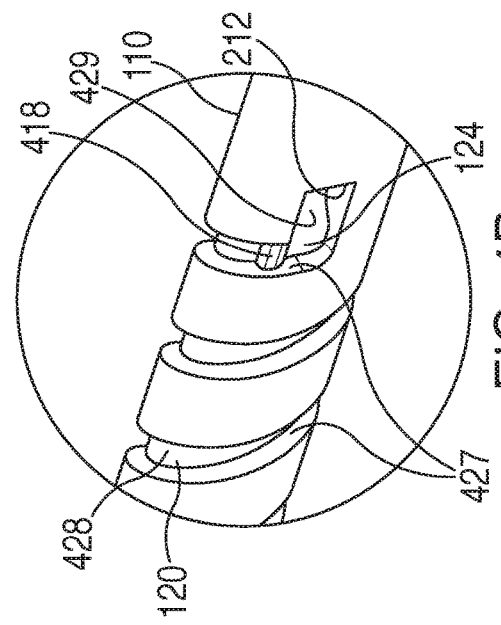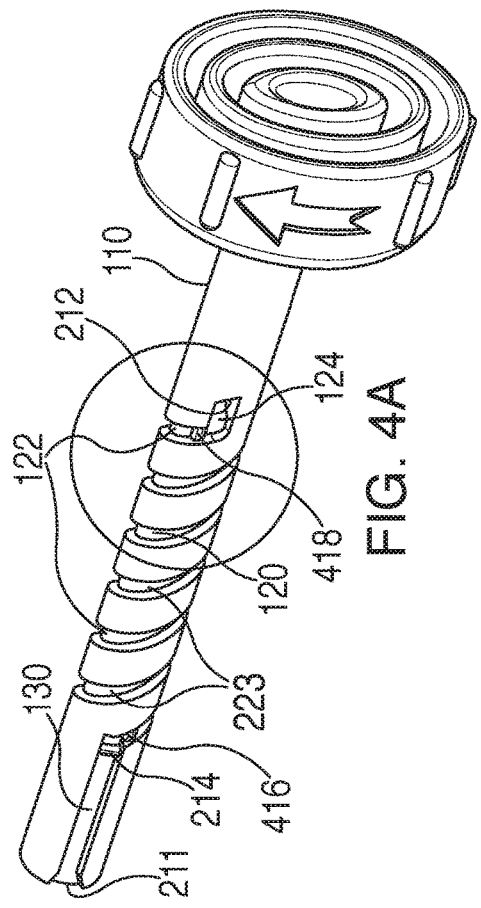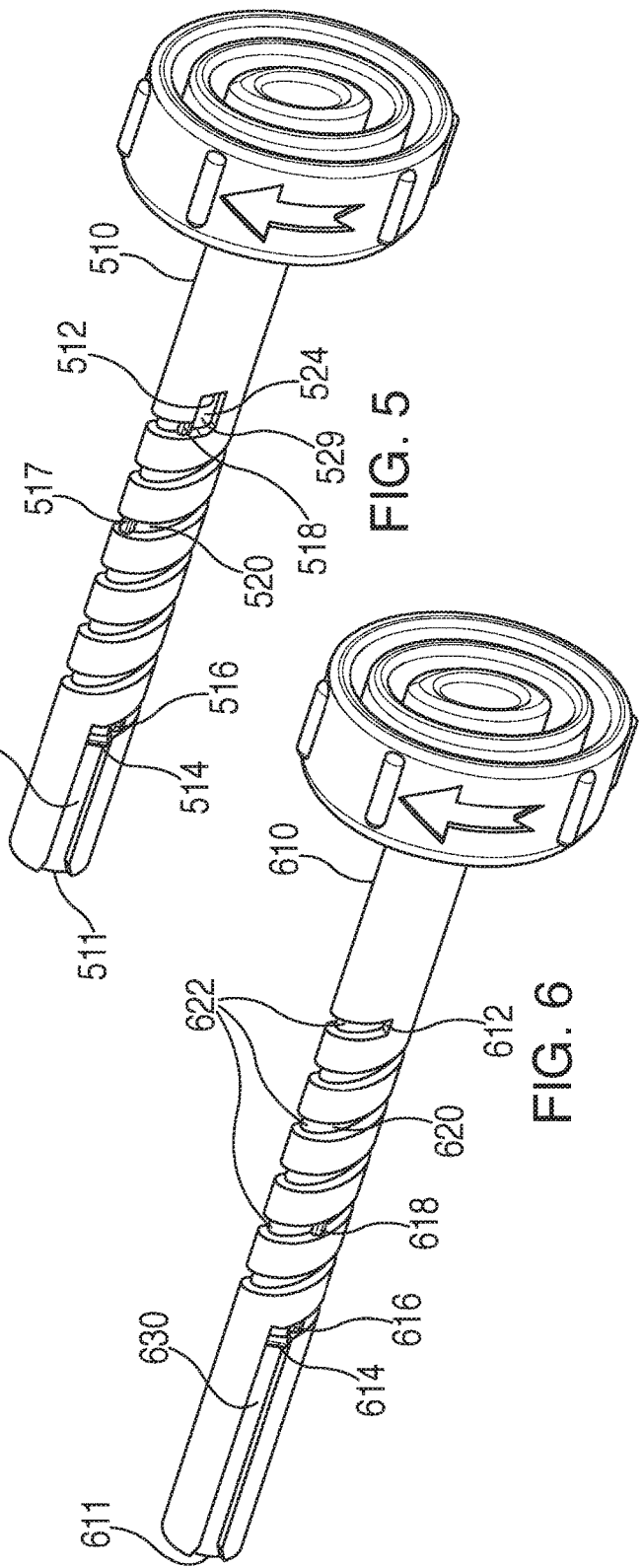

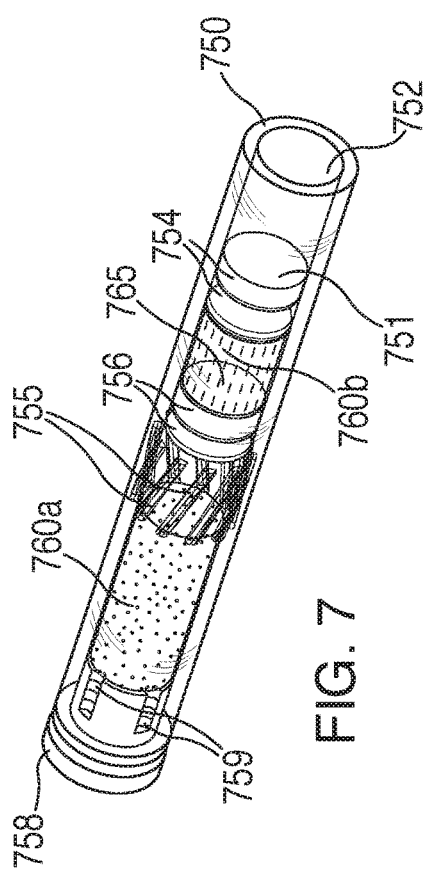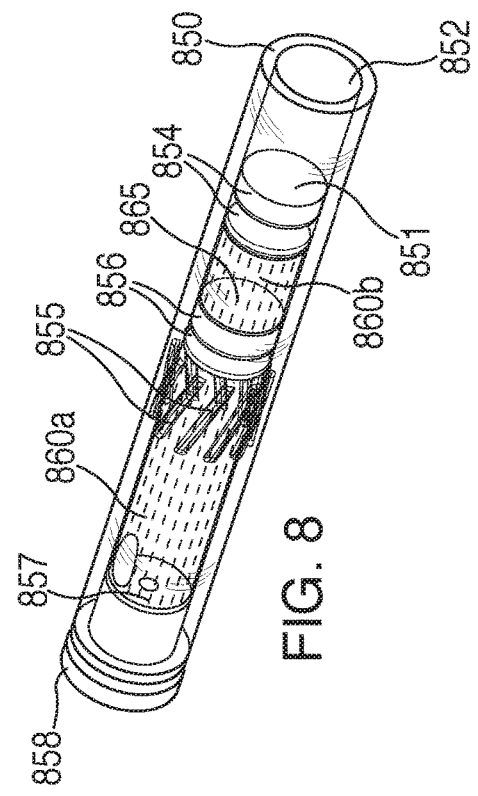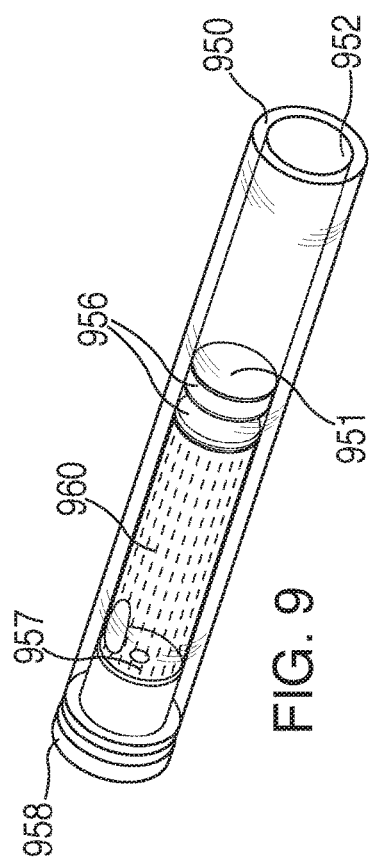

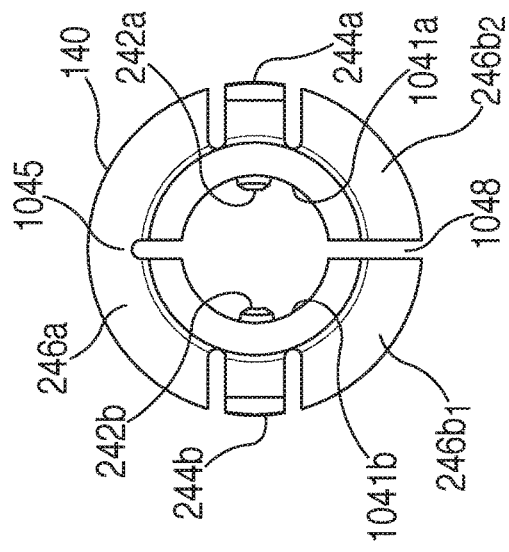
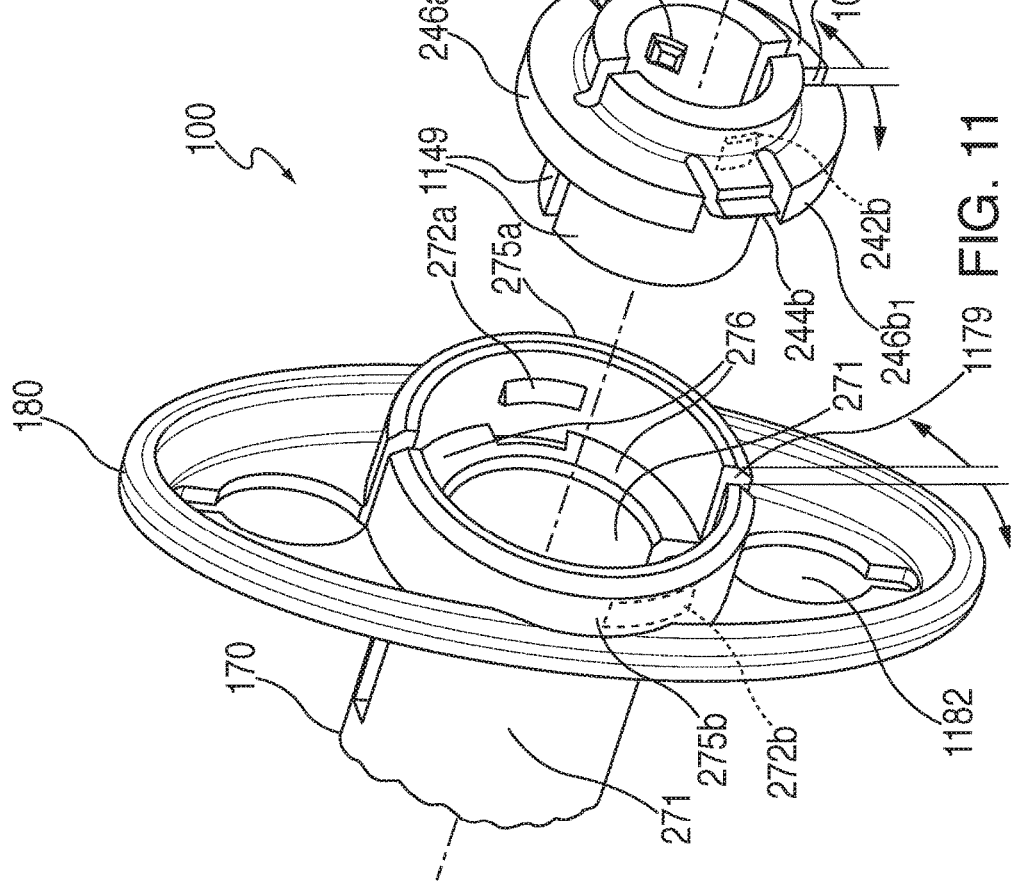

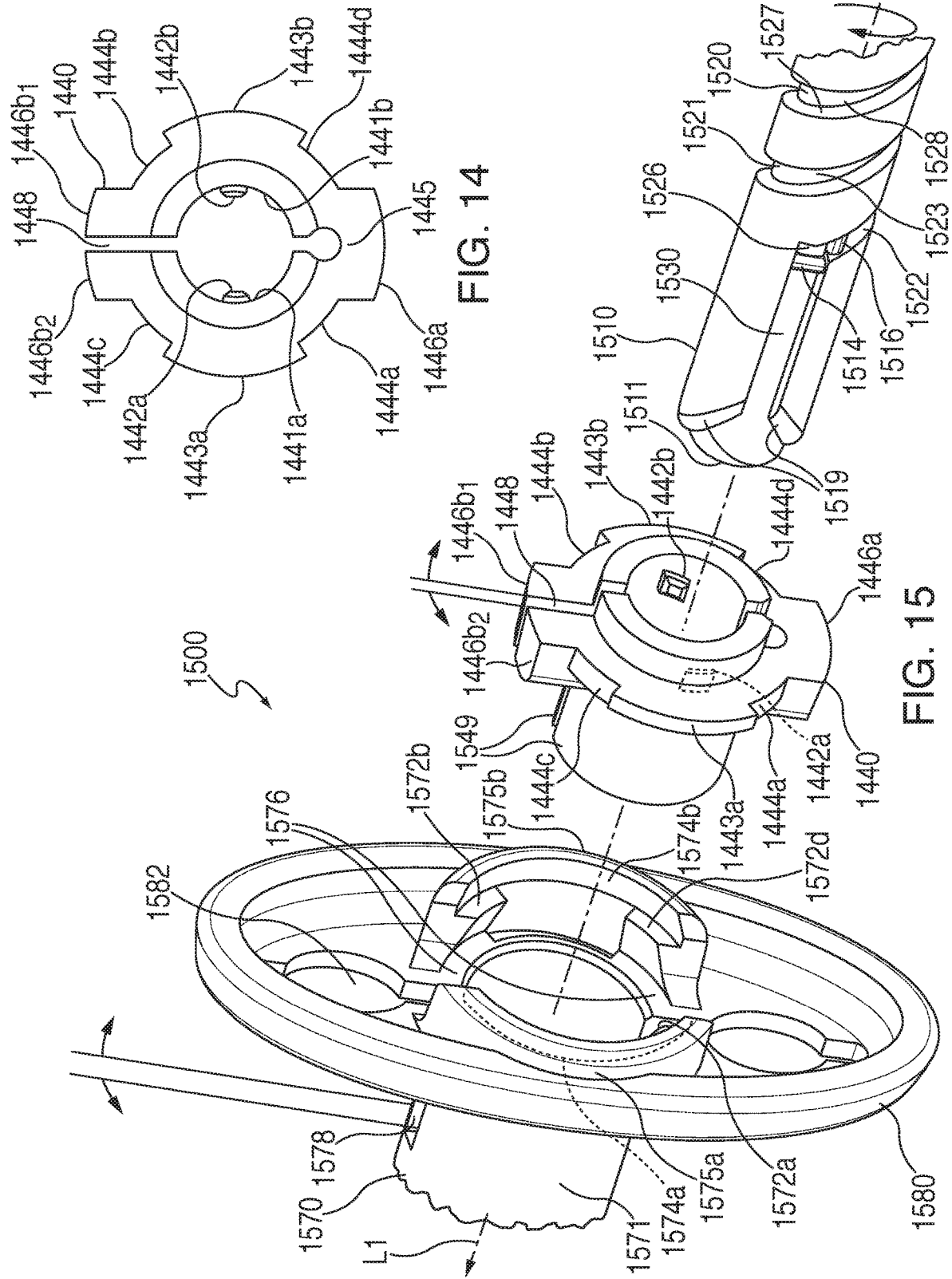

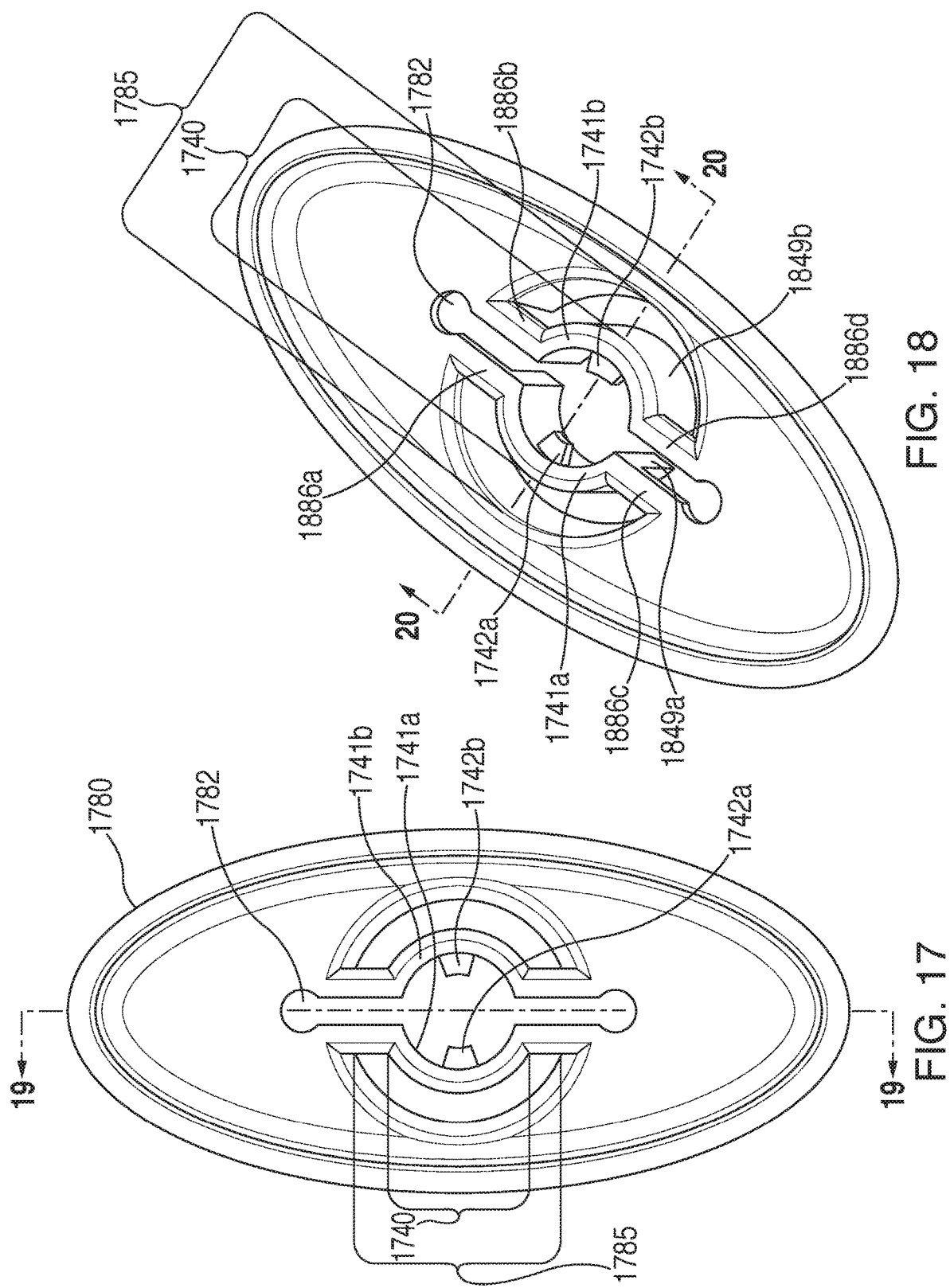

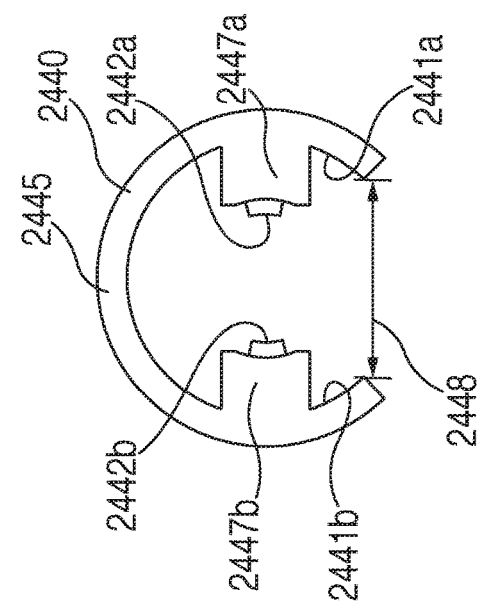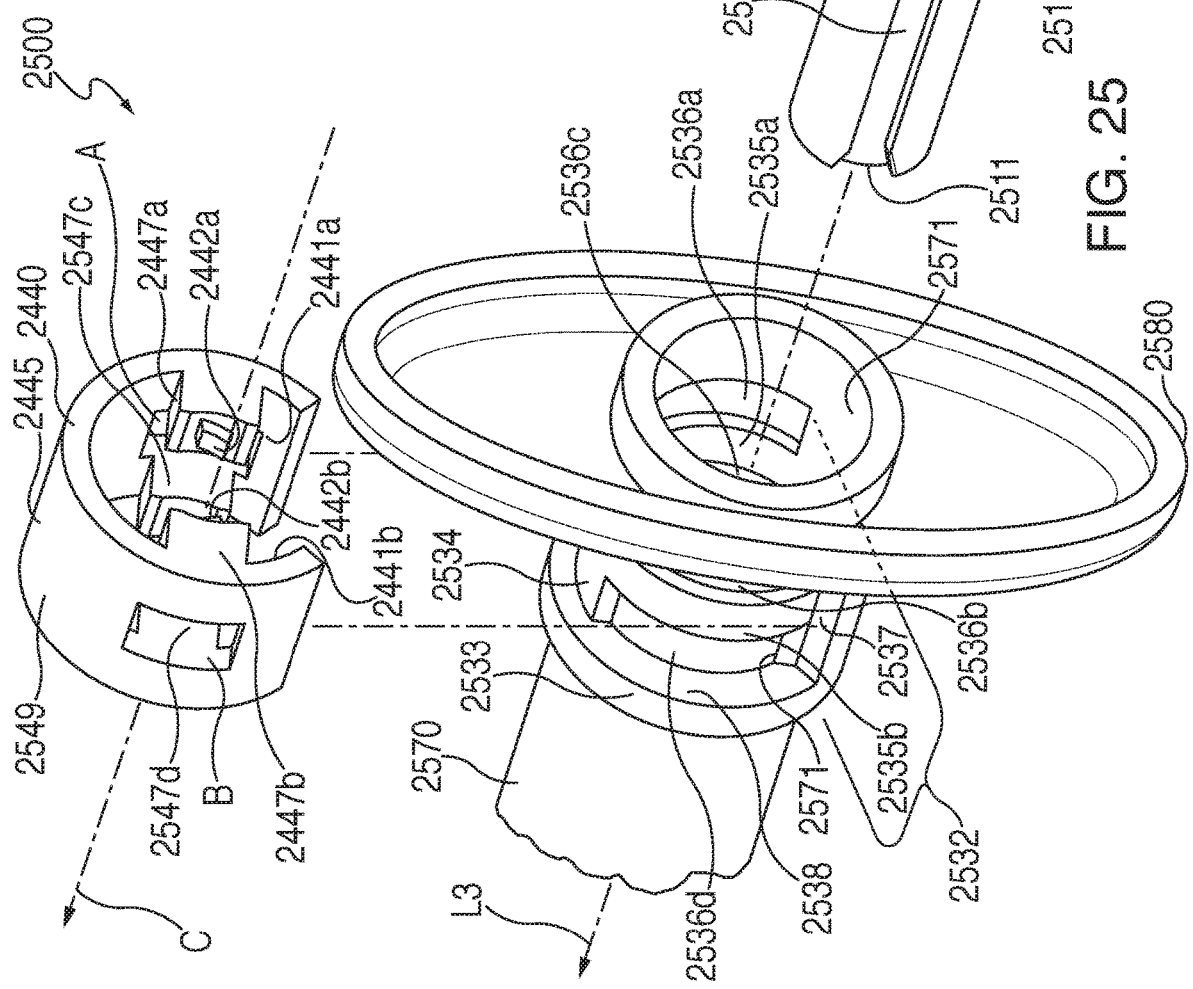

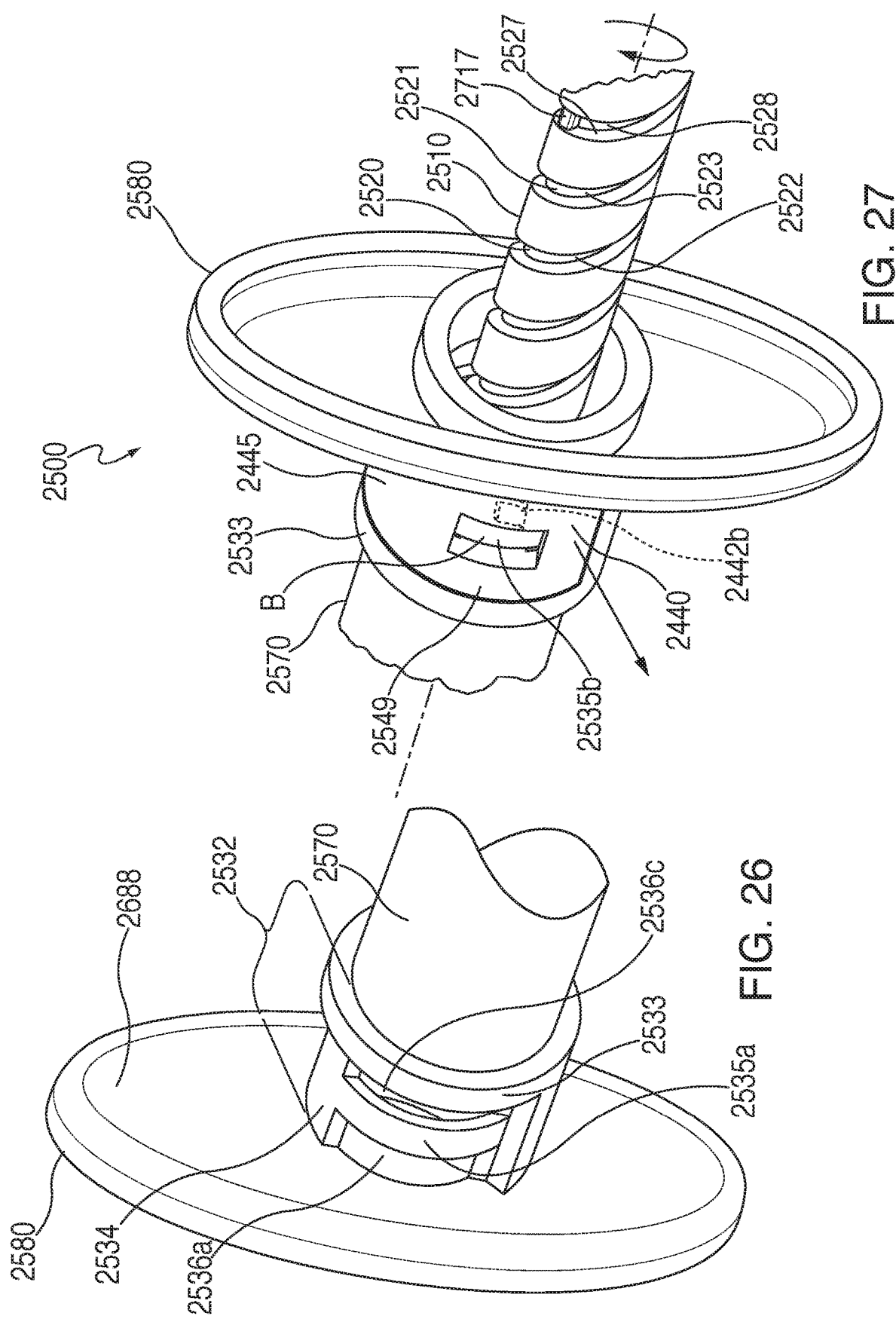

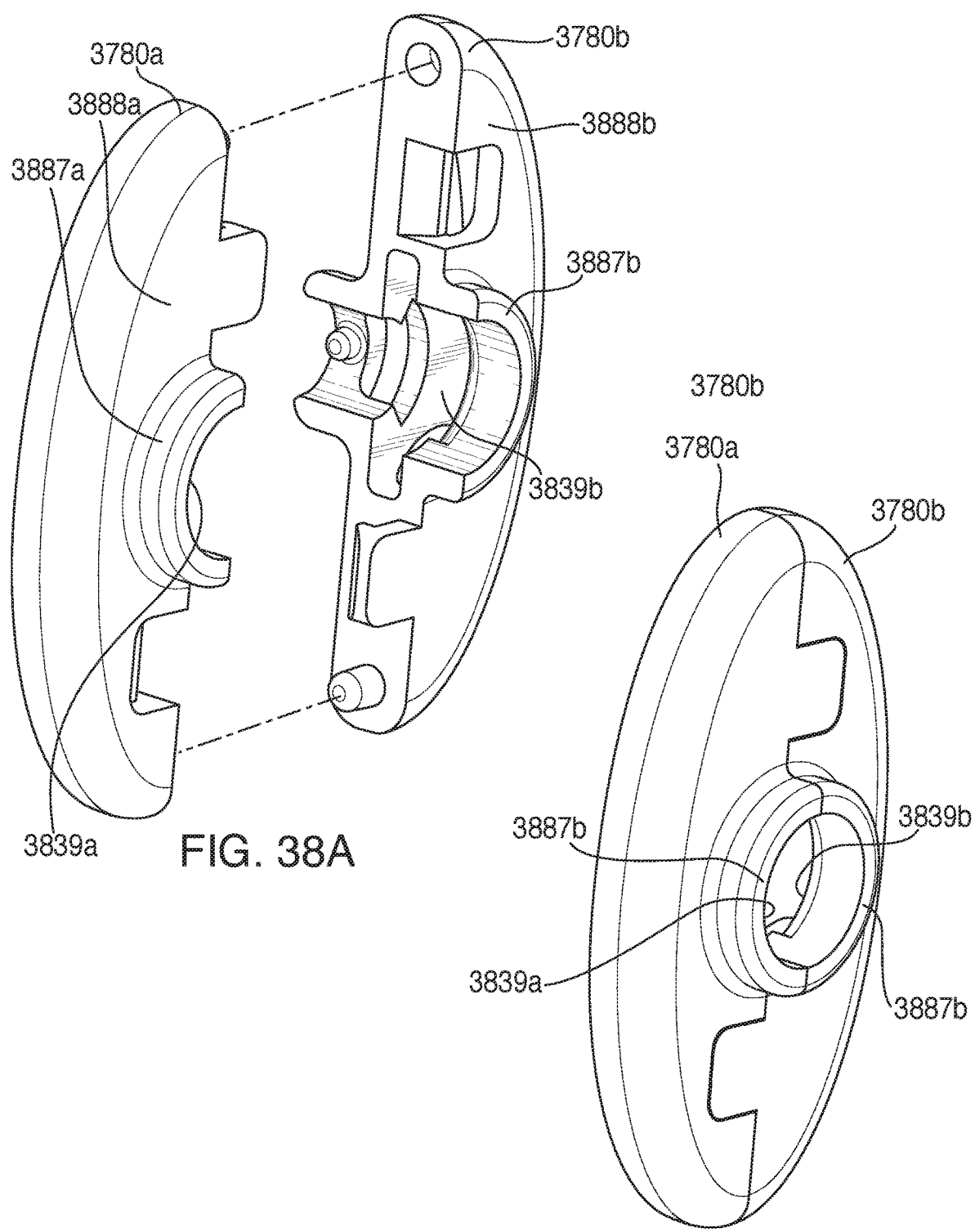

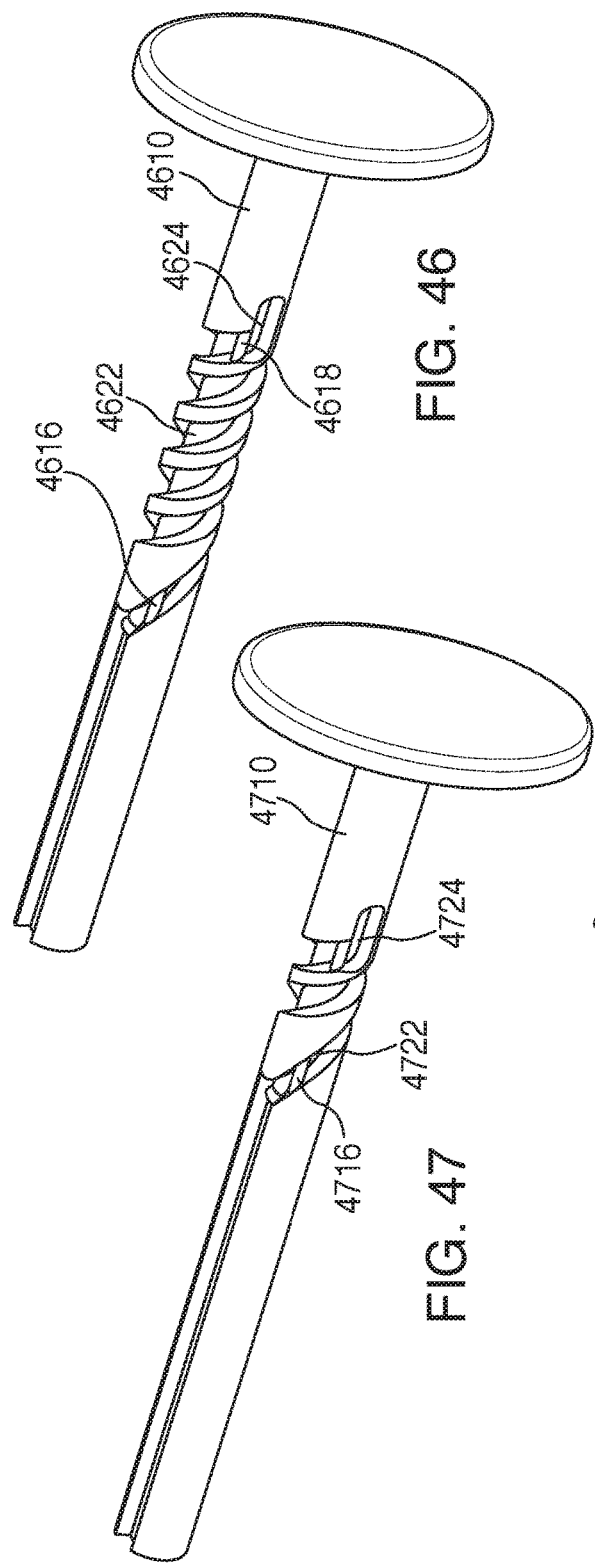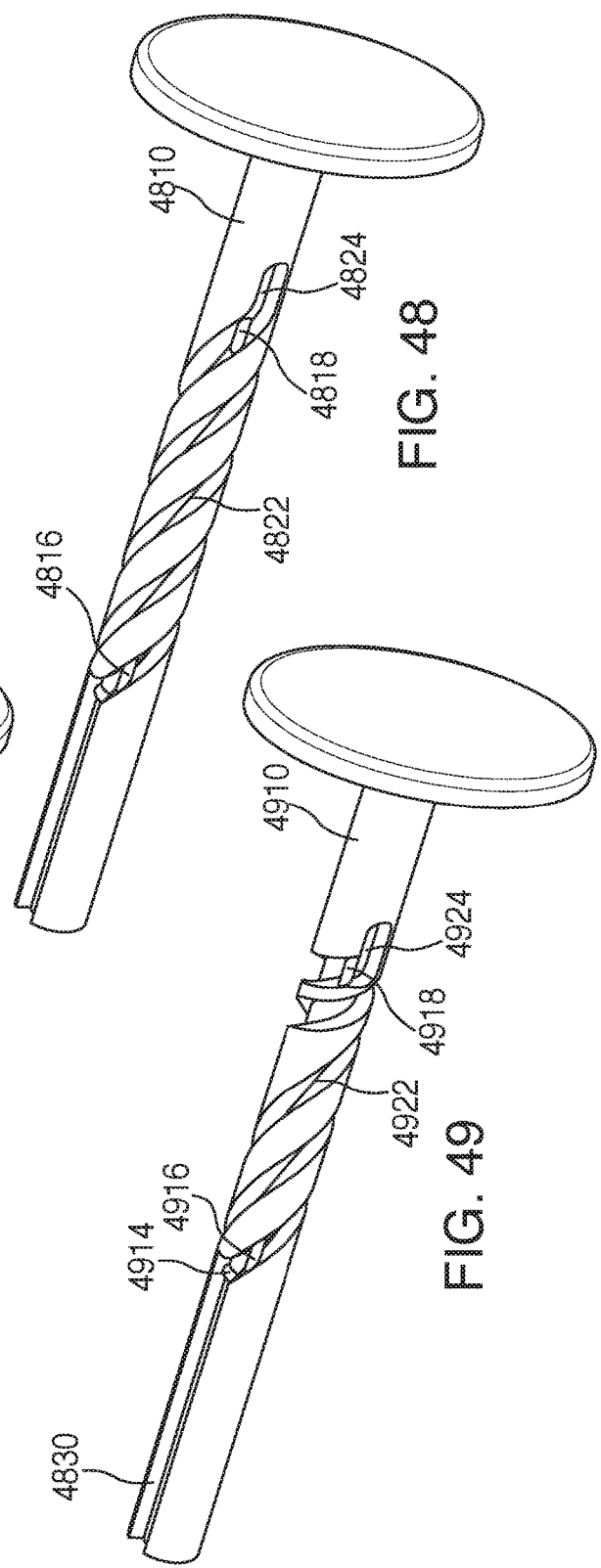

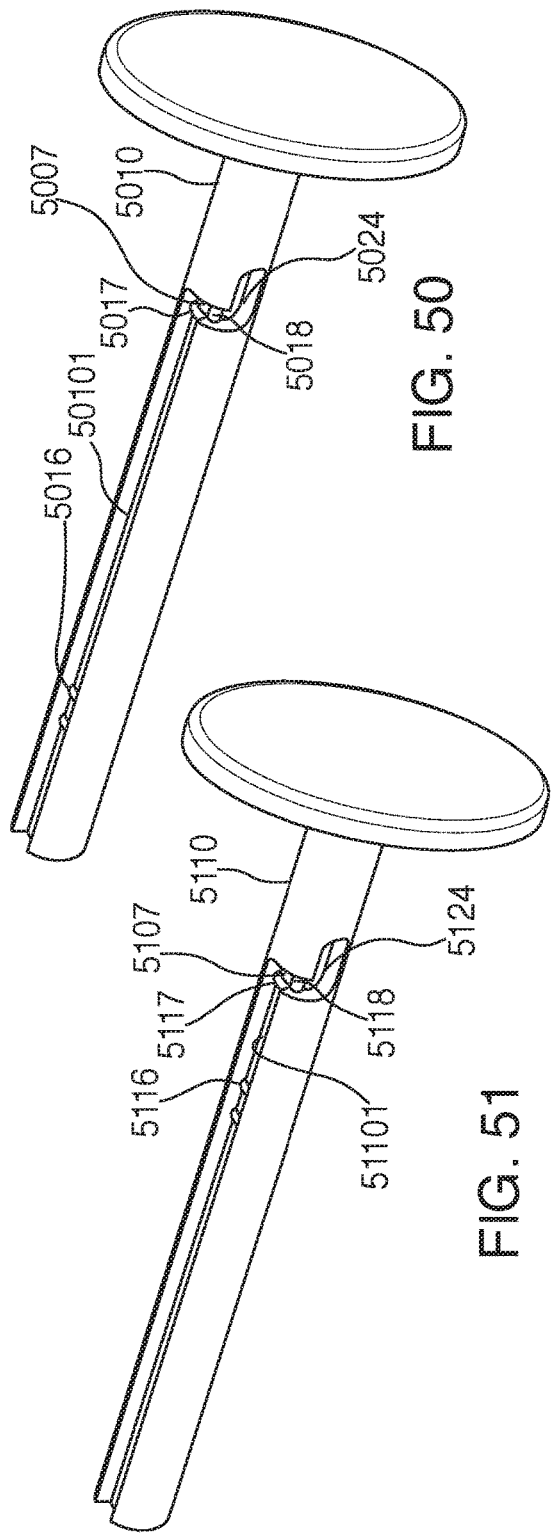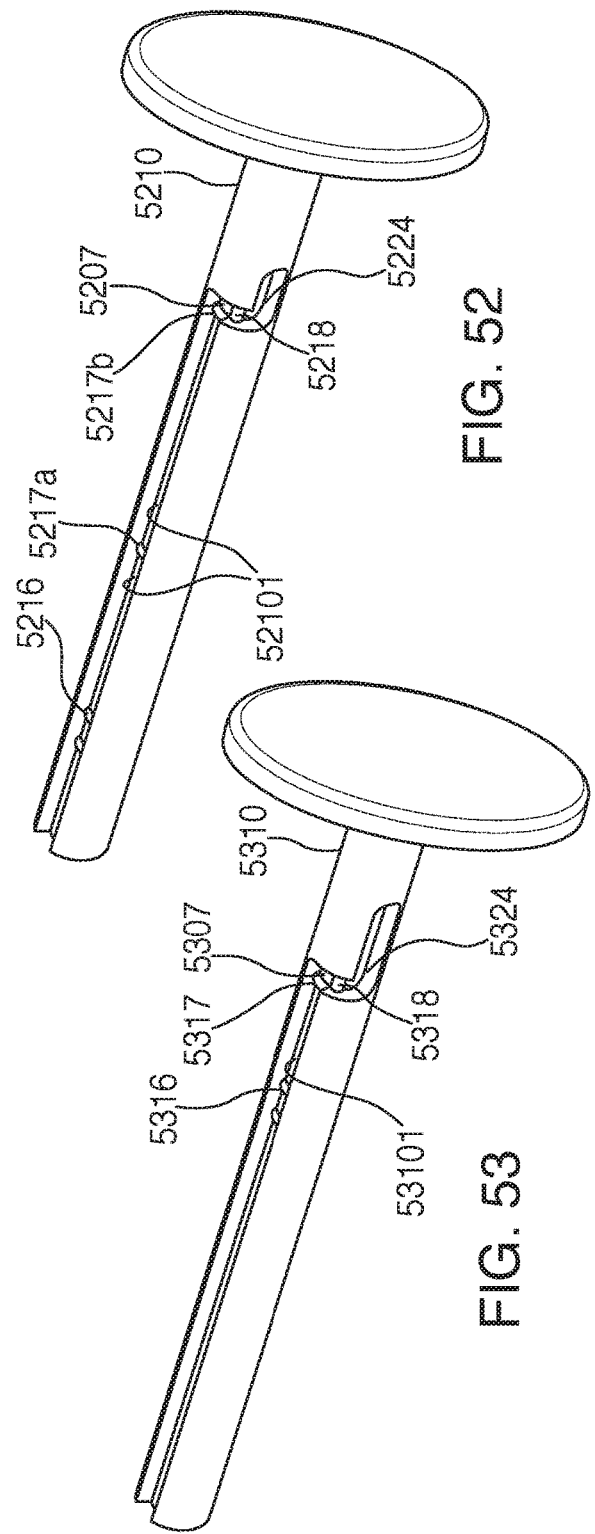

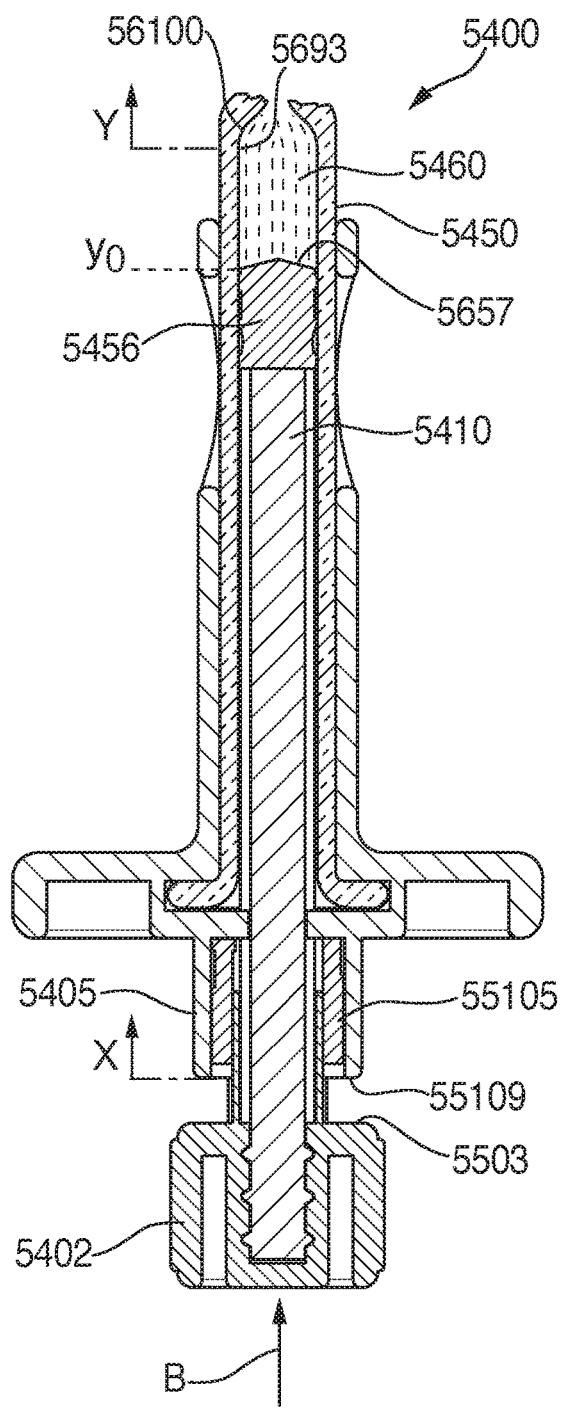
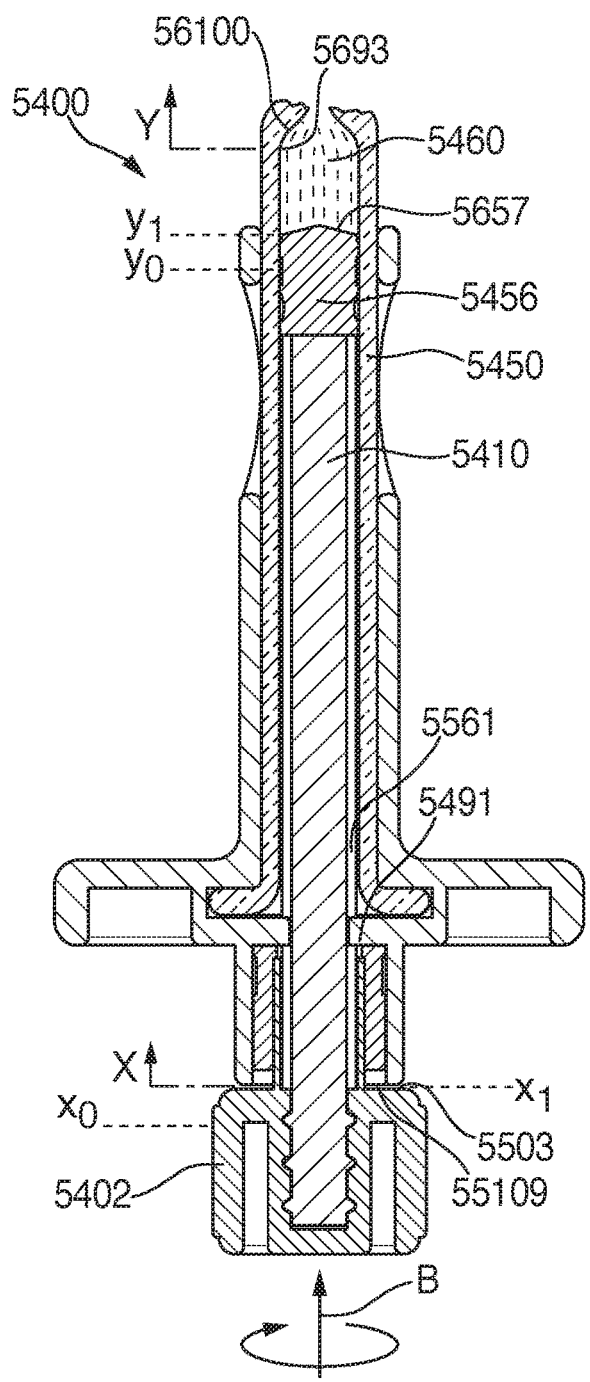
FIG. 56
FIG. 57

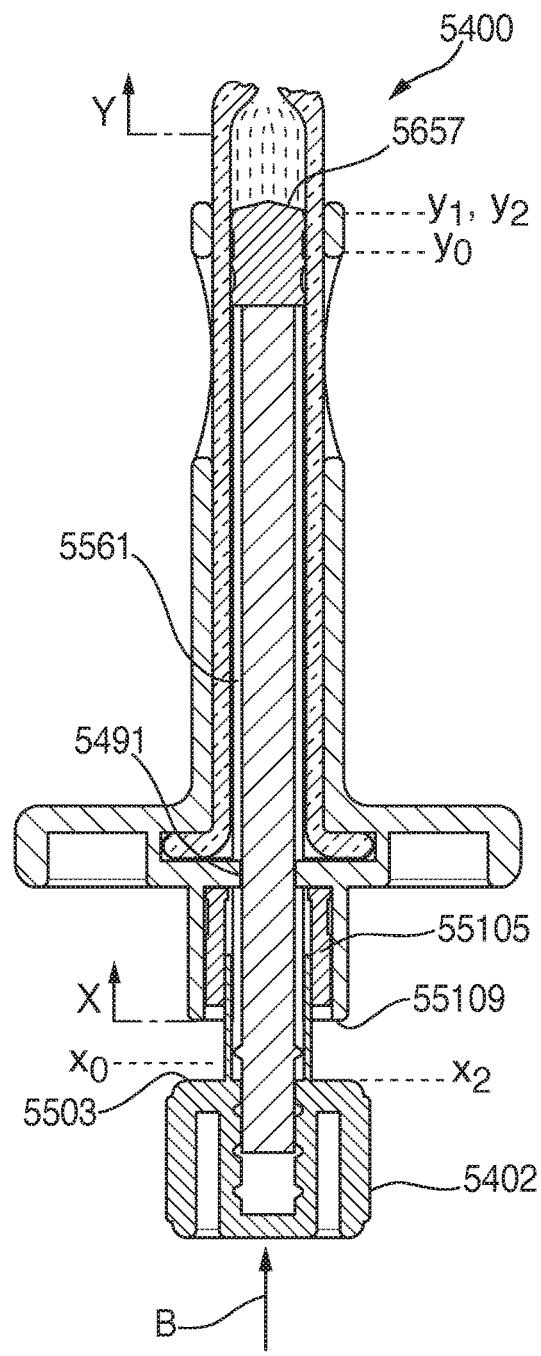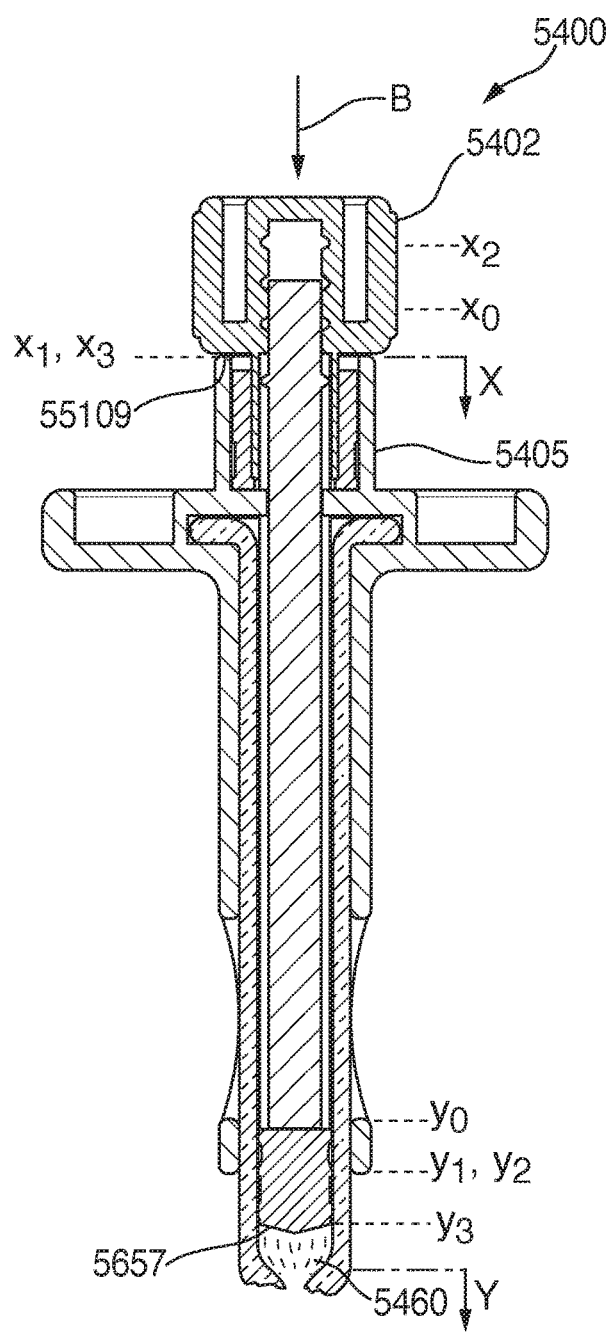
FIG. 58
FIG. 59

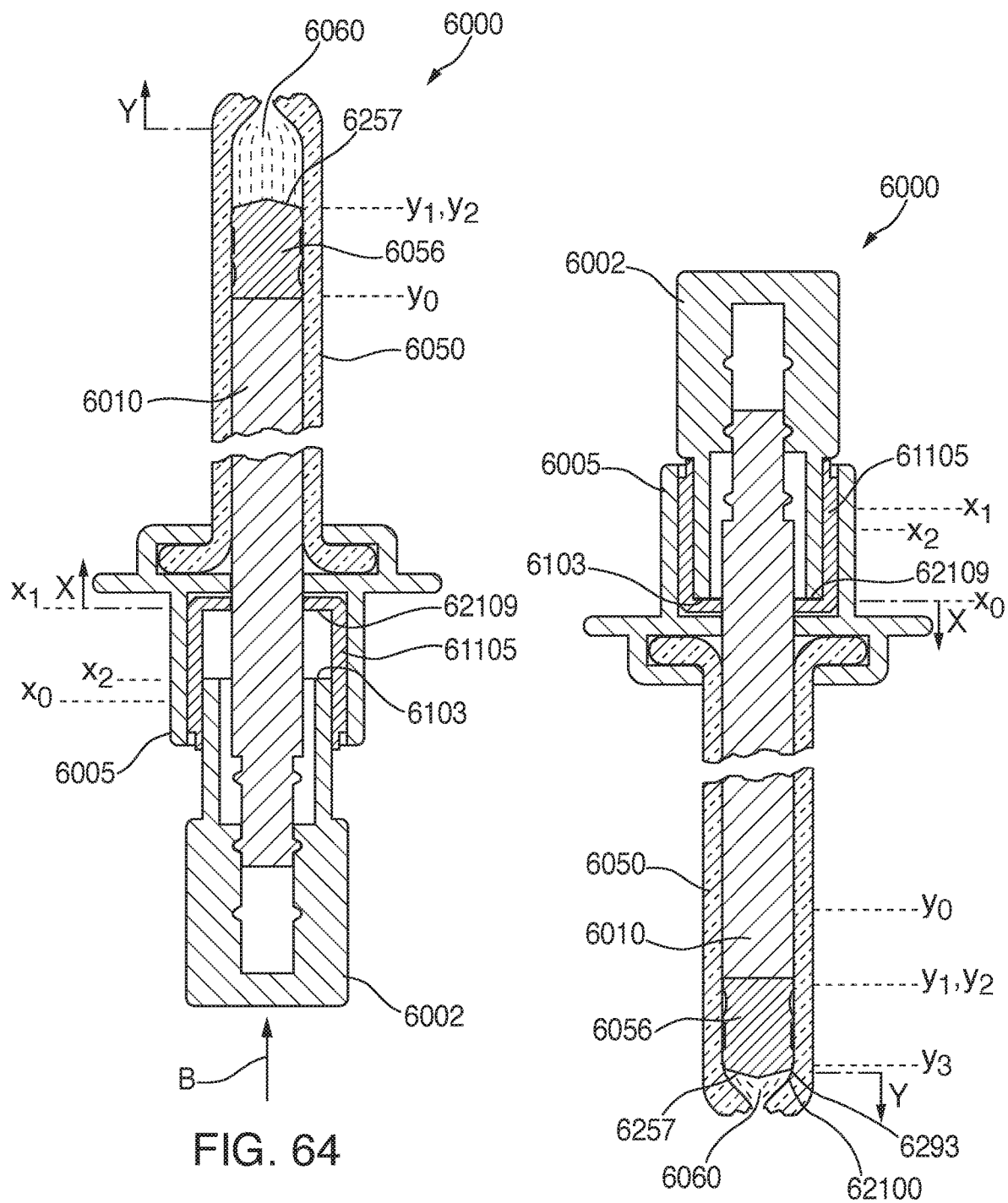

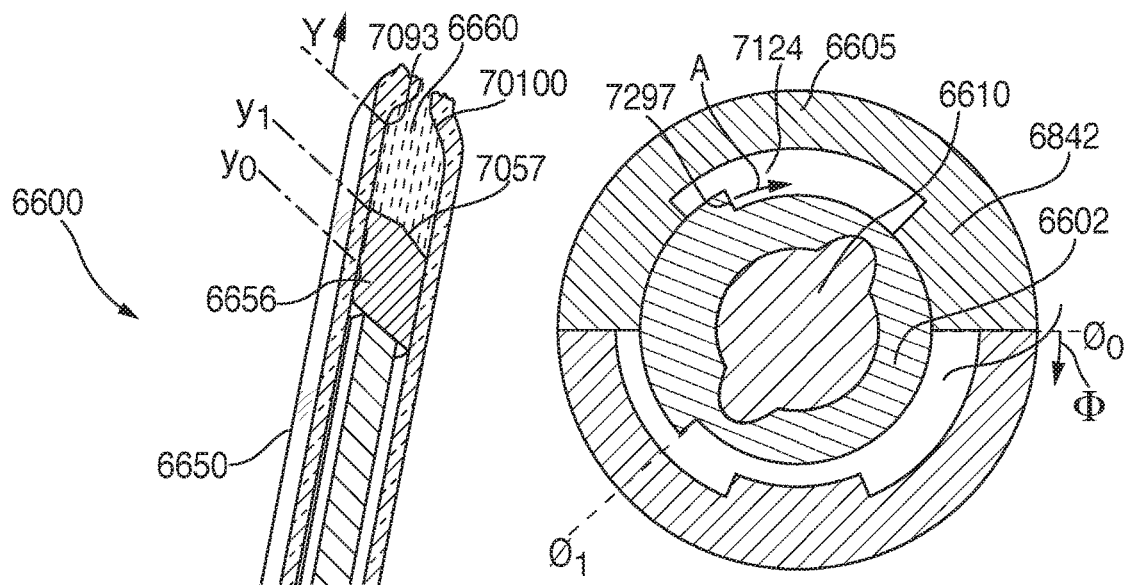
FIG. 74
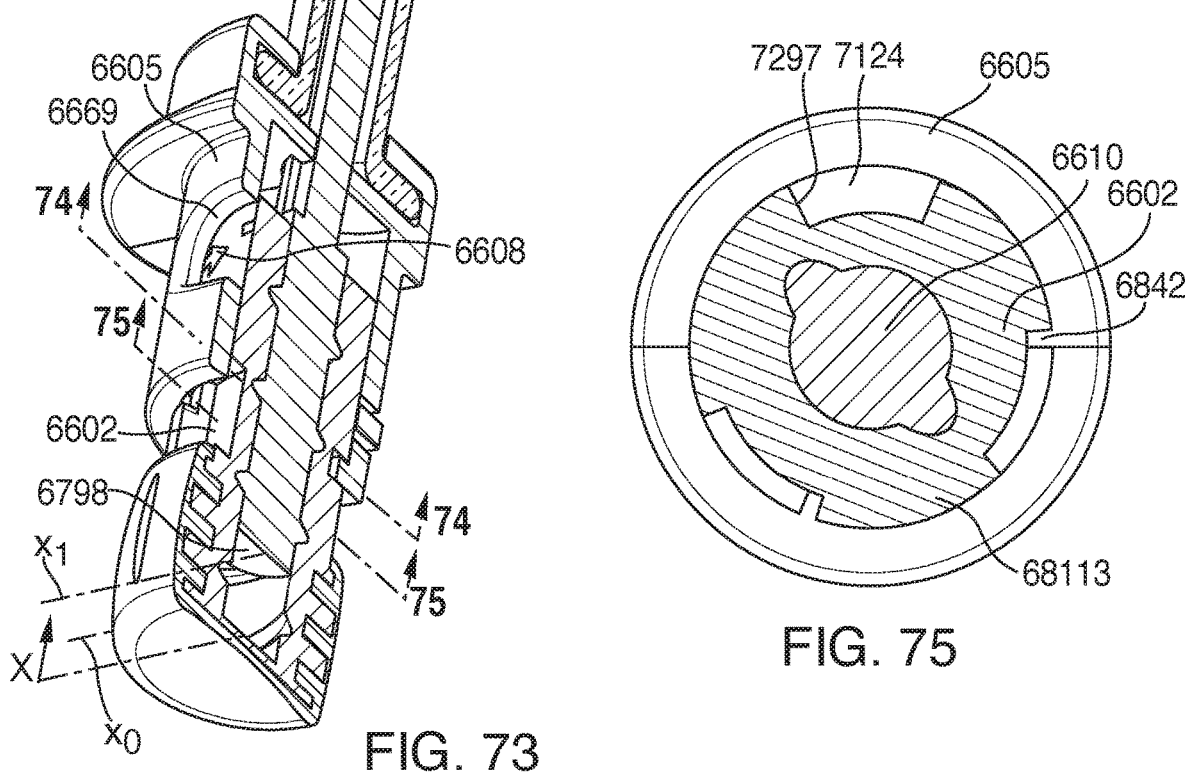
FIG. 75
FIG. 73

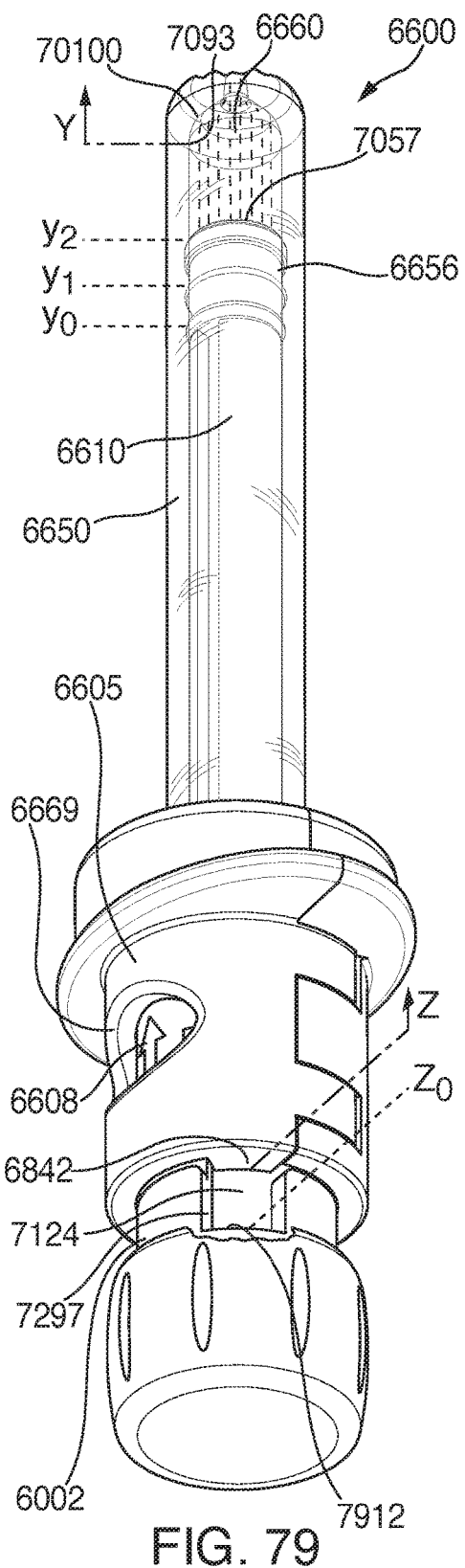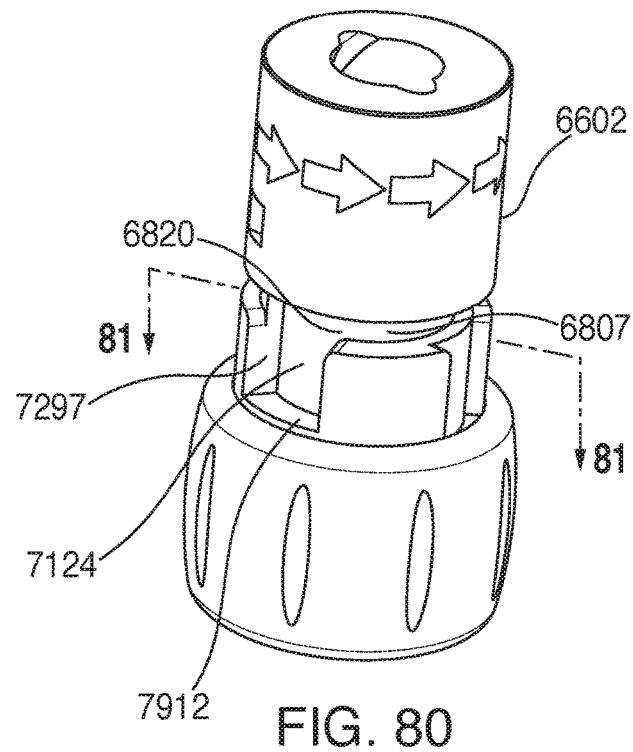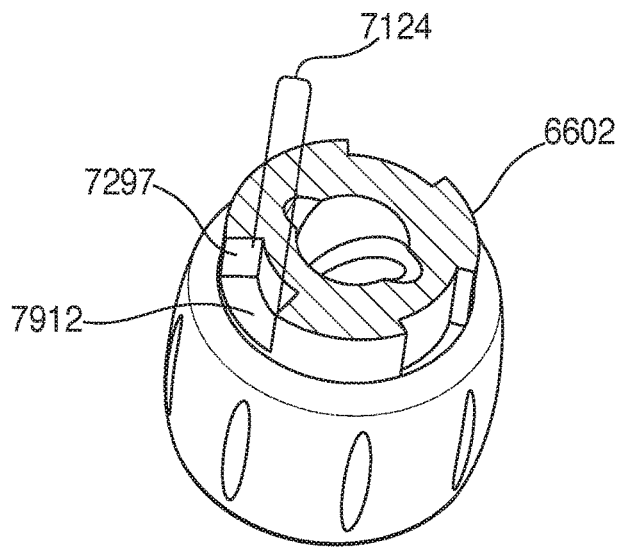
FIG. 79
FIG. 80
FIG. 81

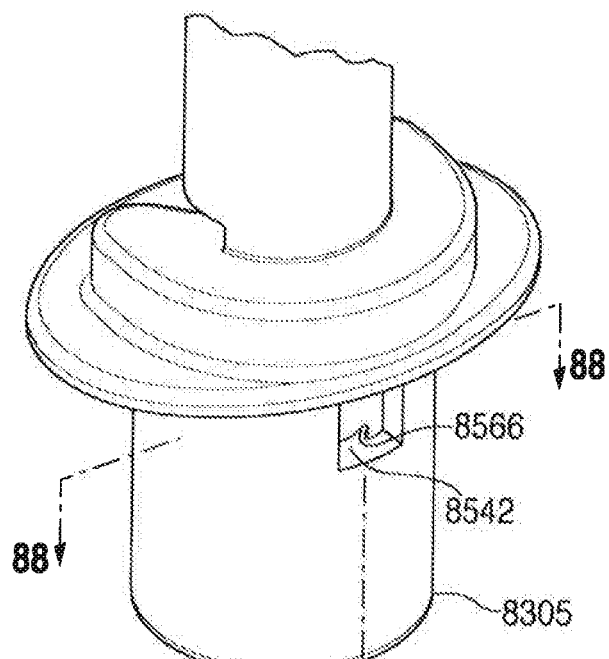
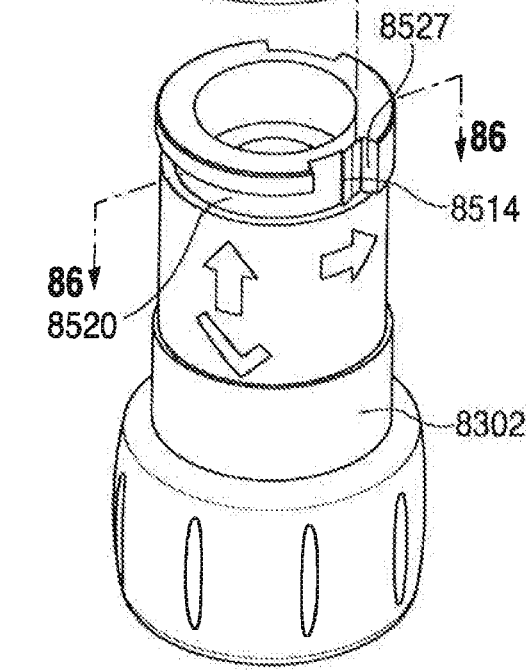
FIG. 85
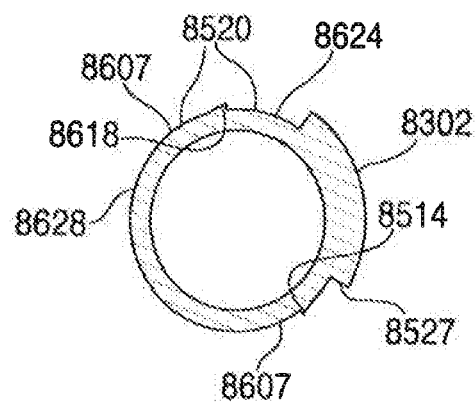
FIG. 86
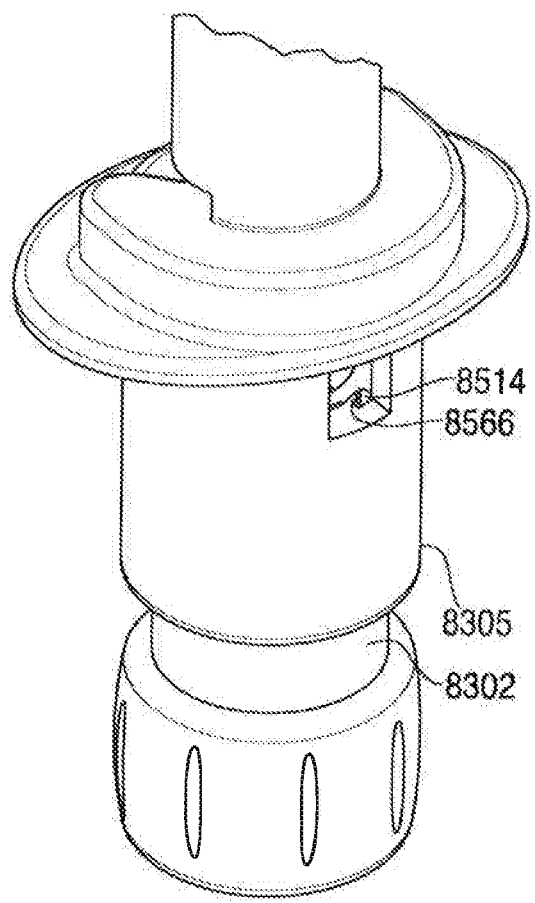
FIG. 87

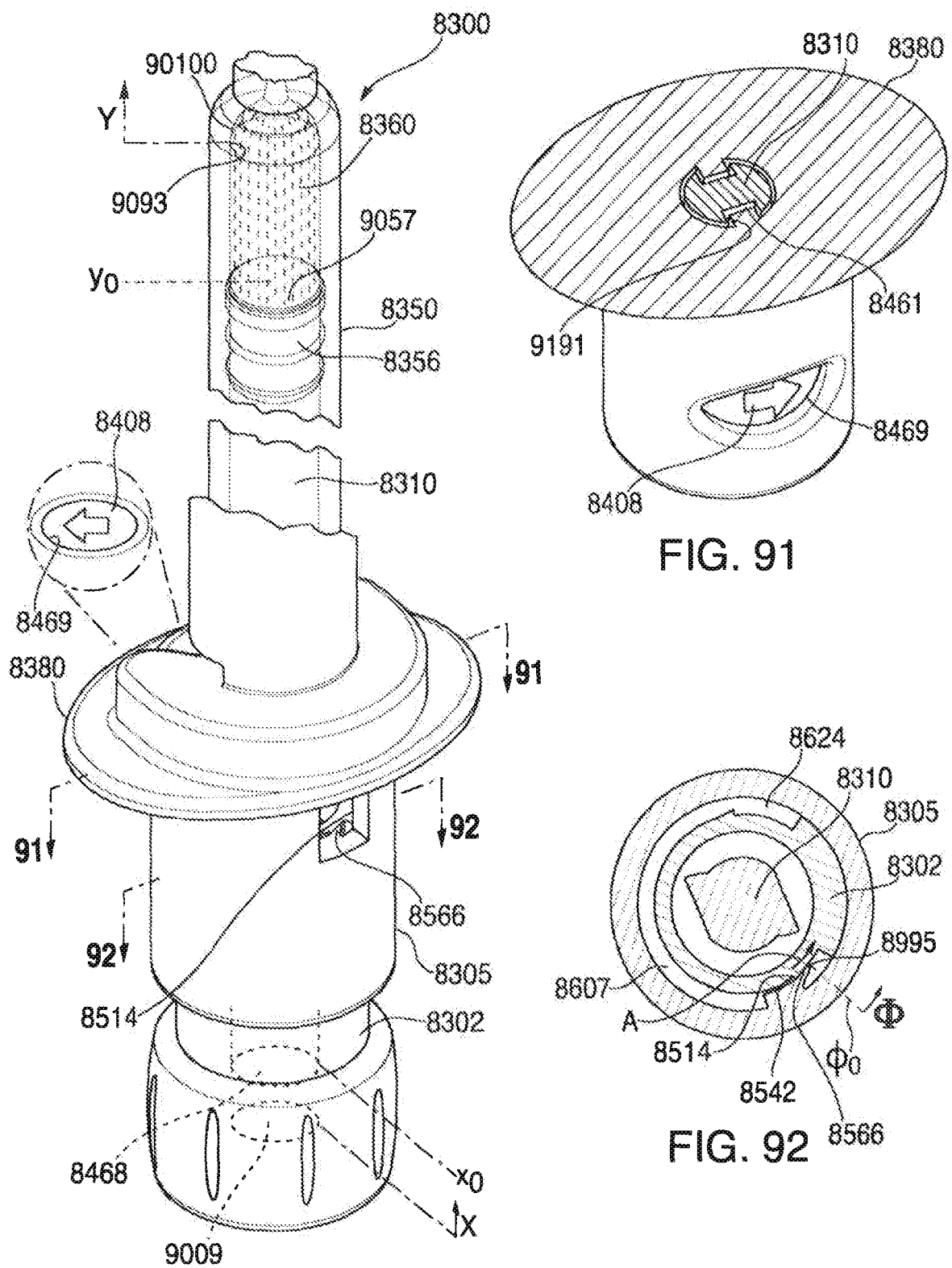

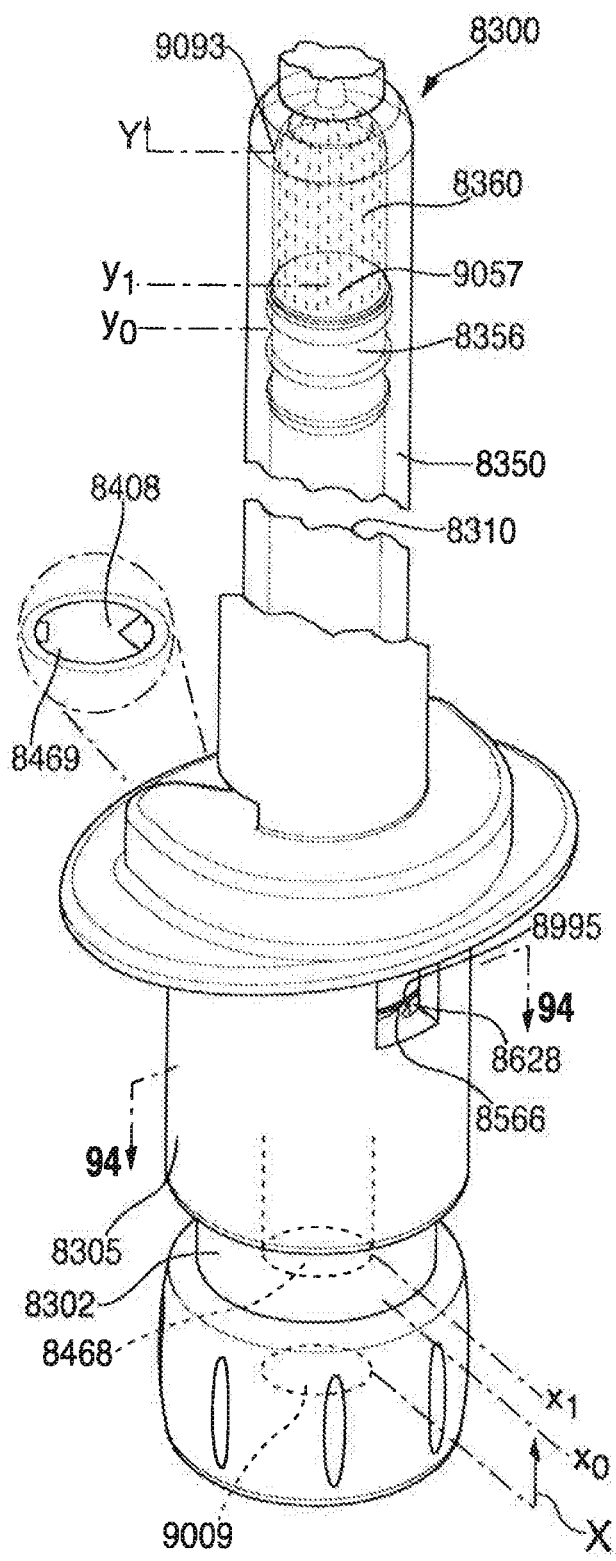
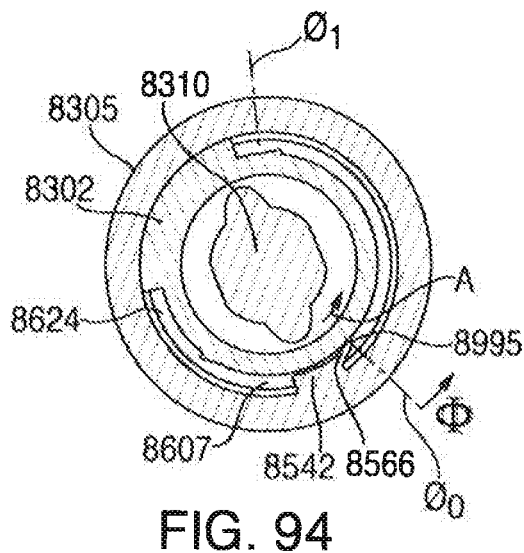
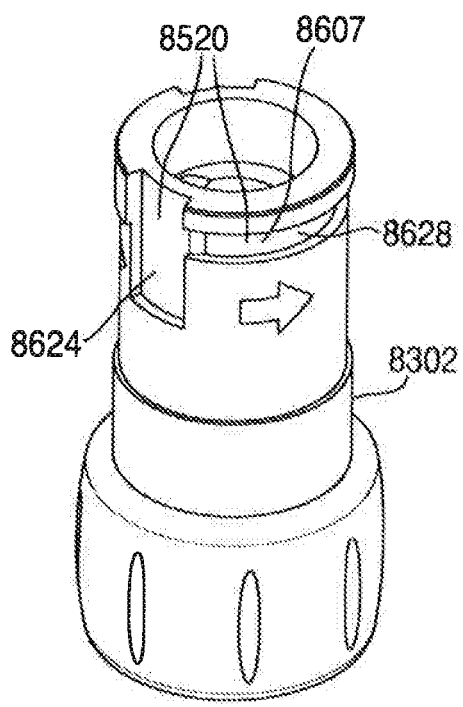
FIG. 93
FIG. 94
FIG. 93A

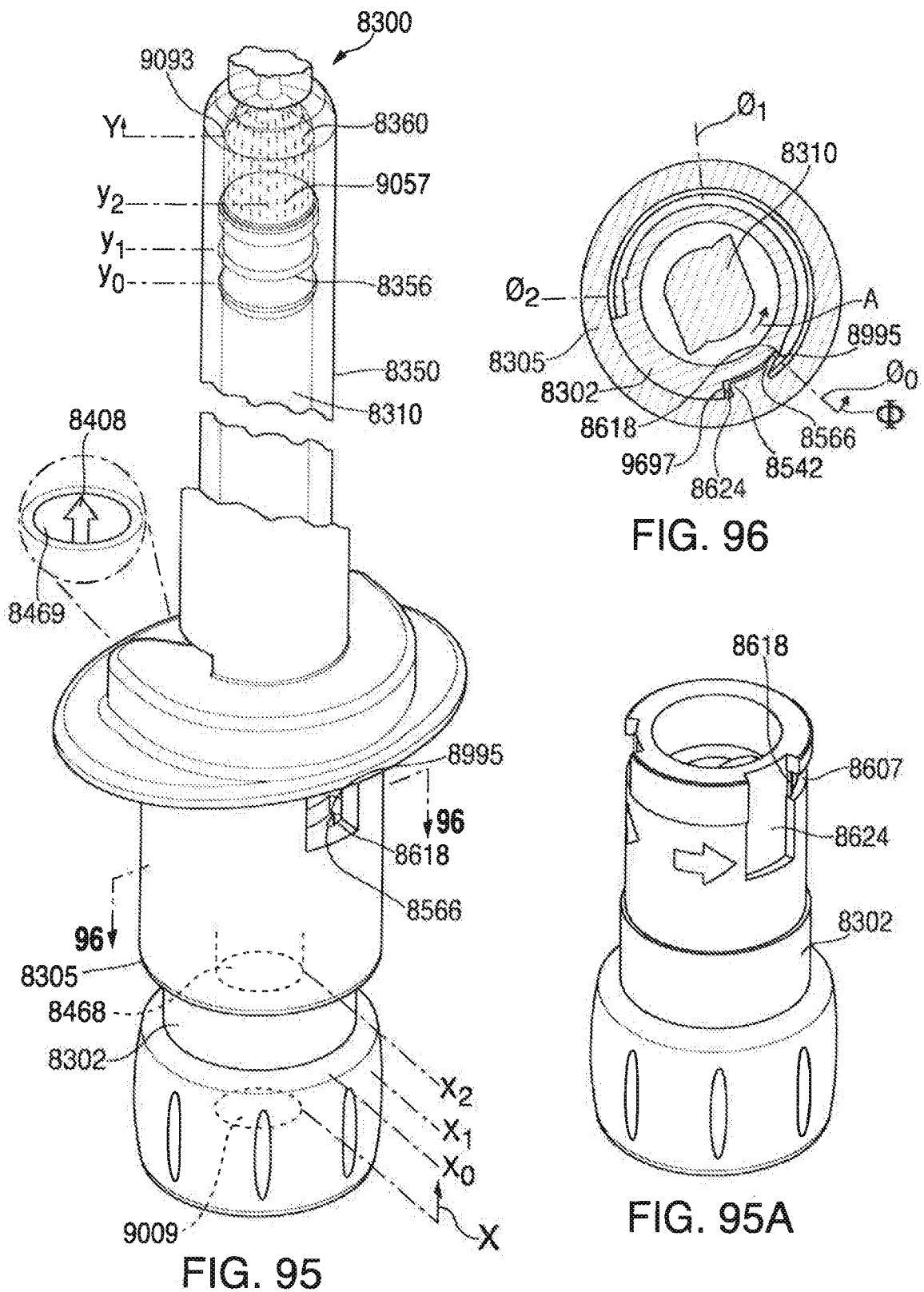

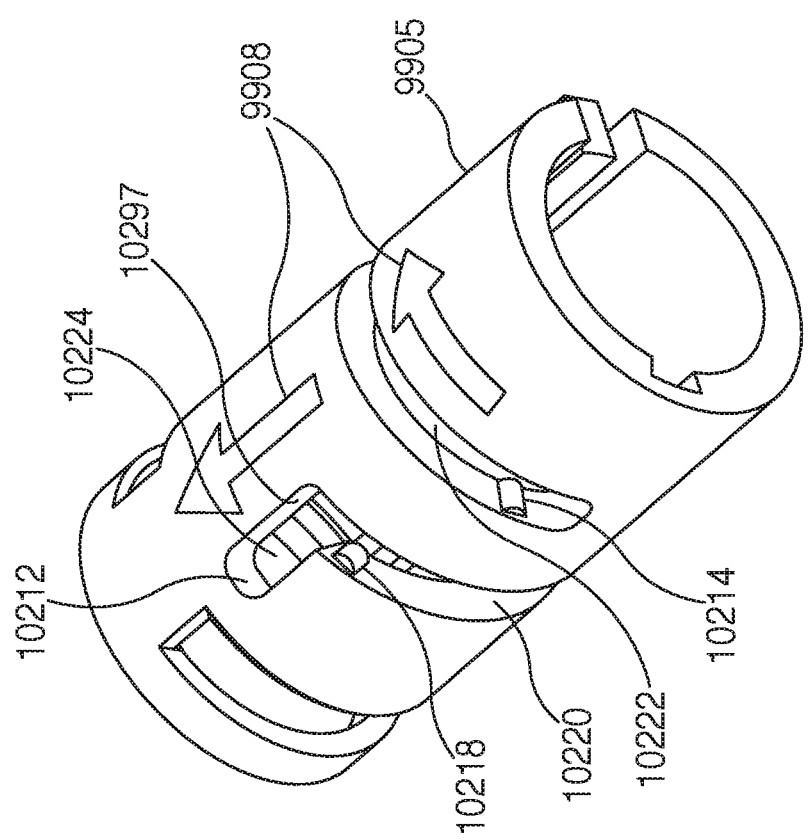

VERSATILE SYRINGE PLATFORM

CROSS-REFERENCE TO OTHER APPLICATIONS

This application is a nonprovisional of U.S. Application No. 62/088,844, which was filed on Dec. 8, 2014, and is hereby incorporated by reference herein in its entirety.

BACKGROUND

A pre-filled syringe is often used to deliver medicament into a patient by discharge of the medicament from the syringe.

Prior to discharge, the pre-filled syringe often contains the medicament in a dischargeable form or, alternatively, in a form requiring conversion to the dischargeable form. The conversion often involves mixing together medicament components initially maintained apart within the syringe.

Prior to discharge, the dischargeable form of the medicament is often contained within the syringe between a slideable syringe plunger and a distal inner end of the syringe defining a discharge orifice, the plunger sealing circumferentially against an interior wall of the syringe.

A seal may require force to be dislodged from the interior wall if static friction is substantial. If the force is applied by a longitudinal impulse, such as a push by an operator's thumb, the impulse may provide enough energy to dislodge the seal, but may also compromise the operator's control over the displacement of the plunger once the seal is dislodged.

With the syringe oriented distal end up, discharge of air from the syringe ("priming") may be effected by displacement of the plunger toward the distal inner end. Priming drives the air out through the discharge orifice and a distally attached delivery needle, thus filling the needle with the medicament.

After priming, before initiation of delivery of the medicament, the needle is inserted into the patient. Delivery of the medicament is effected by further displacement of the plunger toward the distal inner end. An extent of displacement of the plunger toward the distal inner end determines a volume of medicament delivered to the patient.

Typically, the extent of the plunger displacement delivering the medicament ("delivery stroke") is limited by the plunger "bottoming out" against the distal inner end. Bottoming out typically involves deformation of a pliant material of the plunger, often against the distal inner end, which may include a pliant material of a needle-penetrated distal stopper.

The extent of the delivery stroke and, thereby, the volume of medicament delivered are often sensitive to deformation of the plunger and/or the stopper. Extent of such deformation is often not reliably repeatable. Bottoming out may not provide a reliable delivery mechanism for low volume of the medicament.

Operator manipulation to effect stages of syringe operation—such as mixing, priming or delivery—impacts volume of medicament remaining in the syringe at initiation of delivery. Typically, there is little or no feedback indicating to an operator when, during the manipulation, pre-delivery stages have been completed and when to initiate delivery. Without such indication of progress of stages of syringe operation, medicament to be delivered may be lost before initiation of delivery. Alternatively, the volume of medicament remaining in the syringe after pre-delivery stages may exceed a desired delivery volume. For low volume delivery, such loss or excess of medicament may represent a significant portion of the desired volume.

It would be desirable, therefore, to provide apparatus and methods for low volume medicament delivery with improved reliability over bottoming out.

It would also, therefore, be desirable to provide apparatus and methods for increasing the operator's control over the plunger displacement while dislodging the seal from the container wall.

Also, it would be desirable, therefore, to provide apparatus and methods providing indication of progress of stages of syringe operation.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 2A is a partial cross-sectional view of the apparatus shown in FIG. 2, the view taken along lines A-A (shown in FIG. 2);

FIG. 2B is a partial cross-sectional view of the apparatus shown in FIG. 2, the view taken along lines B-B (shown in FIG. 2);

FIG. 2C is a partial cross-sectional view of the apparatus shown in FIG. 2, the view taken along lines C-C (shown in FIG. 2);

FIG. 4A is a perspective view of apparatus in accordance with the principles of the invention;

FIG. 4B is an enlarged detail of the apparatus shown in FIG. 4A;

FIG. 5 is a perspective view of apparatus in accordance with the principles of the invention;

FIG. 6 is a perspective view of apparatus in accordance with the principles of the invention;

FIG. 7 is a perspective view of apparatus in accordance with the principles of the invention;

FIG. 8 is a perspective view of apparatus in accordance with the principles of the invention;

FIG. 9 is a perspective view of apparatus in accordance with the principles of the invention;

FIG. 10 is an end-view of apparatus in accordance with the principles of the invention;

FIG. 11 is an exploded, perspective view of apparatus in accordance with the principles of the invention, including the apparatus shown in FIG. 10;

FIG. 14 is an end-view of apparatus in accordance with the principles of the invention;

FIG. 15 is an exploded, perspective view of apparatus in accordance with the principles of the invention, including the apparatus shown in FIG. 14;

FIG. 17 is an end-view of apparatus in accordance with the principles of the invention;

FIG. 18 is a perspective view of the apparatus shown in FIG. 17;

FIG. 24 is an end-view of apparatus in accordance with the principles of the invention;

FIG. 25 is an exploded perspective view of apparatus in accordance with the principles of the invention, including the apparatus shown in FIG. 24;

FIG. 26 is another perspective view of apparatus shown in FIG. 25;

FIG. 27 is another perspective view of the apparatus shown in FIG. 25;

FIG. 29A is another perspective view of apparatus shown in FIG. 28;

FIG. 38A is a perspective view of apparatus in accordance with the principles of the invention;

FIG. 38B is a perspective view of apparatus in accordance with the principles of the invention;

FIG. 46 is a perspective view of apparatus in accordance with the principles of the invention;

FIG. 47 is a perspective view of apparatus in accordance with the principles of the invention;

FIG. 48 is a perspective view of apparatus in accordance with the principles of the invention;

FIG. 49 is a perspective view of apparatus in accordance with the principles of the invention;

FIG. 50 is a perspective view of apparatus in accordance with the principles of the invention;

FIG. 51 is a perspective view of apparatus in accordance with the principles of the invention;

FIG. 52 is a perspective view of apparatus in accordance with the principles of the invention;

FIG. 53 is a perspective view of apparatus in accordance with the principles of the invention;

FIG. 56 is a partial cross-sectional view of apparatus in accordance with the principles of the invention;

FIG. 57 is a partial cross-sectional view of apparatus in accordance with the principles of the invention;

FIG. 58 is a partial cross-sectional view of apparatus in accordance with the principles of the invention;

FIG. 59 is a partial cross-sectional view of apparatus in accordance with the principles of the invention;

FIG. 64 is a partial cross-sectional view of apparatus in accordance with the principles of the invention;

FIG. 65 is a partial cross-sectional view of apparatus in accordance with the principles of the invention;

FIG. 73 is a partial cross-sectional, perspective view of apparatus in accordance with the principles of the invention;

FIG. 74 is a cross-sectional view of the apparatus shown in FIG. 73, the view taken along lines 74-74 (shown in FIG. 73);

FIG. 75 is a partial cross-sectional view of the apparatus shown in FIG. 73, the view taken along lines 75-75 (shown in FIG. 73);

FIG. 79 is a perspective view of apparatus in accordance with the principles of the invention;

FIG. 80 is a perspective view of apparatus in accordance with the principles of the invention;

FIG. 81 is a partial cross-sectional, perspective view of apparatus shown in FIG. 80, the view taken along lines 81-81 (shown in FIG. 80);

FIG. 85 is a partial exploded, perspective view of the apparatus shown in FIG. 83;

FIG. 86 is a cross-sectional view of the apparatus shown in FIG. 85, the view taken along lines 86-86 (shown in FIG. 85);

FIG. 87 is a perspective view of apparatus in accordance with the principles of the invention;

FIG. 90 is a perspective view of apparatus in accordance with the principles of the invention;

FIG. 91 is a partial cross-sectional, perspective view of the apparatus shown in FIG. 90, the view taken along lines 91-91 (shown in FIG. 90);

FIG. 92 is a cross-sectional view of the apparatus shown in FIG. 90, the view taken along lines 92-92 (shown in FIG. 90);

FIG. 93 is a perspective view of apparatus in accordance with the principles of the invention;

FIG. 93A is a perspective view of apparatus in accordance with the principles of the invention;

FIG. 94 is a cross-sectional view of the apparatus shown in FIG. 93, the view taken along lines 94-94 (shown in FIG. 93);

FIG. 95 is a perspective view of apparatus in accordance with the principles of the invention;

FIG. 95A is a perspective view of apparatus in accordance with the principles of the invention;

FIG. 96 is a cross-sectional view of the apparatus shown in FIG. 95, the view taken along lines 96-96 (shown in FIG. 95);

FIG. 102 is a perspective view of apparatus in accordance with the principles of the invention.

DETAILED DESCRIPTION

Figure 1:
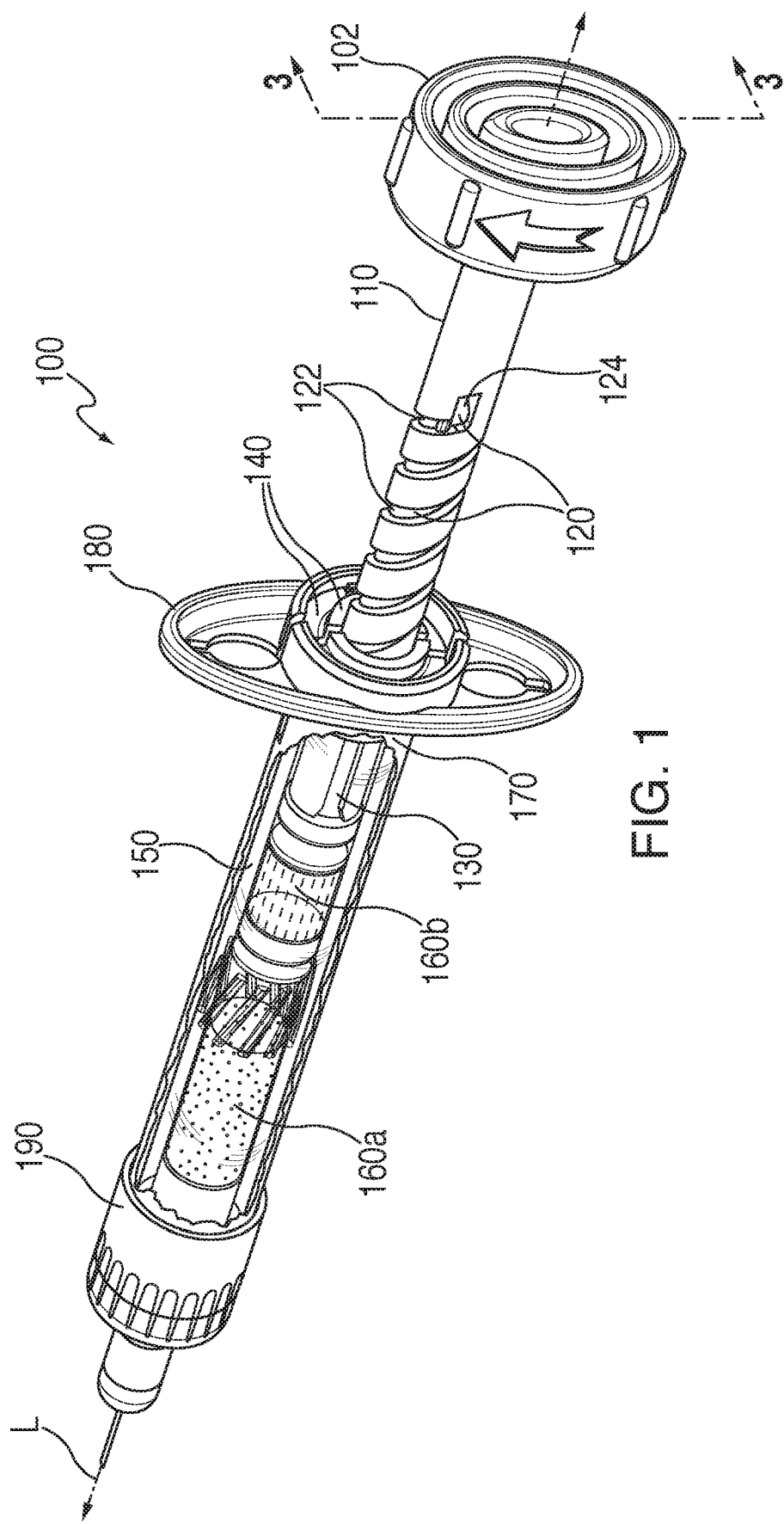
FIG. 1 is a perspective view of apparatus in accordance with principles of the invention, including a cutaway of external features providing a view of internal features of the apparatus.

Apparatus and methods for low volume medicament delivery are provided. The apparatus may be used to perform one or more steps of the methods. The methods may include methods for manufacture of one or more of the apparatus.

Exemplary embodiments are shown and described below. Features, including structures, materials, volumes, functions and other attributes that are shown and described in connection with any of the embodiments may be combined, in whole or in part, with each other or included, in whole or in part, in other embodiments.

The apparatus and methods may deliver a predetermined low volume of medicament. The predetermined low volume of medicament may include a predetermined amount of the medicament. The predetermined low volume of medicament may include a target amount of the medicament. The delivery may involve a syringe delivery stroke. The delivery stroke may involve distal displacement of the medicament by a plunger rod. The plunger rod may include a track. The track may have a predetermined length along the rod. The track may include a terminal surface. The terminal surface may proximally limit the predetermined length.

The operator may distally displace the rod through a plunger rod guide. The plunger rod guide may include a boss. The boss may be engaged with the track. Distal displacement of the rod and, thus, the delivery stroke, may be terminated by abutment of the terminal surface against the boss. The abutment may leave a predetermined residual volume of undelivered medicament in a space between a distal syringe stopper configured for medicament discharge and a slideable syringe plunger distally displaced by the rod toward the stopper.

Hardness of materials of the rod and of the guide over materials of the plunger and of the stopper may facilitate reliable setting of the delivery stroke and, thus, of the volume of delivered medicament, without volume uncertainties that may be associated with bottoming out of the plunger against the stopper.

The apparatus and methods may provide the operator indication of progress of stages of syringe operation, such as initiation and/or completion of stages of rod displacement, including the delivery stroke and pre-delivery stages such as priming. The guide may be configured to deflect in response to interaction of the boss with a trigger disposed along the track. The trigger may be disposed at a position corresponding to initiation and/or completion of one of the stages. Deflection of the guide may indicate, for example, when to transition from syringe priming to the delivery stroke.

The apparatus may include, and the methods may involve, a delivery device for delivery of the medicament. The device may define a longitudinal axis. The longitudinal axis may define a proximal direction and a distal direction. The longitudinal axis may define a radial direction normal to the longitudinal axis. The longitudinal axis may define a circumferential direction about the longitudinal axis. The device may have a distal end. The device may be configured to distally deliver the predetermined amount of the medicament. The amount may have any suitable volume, such as any of the volumes set forth above.

The device may include the plunger rod. The device may include a knob. The knob may include any suitable material, including that referred to above in connection with the rod. The knob may be disposed at a proximal end of the device. The knob may be attached to the rod. The knob may be integral to the rod. The rod and knob may constitute a unitary piece.

The knob may be turned about the axis. Turning the knob may turn the rod about the axis. The knob may be pushed distally along the axis. Pushing the rod distally may move the rod distally along the axis.

The knob may have a cross-section transverse to the axis. The cross-section may be circular. The cross-section may be elliptical. The cross-section may be of any suitable shape. Any suitable shape may include a polygonal shape. The cross-section may be bordered by a perimeter.

The knob may include turn ridges along the perimeter. The turn ridges may facilitate traction on the knob. The turn ridges may facilitate gripping the knob. The turn ridges may facilitate turning the knob.

The knob may include a proximal end of the knob. The proximal end may include push features. The push features may facilitate pushing the rod. The push features may facilitate traction on the knob. The push features may include a push pad. The push pad may be smoothly contoured. The push features may include push ridges. The push ridges may be concentric about the axis.

The rod may define the track. The track may include a recess in the rod. The recess may extend radially into a cylindrical surface of the rod. The recess may extend along the cylindrical surface of the rod. The recess may be a groove extending along the cylindrical surface. A radial distance of a floor of the recess from the longitudinal axis may be less than a cylindrical radius of the rod.

The track may include a raised element. The raised element may extend radially outward from the cylindrical surface. The raised element may extend along the cylindrical surface. The raised element may be a rib running along the cylindrical surface. A radial distance of a top of the raised element from the longitudinal axis may be greater than the rod radius.

The track may define the trigger. A border of the recess may define the trigger. A portion of the raised element may define the trigger.

The track may include the trigger. The track may support the trigger. The track may directly support the trigger. A border of the recess may support the trigger. A portion of the raised element may support the trigger.

The track may indirectly support the trigger. The track may include a flexible panel. The track may support the flexible panel. The flexible panel may support the trigger.

The track may be a first track. The rod may define a second track. The rod may define more than two tracks. The two or more tracks may be disposed parallel to each other along the cylindrical surface.

The device may include the plunger rod guide. The guide may define a passageway. The rod may be disposed in the passageway. The rod may be coaxial with the longitudinal axis. The rod may be disposed, relative to the longitudinal axis, distal-to-proximal parallel to the device. The track may be proximal, along the cylindrical surface of the rod, to a distal end of the rod.

The guide may support the boss. The boss may be of a shape that is, at least in part, cylindrical, cubic, pyramidal, tetrahedral, ellipsoidal, hemispherical or any other suitable shape. Any other suitable shape may include prismatic. Any other suitable shape may include an irregular form of any of the listed shapes. Any other suitable shape may include a truncated form of any of the listed shapes. Any other suitable shape may include a combination of two or more of any of the listed shapes. The combination may include dome-capped cylindrical. The combination may include rounded-apex stepped tetrahedral.

The boss may engage the rod at the track. The boss may be positioned against a side of the track. The boss may be maintained alongside the side of the track. The flexible panel may be supported by the side of the track. The flexible panel may be substantially coplanar with the side of the track. The boss may be positioned against a running surface of the track. The boss may be maintained against a running surface of the track. The flexible panel may be supported by the running surface of the track. The flexible panel may be substantially coplanar with the running surface of the track. The running surface may be the floor of the recess. The running surface may be the top of the raised element.

The boss may extend radially into the track. The boss may extend into the recess. The boss may be positioned within the recess. The boss may be maintained within the recess.

The boss may be positioned adjacent the raised element. The boss may be maintained adjacent the raised element. The boss may be positioned against a top of the raised element. The boss may be positioned alongside the rib. The boss may be maintained alongside the rib. The boss may be positioned straddling the rib.

The boss and the trigger may interact. The guide may be configured to deflect responsive to interaction between the boss and the trigger. The guide may be configured to deflect radially relative to the longitudinal axis.

The flexible panel may be configured to deflect responsive to the interaction between the boss and the trigger. The flexible panel may be configured to deflect radially relative to the longitudinal axis. The flexible panel may be configured to deflect radially relative to the rod. The flexible panel may be configured to deflect radially relative to the running surface of the track. The flexible panel may be configured to deflect laterally relative to the longitudinal axis. The flexible panel may be configured to deflect laterally relative to the side of the track.

Deflection of the guide and deflection of the flexible panel may occur simultaneously, each responsive to the interaction of the boss and the trigger.

The guide may be configured such that the boss does not substantially deflect in response to the interaction of the boss and the trigger. Deflection of the flexible panel may be enhanced by the guide being configured such that the boss does not substantially deflect in response to the interaction of the boss and the trigger.

The rod may be configured without the flexible panel.

The trigger may include a protrusion. The protrusion may be supported by a border of the recess. The protrusion may be supported by a portion of the raised element. The protrusion may be supported by a portion of the flexible panel. The protrusion may be of any suitable shape for interaction with the boss. The trigger may include a thickened side of the track. The trigger may define a constriction in a width of the track.

The interaction may be an interference between the boss and the trigger. The guide may be configured to deflect away from the longitudinal axis. The flexible panel may be configured to deflect toward the longitudinal axis.

The trigger may include a depression. The depression may be defined by a border of the recess. The depression may be defined by a portion of the raised element. The depression may be defined by a portion of the flexible panel. The depression may be of any suitable shape for interaction with the boss. The trigger may include a thinned side of the track. The trigger may define a widening of the track.

The interaction may be an urging of the boss against the trigger. The guide may be configured to deflect toward the longitudinal axis. The flexible panel may be configured to deflect away from the longitudinal axis.

The device may include a housing. The housing may be disposed coaxial with the longitudinal axis. The housing may be disposed, relative to the longitudinal axis, distal-to-proximal parallel to the device. The housing may define an opening. The opening may be disposed proximally on the housing. The opening may be a proximal housing opening. The guide may be disposed in the proximal housing opening.

The guide may be part of the housing. The guide may be manufactured as part of the housing. Manufacture of the guide as part of the housing may be accomplished through a molding process. Manufacture of the guide as part of the housing may be accomplished through an injection molding process. Manufacture of the guide as part of the housing may be accomplished through an overmolding process. The manufacture of the guide as part of the housing may be accomplished through a coinjection process.

The guide may be separate from the housing. The guide may be manufactured separately from the housing. The guide may be molded separately from the housing. The guide may be affixed to the housing. The guide may include guide-anchoring elements. The housing may include guide-anchor-accepting elements structurally complementary to the guide-anchoring elements. The guide may be affixed to the housing by mating the guide-anchoring elements with the guide-anchoring-accepting elements.

The device may include a medicament container. The container may be disposed in the housing. The container may be disposed distal the guide. The container may define a bore. The bore may be bound by an interior wall. The interior wall may define a substantially uniform diameter along a segment of the interior wall.

The rod may be configured to be displaced distally, relative to the housing, within the bore to discharge medicament from the container. The rod may be displaced distally until the boss abuts the terminal surface of the track.

The track may include the terminal surface. The track may support the terminal surface. The track may support the terminal surface proximally to the trigger. The terminal surface may be a distal surface of a proximal end-wall of the track. The end-wall may be a sidewall of the track. The end-wall may be orthogonal to the side of the track. The end-wall may be orthogonal to the running surface of the track. The end-wall may block relative proximal movement, beyond the distal surface of the end-wall, of the boss along the track.

Abutment of the boss against the terminal surface may substantially limit motion of the rod in a distal direction. The track may include sidewalls. The sidewalls adjacent the terminal surface may substantially limit motion of the rod in a distal direction when the boss abuts the terminal surface. Track sidewalls adjacent to the terminal surface may substantially limit motion of the rod in a circumferential direction when the boss abuts the terminal surface. Track sidewalls distal to the terminal surface may substantially limit motion of the rod in a distal direction when the boss abuts the terminal surface. Track sidewalls distal to the terminal surface may substantially limit motion of the rod in a circumferential direction when the boss abuts the terminal surface.

Abutment of the boss against the terminal surface may substantially limit motion of the rod, subsequent to the abutting, to movement in a proximal direction away from the boss. The boss abutting the terminal surface may limit motion of the boss, relative to the rod, to movement substantially axially away from the terminal surface.

The segment of the interior wall may include a distal portion. The distal portion may, in operation of the device, contact a bulk liquid residuum of the medicament after the boss abuts the terminal surface. The distal portion may be wetted by the bulk liquid residuum even after the boss abuts the terminal surface. The distal portion may directly contact the residuum. The distal portion may directly contact the residuum even after the boss abuts the terminal surface.

The device may include the plunger. The plunger may be at least one plunger slideably sealing against the interior wall. The plunger may be disposed within the container. The plunger may be disposed distal the rod. The plunger may be configured to slide distally responsive to distal displacement of the rod.

The device may include the stopper. The stopper may seal a distal end of the container. The distal end of the container may define a distal container opening. A proximal body-section of the distal stopper may be disposed within the distal container opening. The proximal body section of the distal stopper may seal against the interior wall of the container proximal to the distal container opening.

The stopper may include a distal surface. The distal surface may be disposed transverse to the axis. A distal body-section of the stopper proximal to the distal surface of the stopper may have an outer diameter greater than an outer diameter of the distal end of the container. A proximal rim of the distal body-section of the stopper may seal against an end-wall of the container surrounding the distal container opening.

The housing may include a distal retaining ridge. The distal retaining ridge may be disposed transverse to the axis. The distal retaining ridge may be part of an interior of a wall of the housing. The distal retaining ridge may be proximal to a distal end-wall of the housing surrounding a distal opening of the housing. The distal opening of the housing may be a distal housing opening. The distal housing opening may have an inner diameter. The inner diameter of the distal housing opening may be smaller than an outer diameter of the distal body-section of the distal stopper. The outer diameter of the distal body-section of the distal stopper may be substantially the same as an outer diameter of the container. The outer diameter of the container may be smaller than an inner diameter of the housing proximal to the distal retaining ridge. The container, with the distal end of the container sealed by the distal stopper, may be disposed within the housing between a distal aspect of the guide and the distal retaining ridge.

Prior to discharge of the medicament, the medicament may be sealed within the container between the stopper and the at least one plunger. The stopper may configured to be penetrated by a needle. The needle may have a cannula. The cannula may be configured to distally transfer medicament discharged from the container.

The cannula may be configured to transfer medicament directly through the needle to the patient.

The cannula may be configured to transfer medicament indirectly through the needle to the patient. The needle may be a first needle. The device may include a second needle. The cannula of the first needle may be configured to transfer medicament to the second needle. The second needle may be configured to transfer medicament directly to the patient. The device may include a filter. The filter may be an in-line filter. The filter may be disposed between the first needle and the second needle. The filter may receive medicament discharged from the cannula of the first needle. The filter may filter medicament discharged from the cannula of the first needle. The second needle may receive medicament filtered by the filter. The second needle may transfer the medicament filtered by the filter to the patient.

The medicament may include a formulation of one or more compounds. The compounds may include naturally occurring substances. The compounds may include substances derived from naturally occurring substances. The compounds may include synthetically produced substances. The compounds may include chimeric substances. The compounds may include engineered substances. The compounds may include humanized substances. The compounds may include substances produced by recombinant techniques. The compounds may include substances modified by recombinant techniques.

The compounds may include a drug accepted for therapeutic treatment of a patient. The compounds may include a substance used in a therapeutic protocol. The compounds may include a substance used in a diagnostic protocol. The compounds may include a substance used in an experimental protocol. The compounds may include a substance compatible for use with apparatus and methods of the invention.

The medicament may include any medical agent listed herein, either alone or in combination with one or more other listed medical agents or with one or more other, non-listed, medical agents. The medical agents may include anti-glaucoma medications, other ocular agents, neuroprotective agents, antimicrobial agents, anti-inflammatory agents (including steroids and non-steroidal compounds), and biological agents including hormones, enzymes or enzyme-related components, antibodies or antibody-related components, oligonucleotides (including DNA, RNA, short-interfering RNA, and other suitable oligonucleotides, such as antisense oligonucleotides), DNA/RNA vectors, viruses or viral vectors, peptides, and proteins. The medical agents may include anti-angiogenesis agents, including angiostatin, anecortave acetate, thrombospondin, vascular endothelial growth factor (VEGF) receptor tyrosine kinase inhibitors, and anti-VEGF drugs, such as ranibizumab (LUCENTIS®), bevacizumab (AVASTIN®), pegaptanib (MACUGEN®), sunitinib, and sorafenib, and any of a variety of known small-molecule and transcription inhibitors having an anti-angiogenesis effect; ophthalmic drugs, including glaucoma agents, such as adrenergic antagonists, including beta-blocker agents such as atenolol, propranolol, metipranolol, betaxolol, carteolol, levobetaxolol, levobunolol and timolol. The medical agents may include platelet-derived growth factor (PDGF) inhibitors and anti-PDGF drugs. The medical agents may include transformation growth factor (TGF) inhibitors and anti-TGF drugs. The medical agents may include anti-inflammatory agents including glucocorticoids and corticosteroids, such as betamethasone, cortisone, dexamethasone, dexamethasone 21-phosphate, methylprednisolone, prednisolone 21-phosphate, prednisolone acetate, prednisolone, loteprednol, medrysone, fluocinolone acetonide, triamcinolone acetonide, triamcinolone, beclomethasone, budesonide, flunisolide, fluorometholone, fluticasone, hydrocortisone, hydrocortisone acetate and rimexolone; and non-steroidal anti-inflammatory agents including diclofenac, flurbiprofen, ibuprofen, bromfenac, nepafenac, ketorolac, salicylate, indomethacin, naxopren, naproxen, piroxicam and nabumetone. The medical agents may include anti-cytokine agents; the medical agents may include anti-interleukin-6 agents such as tocilizumab (ACTEMR). The medical agents may include anti-complement agents, including those targeting complement factor D (such as an anti-complement factor D antibody or an antigen-binding fragment thereof) such as lampalizumab, and those targeting complement factor H (such as an anti-complement factor H antibody or an antigen-binding fragment thereof). The medical agents may include angiopoietin-specific agents, such as an angiopoietin-2 antibody or an antigen-binding fragment thereof. The medical agents may include human growth hormone. The medical agents may include any suitable medical agent.

The medicament may include one or more derivatives of any of the above-mentioned medical agents. The medicament may include advanced forms of any of the above-mentioned medical agents. The medicament may include mutated forms of any of the above-mentioned medical agents. The medicament may include combinations of any of the above-mentioned medical agents. The combinations may be incorporated into a multi-specific molecule. The multi-specific molecule may exhibit properties of its constituent parts. The multi-specific molecule may exhibit properties different from any if its constituent parts. The medicament may include depots, hydrogels and pegylated forms of any of the above medical agents. The medicament may include any suitable form of any of the above medical agents.

Prior to discharge of the medicament, the medicament may be stored within the container. The medicament may be stored in a dischargeable form of the medicament. The dischargeable form of the medicament may include all medical agents desired in a scenario—therapeutic, experimental or otherwise—for delivery, under desired conditions. Desired conditions may include therapeutic activity, medical agent concentration(s), viscosity, pH, ionic strength or any other suitable condition.

The medicament may be stored in a storage form of the medicament. The storage form of the medicament may require preparation of the medicament for discharge. The preparation of the medicament for discharge may include conversion of the medicament from the storage form of the medicament to the dischargeable form of the medicament.

The storage form of the medicament may include a first component. The first component may be stored in the medicament container. The storage form of the medicament may include a second component. The second component may be stored in the medicament container. The second component may be stored apart from the first component.

The first component may be a formulation of any of the above-mentioned medical agents. The second component may be a formulation of any of the above-mentioned medical agents. The first component may be a formulation that, upon mixing with the second component, adjusts conditions of the second component. The second component may be a formulation that, upon mixing with the first component, adjusts conditions of the first component. Conditions may include therapeutic activity, medical agent concentration(s), viscosity, pH and ionic strength.

The preparation of the medicament may include mixing the first component and the second component. A mixture of the first component and the second component may include the dischargeable form of the medicament.

The storage form of the medicament may include a lyophilized product that, when reconstituted, includes the dischargeable form of the medicament. Reconstitution of the lyophilized product may involve mixing the lyophilized product with a reconstituting solution. The lyophilized product may be the first component. The reconstituting solution may be the second component. The second component may be in a liquid state.

The device may include a rod-contacting face. The distal end of the rod may contact the rod-contacting face. The distal end of the rod may connect with the rod-contacting face. The distal end of the rod may couple with the rod-contacting face. The rod-contacting face may be distally displaced within the container in response to distal displacement of the rod within the container.

The at least one plunger may include a proximal plunger. The rod-contacting face may be associated with a proximal face of the proximal plunger. The proximal face of the proximal plunger may include the rod-contacting face. The proximal plunger may be distally displaced within the container in response to distal displacement of the rod-contacting face within the container. The proximal plunger may be distally displaced within the container in response to distal displacement of the rod within the container.

The at least one plunger may include a discharge plunger. The discharge plunger may be disposed within the container distal to the proximal plunger. There may be no other plunger within the container between the discharge plunger and the stopper.

Prior to the mixing of the first component and the second component, the first component and the second component may be separated by the discharge plunger. The first component may be sealed within the container between the stopper and the discharge plunger. The second component may be sealed within the container between the discharge plunger and the proximal plunger.

The container may include a bypass feature. The bypass feature may be configured to facilitate fluid communication bypassing a sealing surface of the discharge plunger. The bypass feature may include one or more grooves, at least partly longitudinal with respect to the axis, recessed into the interior wall. Prior to mixing, the sealing surface of the discharge plunger may be disposed proximal to a proximal-most aspect of the bypass feature, sealing against the interior wall and maintaining the second component apart from the first component.

The mixing may involve orienting the device with its distal end up and penetrating the stopper to dispose the cannula through the stopper. The mixing may involve distal displacement of the rod-connecting face via distal displacement of the rod. Distal displacement of the rod-connecting face may distally displace the proximal plunger. Distal displacement of the proximal plunger may distally displace the second component. Distal displacement of the second component may distally displace the discharge plunger. Distal displacement of the discharge plunger may slide a proximal-most circumferential portion of the sealing surface of the discharge plunger along the interior wall to a position just distal to the proximal-most aspect of the bypass feature, facilitating distal flow along the bypass feature of the second component into the first component. Further distal displacement of the proximal plunger may not substantially displace the discharge plunger while the second component remains between the proximal plunger and the discharge plunger. While the second component remains between the proximal plunger and the discharge plunger, distal displacement of the proximal plunger may distally displace the second component along the bypass feature, facilitating mixing of the second component with the first component.

A distal face of the proximal plunger may be complementary to a proximal face of the discharge plunger. Upon encounter of the distal face of the distally displaced proximal plunger with the proximal face of the discharge plunger, substantially no second component may remain between the proximal plunger and the discharge plunger. When substantially no second component remains between the proximal plunger and the discharge plunger, the mixture may include the dischargeable form of the medicament.

When substantially no second component remains between the proximal plunger and the discharge plunger, further distal displacement of the proximal plunger may further distally displace the discharge plunger. A distal face of the discharge plunger may, upon being distally displaced toward the stopper, distally displace the dischargeable form of the medicament.

A scenario in which the medicament is stored during device manufacture in the storage form may be accommodated by a configuration of the device in which the at least one plunger includes the proximal plunger and the discharge plunger and in which the container includes the bypass feature. Such a configuration of the device may be termed a mixing configuration. In the mixing configuration, the rod-contacting face may be associated with the proximal plunger.

A scenario in which the medicament is stored during device manufacture in the dischargeable form may require, in the container, neither multiple plungers for sequestration of storage form components nor the bypass feature for mixing of components. When no mixing is to be performed, the plunger may include only the discharge plunger. A configuration of the device in which the plunger is the discharge plunger and in which the interior wall does not include the bypass feature, may be termed a non-mixing configuration. In the non-mixing configuration, the rod-connecting face may be associated with the discharge plunger. The rod-contacting face may be associated with a proximal face of the discharge plunger. The proximal face of the discharge plunger may include the rod-contacting face. The discharge plunger may be distally displaced by distal displacement of the rod contacting the proximal face of the discharge plunger.

The device may be manufactured as a "pre-filled" device. The device may be manufactured with the container configured to store a volume of the medicament. The volume may be substantially determined during manufacture. The volume may be set with anticipation of loss of medicament that may result from manipulations of the device prior to performance of the delivery stroke. Such manipulations may include mixing and priming. The volume may depend on the scenario for which the device is intended. Illustrative ranges of value of the volume may include about 0.025 milliliter to about 0.05 milliliter, about 0.05 milliliter to about 0.1 milliliter, about 0.1 milliliter to about 0.25 milliliter, about 0.25 milliliter to about 0.5 milliliter, about 0.5 milliliter to about 1 milliliter, about 1 milliliter to about 2 milliliters, about 2 milliliters to about 3 milliliters, about 3 milliliters to about 4 milliliters, about 4 milliliters to about 5 milliliters, about 5 milliliters to about 6 milliliters, about 6 milliliters to about 7 milliliters, about 7 milliliters to about 8 milliliters, about 8 milliliters to about 9 milliliters, about 9 milliliters to about 10 milliliters, or any other suitable ranges.

The housing may include a housing wall. The housing wall may be configured to deflect in response to deflection of the guide. The housing wall may include a section that is displaced radially relative to the longitudinal axis during the deflection of the guide. The section may be a first section. The housing wall may include a second section that is displaced radially relative to the longitudinal axis during the deflection of the guide. Radial direction of displacement of the section or sections relative to the longitudinal axis may conform to radial direction of the deflection of the guide relative to the longitudinal axis. The displacement of the section or sections may be radially outward. The displacement of the section(s) may be radially inward.

The device may include a finger flange. The finger flange may be part of the housing. The finger flange may be manufactured as part of the housing. Manufacture of the finger flange as part of the housing may be accomplished through a molding process. Manufacture of the finger flange as part of the housing may be accomplished through an injection molding process. Manufacture of the finger flange as part of the housing may be accomplished through an overmolding process. The manufacture of the finger flange as part of the housing may be accomplished through a coinjection process.

The finger flange may be separate from the housing. The finger flange may be manufactured separately from the housing. The finger flange may be molded separately from the housing. The finger flange may be affixed to the housing. The finger flange may have finger flange-anchoring elements. The housing may have finger flange-anchor-accepting elements structurally complementary to the finger flange-anchoring elements. The finger flange may be affixed to the housing by mating the finger flange-anchoring elements with the finger flange-anchoring-accepting elements.

The finger flange may be supported by the housing wall. The finger flange may encompass the section(s). The finger flange may be configured to deflect in response to the displacement of the section(s). The finger flange may be configured to deflect in response to the deflection of the guide.

The guide may include an arm. The arm may be curved. The arm may support the boss. The arm may define the passageway. The arm may be a first arm. The guide may include a second arm. The second arm may be curved. The second arm may define the passageway.

The first arm and the second arm may be joined at a hinge. The first arm may support the boss apart from the hinge. The hinge may be resilient. The first arm and the second arm may define a gap. The first arm may support the boss apart from the gap. The gap may be opposite the hinge. A width of the gap may change during the deflection of the guide. The gap may widen during the deflection of the guide. The gap may narrow during the deflection of the guide.

The housing wall may define a slot. The slot may be circumferentially aligned with the gap. A width of the slot may change during the deflection of the guide. The slot may widen during the deflection of the guide. The slot may narrow during the deflection of the guide.

The finger flange may define an internal bay. The guide may be suspended across the bay. The guide may be suspended at an end of the guide. The arm of the guide may support the boss apart from the end of the guide.

The guide may be suspended across the bay by a support member. The support member may extend in a first direction. The bay may accommodate the deflection of the guide. The bay may accommodate the deflection of the guide in a second direction. The first direction may be substantially orthogonal to the second direction.

The support member may be configured to deform in response to the deflection of the guide. Deformation of the support member may relieve stress in the finger flange. The deformation of the support member may increase stress in the finger flange.

The finger flange may include an annular border. The border may define a hole. The hole may be adjacent the support member. The border may be configured to deform in response to deflection of the guide. Deformation of the border may relieve stress in the finger flange. The deformation of the border may increase stress in the finger flange.

The support member may be a first support member. The guide may be suspended across the bay by the first support member and by a second support member. The guide, the support member(s) and the finger flange may be manufactured as an integral piece. Manufacture of the integral piece may be accomplished through a molding process. Manufacture of the integral piece may be accomplished through an injection molding process. Manufacture of the integral piece may be accomplished through an overmolding process. The manufacture of the integral piece may be accomplished through a coinjection process.

The housing may include a frame. The frame may define the proximal housing opening. The frame may be disposed proximally on the housing. The proximal housing opening may be defined, by the frame, in the housing wall.

The frame may be disposed coaxial with the longitudinal axis. The proximal housing opening may be disposed coaxial with the longitudinal axis. The frame may be disposed circumferentially about the longitudinal axis. The proximal housing opening may be disposed circumferentially about the longitudinal axis.

The guide may include a clip. The clip may be clipped onto the frame. The clip may be clipped onto the frame such that a central axis of the clip aligns with the longitudinal axis. The clip may be clipped onto the frame such that the boss extends radially inward through the proximal housing opening toward the longitudinal axis. The clip may be clipped onto the frame such that the boss engages the rod through the proximal housing opening. The clip may be clipped onto the frame such that the boss extends into close proximity of the track through the proximal housing opening.

The clip may be a C-shaped clip. The C-shaped clip may be clipped onto the frame in a direction transverse to the longitudinal axis.

The guide may be configured to deflect within the proximal housing opening. The guide may be configured to deflect relative to the housing. An exterior surface of the guide may be configured to deflect relative to the housing. An interior surface of the guide may be configured to deflect relative to the housing. The guide may be configured to deflect beyond a surface of the housing. The guide may be configured to deflect outwardly beyond an exterior surface of the housing. The guide may be configured to deflect inwardly beyond an interior surface of the housing.

The track may include a tract. A length along the tract may correspond to the delivery stroke of the rod. The length along the tract may correspond to an extent of the delivery stroke. Movement of the boss relative to the length may correspond to performance of the delivery stroke. Performance of a full extent of the delivery stroke may discharge from the container a dose amount of the medicament. The delivery stroke may set the dose amount.

The length along the tract may be distal to the terminal surface. The length along the tract may be adjacent to the terminal surface. The length along the tract may be between the trigger and the terminal surface. The length along the tract may be predetermined. The length along the tract may be predetermined during manufacture of the device.

The delivery stroke may be predetermined during the manufacture of the device. Mechanical properties of the materials of, and manufactured configuration of, the container and its associated stopper and plunger(s) and of the housing, guide and rod, may determine the delivery stroke. The full extent of the delivery stroke may be predetermined in manufacturing.

The boss may provide a reactive surface. With the boss abutting the terminal surface, the reactive surface may limit distal displacement of the rod within the container. With the boss abutting the terminal surface, the reactive surface may mechanically terminate the delivery stroke.

At termination of the delivery stroke, the distal face of the discharge plunger may be proximal to, and at a non-zero distance from, a proximal face of the stopper. At termination of the delivery stroke, the bulk liquid residuum of the medicament contacting the distal portion of the segment of the interior wall of the container may be maintained between the distal face of the discharge plunger and the proximal face of the stopper.

The tract may be substantially parallel to the longitudinal axis. With the boss engaging the rod at the tract, the reactive surface may limit rotational movement of the rod about the longitudinal axis. With the boss extending into the tract, the reactive surface may limit rotational movement of the rod about the longitudinal axis. A length corresponding to the delivery stroke may be a longitudinal length along the tract. The length corresponding to the delivery stroke along the longitudinal tract may be between the trigger and the terminal surface.

The tract may be substantially helical about the longitudinal axis. With the boss engaging the rod at the tract, the reactive surface may convert rotational movement of the rod about the longitudinal axis into axial movement of the rod along the longitudinal axis. With the boss extending into the tract, the reactive surface may convert rotational movement of the rod about the longitudinal axis into axial movement of the rod along the longitudinal axis. The length corresponding to the delivery stroke may follow a helical path along the tract. The length corresponding to the delivery stroke along the helical tract may be given by an arithmetic product of a helical pitch of the helical path and a number of helical turns (including any partial turns) between the trigger and the terminal surface.

The device may be configured to provide indication of completion of the delivery stroke. Indication of completion of the delivery stroke may be tactile. Indication of completion of the delivery stroke may be acoustic.

Abutment of the boss against the terminal surface may indicate completion of the delivery stroke. Upon the boss abutting the terminal surface, configuration and material(s) of the boss in conjunction with configuration and material(s) of the track supporting the terminal surface may provide an operator-detectable mechanical vibration transmitted through the device and/or an audible sound. In scenarios in which a noise associated with the syringe during medicament delivery may be undesirable (for example, if such a noise may startle the patient), configuration and material(s) of the boss in conjunction with configuration and material(s) of the track supporting the terminal surface may provide the operator-detectable mechanical vibration absent the audible sound or may provide neither the operator-detectable mechanical vibration nor the audible sound.

Deflection of the guide associated with the boss approaching abutment against the terminal surface may provide indication of the abutment. A radial distance, from the axis, of the running surface of the track may vary along a length of the track distal the terminal surface. The guide may deflect radially relative to the axis in response to interaction between the boss and the running surface.

The radial distance may decrease proximally toward the terminal surface along the length of track distal to the terminal surface. The interaction may include an urging of the boss against the running surface. The guide may deflect toward the axis as the boss is brought into abutment against the terminal surface. Deflection of the guide toward the axis as the boss is brought into abutment against the terminal surface may provide indication of completion of the delivery stroke.

The radial distance may reach a minimum at a position of the boss against the track corresponding to the boss abutting the terminal surface. The minimum may be a local minimum. The minimum may be maintained along the remainder of the track adjacent the terminal surface. The running surface may be configured such that the boss, having reached the minimum, is locked into its position at the minimum. The boss may be blocked proximally by the terminal surface and distally by a slope of the running surface. The running surface may be configured such that the rod is blocked from proximal movement along the axis upon the boss reaching the minimum.

The track may include a distal longitudinal tract. The distal longitudinal tract may be substantially parallel to the longitudinal axis. The track may include a proximal longitudinal tract. The proximal longitudinal tract may be substantially parallel to the longitudinal axis.

The track may be a helix-containing track. The helix-containing track may include a helicoidal tract. The helicoidal tract may be substantially helical about the longitudinal axis. The helicoidal tract may be disposed medially on the rod. The helicoidal tract may be disposed proximally to the distal longitudinal tract. The distal longitudinal tract may have a proximal portion. The proximal portion may be adjacent, along the helix-containing track, to a distal portion of the helicoidal tract. The proximal portion of the distal longitudinal tract may be continuous, along the helix-containing track, with the distal portion of the helicoidal tract. The helicoidal tract may be disposed distally to the proximal longitudinal tract. The proximal longitudinal tract may have a distal portion. The distal portion may be adjacent, along the helix-containing track, to a proximal portion of the helicoidal tract. The distal portion of the proximal longitudinal tract may be continuous, along the helix-containing track, with the proximal portion of the helicoidal tract. The helix-containing track may be continuous along the distal longitudinal tract, the helicoidal tract and the proximal longitudinal tract.

The helix-containing track may be a rotary-delivery track. The rotary-delivery track may include the helicoidal tract disposed proximal and adjacent, and continuous with, the distal longitudinal tract, absent the proximal longitudinal tract.

The track may be a collinear track. In the collinear track, a proximal portion of the distal longitudinal tract may be adjacent, along the track, to a distal portion of the proximal longitudinal tract, absent the helicoidal tract. The distal portion of the proximal longitudinal tract may be continuous, along the collinear track, with the proximal portion of the distal longitudinal tract. The collinear track may be continuous along the distal longitudinal tract and the proximal longitudinal tract. The distal longitudinal tract and the proximal longitudinal tract may be collinear.

The trigger may be a first trigger. The proximal portion of the distal longitudinal tract may include the first trigger. The first trigger may be defined by the proximal portion of the distal longitudinal tract. The first trigger may be supported by the proximal portion of the distal longitudinal tract. The first trigger and the boss may interact. Responsive to interaction of the first trigger and the boss, the guide may deflect. The guide deflecting responsive to interaction of the first trigger and the boss may be a first guide-deflection.

The flexible panel may include the first trigger. The first trigger may be defined by the flexible panel. The first trigger may be supported by the flexible panel. Responsive to interaction of the first trigger and the boss, the flexible panel may deflect. The flexible panel deflecting responsive to interaction of the first trigger and the boss may be a first panel-deflection.

The first guide-deflection and/or the first panel-deflection may correspond to a first stage of distal displacement of the rod in the container. The first stage may be an initial distal displacement of the rod. The initial displacement may position the rod in the device prior to operation of the device.

The initial displacement may position the rod with the boss engaging the rod such that likelihood of inadvertent proximal slippage of the rod out of the device is reduced. The initial displacement may position the rod with the boss engaging the rod such that the rod is substantially blocked from inadvertent further distal displacement. The initial displacement may position the rod with the boss engaging the rod such that further displacement of the rod may involve intentional manipulation on the part of the operator. The initial displacement may be performed as a manufacturing step.

The rod may include a second trigger. The second trigger may have none, some or all of the features and functions of the first trigger. The track may include the second trigger. The track may define the second trigger. The track may support the second trigger. The flexible panel may include the second trigger. The flexible panel may define the second trigger. The flexible panel may support the second trigger.

The second trigger and the boss may interact. Responsive to interaction of the second trigger and the boss, the guide may deflect. The guide deflecting responsive to interaction of the second trigger and the boss may be a second guide-deflection.

Responsive to interaction of the second trigger and the boss, the flexible panel may deflect. The flexible panel deflecting responsive to interaction of the second trigger and the boss may be a second panel-deflection.

The second guide-deflection and/or the second panel-deflection may correspond to a second stage of distal displacement of the rod in the container. The second stage may be a second distal displacement of the rod. The second displacement may position the rod in the device during operation of the device. The second displacement may be performed during operation of the device. The second displacement may be performed by the operator.

A role of the second stage among the stages of syringe operation of the device may be determined by the configuration (mixing or non-mixing) of the device, geometry (helix-containing or collinear) of the track and location of the second trigger along the track.

Along the helix-containing track, the second trigger may be supported by the distal portion of the helicoidal tract. Along the collinear track, the second trigger may be supported by the distal portion of the proximal longitudinal tract. The second stage may be an initiation of operation of the device. For the mixing configuration, the initiation may include commencement of preparation of the medicament for discharge. For the non-mixing configuration, the initiation may include commencement of priming of the device for delivery of the medicament.

Along the helix-containing track, the second trigger may be supported by a medial portion of the helicoidal tract. Along the collinear track, the second trigger may be supported by a medial portion of the proximal longitudinal tract. For the mixing configuration, the second stage may be performed subsequent to the preparation of the medicament and may include the priming. For the mixing configuration, the medial portion of the proximal longitudinal tract may be a first medial portion of the proximal longitudinal tract disposed distal to a second medial portion of the proximal longitudinal tract. For the non-mixing configuration, the second stage may include the delivery of the medicament.

Along the helix-containing track, the second trigger may be supported by the proximal portion of the helicoidal tract. Along the collinear track, the second trigger may be supported by the second medial portion of the proximal longitudinal tract. For the mixing configuration, the second stage may be performed subsequent to the priming and may include the delivery of the medicament.

A proximal portion of the proximal longitudinal tract may support the terminal surface proximal to the second trigger. A proximal end-wall of the proximal longitudinal tract may support the terminal surface.

Along the helix-containing track, the length corresponding to the delivery stroke may be a length along the proximal longitudinal tract between the second trigger, supported by the proximal portion of the helicoidal tract, and between the terminal surface supported, proximal the second trigger, by the proximal portion of the proximal longitudinal tract.

Along the collinear track, the length corresponding to the delivery stroke may be a length along the proximal longitudinal tract between the second trigger, supported by the second medial portion of the proximal longitudinal tract, and between the terminal surface supported, proximal the second trigger, by the proximal portion of the proximal longitudinal tract.

Along the rotary-delivery track, the proximal portion of the helicoidal tract may support the terminal surface proximal to the second trigger. A proximal end-wall of the proximal portion of the helicoidal tract may support the terminal surface. The length corresponding to the delivery stroke may be a length along the proximal portion of the helicoidal tract between the second trigger, supported by the proximal portion of the helicoidal tract, and between the terminal surface supported, proximal the second trigger, by the proximal portion of the helicoidal tract.

The track may be a first track. The rod may further define a second track. The second track may have none, some or all of the features and functions of the first track. The second track may be disposed on the rod apart from the first track. The second track may be disposed parallel to the first track.

The first trigger may be supported by the first track. The second trigger may be supported by the second track.

The flexible panel may be a first flexible panel. The first track may include the first flexible panel. The first track may support the first flexible panel. The first flexible panel may support the first trigger. The second track may include a second flexible panel. The second track may support the second flexible panel. The second flexible panel may have none, some or all of the features and functions of the first flexible panel. The second flexible panel may support the second trigger.

The boss may be a first boss. The first boss may engage the rod at the first track. The first boss may be positioned against a side of the first track. The first boss may be maintained against the side of the first track. The first boss may extend radially inward into the first track. The first boss may be positioned against a running surface of the first track. The first boss may be maintained against the running surface of the first track.

The device may include a second boss. The guide may support the second boss. The second boss may have none, some or all of the features and functions of the first boss. The second arm of the guide may support the second boss.

The second boss may be disposed, relative to the longitudinal axis, diametrically opposite the first boss. The second boss may engage the rod at the second track. The second boss may be positioned against a side of the second track. The second boss may be maintained against the side of the second track. The second boss may extend radially inward into the second track. The second boss may be positioned against a running surface of the second track. The second boss may be maintained against the running surface of the second track.

The interaction may include a first interaction. The first interaction may involve the first boss and the first trigger interacting with each other. The first guide-deflection may be responsive to the first interaction. The first guide-deflection may include a movement of the first boss relative to the longitudinal axis. The first guide-deflection may include a movement of the guide relative to the longitudinal axis. The first panel-deflection may be responsive to the first interaction. The first panel-deflection may include a movement of the first flexible panel relative to the longitudinal axis.

The interference may include a first interference. The first interference may involve the first boss and the first trigger interfering with each other. The first guide-deflection may be responsive to the first interference. The first guide-deflection may include a movement of the first boss away from the longitudinal axis. The first guide-deflection may include a movement of the guide away from the longitudinal axis. The first panel-deflection may be responsive to the first interference. The first panel-deflection may include a movement of the first flexible panel toward the longitudinal axis.

The urging may include a first urging. The first urging may involve the first boss and the first trigger being urged against each other. The first guide-deflection may be responsive to the first urging. The first guide-deflection may include a movement of the first boss toward the longitudinal axis. The first guide-deflection may include a movement of the guide toward the longitudinal axis. The first panel-deflection may be responsive to the first urging. The first panel-deflection may include a movement of the first flexible panel away from the longitudinal axis.

The interaction may include a second interaction. The second interaction may involve the second boss and the second trigger interacting with each other. The second guide-deflection may be responsive to the second interaction. The second guide-deflection may include a movement of the second boss relative to the longitudinal axis. The second guide-deflection may include a movement of the guide relative to the longitudinal axis. The second panel-deflection may be responsive to the second interaction. The second panel-deflection may include a movement of the second panel relative to the longitudinal axis.

The interference may include a second interference. The second interference may involve the second boss and the second trigger interfering with each other. The second guide-deflection may be responsive to the second interference. The second guide-deflection may include a movement of the second boss away from the longitudinal axis. The second guide-deflection may include a movement of the guide away from the longitudinal axis. The second panel-deflection may be responsive to the second interference. The second panel-deflection may include a movement of the second flexible panel toward the longitudinal axis.

The urging may include a second urging. The second urging may involve the second boss and the second trigger being urged against each other. The second guide-deflection may be responsive to the second urging. The second guide-deflection may include a movement of the second boss toward the longitudinal axis. The second guide-deflection may include a movement of the guide toward the longitudinal axis. The second panel-deflection may be responsive to the second urging. The second panel-deflection may include a movement of the second flexible panel away from the longitudinal axis.

The first and second tracks, first and second triggers and first and second bosses may be configured to provide the first guide-deflection and the second guide-deflection substantially simultaneously. The first and second tracks, first and second triggers and first and second bosses may be configured to produce the first guide-deflection and the second guide-deflection non-simultaneously.

The first and second tracks, first and second flexible panels, first and second triggers and first and second bosses may be configured to provide the first panel-deflection and the second panel-deflection substantially simultaneously. The first and second tracks, first and second flexible panels, first and second triggers and first and second bosses may be configured to produce the first panel-deflection and the second panel-deflection non-simultaneously.

The first and second tracks, first and second flexible panels, first and second triggers and first and second bosses may be configured to produce substantially simultaneity among the first guide-deflection, the first panel-deflection, the second guide-deflection and the second panel-deflection. The first and second tracks, first and second flexible panels, first and second triggers and first and second bosses may be configured to produce a predetermined sequence of occurrence and/or of indication among the first guide-deflection, the first panel-deflection, the second guide-deflection and the second panel-deflection. The sequence of occurrence and/or of indication may be predetermined during the manufacture of the device.

The device may be configured to indicate stages of the syringe operation. The device may be configured to provide indication of stages of the syringe operation. The device may be configured to indicate stages of the displacement of the rod. The device may be configured to provide indication of stages of the displacement of the rod. The device may be configured to indicate the interaction of the boss(es) and the trigger(s). The device may be configured to provide indication of the interaction of the boss(es) and the trigger(s).

The indication of the interaction may signal initiation of the stage associated with the interaction. The indication of the interaction may signal completion of the stage. The indication of the stage may be tactile. The indication of the stage may be acoustic. The indication of the stage may be visual.

Deflection of the guide and/or of the flexible panel(s) in response to the interaction of the boss(es) and the trigger(s) may include indication of the interaction. For example, the operator may receive tactile indication of interaction by feeling the deflection against the operator's fingers during syringe operation.

The deflection of the guide and/or of the flexible panel(s) in response to the interaction of the boss(es) and the trigger(s) may produce indication of the interaction. The deflection may cause components of the device other than the guide and/or the flexible panel(s) to deflect, transmitting and/or amplifying the deflection. The deflection and/or the other components deflecting may cause operator-detectable mechanical vibration in the device. The deflection and/or the other components deflecting may produce an audible sound, such as a snap and/or a click.

The indication may be concomitant of the deflection. The boss(es) moving along the trigger(s) may produce the indication of the interaction. The boss(es) moving along the trigger(s) may produce the operator-detectable mechanical vibration. The boss(es) moving along the trigger(s) may produce the audible sound. The other components may deflect closely upon the deflection.

The indication may be attendant upon the deflection. The guide may produce the indication in returning to a non-deflected state after the deflection. The flexible panel(s) may produce the indication in returning to the non-deflected state after the deflection. After the deflection, the boss(es) may re-contact sidewalls and/or running surfaces from which the boss(es) had been shifted by the interaction. Re-contacting the sidewalls and/or running surfaces may produce the mechanical vibration. Re-contacting the sidewalls and/or running surfaces may produce the audible sound.

The deflection of the guide and/or a return of the guide after deflection to the non-deflected state, may provide the operator-detectable mechanical vibration transmitted through the device and/or the audible sound. The deflection of the flexible panel(s) and/or return of the flexible panel(s) after deflection to a non-deflected state, may provide the operator-detectable mechanical vibration transmitted through the device and/or the audible sound. Deflection of the guide may cause deflection of the section or sections of the housing. The deflection of the section or sections may provide the operator-detectable mechanical vibration transmitted through the device and/or the audible sound. Return of the section or sections, after deflection, to the non-deflected state may provide the operator-detectable mechanical vibration transmitted through the device and/or the audible sound. Deflection of the guide may cause deflection of the finger flange. The deflection of the finger flange and/or return of the finger flange after deflection to the non-deflected state, may provide the operator-detectable mechanical vibration transmitted through the device and/or the audible sound.

Different stages of the displacement of the rod may have different indications associated with them. Different indications may differ by duration, amplitude or other suitable qualities. Other suitable qualities may include audio pitch.

One or more properties of one or more of the boss(es), the guide, the trigger(s), the track(s), the rod, the flexible panel(s) and the housing, may determine one or more of a duration of the indication, an amplitude of the indication and, for acoustic indication, an acoustic pitch of the indication. The properties may include geometry, lubricity, resilience and other relevant properties. Other relevant properties may include hardness. The properties may be set in the manufacture of the device to provide a desired indication of a stage of the displacement of the rod. The properties may be set in the manufacture of the device to provide different desired indications of different stages of the displacement of the rod. For example, the trigger may be configured with a rough surface over which the boss would bump several times in running against and along the trigger. The trigger may be a protrusion with a steep proximal slope configured to return the boss running over the trigger to the running surface with a snap.

Steps of an illustrative method of use of the mixing configuration of the device are presented. The steps of the illustrative method described herein may be performed in an order other than the order described herein. Some of the steps described herein may be combined. Some of the steps described herein may be omitted. Some embodiments of the invention may include steps that are not described in connection with the illustrative method.

Components of the apparatus of the illustrative method may be packaged at manufacture in sterile packaging. The apparatus may be intended for an ocular therapeutic scenario, the delivery stroke to deliver a desired dose of an ocular medicament into the eye of a patient. The device may have been pre-filled with the ocular medicament as a lyophilized product sequestered from a reconstituting solution.

The pre-filled device may have been packaged with the rod distally displaced through the guide into the container to the initial distal displacement just beyond the first trigger. Proximal to the first trigger, the track may include a distal helicoidal tract and a proximal longitudinal tract. The helicoidal tract may include a distal operation-initiation trigger adjacent to the first trigger. The helicoidal tract may also include a medial priming-initiation trigger. The helicoidal tract may also include a proximal delivery-initiation trigger adjacent to a distal portion of the longitudinal tract. A proximal portion of the longitudinal tract may proximally end in the terminal surface supported by a proximal-most end-wall of the track.

A needle hub that includes the first needle and the second needle may be packaged as a separate component from the pre-filled device. All distal displacements in the method may be relative to the medicament container and/or to the device housing. The patient's eye is assumed to have been prepared for injection. For purposes of simplicity of presentation, all steps are presented as performed by a single operator.

The method of use may involve one or more of the following steps:

The operator may unpackage the pre-filled device and the needle hub. A protective sterility cap may be removed from the distal end of the pre-filled device to expose a distal exterior of the stopper. The operator may orient the distal end of the pre-filled device substantially vertically upwards above the proximal end of the device, and penetrate the stopper with the first needle by securely affixing the needle hub to the distal end of the housing.

Maintaining the orientation of the device, the operator may begin to turn the rod about the device axis to cause interaction of the boss and the operation-initiation trigger.

The interaction may be indicated acoustically. The interaction may be indicated acoustically by the audible sound. The sound may be a click. The sound may be a snap. The interaction may be indicated tactilely. The interaction may be indicated tactilely by a device-mediated mechanical vibration. With further turning of the rod, the operator may displace the rod distally within the container, distally displacing the proximal plunger, the reconstituting solution and the discharge plunger until a proximal-most circumferential portion of the sealing surface of the discharge plunger passes the proximal-most aspect of the bypass feature, at which point the discharge plunger may stop being responsive to distal displacement of the rod. As the operator further turns the rod, the proximal plunger and the reconstitution solution may be displaced, the proximal plunger approaching the substantially immobilized discharge plunger and the reconstituting solution flowing around the discharge plunger along the bypass feature. The reconstituting solution may mix with the lyophilized product to reconstitute the ocular medicament. When the operator has displaced all the reconstituting solution by turning the rod until the distal face of the proximal plunger encounters the complementary proximal face of the discharge plunger, the medicament may be reconstituted to the therapeutic activity, medical agent concentration(s), viscosity, pH and ionic strength desired for the scenario.

Maintaining the orientation of the device, the operator may further turn the rod just beyond the point of reconstitution to cause interaction of the boss and the priming-initiation trigger. The interaction may be indicated acoustically by the audible sound and/or tactilely by the device-mediated mechanical vibration. Indication of the interaction may be different from the previous indication in amplitude, tone or other properties. The operator may tap the device to dislodge air bubbles from the interior wall to facilitate their gathering together at a highest elevation in the distal-end-up device. The operator further turning the rod may distally displace the proximal plunger, the discharge plunger abutted proximally by the proximal plunger and the reconstituted ocular medicament, all toward the needle-penetrated stopper, priming the device by discharging the air out the first needle and then out the second needle and filling the first and second needles with reconstituted ocular medicament.

At the point of the second needle filling with the reconstituted ocular medicament, the operator further turning the rod may cause interaction of the boss and the delivery-initiation trigger. The interaction may be indicated acoustically with the audible sound and/or tactilely with the device-mediated mechanical vibration. Indication of the interaction may be different from one or both of the previous indications in amplitude, tone or other properties. Immediately after the interaction of the boss and the delivery-initiation trigger, the boss may be engaged with the longitudinal tract, blocking further turning of the rod. The indication of delivery initiation may serve to cue the operator to bring the primed device into close proximity to the patient and, with whatever orientation of the device is most suitable for injection in this ocular therapeutic scenario, to carefully engage the second needle with the patient's eye.

With the second needle engaged with the patient's eye, the operator may initiate the delivery stroke by beginning to push the rod distally along the device axis. The operator pushing the rod distally may distally displace the rod, the proximal plunger, the discharge plunger abutted proximally by the proximal plunger and the reconstituted ocular medicament, all toward the needle-penetrated stopper, discharging the reconstituted ocular medicament through the first needle and delivering the reconstituted ocular medicament into the patient's eye through the second needle.

The operator pushing the rod distally may move the terminal surface closer to the boss engaged with the longitudinal tract. The operator may continue to push the rod distally until bringing the terminal surface and the boss into abutment. The abutment of the terminal surface and the boss may terminate the delivery stroke. The abutment of the terminal surface and the boss may complete delivery of the desired dose of the ocular medicament. The abutment of the terminal surface and the boss may be indicated by the cessation of distal movement of the rod and by an operator-detectable device-mediated mechanical vibration.

The second needle may be disengaged from the patient's eye, the device may be put aside, and the operator may tend to the patient's post-injection care.

The methods may include methods of manufacture of the medicament delivery device. The methods may include positioning a resilient arm that supports a boss, such that the boss is disposed at a radial distance from the axis less than an inner radius of the device housing. The arm may define a passageway that is configured to guide the plunger rod that supports a track that supports a trigger. The methods may include molding a plunger rod guide that includes the arm and accommodates the passageway.

The methods may include securing the arm relative to the housing against rotational displacement about the axis and against axial displacement along the axis. The arm may be configured to deflect radially relative to the axis in response to interaction of the boss and the trigger.

The methods may include securing the arm by molding the guide onto the housing.

The methods may include securing the arm by fixing the guide to a proximal segment of the housing. Fixing the guide may include insertion of the guide axially, relative to the axis, into an opening in the proximal segment. Fixing the guide may include insertion of the guide transversely, relative to the axis, into an opening in the proximal segment.

The methods may include providing the rod. Providing the rod may include molding the rod. The rod may be configured to be displaced within the housing toward a distal end of the housing. The rod may support a terminal surface, such that, with the boss engaging the rod at the track and with the boss abutting the terminal surface, the boss may provide a reactive surface that limits further distal displacement of the rod. With the boss abutting the terminal surface, movement of the boss relative to the rod may be limited to substantially axial movement away from the terminal surface. With the boss engaging a longitudinal tract of the track, the boss may provide a reactive surface that limits rotational movement of the rod about the axis. With the boss engaging a helicoidal tract of the track, the boss may provide a reactive surface that converts rotational movement of the rod about the axis into axial movement of the rod along the axis. The boss may engage the track by extending radially into the track. The boss may be engaged with the longitudinal tract by extending radially into the longitudinal tract. The boss may be engaged with the helicoidal tract by extending radially into the helicoidal tract.

The methods may involve election of materials for manufacture of components of the apparatus. The materials may be elected for their material properties. The material properties for which the materials may be elected may facilitate operation of the apparatus. Material properties that facilitate operation of the apparatus may include chemical inertness, resilience, transparency and other suitable properties. Other suitable properties may include hardness.

The plunger or plungers may include a plunger material. The plunger material may include polymeric material. The plunger material may include elastomeric material. The plunger material may include thermoplastic elastomer (TPE). The plunger material may include natural rubber. The plunger material may include a compound made from natural rubber. The plunger material may include synthetic rubber. The plunger material may include a compound made from synthetic rubber. The plunger material may include silicone rubber. The plunger material may include a compound made from silicone rubber. The plunger material may include butyl rubber. The plunger material may include a compound made from butyl rubber. The plunger material may include a material elected to reduce interaction of the plunger or plungers with the medicament. The plunger material may include a resilient material. The plunger material may include a material with a hardness less than about 80 Shore A durometer (ASTM D2240 type A hardness scale). The plunger material may facilitate movement of the plunger or plungers within the container. The plunger material may facilitate engagement of the plunger or plungers with the inner wall of the container. The plunger material may facilitate sealing of the plunger or plungers against the inner wall of the container.

The plunger material may include a plunger lubricious coating. The plunger lubricious coating may coat the plunger material. The plunger material may bear the plunger lubricious material. The plunger lubricious material may include polytetrafluoroethylene (PTFE). The plunger lubricious material may include ethylene tetrafluoroethylene (ETFE). The plunger lubricious coating may include a material elected to reduce interaction of the plunger or plungers with the medicament. The plunger lubricious material may facilitate movement of the plunger or plungers within the container. The plunger lubricious material may facilitate engagement of the plunger or plungers with the inner wall of the container. The plunger lubricious material may facilitate sealing of the plunger or plungers against the inner wall of the container.

The stopper may include a stopper material. The stopper material may include polymeric material. The stopper material may include elastomeric material. The stopper material may include TPE. The stopper material may include natural rubber. The stopper material may include a compound made from natural rubber. The stopper material may include synthetic rubber. The stopper material may include a compound made from synthetic rubber. The stopper material may include silicone rubber. The stopper material may include a compound made from silicone rubber. The stopper material may include butyl rubber. The stopper material may include a compound made from butyl rubber. The stopper material may include a material elected to reduce interaction of the stopper with the medicament. The stopper material may include a resilient material. The stopper material may include a material with a hardness less than about 80 Shore A durometer. The stopper material may facilitate movement of the stopper into the container. The stopper material may facilitate engagement of the stopper with the inner wall of the container. The stopper material may facilitate sealing of the stopper against the inner wall of the container. The stopper material may facilitate sealing of the stopper against a distal end-wall of the container. The stopper material may be self-sealing around the first needle.

The stopper material may include a stopper lubricious coating. The stopper lubricious coating may coat the stopper material. The stopper material may bear the stopper lubricious material. The stopper lubricious material may include PTFE. The stopper lubricious material may include ETFE. The stopper lubricious coating may include a material elected to reduce interaction of the stopper with the medicament. The stopper lubricious material may facilitate movement of the stopper into the container. The stopper lubricious material may facilitate engagement of the stopper with the inner wall of the container. The stopper lubricious material may facilitate sealing of the stopper against the inner wall of the container. The stopper lubricious material may facilitate sealing of the stopper against the distal end-wall of the container.

The guide may include a guide material. The guide material may include polymeric material. The guide material may include thermoplastic polymer. The guide material may include delrin. The guide material may include polypropylene. The guide material may include nylon. The guide material may include teflon. The guide material may include acrylonitrile butadiene styrene (ABS). The guide material may include polycarbonate. The guide material may include polysulfone. The guide material may include acrylic polymer. The guide material may include polymethylmethacrylate (PMMA). The guide material may include a stiff material. The guide material may include a material with a hardness more than about 80 Shore A durometer. The guide material may include a material with a low coefficient of friction. The guide material may include a material with a coefficient of friction of about 0.01 to about 0.5.

The rod may include a rod material. The rod material may include polymeric material. The rod material may include thermoplastic polymer. The rod material may include delrin. The rod material may include polypropylene. The rod material may include nylon. The rod material may include teflon. The rod material may include ABS. The rod material may include polycarbonate. The rod material may include polysulfone. The rod material may include acrylic polymer. The rod material may include PMMA. The rod material may include a stiff material. The rod material may include a material with a hardness more than about 80 Shore A durometer. The rod material may include a material with a low coefficient of friction. The rod material may include a material with a coefficient of friction of about 0.01 to about 0.5.

The housing may include a housing material. The housing material may include polymeric material. The housing material may include thermoplastic polymer. The housing material may include delrin. The housing material may include polypropylene. The housing material may include nylon. The housing material may include teflon. The housing material may include ABS. The housing material may include polycarbonate. The housing material may include polysulfone. The housing material may include acrylic polymer. The housing material may include PMMA. The housing material may include a stiff material. The housing material may include a material with a hardness more than about 80 Shore A durometer. The housing material may include a material with a low coefficient of friction. The housing material may include a material with a coefficient of friction of about 0.01 to about 0.5. The housing material may include a material that is translucent. The housing material may include a material that is transparent.

The container may include a container material. The container material may include polymeric material. The plunger material may include amorphous material. The housing material may include thermoplastic polymer. The container material may include glass. The container material may include type 1 borosilicate glass. The container material may include cyclic olefin copolymer (COC). The container material may include polypropylene. The container material may include PMMA. The container material may include a material that is translucent. The container material may include a material that is transparent.

The container material may include a container lubricious coating. The container lubricious coating may coat the container material. The container material may bear the container lubricious material. The container lubricious coating may include silicone oil. The container lubricious material may facilitate movement of the plunger or plungers within the container.

For example, some embodiments may feature an ABS plunger rod disposed in a passageway of a delrin guide affixed to a PMMA housing. The embodiments may feature, in a borosilicate glass container, silicone rubber plungers with PTFE coatings and a butyl rubber stopper with an ETFE coating. The embodiments may feature ABS trigger protrusions integral to the ABS rod, the protrusions supported by parallel helicoidal tracts of parallel helix-containing tracks of the mixing configuration. The embodiments may feature ABS end-walls of parallel longitudinal tracts of the helix-containing tracks, the end-walls serving as terminal surfaces of the helix-containing tracks. The embodiments may feature delrin bosses integral to the delrin guide, the delrin bosses of truncated pyramidal shape and oriented within the guide in conformity with a helical pitch of the helicoidal tracts of the tracks. Some embodiments may feature any other suitable combination of materials and/or geometries.

The apparatus may include, and the methods may involve, determination of the extent of the delivery stroke by abutment of the rod material with the guide material, the guide material fixed in place axially and rotationally relative to the housing. The greater hardness of rod material, guide material and housing material compared to the plunger material and the stopper material, may provide a greater reliability of low volume delivery through abutment of the boss against the terminal surface than provided by bottoming out a typical syringe plunger against a distal inner end of a typical syringe.

The apparatus may include, and the methods may involve, a delivery device for delivering a target amount of medicament from a distal end of the device.

The device may include a collar. The collar may include any suitable material, including that referred to above in connection with the guide. The collar may be disposed coaxial with the axis. The collar may include the boss and a projection. The device may include the plunger rod. The plunger rod may be threadingly engaged, coaxially within the collar, with the proximal knob. The proximal knob may include a track. The track may include an annular tract. The track may include a longitudinal tract. The boss may slidingly engage the annular tract to longitudinally retain the knob during a rotation of the knob about the axis. The boss may slidingly engage the longitudinal tract during a longitudinal translation of the knob. The projection may slidingly engage a longitudinally extending structure of the rod to rotationally retain the rod during the rotation. The rotation may drive the rod toward the distal end.

The translation may be delimited by interference between the boss and a proximal terminal surface of the longitudinal tract. The translation may advance the target amount out of the distal end.

The longitudinal tract may intersect the annular tract. The rotation may be delimited by abutment of the boss against a lateral surface of the longitudinal tract. The longitudinal tract may retain the knob rotationally during the translation and may corresponds, in longitudinal extent, from the location of the abutment, to the target amount. The interference may limit motion of the boss, relative to the knob, to motion that is directed away from the terminal surface and parallel to the axis. The interference may terminate advancement of medicament out of the distal end.

The collar may include a bracket configured to retain, coaxially with the knob, a medicament container. The container may define a bore bound by an interior sidewall that defines, along a segment of the sidewall, a uniform diameter. A distal end of the rod may abut a plunger within the container. The plunger may be slidingly engaged with the sidewall.

Before the translation, the plunger may seal a pre-delivery amount of the medicament between an inner distal end-wall of the container and the plunger. After the translation, a distal portion of the segment may contact a bulk liquid residuum contained between the inner distal end-wall and the plunger. The amount of the medicament in the residuum may be an amount that is no greater than the pre-delivery amount less the target amount.

The rotation may set the pre-delivery amount. The rotation may prepare the medicament for delivery. The preparation may include mixing components of the medicament within the container.

The plunger may be the first plunger and, distal to the first plunger, the second plunger may slidingly engage with the segment.

Prior to the mixing, a liquid component of the medicament may be sealed within the container between the first plunger and the second plunger. The mixing may include transfer of the liquid component, within the container, distally past the second plunger. After the mixing, the distal face of the first plunger may abut the proximal face of the second plunger.

The preparing may include priming the container.

The priming may include the distal discharge of air from the container.

The knob may include the signage. The signage may provide an indication of a stage of device operation. The collar may define a window. The window may expose a portion of the signage. The portion may indicate, prior to the rotation, a medicament preparation stage of the device operation. The portion may indicate, during the rotation, continuation of the preparation stage. The portion may indicate, after the rotation, a medicament delivery stage of the device operation.

The portion may indicate, after the rotation and prior to the translation, commencement of the delivery stage. The portion may indicate, after the translation, completion of the delivery stage.

The abutment may provide tactile indication of completion of a medicament preparation stage of device operation. The abutment may provide acoustic indication of completion of a medicament preparation stage of device operation.

The interference may provide an indication of completion of a medicament delivery stage of device operation.

The longitudinally extending structure may extend along a length of the rod that is disposed between a proximal thread of the rod and a distal end of the rod.

The longitudinally extending structure may support a surface feature configured to interfere with the projection to longitudinally retain the rod from proximal movement.

The surface feature may have a proximal stop surface. The proximal stop surface may provide blockage against distal movement of the projection relative to the surface feature. Distal to the stop surface, the surface feature may provide passage for proximal movement of the projection relative to the surface feature.

The projection may project radially inward. The projection may have a distal stop surface. The distal stop surface may provide blockage against distal movement of the projection relative to the surface feature. Proximal to the stop surface, the projection may provide passage for proximal movement of the projection relative to the surface feature.

The longitudinally extending structure may include a slot. The slot may extend radially inward. The surface feature may extend, in a plane transverse to the axis, into the slot.

The longitudinally extending structure may include a rail. The rail may extend radially outward. The surface feature may extend, in a plane transverse to the axis, radially outward from the rail.

The boss may include a flexible panel. The flexible panel may include a free end. The free end may be disposed more radially inward than any other surface of the boss. The free end may be disposed more radially inward than any other part of the boss.

A running surface of the track may support the trigger. The free end may be configured to, responsive to interaction between the free end and the trigger, deflect relative to the axis when the panel passes by the trigger.

The trigger may have a stop surface. The stop surface may be disposed on a plane transverse to the axis. The stop surface may be configured to block passage of the free end in a direction opposite to the rotation.

The trigger may include the protrusion. The interaction may involve an interference between the free end and the trigger. During the rotation, the panel may pass by the stop surface after passing by all other surfaces of the trigger.

The trigger may include a recess. The interaction may include an urging of the free end against the recess. During the rotation, the panel may pass by the stop surface before passing by any other surface of the trigger.

The interaction may occur upon initiation of the rotation.

Prior to the interaction, the boss may be disposed adjacent a portion of the annular tract that is circumferentially most distant, in the direction of the rotation, from the longitudinal tract. Prior to the interaction, the trigger may limit motion of the free end along the track.

The interaction may occur upon completion of the rotation.

The trigger may be disposed on the annular tract at a juncture of the annular tract and the longitudinal tract. The trigger, following the interaction, may limit rotary motion of the knob in a direction opposite the rotation.

The deflection may provide an indication of the interaction. The indication may be tactile. The indication may be acoustic.

The apparatus may include, and the methods may involve, a medicament delivery device having the longitudinal axis.

The device may include the collar. The collar may be disposed coaxial with the axis. The collar may support a flexible panel and a projection. The device may include the plunger rod. The plunger rode may be threadingly engaged, coaxially within the collar, with the proximal knob. The proximal knob may include the track that supports the trigger.

The panel may be configured to deflect, responsive to interaction with the trigger, relative to the axis. The panel may slidingly engage the track to longitudinally retain the knob during a rotation of the knob about the axis. The rod may include a longitudinally extending structure. The projection may slidingly engage the longitudinally extending structure to rotationally retain the rod during the rotation. The rotation may drive the rod toward the distal end.

The track may include the annular tract. The track may include the longitudinal tract. The annular tract may intersect the longitudinal tract. The panel may slidingly engage the annular tract during the rotation. The panel may slidingly engage the longitudinal tract during a longitudinal translation of the knob. The longitudinal tract may retain the knob rotationally during the translation and may corresponds, in longitudinal extent, from the intersecting, to the target amount. The translation may be delimited by interference between the panel and the proximal terminal surface of the longitudinal tract. The interference may limit motion of the panel, relative to the knob, to motion that is directed away from the terminal surface and parallel to the axis. The interference may terminate advancement of medicament out of the distal end.

The collar may support the bracket. The bracket may be configured to retain, coaxially with the knob, the medicament container. The container may define a bore bound by an interior sidewall that defines, along a segment of the sidewall, a uniform diameter. The distal end of the rod may abut the plunger within the container. The plunger may be slidingly engaged with the sidewall. Before the translation, the plunger may seal the pre-delivery amount of the medicament between the inner distal end-wall of the container and the plunger. After the translation, the distal portion of the segment may contact the bulk liquid residuum contained between the inner distal end-wall and the plunger.

The amount of the medicament in the residuum may be an amount that is no greater than the pre-delivery amount less the target amount. The distal portion of the segment may directly contact the residuum.

The rotation may set the pre-delivery amount. The rotation may prepare the medicament for delivery.

The preparation may include mixing components of the medicament within the container.

The device may include the first plunger and, distal to the first plunger, the second plunger is slidingly engaged with the segment.

Prior to the mixing, a liquid component of the medicament may be sealed within the container between the first plunger and the second plunger. The mixing may include transfer of the liquid component, within the container, distally past the second plunger. After the mixing, the distal face of the first plunger may abut the proximal face of the second plunger.

The preparing may include priming the container.

The priming may include distal discharge of air from the container. The priming may include distal discharge of an inert gas from the container.

The knob may include the signage. The signage may provide the indication. The indication may be an indication of a stage of device operation. The collar may define the window. The window may expose the portion of the signage. The portion may indicate, prior to the rotation, the medicament preparation stage of the device operation. The portion may indicate, after the rotation, the medicament delivery stage of the device operation.

The portion may indicate, during the rotation, continuation of the preparation stage.

The portion may indicate, after the rotation and prior to the translation, commencement of the delivery stage. The portion may indicate, after the translation, completion of the delivery stage.

The longitudinally extending structure may extend along a length that is disposed between a proximal thread of the rod and a distal end of the rod. The longitudinally extending structure may support the surface feature configured to interfere with the projection to longitudinally retain the rod from proximal movement.

The surface feature may include a proximal stop surface. The proximal stop surface may provide blockage against distal movement of the projection relative to the surface feature. Distal to the stop surface, the surface feature may provide passage for proximal movement of the projection relative to the surface feature.

The projection may project radially inward. The projection may include the distal stop surface. The distal stop surface may provide blockage against distal movement of the projection relative to the surface feature. Proximal to the stop surface, the projection may provide passage for proximal movement of the projection relative to the surface feature.

The longitudinally extending structure may include the slot that extends radially inward. The surface feature may extend, in the plane transverse to the axis, into the slot.

The longitudinally extending structure may include the rail that extends radially outward. The surface feature may extend, in the plane transverse to the axis, out from the rail.

The panel may be supported by the boss that is supported by the collar. In the rotation, the boss may be in sliding engagement with the annular tract. In the rotation, the panel may trail all other surfaces of the boss. In the rotation, the panel may trail all other parts of the boss. The panel may include the free end. The free end may be disposed more radially inward than any other surface of the panel. The free end may be disposed more radially inward than any other part of the panel.

In the rotation, the free end may trail all other surfaces of the panel. In the rotation, the free end may trail all other parts of the panel.

The running surface of the track may support the trigger. The free end may interact with the trigger to produce the deflection when the panel passes by the trigger.

The trigger may include the stop surface. The stop surface may be disposed on the plane transverse to the axis. The stop surface may be configured to block passage of the free end in a direction opposite to the rotation.

The trigger may include the protrusion. The interaction may be an interference between the free end and the trigger. During the rotation, the panel may pass by the stop surface after passing by all other surfaces of the trigger. During the rotation, the panel may pass by the stop surface after passing by all other parts of the trigger.

The trigger may include a recess. The interaction may include urging the free end against the recess. During the rotation, the panel may pass by the stop surface before passing by any other surface of the trigger. During the rotation, the panel may pass by the stop surface before passing by any other part of the trigger.

The interaction may occur upon initiation of the rotation. Prior to the interaction, the boss may be disposed adjacent a portion of the annular tract that is circumferentially most distant, in the direction of the rotation, from the longitudinal tract. Prior to the interaction, the trigger may limit motion of the free end along the track.

The interaction may occur upon completion of the rotation.

The trigger may be disposed on the annular tract at a juncture of the annular tract and the longitudinal tract. Following the interaction, the trigger may limit rotary motion of the knob in a direction opposite the rotation.

Following the interaction, the panel may be circumferentially aligned with the longitudinal tract.

The deflection may provide the indication of the interaction. The indication may be tactile. The indication may be acoustic.

The longitudinal tract may include a lateral surface. The rotation may be delimited by abutment of the boss against the lateral surface. The abutment may circumferentially align the boss with the longitudinal tract.

The abutment may provide tactile indication of completion of the medicament preparation stage of device operation. The abutment may provide acoustic indication of completion of the medicament preparation stage of device operation.

The interference may provide indication of completion of the medicament delivery stage of device operation.

The methods may include a method of manufacturing a medicament delivery device. The methods may include providing the knob having the annular recess that includes the surface from which extends the protrusion. The methods may include providing the collar that supports the flexible panel that extends into an interior of the collar. The methods may include positioning the knob coaxially within the collar so that a free end of the panel extends radially inward beyond the protrusion and is deflectable by the protrusion when the knob rotates relative to the collar. The methods may include threadingly engaging the plunger rod with the knob. The methods may include securing the rod against rotation relative to the knob.

The providing a knob may include providing a knob that has a longitudinal recess. The longitudinal recess may intersect the annular recess. The longitudinal recess may support the terminal surface configured to abut the panel.

The providing a collar may include providing a collar that includes the projection. The securing may include engaging the projection with the longitudinally extending structure of the rod.

The longitudinally extending structure may include the slot. The engaging may include insertion of the projection into the slot.

The longitudinally extending structure may include the rail. The engaging may include positioning the projection alongside the rail.

The methods may include providing a rod that includes an end supporting a thread that is engageable with the knob.

The apparatus may include, and the methods may involve, a delivery device for delivering a target amount of medicament from a distal end of the device. The device may include the collar disposed coaxial with the axis. The collar may include the projection and the track. The track may include an annular tract and a longitudinal tract. The device may include the plunger rod. The plunger rode may be threadingly engaged, coaxially within the collar, with the proximal knob. The proximal know may include the boss.

The boss may slidingly engage the annular tract to longitudinally retain the knob during a rotation of the knob about the axis. The boss may slidingly engage the longitudinal tract during a longitudinal translation of the knob. The projection may slidingly engage the longitudinally extending structure of the rod to rotationally retain the rod during the rotation. The rotation may drive the rod toward the distal end. The translation may be delimited by interference between the boss and the proximal terminal surface of the longitudinal tract. The translation may advance the target amount out of the distal end.

The longitudinal tract may intersects the annular tract. The rotation may be delimited by abutment of the boss against the lateral surface of the longitudinal tract. The abutment may circumferentially align the boss with the longitudinal tract. The longitudinal tract may retain the knob rotationally during the translation and corresponds in longitudinal extent, from a location of the abutment, to the target amount The interference may limit motion of the boss, relative to the collar, to motion that is directed away from the terminal surface and parallel to the axis. The interference may terminate advancement of medicament out of the distal end.

The collar may include the bracket. The bracket may be configured to retain, coaxially with the knob, a medicament container. The container may define a bore bound by an interior sidewall that defines, along a segment of the sidewall, a uniform diameter. The distal end of the rod may abut a plunger within the container. The plunger may be slidingly engaged with the sidewall.

Before the translation, the plunger may seal a pre-delivery amount of the medicament between the inner distal end-wall of the container and the plunger. After the translation, a distal portion of the segment may contact the bulk liquid residuum contained between the inner distal end-wall and the plunger. The amount of the medicament in the residuum may be an amount that is no greater than the pre-delivery amount less the target amount.

The rotation may set the pre-delivery amount. The rotation may prepare the medicament for delivery. The preparing may include mixing components of the medicament within the container.

The plunger may be the first plunger and, distal to the first plunger, the second plunger may be slidingly engaged with the segment.

Prior to the mixing, a liquid component of the medicament may be sealed within the container between the first plunger and the second plunger. The mixing may include transfer of the liquid component, within the container, distally past the second plunger. After the mixing, the distal face of the first plunger may abut the proximal face of the second plunger.

The preparing may include priming the container. The priming may include distal discharge of air from the container. The priming may include distal discharge of inert gas from the container.

The knob may include signage that provides an indication of the stage of device operation. The collar may defines the window exposing the portion of the signage. The portion may indicate, prior to the rotation, a medicament preparation stage of the device. The portion may indicate, after the rotation, a delivery stage of the device. The portion may indicate, during the rotation, continuation of the medicament preparation stage.

The portion may indicate, after the rotation and prior to the translation, commencement of the delivery stage. The portion may indicate, after the translation, completion of the delivery stage.

The abutment may provide tactile indication of completion of the medicament preparation stage. The abutment may provide acoustic indication of completion of the medicament preparation stage. The interference may provide the indication of completion of the medicament delivery stage of device operation.

The longitudinally extending structure may include the slot that extends along a length that is disposed between the proximal thread of the rod and the distal end of the rod. The longitudinally extending structure may include a rail that extends along a length that is disposed between the proximal thread of the rod and the distal end of the rod.

The apparatus may include, and the methods may involve a medicament delivery device having the longitudinal axis.

The medicament delivery device may include the plunger rod guide. The plunger rod guide may include the passageway. The plunger rod guide may support the boss. The passageway may be coaxial with the axis and may be configured to receive the plunger rod. The plunger rod may define the track that supports the trigger. The guide may be configured to deflect, responsive to interaction between the boss and the trigger, radially relative to the axis.

The device may include the finger flange. The finger flange may supports the guide. The finger flange may include a surface that defines, distal to the guide, a recess configured to receive a proximal portion of the medicament container. The recess may extend transverse to the axis. The container may be disposed coaxial with the axis.

Track may extend: radially inward from a cylindrical surface of the rod; and along the cylindrical surface.

The trigger may include a protrusion. The interaction may be an interference between the boss and the trigger. The guide may be configured to deflect away from the axis.

The container may define a bore. The bore may be bound by an interior uniform diameter. The rode may be disposed in the passageway. The rod may be configured to be displaced distally, within the bore, to discharge medicament from the container until the boss abuts a terminal surface of the track. This may limit motion of the boss, relative to the rod, to motion that is directed away from the terminal surface and parallel to the axis.

The segment may include a distal portion that, in operation, may contact a bulk liquid residuum of the medicament after the boss abuts the terminal surface. The distal portion of the segment may directly contact the residuum.

The device may include one or more plunger. The plunger may slideably seal against the interior wall. The plunger may be disposed distal the rod. The plunger may be configured to slide distally responsive to distal displacement of the rod.

The device may include the stopper. The stopper may seal a distal end of the container. The medicament, prior to discharge of the medicament, may be sealed within the container between the stopper and the at least one plunger. The distal end of the container may be configured to be associated with the needle. The needle may have a cannula. The cannula may be configured to distally transfer the dose amount of the medicament. The dose amount may be discharged from the container.

The boss may abut the terminal surface prior to interference of a distal face of the plunger with an inner distal wall of the container. The inner distal wall may have a component transverse to the axis.

The finger flange may be configured to maintain the container at least partly coaxial with the axis. The proximal portion of the medicament container may include a flanged lip. A contour of a section of the flanged lip may be complementary to a region of the surface defining the recess.

A proximal section of the rod may include a cylindrical surface. The cylindrical surface may support the knob. The knob may encompass the section. The knob may be coaxial with the axis.

The knob may be configured to be rotated about the axis and to be longitudinally translated along the axis, the rod being configured to move, relative to the medicament container, in response to motion of the knob.

The knob may include signage. The signage may indicate a direction of rotation about the axis associated with distal displacement of the rod.

The rod may be disposed in the passageway after the proximal portion of the medicament container is received by the recess.

The finger flange may include two or more sections that are configured to snap together onto the proximal portion of the medicament container. The The two or more sections may be mechanically complementary. The two or more sections may be mechanically identical.

The finger flange may define an internal bay. The guide may be suspended across the bay by a support extending in a first direction, and, in a second direction, the guide may be configured to deflect responsive to the interaction between the boss and the trigger.

The first direction may be transverse to a proximal face of the finger flange. The proximal face of the finger flange may be transverse to the axis.

In the second direction, the bay may accommodate deflection of the guide.

The support may be a first support. The guide may be suspended by the first support and by a second support. The guide may be suspended between the first support and by a second support.

The guide may be suspended proximal to the bay. The guide may be suspended at least partly within the bay.

The first direction may be transverse to the second direction.

The support may be configured to deform in response to the deflection. Deformation of the support may relieve stress in the finger flange.

The guide may include an arm. The arm may define the passageway. The arm may support the boss apart from an end of the guide from which the guide is suspended.

The rod second track may be disposed parallel to the first track and may supports the second trigger. The first boss may engage the rod at the first track. The guide may support the second boss. The second boss may engage the rod at the second track.

A first deflection of the guide relative to the axis may be responsive to the first interaction between the first boss and the first trigger. A second deflection of the guide relative to the axis may be responsive to a second interaction between the second boss and the second trigger.

The tracks, triggers and bosses may be configured to provide the first deflection and the second deflection approximately simultaneously.

The track may be proximal, along a cylindrical surface of the rod, to a distal end of the rod. The track may support the terminal surface proximal the trigger. A length, along a tract of the track that is disposed between the trigger and the terminal surface may correspond to a delivery stroke of the rod. The delivery stroke may discharge from the container a dose amount of the medicament. The boss may engage the rod at the track and provides a reactive surface that, with the boss abutting the terminal surface, delimits distal displacement of the rod within the container, thus terminating the delivery stroke.

The boss may engage the rod at the track by being positioned against a side of the track. The boss may engage the rod at the track by extending into the track.

The tract may be substantially parallel to the axis; and, with the boss engaging the tract, the reactive surface may limit rotational movement of the rod about the axis.

The tract may be helicoidal about the axis; and, with the boss engaging the tract, the reactive surface may convert rotational movement of the rod about the axis into axial movement of the rod along the axis.

The track may support the second trigger. The first deflection of the guide, responsive to the boss interacting with the first trigger, may correspond to the first stage of distal displacement of the rod in the container. The second deflection of the guide, responsive to the boss interacting with the second trigger, may correspond to the second stage of distal displacement of the rod in the container.

The track may be disposed proximal, along the cylindrical surface of the rod, to the distal end of the rod. The first trigger may be supported by a proximal portion of the distal longitudinal tract of the track. The proximal portion may be adjacent a distal portion of an intermediate tract of the track. The intermediate tract may be disposed along the cylindrical surface between the distal tract and a proximal tract of the track. The first stage may be an initial distal displacement of the rod. The initial displacement may position the rod in the device prior to operation.

The second trigger may be supported by a distal portion of the intermediate tract. The second stage may be an initiation of operation of the device.

The intermediate tract may be helicoidal about the axis. A helical pitch of a portion of the intermediate tract may be sufficiently high to transduce, with the boss providing a reactive surface in engagement with the high pitched portion of the intermediate tract, a distally directed longitudinal force applied to a proximal end of the rod into a rotary force. In operation, the rotary force may drive a rotation of the rod. The rotation may be included in the second stage.

The initiation may include preparation, for discharge, of the medicament. The preparation may include conversion of the medicament from a storage form of the medicament to a dischargeable form of the medicament.

The storage form of the medicament may include: the first component; and the second component stored apart from the first component. A mixture of the first component and the second component may include the dischargeable form of the medicament.

The preparation may include discharge of air from the container prior to delivery of the medicament.

The second trigger may be supported by the proximal portion of the intermediate tract. The proximal portion of the intermediate tract may be adjacent the distal portion of the proximal tract. The proximal tract may support the terminal surface.

The second stage may be initiation of delivery of the medicament.

A length along the proximal tract proximal to the second trigger and distal to the terminal surface may correspond to the delivery stroke of the rod, the delivery stroke discharging from the container the dose amount of the medicament.

The intermediate tract may be at least partly parallel to the axis. The intermediate tract may be at least in part parallel to the axis. The proximal tract may be at least partly parallel to the axis. The proximal tract may be at least in part parallel to the axis. The proximal tract may be circumferentially displaced from the intermediate tract. The proximal portion of the intermediate tract and the distal portion of the proximal tract may be conjoined by an at least partly circumferential tract of the track.

In operation, the delivery stroke may be enabled by a rotation of the rod that shifts the boss, which may be engaged with the track, from the intermediate tract through the circumferential tract to the proximal tract.

The proximal tract may be displaced by about 90 degrees from the intermediate tract.

Tactile indication of completion of the delivery stroke may be provided by abutment of the boss against the terminal surface.

Deflection of the guide, responsive to the interaction occurring at a stage of a distal displacement of the rod within the bore, may produce an indication of the interaction, signaling initiation of the stage. The indication may be tactile.

One or more properties of one or more of the boss, the guide, the trigger, the track, the rod, the finger flange and the container may determine one or more of an amplitude of the indication and a duration of the indication. The properties may include geometry, lubricity and resilience.

The indication is may be acoustic.

One or more properties of one or more of the boss, the guide, the trigger, the track, the rod, the finger flange and the container, may determine one or more of an amplitude of the indication, a pitch of the indication and a duration of the indication. The properties may include geometry, lubricity and resilience.

The apparatus may include, and the methods may involve, a delivery device for delivering the target amount of medicament from the distal end of the device.

The collar may be disposed coaxial with the longitudinal axis. The collar may include a radial projection. The plunger rod may be threadingly engaged, coaxially within the collar, with the knob. The knob may be a proximal knob. The proximal knob may include an abutment surface. The abutment surface may be a distal abutment surface. The projection may slidingly engage a longitudinally extending structure of the rod to rotationally retain the rod during a rotation of the knob about the axis. The longitudinally extending structure may extend along a length that is disposed between a proximal thread of the rod and a distal end of the rod. The projection may interact with a surface feature of the longitudinally extending structure to longitudinally retain the rod from proximal movement. The rotation may axially displace the abutment surface proximally from a device index surface by a distance corresponding to the target amount. Interference between the abutment surface and the index surface may limit the distance an extent of distal translation of the rod, the translation advancing the target amount out of the distal end.

The surface feature may include a proximal stop surface. The proximal stop surface may provide blockage against distal movement of the projection relative to the surface feature. Distal to the proximal stop surface, the surface feature may provide passage for proximal movement of the projection relative to the surface feature.

The projection may include a distal stop surface. The distal stop surface may provide blockage against distal movement of the projection relative to the surface feature. Proximal to the distal stop surface, the surface feature may provide passage for proximal movement of the projection relative to the surface feature.

The collar may include a bracket, distal to the projection. The bracket may be configured to retain, coaxially with the knob, a medicament container. The container may define a bore bound by an interior sidewall. The sidewall may define, along a segment of the sidewall, a uniform diameter. A distal end of the rod may abut the plunger within the container. The plunger may be slidingly engaged with the sidewall.

Before the translation, the plunger may seal a pre-delivery amount of the medicament between an inner distal end-wall of the container and the plunger. After the translation, a distal portion of the segment may contact a bulk liquid residuum contained between the inner distal end-wall and the plunger. An amount of the medicament in the residuum may be an amount that is no greater than the pre-delivery amount less the target amount.

The index surface, prior to the rotation, may be longitudinally offset from the abutment surface and may be abutted against the abutment surface by a nonrotary distal shift of the knob toward the collar. The shift may set the pre-delivery amount. The shift may prepare the medicament for delivery. The preparation may include mixing components of the medicament within the container.

The plunger may be a first plunger and, distal to the first plunger, a second plunger may be slidingly engaged with the segment.

Prior to the mixing, a liquid component of the medicament may be sealed within the container between the first plunger and the second plunger. The mixing may include transfer of the liquid component, within the container, distally past the second plunger.

After the after the mixing, a distal face of the first plunger may abut a proximal face of the second plunger.

The preparing may include priming the container. The priming may include distal discharge of air from the container. The preparing may include priming the container. The priming may include distal discharge of inert gas from the container.

The device may include a rotatable indicator. The rotatable indicator may be coaxially disposed within the collar. The collar may define a window. The window may expose a sector of the indicator. The rotatable indicator may be longitudinally retained by the collar. The rotatable indicator may be rotationally linked to the knob.

The sector may provide signage. The signage may indicate, prior to the rotation, a medicament preparation stage of device operation. The signage may indicate, after the rotation, the target amount.

The indicator may be configured to provide tactile indication of completion of a medicament preparation stage.

The indicator may be configured to provide acoustic indication of completion of a medicament preparation stage.

The indicator may be configured to provide tactile indication of selection of the target amount.

The indicator may be configured to provide acoustic indication of selection of the target amount.

The index surface may be a distal internal surface of the indicator. The index surface may be a proximal external surface of the collar. The index surface may be oriented transverse to the axis.

Nonrotary distal movement of the knob toward the collar may abut the index surface against the abutment surface. The interference may terminate advancement of the medicament out of the distal end. The interference may provide tactile indication of termination of the advancement.

The apparatus may include, and the methods may involve, a medicament delivery device for delivering a target amount of medicament from a distal end of the device.

The device may include the collar. The collar may be disposed coaxial with the axis. The collar may have a track. The track may include a helical tract. The track may include the longitudinal tract. The device may include the plunger rod. The plunger rod may be disposed coaxially within the collar. The rod may be engaged with the proximal knob. The proximal knob may include the boss. The boss may slidingly engage the helical tract during a rotation of the knob about the axis, the rotation advancing the boss toward the longitudinal tract. The boss may slidingly engage the longitudinal tract during a longitudinal translation of the knob.

The translation may be delimited by interference between the boss and a distal terminal surface of the longitudinal tract. The translation may advance the target amount out of the distal end.

The longitudinal tract may intersect the helical tract. The rotation may be delimited by abutment of the boss against the lateral surface of the longitudinal tract. The abutment may circumferentially align the boss with the longitudinal tract. The longitudinal tract may retains the knob rotationally during the translation. The longitudinal tract may correspond in longitudinal extent, from a location of the abutment, to the target amount.

The interference may limit motion of the boss, relative to the collar, to motion that is directed away from the terminal surface and parallel to the axis. The interference may terminate advancement of medicament out of the distal end.

The collar may include a bracket configured to retain, coaxially with and distal the knob, a medicament container. The container may define a bore bound by an interior sidewall that defines, along a segment of the sidewall, a uniform diameter. The distal end of the rod may abut the plunger within the container. The plunger may be slidingly engaged with the sidewall.

Before the translation, the plunger may seal a pre-delivery amount of the medicament between the inner distal end-wall of the container and the plunger. After the translation, the distal portion of the segment may contact a bulk liquid residuum contained between the inner distal end-wall and the plunger. The amount of the medicament in the residuum may be an amount that is no greater than the predetermined amount less the target amount.

The rotation may set the pre-delivery amount. The rotation may prepare the medicament for delivery. The preparing may include mixing components of the medicament within the container.

The plunger may be the first plunger and, distal to the first plunger, the second plunger may be slidingly engaged with the segment.

Prior to the mixing, a liquid component of the medicament may be sealed within the container between the first plunger and the second plunger. The mixing may include transfer of the liquid component, within the container, distally past the second plunger. After the mixing, the distal face of the first plunger may abuts the proximal face of the second plunger.

The preparing may include priming the container.

The priming may include distal discharge of air from the container. The priming may include distal discharge of inert gas from the container.

The helical tract may extend radially inward from an outer surface of the collar. The longitudinal tract may extend radially inward from the outer surface.

The knob may be disposed, along a length of the knob, concentrically surrounding the collar. The slidingly engaged boss may extend radially inward.

The collar may include a longitudinal dock distal the terminal surface. The dock may be circumferentially aligned with the longitudinal tract. The knob may support the boss on a longitudinal arm extending distally beyond the boss. The longitudinal arm may include a contour. The contour may be complementary to a contour of the dock.

The abutment may circumferentially align the arm with the dock. This may provide an indication of completion of the rotation. The translation may advance the arm into the dock.

The helical tract may extend radially outward from the inner surface of the collar. The longitudinal tract may extend radially away, outward, from the inner surface.

The knob may be disposed, along a length of the knob, concentrically within the collar. The slidingly engaged boss may extend radially outward.

The collar may have, along the outer cylindrical surface, signage. A portion of the signage adjacent the helical tract may indicate the medicament preparation stage of device operation. A portion of the signage adjacent the longitudinal tract may indicate a medicament delivery stage of the device operation. The location of the slidingly engaged boss relative to the signage may provide the indication of the stage of the device operation.

The helical tract may support the trigger. The boss may be supported by an arm configured to deflect responsive to interaction between the boss and the trigger. The interaction may provide an indication of engagement of the boss at a location of the trigger.

The location of the trigger may be adjacent an end of the helical tract. The end may be a proximal end, the indication corresponding to commencement of the rotation. The end may be a distal end, the indication corresponding to commencement of the rotation.

The indication may be tactile. The indication may be acoustic. The abutment may provide tactile indication of completion of the medicament preparation stage of device operation. The abutment may provide acoustic indication of completion of the medicament preparation stage of device operation.

The interference may provide indication of completion of the medicament delivery stage of device operation.

Apparatus and methods described herein are illustrative. Apparatus and methods in accordance with the invention will now be described in connection with the FIGs. The FIGs. show illustrative features of apparatus and method steps in accordance with the principles of the invention.

The steps of the methods may be performed in an order other than the order shown and/or described herein. Some embodiments may omit steps shown and/or described in connection with the illustrative methods. Some embodiments may include steps that are neither shown nor described in connection with the illustrative methods. Illustrative method steps may be combined. For example, one illustrative method may include steps shown in connection with another illustrative method.

Some apparatus may omit features shown and/or described in connection with illustrative apparatus. Some embodiments may include features that are neither shown nor described in connection with the illustrative methods. Features of illustrative apparatus may be combined. For example, one illustrative embodiment may include features shown in connection with another illustrative embodiment.

Apparatus may involve some or all of the features of the illustrative apparatus and/or some or all of the steps of the illustrative methods. Methods may involve some or all of the features of the illustrative methods and/or some or all of the steps of the illustrative apparatus.

The apparatus and methods of the invention will be described in connection with embodiments and features of illustrative devices. The devices will be described now with reference to the accompanying drawings in the FIGs., which form a part hereof. It is to be understood that other embodiments may be utilized and that structural, functional and procedural modifications may be made without departing from the scope and spirit of the present invention.

FIG. 1 shows illustrative medicament delivery device 100. Delivery device 100 may define longitudinal axis L. Delivery device 100 is shown in a state that may be a pre-operational state. In the pre-operational state, delivery device 100 may be fully assembled. In the pre-operational state, delivery device 100 may be prepared for discharge of medicament. In the pre-operational state, discharge of medicament from delivery device 100 may not have begun.

Delivery device 100 may include proximal knob 102. Knob 102 may be disposed coaxial with axis L.

Delivery device 100 may include plunger rod 110. Rod 110 may be a component of a mixing configuration. Knob 102 may be attached to rod 110. Knob 102 may be part of rod 110. Knob 102 and rod 110 may be components of a unitary body.

Rod 110 may be disposed coaxial with axis L. Rotation of knob 102 about axis L may result in rotation of rod 110 about axis L. Longitudinal translation of knob 102 along axis L may result in longitudinal translation of rod 110 along axis L.

Rod 110 may define operational track 120. Operational track 120 may extend along a cylindrical surface of rod 110. Operational track 120 may include a section that is substantially helical about axis L. The section of operational track 120 that is substantially helical about axis L may include helicoidal tract 122. Operational track 120 may include a section that is substantially parallel to axis L. The section of operational track 120 that is substantially parallel to axis L may include longitudinal tract 124. Rod 110 may define pre-operational track 130. Pre-operational track 130 may extend along a cylindrical surface of rod 110.

Delivery device 100 may include plunger rod guide 140. Rod 110 may be disposed in guide 140. Rod 110 may pass through guide 140. Guide 140 may define a passageway (not shown) in which rod 110 is disposed and through which rod 110 passes.

Delivery device 100 may include medicament container 150. Container 150 may be a component of a mixing configuration. Container 150 may be disposed coaxial with axis L. Container 150 may be cylindrical. A distal portion of rod 110 may be disposed within container 150. The distal portion of rod 110 may define pre-operational track 130. In the pre-operational state, pre-operational track 130 may already have been passed through guide 140 into container 150. In the pre-operational state, operational track 120 may not yet have been passed through guide 140.

Container 150 may contain medicament component 160a. Container 150 may contain medicament component 160b. Container 150 may contain medicament component 160a apart from medicament component 160b. In the pre-operational state, medicament component 160a may be maintained apart from medicament component 160b.

Delivery device 100 may include device housing 170. Housing 170 may be disposed coaxial with axis L. Housing 170 may be cylindrical. Guide 140 may be disposed in housing 170. Container 150 may be disposed in housing 170.

Delivery device 100 may include finger flange 180. Finger flange 180 may be separate from housing 170. Finger flange 180 may be attached to housing 170. Finger flange 180 may be integral to housing 170.

Delivery device 100 may include needle hub 190. Needle hub 190 may be disposed coaxial with axis L. Needle hub 190 may be attached to housing 170.

Figure 2:
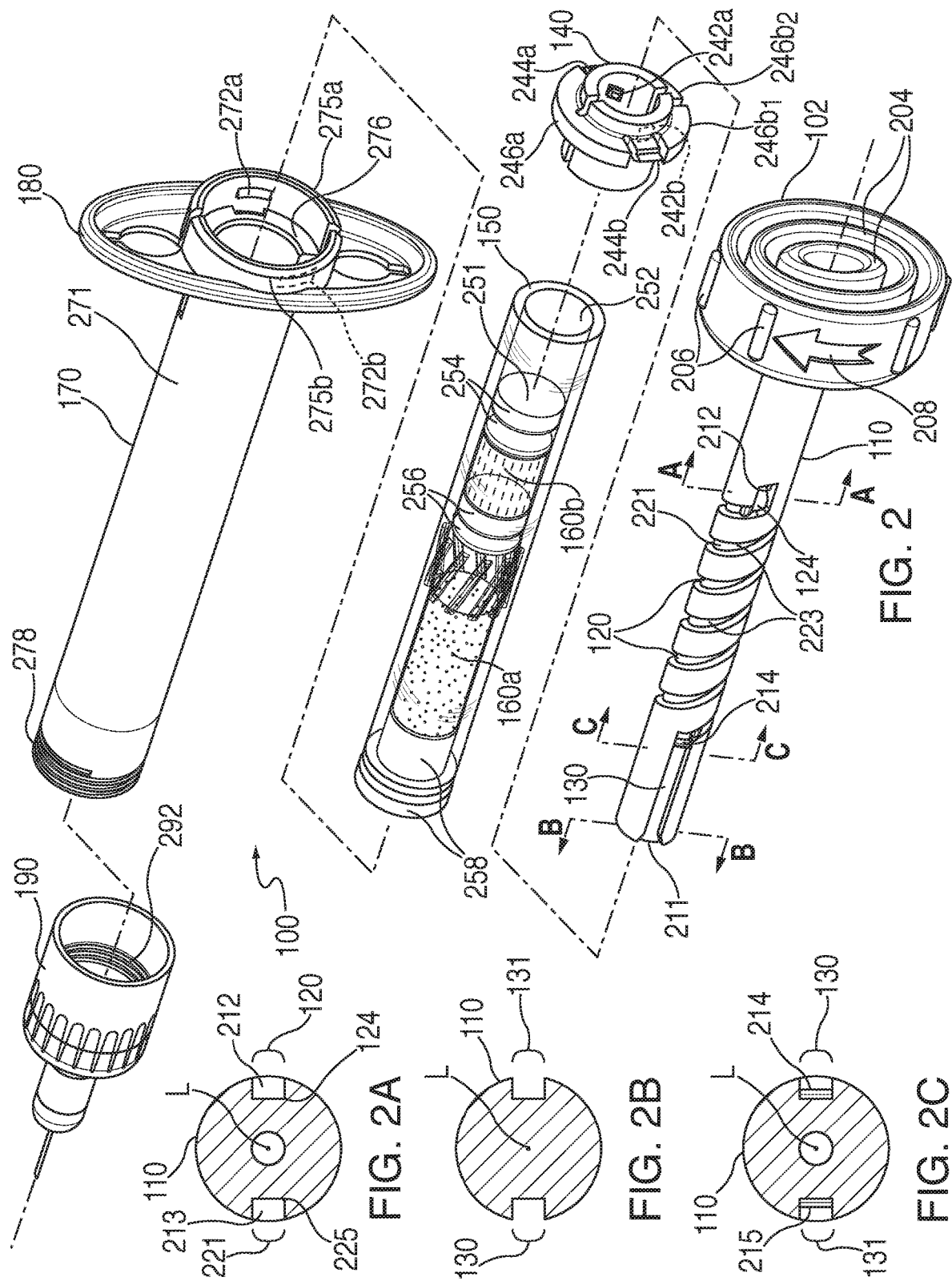
FIG. 2 is an exploded perspective view of the apparatus shown in FIG. 1.

FIG. 2 shows features of delivery device 100.

FIG. 2 shows knob 102. Knob 102 may have an elliptical shape about axis L (shown in FIG. 1). The elliptical shape may provide an operator of delivery device 100 tactile cues as to the circumferential orientation of rod 110 about axis L during an operational state of delivery device 100. The elliptical shape may provide the operator visual cues as to the circumferential orientation of rod 110 about axis L during the operational state.

Knob 102 may include push ridges 204. Push ridges 204 may be utilized by the operator to effect distal longitudinal translation of rod 110 along axis L. Push ridges 204 may contribute to traction on knob 102 for effecting longitudinal translation of rod 110. Push ridges 204 may contribute to ergonomic finger contact of the operator with knob 102 for effecting longitudinal translation of rod 110. The finger contact with knob 102 through push ridges 204 may conduct tactile feedback to the operator of an extent of distal longitudinal translation of rod 110 along axis L.

Knob 102 may include turn ridges 206. Turn ridges 206 may be utilized by the operator to effect rotation of rod 110 about axis L. Turn ridges 206 may contribute to traction on knob 102 for effecting rotation of rod 110. Turn ridges 206 may contribute to ergonomic finger contact of the operator with knob 102 for effecting rotation of rod 110. The finger contact with turn ridges 206 may conduct tactile feedback to the operator of an extent of rotation of rod 110 about axis L.

Turn ridges 206 may be spaced circumferentially around knob 102. Turn ridges 206 may be spaced regularly around a circumference of knob 102. Turn ridges 206 being spaced regularly about the circumference of knob 102 may provide the operator a measure of an extent of rotation performed.

Knob 102 may include turn direction signage 208. In the operational state, delivery device 100 may effect distal displacement of rod 110 within container 150 in response to rotation of rod 110 about axis L in only one of two rotational directions. Turn direction signage 208 may provide the operator with cues as to an effective rotational direction. The cues may serve as reminders before and/or during the operational state. The cues may be visual. The cues may be tactile.

As depicted, the effective rotational direction for distal displacement of rod 110 within container 150 in response to rotation of rod 110 about axis L may be clockwise for delivery device 100. (For some embodiments, not shown, featuring operational tracks with a screw-sense opposite that depicted for helical sections of rod 110, counter-clockwise rotation may the effective rotational direction. For some embodiments, turn direction signage may provide cues for counter-clockwise rotation.)

Rod 110 may include terminal surface 212. Terminal surface 212 may be a proximal end of operational track 120. Operational track 120 may support terminal surface 212. Terminal surface 212 may be a sidewall of operational track 120. Terminal surface 212 may be the sidewall most proximally situated along operational track 120. Terminal surface 212 may be an end-wall of operational track 120. Terminal surface 212 may be a sidewall of longitudinal tract 124. Terminal surface 212 may be the sidewall most proximally situated along longitudinal tract 124. Terminal surface 212 may be an end-wall of longitudinal tract 124.

Rod 110 may define second operational track 221. Second operational track 221 may extend parallel to operational track 120 along the cylindrical surface of rod 110. Second operational track 221 may be disposed diametrically opposite to operational track 120 along the cylindrical surface of rod 110.

Second operational track 221 may include a section that is substantially helical about axis L. The section of second operational track 221 that is substantially helical about axis L may be helicoidal tract 223. Second operational track 221 may include a section (not shown) that is substantially parallel to axis L.

Distal rod end 211 may define a distal end of pre-operational track 130. Pre-operational trigger 214 may demarcate a proximal end to pre-operational track 130. Pre-operational trigger 214 may be a protrusion supported by pre-operational track 130.

FIG. 2A shows rod 110 in a cross-sectional view taken along lines A-A (viewed along axis L toward knob 102) shown in FIG. 2. Rod 110 may have a hollow core coaxial with axis L. The drawing presents an end-on view of terminal surface 212 as the proximal end of operational track 120. The section of operational track 120 terminated proximally by terminal surface 212 may be longitudinal tract 124. Longitudinal tract 124 may be disposed symmetrically on the circumference of rod 110 about axis L relative to longitudinal tract 225. Longitudinal tract 225 may be the section of second operational track 221 that is substantially parallel to axis L. Longitudinal tract 225 may be disposed on the circumference of rod 110 diametrically opposite longitudinal tract 124. Rod 110 may include second terminal surface 213. Second terminal surface 213 may be a proximal end of second operational track 221. Second terminal surface 213 may be a proximal end of longitudinal tract 225. Second operational track 221 may support second terminal surface 213. Second terminal surface 213 may be a sidewall of second operational track 221. Second terminal surface 213 may be the sidewall most proximally situated along second operational track 221. Second terminal surface 213 may be an end-wall of second operational track 221. Terminal surface 213 may be a sidewall of longitudinal tract 225. Second terminal surface 213 may be the sidewall most proximally situated along longitudinal tract 225. Second terminal surface 213 may be an end-wall of longitudinal tract 225. Second terminal surface 213 may be disposed along rod 110 at a distance from distal rod end 211 substantially equal to a distance of terminal surface 212 from distal rod end 211.

FIG. 2B shows rod 110 in a cross-sectional view taken along lines B-B (viewed along axis L toward distal end 211) shown in FIG. 2. The hollow core of rod 110 (shown in FIG. 2A) may not extend distally to lines B-B. Pre-operational track 130 may be disposed symmetrically about axis L on the circumference of rod 110 relative to second pre-operational track 131. Second pre-operational track 131 may be disposed on the circumference of rod 110 diametrically opposite pre-operational track 130. Second pre-operational track 131 may extend along a cylindrical surface of rod 110. Distal rod end 211 may define a distal end of second pre-operational track 131.

FIG. 2C shows rod 110 in a cross-sectional view taken along lines C-C (viewed along axis L toward knob 102). The drawing presents an end-on view of pre-operational trigger 214 as demarcating the proximal end of pre-operational track 130. Pre-operational trigger 214 may be disposed symmetrically about axis L on the circumference of rod 110 relative to second pre-operational trigger 215. Second pre-operational trigger 215 may be disposed on the circumference of rod 110 diametrically opposite pre-operational trigger 214. Second pre-operational trigger 215 may be a protrusion supported by second pre-operational track 131. Second pre-operational trigger 215 may be disposed along rod 110 at a distance from distal rod end 211 substantially equal to a distance of pre-operational trigger 214 from distal rod end 211.

FIG. 2 shows that distal rod end 211 may be inserted through guide 140. Guide 140 may define a passageway through which distal rod end 211 may be inserted. The passageway through which distal rod end 211 may be inserted may be the passageway in which rod 110 may be disposed.

Guide 140 may include boss 242a. Guide 140 may include boss 242b (indicated in phantom lines). Boss 242a and boss 242b may be symmetrically disposed relative to each other about axis L about an interior of guide 140. Boss 242b may be disposed diametrically opposite boss 242a within the interior of guide 140. With insertion of distal rod end 211 through guide 140, boss 242a may engage rod 110 at second pre-operational track 131 (shown in FIG. 2B). Boss 242a may extend radially into second pre-operational track 131. With insertion of distal rod end 211 through guide 140, boss 242b may engage rod 110 at pre-operational track 130. Boss 242b may extend radially into pre-operational track 130.

Guide 140 may include guide-tab 244a. Guide 140 may include guide-tab 244b. Guide-tab 244a and guide-tab 244b may be symmetrically disposed relative to each other about axis L about an exterior of guide 140. Guide-tab 244b may be disposed diametrically opposite guide-tab 244a about the exterior of guide 140. Guide 140 may include seating collar section 246a, seating collar section 246b1 and seating collar section 246b2.

A distal aspect of guide 140 may face a proximal opening of container 150. A distal surface of guide 140 may abut a proximal end-wall surrounding a proximal opening of container 150. Container 150 may define a bore bound by interior wall 252. A proximal portion of interior wall 252 may define the proximal opening of container 150. A distal portion of interior wall 252 may define a distal opening of container 150.

An exterior circumferential surface of proximal plunger 254 may slideably seal against interior wall 252. A proximal face of proximal plunger 254 may be configured to contact distal rod end 211. Rod-contacting face 251 may be configured to contact distal rod end 211. Proximal plunger 254 may include rod-contacting face 251. The proximal face of proximal plunger 254 may include rod-contacting face 251.

An exterior circumferential surface of discharge plunger 256 may slideably seal against interior wall 252. In the pre-operational state, discharge plunger 256 may sealingly maintain medicament component 160a apart from medicament component 160b. In the pre-operational state, medicament component 160b may be sealingly maintained between proximal plunger 254 and discharge plunger 256. In the pre-operational state, medicament component 160a may be sealingly maintained between discharge plunger 256 and needle-penetrable stopper 258.

Needle-penetrable stopper 258 may seal the distal opening of container 150. Needle-penetrable stopper 258 may abut a distal end-wall surrounding the distal opening of container 150. An exterior circumferential surface of a proximal body-section of needle-penetrable stopper 258 may seal against the distal portion of interior wall 252. A distal body-section of needle-penetrable stopper 258 may have a diameter substantially greater than a uniform diameter of the bore of container 150. A proximal surface of a rim of the distal body-section of needle-penetrable stopper 258 may seal against the distal end-wall of container 150.

Container 150 may be disposed in housing 170 distal to guide 140. Container 150 may be disposed in housing 170 between guide 140 and a distal retaining ridge (not shown) of housing 170. The proximal end-wall of container 150 surrounding the proximal opening of container 150 may abut the distal surface of guide 140. A distal rim of the distal body-section of needle-penetrable stopper 258 may abut the distal retaining ridge of housing 170.

Guide 140 may be disposed in housing 170 in a proximal opening of housing wall 271. Housing wall 271 may support finger flange 180. Housing wall 271 may include a first wall section 275a. Wall section 275a may be arcuate in cross-section transverse to axis L. Housing wall 271 may include a second wall section 275b. Wall section 275b may be arcuate in cross-section transverse to axis L. Wall section 275a and wall section 275b may be symmetrically disposed relative to each about axis L.

Guide 140 may be disposed in housing 170 between wall section 275a and wall section 275b. When guide 140 is disposed in housing 170 between wall section 275a and wall section 275b, guide-tab 244a may be blocked from axially proximal movement by guide-tab lock 272a. A proximal side of a circumferential edge of guide-tab 244a may be maintained distal to a distal edge of guide-tab lock 272a. Guide-tab 244b may be blocked from axially proximal movement by guide-tab lock 272b (indicated in phantom lines). A proximal side of a circumferential edge of guide-tab 244b may be maintained distal to a distal edge of guide-tab lock 272b.

Guide 140 may be seated in housing 170 against seating surface 276. When guide 140 is seated in housing 170, seating surface 276 may abut each of seating collar section 246a, seating collar section 246b1 and seating collar section 246b2. Seating collar section 246a and seating collar section 246b1 may be blocked from rotational movement about axis L relative to housing 170 by guide-tab lock 272b. Seating collar section 246a and seating collar section 246b2 may be blocked from rotational movement about axis L relative to housing 170 by guide-tab lock 272a. Seating collar section 246a and/or seating collar section 246b1 and/or seating collar section 246b2 being blocked from rotational movement about axis L relative to housing 170 may block guide 140 from rotational movement about axis L relative to housing 170.

Housing 170 may include housing thread 278. Needle hub 190 may include hub thread 292. Needle hub 190 may be affixed to housing 170 by threading together housing thread 278 and hub thread 292.

Figure 3:
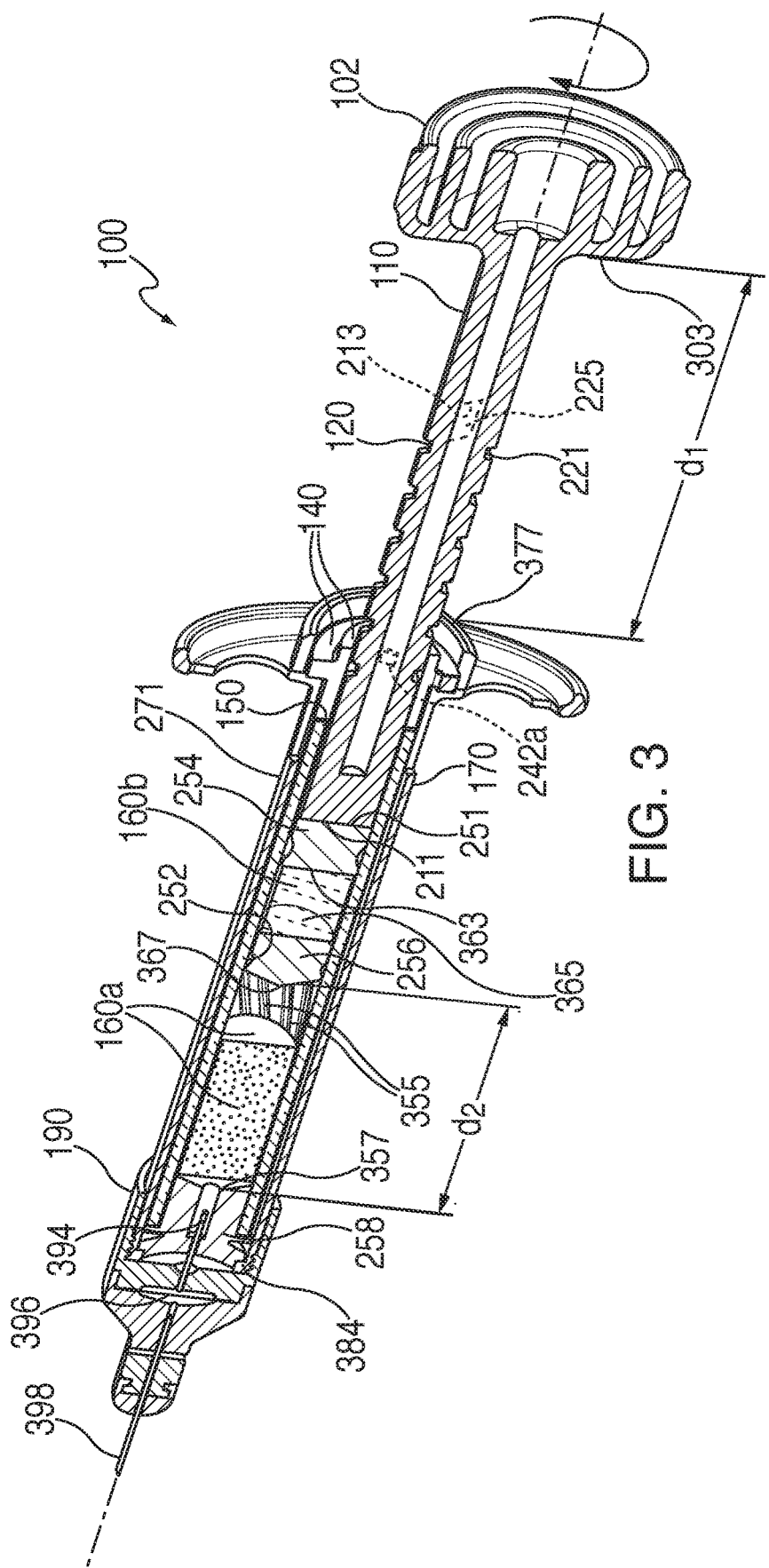
FIG. 3 is a partial cross-sectional view of the apparatus shown in FIG. 1, the view taken along lines 3-3 (shown in FIG. 1)

FIG. 3 shows delivery device 100 in a cross-sectional view taken along lines 3-3 (shown in FIG. 1). FIG. 3 shows the proximal end-wall of container 150 disposed distal to guide 140. The proximal end-wall of container 150 may abut the distal surface of guide 140. Needle-penetrable stopper 258 may be disposed proximal to distal retaining ridge 384. Distal retaining ridge 384 may be disposed interior to housing 170. Distal retaining ridge 384 may include a radially inward thickened portion of wall 271. Distal retaining ridge 384 may be disposed circumferentially surrounding a distal opening of housing 170.

A distal surface of the distal body-section of needle-penetrable stopper 258 may abut distal retaining ridge 384. The distal rim of the distal body-section of needle-penetrable stopper 258 may be compressed between distal retaining ridge 384 and the distal end-wall of container 150. A distal surface of the rim of the distal body-section of needle-penetrable stopper 258 may be deformed by distal retaining ridge 384. Container 150 may be maintained substantially immobile relative to housing 170. Container 150 may be maintained substantially axially immobile relative to housing 170 between the distal surface of guide 140 and distal retaining ridge 384. A spacer (not shown) may be disposed between the distal surface of guide 140 and the proximal end-wall of container 150. The distal surface of guide 140 may abut the spacer. The proximal end-wall of container 150 may abut the spacer.

Knob 102 may include knob distal surface 303. Housing wall 271 may include proximal housing end-wall 377. Knob distal surface 303 may be separated from proximal housing end-wall 377 by linear distance d1 parallel to axis L (shown in FIG. 1). During the operational state, as rod 110 is distally displaced through guide 140, distance d1 may decrease. At the end of the operational state, with completion of medicament delivery, distance d1 may be at a minimum. The minimum may be greater than zero.

The operational state of delivery device 100 may include pre-delivery operation of device 100 and medicament delivery operation of device 100. Pre-delivery operation of device 100 may be carried out with the distal end of delivery device 100 maintained substantially vertically upwards above knob 102. Performance of the delivery stroke may involve whatever orientation of delivery device 100 is most suitable for injection into the patient.

Distal rod end 211 may abut rod-contacting face 251 of proximal plunger 254. As rod 110 is distally displaced through guide 140 in the operational state, distal rod end 211 may distally displace rod-contacting face 251 and, thereby, distally displace proximal plunger 254. During distal displacement of proximal plunger 254, proximal plunger 254 may sealingly slide against interior wall 252. Distal displacement of proximal plunger 254 may distally displace medicament component 160b.

Medicament component 160b may be disposed between distal face 363 of proximal plunger 254 and proximal face 365 of discharge plunger 256. Medicament component 160b may substantially fill a space between distal face 363 and proximal face 365. Medicament component 160b may include a liquid. The liquid may be substantially incompressible. Distal displacement of medicament component 160b may distally displace discharge plunger 256. During distal displacement of discharge plunger 256, discharge plunger 256 may sealingly slide against interior wall 252. Medicament component 160b may be sealed within interior wall 252 between distal face 363 and proximal face 365. Distal face 363 may be structurally complementary to proximal face 365.

With boss 242a (indicated in phantom lines) engaged with operational track 120 and boss 242b (shown in FIG. 2) engaged with second operational track 221, clockwise rotation of knob 102 may displace rod 110 distally through guide 140. Distal displacement of rod 110 may decrease distance d1. Delivery device 100 may be configured such that, even at an end of the operational state, with a maximum distal displacement of rod 110 through guide 140 and into container 150, distance d1 may be greater than zero.

Delivery device 100 may include bypass grooves 355. Bypass grooves 355 may include one or more recesses extending radially outward into interior wall 252. A radial distance of a floor of any of bypass grooves 355 from axis L may be more than a cylindrical radius of interior wall 252. Bypass grooves 355 may have extension with a component parallel to axis L along an inner cylindrical surface of interior wall 252. Pre-operationally, proximal face 365 may be proximal to a proximal-most aspect of the extension of bypass grooves 355 along the inner cylindrical surface of interior wall 252.

In the pre-operational state, a proximal circumferential sealing surface of discharge plunger 256 adjacent to proximal face 365 may seal along its entire perimeter against interior wall 252. In the operational state, as displacement of discharge plunger 256 progresses distally with further clockwise rotation of knob 102, discharge plunger 256 may sealingly slide distally against interior wall 252, maintaining a full perimeter seal, until the proximal circumferential sealing surface of discharge plunger 256 passes the proximal-most aspect of the extension of bypass grooves 355 along the inner cylindrical surface of interior wall 252.

With the proximal circumferential sealing surface of discharge plunger 256 distal to the proximal-most aspect of the extension of bypass grooves 355 along the inner cylindrical surface of interior wall 252, the circumferential sealing surface of discharge plunger 256 may maintain a seal along unrecessed sections of interior wall 252. The circumferential sealing surface of discharge plunger 256 may not maintain a seal across a width of any one of bypass grooves 355. Component 160*b* may be displaced distally via bypass grooves 355 into a space between distal face 367 of discharge plunger 256 and proximal face 357 of stopper 258, mixing with component 160*a*. Component 160*b* may include a reconstituting solution. Component 160*a* may include a lyophilized product that would be progressively reconstituted as more of component 160*b* is distally displaced by further clockwise rotation of knob 102.

Discharge of pressure distal to distal face 367 may be effected by a cannula in discharge needle 394 of needle hub 190. Needle 394 may penetrate distal stopper 258. Distal stopper 258 may seal around an outer perimeter of needle 394. The cannula of needle 394 may be in fluid communication with the space between distal face 367 and proximal face 357. The cannula of needle 394 may be in fluid communication with a cannula of delivery needle 398. The cannula of needle 394 may be in fluid communication with in-line filter 396. Filter 396 may be in fluid communication with the cannula of delivery needle 398.

With the proximal circumferential sealing surface of discharge plunger 256 distal to the proximal-most aspect of the extension of bypass grooves 355 along the inner cylindrical surface of interior wall 252, further clockwise rotation of knob 102 may further distally displace rod 110. The further distal displacement of rod 110 may further distally displace proximal plunger 254. The further distal displacement of proximal plunger 254 may further distally displace component 160*b*. With further distally displaced component 160*b* flowing distally along bypass grooves 355 rather than being sealed proximally to the proximal circumferential sealing surface of discharge plunger 256, discharge plunger 256 may remain substantially immobile until abutted on proximal face 365 by distal face 363 of distally displaced proximal plunger 254.

With abutment of distal face 363 against proximal face 365, substantially none of component 160*b* may remain proximal to proximal face 365, substantially all of component 160*b* having been distally displaced along bypass grooves 355. With substantially all of component 160*b* displaced along bypass grooves 355, component 160*b* and component 160*a* may be mixed into a mixture of component 160*a* and component 160*b*. The mixture of component 160*a* and component 160*b* may be a complete mixture. The mixture of component 160*a* and component 160*b* may be contained in the space between distal face 367 and proximal face 357. Distal face 367 may be separated from proximal face 357 by linear distance d2 parallel to axis L.

Further clockwise rotation of knob 102 may reduce the linear distance d2 by further distally displacing rod 110. The further distal displacement of rod 110 may further distally displace proximal plunger 254. The further distal displacement of proximal plunger 254 may further distally displace discharge plunger 256, bringing distal face 367 closer to proximal face 357, reducing distance d2. Distal face 367 may be structurally complementary to proximal face 357.

The further distal displacement of discharge plunger 256 may distally displace the mixture of component 160*a* and component 160*b*. With the further distal displacement of rod 110, circumferential sealing surfaces of discharge plunger 256 and of proximal plunger 254 may, sequentially, pass distally beyond a distal-most aspect of the extension of bypass grooves 355 along the inner cylindrical surface of interior wall 252. Passing the distal-most aspect of the extension of bypass grooves 355 along the inner cylindrical surface of interior wall 252, circumferential sealing surfaces of discharge plunger 256 and of proximal plunger 254 may, sequentially, effect complete perimeter seals against interior wall 252.

With the complete perimeter seal(s) against interior wall 252, further distal displacement of rod 110 may distally displace the mixture of component 160*a* and component 160*b*, discharging the mixture of component 160*a* and component 160*b* out through, sequentially, needle 394, filter 396 and needle 398.

Further clockwise rotation of knob 102 may bring boss 242*a*, engaged with operational track 120, into engagement with longitudinal tract 124 (shown in FIG. 2) of track 120. The further clockwise rotation of knob 102 may bring boss 242*b* (shown in FIG. 2), engaged with second operational track 221, into engagement with longitudinal tract 225 (indicated in phantom lines) of track 221. Engagement of the boss(es) with the longitudinal tract(s) may block further clockwise rotation of knob 102.

With engagement of the boss(es) with the longitudinal tract(s), knob 102 may be pushed distally along axis L to further distally displace rod 110. Further displacement of rod 110 may constitute performance of the delivery stroke. The further displacement of rod 110 may further distally displace the mixture of component 160*a* and component 160*b*, discharging the mixture of component 160*a* and component 160*b* out through, sequentially, needle 394, filter 396 and needle 398.

Knob 102 may be pushed distally along axis L until boss 242*a* abuts terminal surface 212 (shown in FIG. 2) and/or until boss 242*b* abuts terminal surface 213 (indicated in phantom lines). Abutment of the boss(es) with the terminal surface(es) may block further distal displacement of rod 110 and may block further distal displacement of the mixture of component 160*a* and component 160*b*. The abutment of the boss(es) with the terminal surface(es) may terminate the delivery stroke.

With the abutment of the boss(es) with the terminal surface(es), linear distance d2 may be non-zero. With the abutment of the boss(es) with the terminal surface(es), a residuum of the mixture of component 160*a* and component 160*b* may remain contained within interior wall 252 between distal face 367 and proximal face 357.

FIG. 4A and FIG. 4B show features of rod 110.

FIG. 4A shows pre-operational track 130 of rod 110 distally defined by distal rod end 211 and proximally limited by pre-operational trigger 214. Adjacent pre-operational trigger 214, operation-initiation trigger 416 may be supported by operational track 120 at a distal end of helicoidal tract 122. Track 120 may support delivery-initiation trigger 418 at a proximal end of helicoidal tract 122, adjacent a distal end of longitudinal tract 124, which latter being proximally limited by terminal surface 212.

A proximal end of helicoidal tract 223 may be disposed distal and adjacent longitudinal tract 225 (shown in FIG. 2A and FIG. 3). Diametrically opposite delivery-initiation trigger 418, the proximal end of helicoidal tract 223 may support a second delivery-initiation trigger (not shown) adjacent a distal end of longitudinal tract 225.

FIG. 4B shows details of the view of rod 110 shown in FIG. 4A. Track 120 may be defined by sidewall 427. Track 120 may be defined by running surface 428. Between delivery-initiation trigger 418 and terminal surface 212, running surface 428 may include running surface 429. In approaching terminal surface 212, running surface 429 may be progressively recessed into rod 110. A radial distance of running surface 429 from axis L (shown in FIG. 1) may decrease with increasing proximity, along longitudinal tract 124, of running surface 429 to terminal surface 212.

FIG. 5 and FIG. 6 show details of plunger rods that may be components of configurations of the invention.

FIG. 5 shows plunger rod 510. Rod 510 may be a component of a mixing configuration. Rod 510 may have none, some or all of the features and functions of rod 110 (shown in FIGS. 1, 2, 2A, 2B, 2C, 3, 4A and 4B). Rod 510 may include terminal surface 512, longitudinal tract 524, delivery-initiation trigger 518, operational track 520, operation-initiation trigger 516, pre-operational trigger 514, pre-operational track 530 and distal rod end 511. Rod 510 may define a longitudinal rod axis (not shown).

Rod 510 may include running surface 529 of longitudinal tract 524. A radial distance of running surface 529 from the longitudinal rod axis may remain constant along longitudinal tract 524. Track 520 may support priming-initiation trigger 517. Priming-initiation trigger 517 may be located medially along track 520, proximal to operation-initiation trigger 516 and distal to delivery-initiation trigger 518.

FIG. 6 shows plunger rod 610. Rod 610 may be a component of a non-mixing configuration. Rod 610 may have none, some or all of the features and functions of rod 110 (shown in FIGS. 1, 2, 2A, 2B, 2C, 3, 4A and 4B). Rod 610 may have none, some or all of the features and functions of rod 510 (shown in FIG. 5). Rod 610 may include terminal surface 612, operational track 620, operation-initiation trigger 616, pre-operational trigger 614, pre-operational track 630 and distal rod end 611. Rod 610 may define a longitudinal rod axis (not shown). Operational track 620 may be a rotary-delivery track.

Rod 610 may include helicoidal tract 622. Track 620 may include delivery-initiation trigger 618. Delivery-initiation trigger 618 may be located medially along track 620, proximal to operation-initiation trigger 616 and distal to terminal surface 612. The non-mixing configuration may feature pre-filling with a dischargeable form of medicament (not shown). In the non-mixing configuration, operation of the delivery device may begin with priming. Operation-initiation trigger 616 may be a priming-initiation trigger.

Terminal surface 612 may be a proximal end of operational track 620. Operational track 620 may support terminal surface 612. Terminal surface 612 may be a sidewall of operational track 620. Terminal surface 612 may be an end-wall of operational track 620. Terminal surface 612 may be a sidewall of helicoidal tract 622. Terminal surface 612 may be an end-wall of helicoidal tract 622.

Terminal surface 612 may be an end-wall of track 620 along helicoidal tract 622. A length along helicoidal tract 622 between delivery-initiation trigger 618 and terminal surface 612 may set the extent of the delivery stroke. The delivery stroke may be performed by rotation of rod 110 about the longitudinal axis.

FIG. 7, FIG. 8 and FIG. 9 show details of medicament containers that may be components of configurations of the invention.

FIG. 7 shows medicament container 750. Container 750 may be a component of a mixing configuration. Container 750 may have none, some or all of the features and functions of container 150 (shown in FIGS. 1, 2 and 3). Container 750 may define a bore bound by interior wall 752. Needle-penetrable stopper 758 may seal a distal end of the bore. The distal end of the bore may include a distal portion of interior wall 752. The distal portion of interior wall 752 may define a distal opening of container 750.

Container 750 may include proximal plunger 754, medicament component 760b, discharge plunger 756, bypass grooves 755 and medicament component 760a.

Container 750 may include rod-contacting face 751. Proximal plunger 754 may include rod-contacting face 751. A proximal face of proximal plunger 754 may include rod-contacting face 751. Discharge plunger 756 may include proximal face 765.

Medicament component 760b may include a liquid medicament component formulation. Medicament component 760b may be disposed between proximal face 765 and proximal plunger 754. Medicament component 760b may be sealed between proximal face 765 and proximal plunger 754. Medicament component 760b may substantially fill a space between proximal face 765 and a distal face of proximal plunger 754.

Medicament component 760a may be disposed distal to discharge plunger 756. Medicament component 760a may be disposed between discharge plunger 756 and needle-penetrable stopper 758. Medicament component 760a may be sealed between discharge plunger 756 and needle-penetrable stopper 758.

Displacement of proximal face 765 distally beyond a proximal-most extent of bypass grooves 755 may facilitate flow of medicament component 760b along bypass grooves 755, bypassing discharge plunger 756, to mix with medicament component 760a.

Medicament component 760a may include a solid medicament component formulation. Medicament component 760a may include a lyophilized product. Medicament component 760b may include a reconstituting solution. Medicament component 760a may be reconstituted by mixing with medicament component 760b.

Needle-penetrable stopper 758 may seal the distal opening of container 750 along interior wall 752. A proximal body-section of needle-penetrable stopper 758 may be inserted into container 750 through the distal opening of container 750. A cylindrical surface of the proximal body-section may seal against the distal portion of interior wall 752. A distal circumferential portion of the cylindrical surface may seal along its entire perimeter against interior wall 752.

Needle-penetrable stopper 758 may seal the distal opening of container 750 along a distal end-wall of container 750 surrounding the distal opening of container 750. Needle-penetrable stopper 758 may abut the distal end-wall. A distal body-section of needle-penetrable stopper 758 may have a diameter substantially greater than a uniform diameter of the bore of container 750. A proximal surface of a rim of the distal body-section may seal against the distal end-wall of container 750.

The cylindrical surface of the proximal body-section of needle-penetrable stopper 758 may define voids 759. Voids 759 may be recessed into the cylindrical surface. Voids 759 may have longitudinal extension along the cylindrical surface. Voids 759 may extend proximally from the distal circumferential portion of the cylindrical surface sealing against the distal end-wall of container 750. Voids 759 may extend proximally to a proximal end of needle-penetrable stopper 758.

During a manufacturing step of the mixing configuration, container 750 may be oriented with the distal opening vertically upwards above a proximal end of container 750. Needle-penetrable stopper 758 may be partially inserted (not shown) into the distal end of container 750, leaving a gap between the distal end-wall of container 750 and the proximal surface of the rim of the distal body-section of needle-penetrable stopper 758. The gap may be configured to facilitate gas exchange along voids 759 between an interior of container 750 and an exterior of container 750.

During the manufacturing step, container 750 may be within a lyophilization chamber (not shown). A portion of the interior of container 750 distal to discharge plunger 756 may contain a liquid medicament formulation (not shown) to be lyophilized to produce component 760*a*. During lyophilization, gas may be exchanged along voids 759 from the liquid medicament formulation in the interior of container 750 to the exterior of container 750. The gas may be a lyophilization byproduct. The lyophilization byproduct may be vaporized solvent of the liquid medicament formulation. Lyophilization may continue until the lyophilized product remains in container 750. The lyophilized product may be a caked desiccated medicament. With completion of lyophilization, medicament component 760*a* may have been produced by lyophilization. With the completion of lyophilization, needle-penetrable stopper 758 may be fully inserted into container 750, bringing the rim of the distal body-section of needle-penetrable stopper 758 into abutment with the distal end-wall of container 750.

FIG. 8 shows medicament container 850. Container 850 may be a component of a mixing configuration. Container 850 may have none, some or all of the features and functions of container 150 (shown in FIGS. 1, 2 and 3). Container 850 may have none, some or all of the features and functions of container 750 (shown in FIG. 7). Container 850 may define a bore bound by interior wall 852. Needle-penetrable stopper 858 may seal a distal end of the bore. The distal end of the bore may include a distal portion of interior wall 852. The distal portion of interior wall 852 may define a distal opening of container 850.

Container 850 may include proximal plunger 854, medicament component 860*b*, discharge plunger 856, bypass grooves 855 and medicament component 860*a*.

Container 850 may include rod-contacting face 851. Proximal plunger 854 may include rod-contacting face 851. A proximal face of proximal plunger 854 may include rod-contacting face 851. Discharge plunger 856 may include proximal face 865.

Medicament component 860*b* may include a liquid medicament component formulation. Medicament component 860*b* may be disposed between proximal face 865 and proximal plunger 854. Medicament component 860*b* may be sealed between proximal surface 865 and proximal plunger 854. Medicament component 860*b* may substantially fill a space between proximal surface 865 and a distal face of proximal plunger 854.

Medicament component 860*a* may include a liquid medicament component formulation. Medicament component 860*a* may be disposed distal to discharge plunger 856. Medicament component 860*a* may be disposed between discharge plunger 856 and needle-penetrable stopper 858. Medicament component 860*a* may be sealed between discharge plunger 856 and needle-penetrable stopper 858. Medicament component 860*a* may substantially fill a space between proximal surface 857 of needle-penetrable stopper 858 and a distal face of discharge plunger 856.

Displacement of proximal face 865 distally beyond a proximal-most extent of bypass grooves 855 may facilitate flow of medicament component 860*b* along bypass grooves 855, bypassing discharge plunger 856, to mix with medicament component 860*a*.

Medicament component 860*a* may include a first component of a binary drug system. Medicament component 860*b* may include a second component of the binary drug system. In the pre-operational state, the first and second components of the binary drug system may be maintained apart from each other in container 850. During the operational state, the first and second components of the binary drug system may be mixed in container 850 preparatory to delivery of the binary drug system to the patient.

Medicament component 860*a* may include a medicament formulation of a pH, ionic strength and/or medical agent concentration better suited for storage than for delivery to the patient. Medicament component 860*b* may include a solution, such as a buffering solution, which, when mixed with medical component 860*a*, yields a mixture of a pH, ionic strength and/or medical agent concentration better suited for delivery to the patient than for storage.

Needle-penetrable stopper 858 may seal the distal opening of container 850 along interior wall 852. An exterior circumferential surface of a proximal body-section of needle-penetrable stopper 858 may seal against the distal portion of interior wall 852. The cylindrical surface may seal along its circumferential perimeter against interior wall 852.

Needle-penetrable stopper 858 may seal the distal opening of container 850 along a distal end-wall of container 850 surrounding the distal opening of container 850. Needle-penetrable stopper 858 may abut the distal end-wall. A distal body-section of needle-penetrable stopper 858 may have a diameter substantially greater than a uniform diameter of the bore of container 850. A proximal surface of a rim of the distal body-section may seal against the distal end-wall of container 850.

FIG. 9 shows medicament container 950. Container 950 may be a component of a non-mixing configuration. Container 950 may have none, some or all of the features and functions of container 150 (shown in FIGS. 1, 2 and 3). Container 950 may have none, some or all of the features and functions of container 750 (shown in FIG. 7). Container 950 may have none, some or all of the features and functions of container 850 (shown in FIG. 8). Container 950 may define a bore bound by interior wall 952. Needle-penetrable stopper 958 may seal a distal end of the bore. The distal end of the bore may include a distal portion of interior wall 952. The distal portion of interior wall 952 may define a distal opening of container 950.

Container 950 may include discharge plunger 956 and medicament 960.

Container 950 may include rod-contacting face 951. Discharge plunger 956 may include rod-contacting face 951. A proximal face of discharge plunger 956 may include rod-contacting face 951.

Medicament 960 may include a liquid medicament formulation. Medicament 960 may be disposed distal to discharge plunger 956. Medicament 960 may be disposed between discharge plunger 956 and needle-penetrable stopper 958. Medicament 960 may be sealed between discharge plunger 956 and needle-penetrable stopper 958. Medicament 960 may substantially fill a space between proximal face 957 of needle-penetrable stopper 958 and a distal face of discharge plunger 956.

Needle-penetrable stopper 958 may seal the distal opening of container 950 along interior wall 952. An exterior circumferential surface of a proximal body-section of needle-penetrable stopper 958 may seal against the distal portion of interior wall 952. The cylindrical surface may seal along its circumferential perimeter against interior wall 952.

Needle-penetrable stopper 958 may seal the distal opening of container 950 along a distal end-wall of container 950 surrounding the distal opening of container 950. Needle-penetrable stopper 958 may abut the distal end-wall. A distal body-section of needle-penetrable stopper 958 may have a diameter substantially greater than a uniform diameter of the bore of container 950. A proximal surface of a rim of the distal body-section may seal against the distal end-wall of container 950.

FIG. 10 shows a front view of a proximal face of guide 140. FIG. 10 shows boss 242a and boss 242b disposed diametrically opposite, and extending toward, each other. FIG. 10 shows guide-tab 244a and guide-tab 244b disposed diametrically opposite, and extending away from, each other. FIG. 10 shows seating collar section 246a, seating collar section 246b1 and seating collar section 246b2.

Boss 242a may be supported by arm 1041a. Boss 242b may be supported by arm 1041b. Arm 1041a and arm 1041b may be joined at hinge 1045. Hinge 1045 may be resilient. Arm 1041a and arm 1041b may define gap 1048. Gap 1048 may extend between seating collar section 246b1 and seating collar section 246b2. Gap 1048 may be opposite hinge 1045. Arm 1041a may support boss 242a apart from gap 1048. Arm 1041a may support boss 242a apart from hinge 1045. Arm 1041b may support boss 242b apart from gap 1048. Arm 1041b may support boss 242b apart from hinge 1045.

Guide 140 may be configured to deflect. Arms 1041a and 1041b may be configured to deflect away from each other about hinge 1045. A width of gap 1048 may change during deflection of guide 140. Gap 1048 may widen during the deflection of guide 140. Gap 1048 may narrow during the deflection of guide 140.

FIG. 11 shows features of delivery device 100.

FIG. 11 shows that distal end 211 of rod 110 may be longitudinally inserted through guide 140. With insertion of distal rod end 211 through guide 140, boss 242b (indicated in phantom lines) may engage rod 110 at pre-operational track 130 and/or boss 242a may engage rod 110 at second pre-operational track 131 (shown in FIG. 2B and FIG. 2C). Rod 110 may include chamfers 1119. Chamfers 1119 may facilitate engagement of the boss(es) at the pre-operational track(s) upon insertion of rod 110 through guide 140.

FIG. 11 shows that guide 140 may be inserted into housing 170, with distal guide extension 1149 extending into an interior of housing wall 271. Guide 140 may be inserted into housing 170 until seating surface 276 abuts seating collar section 246a and/or until seating surface 276 abuts seating collar section 246b1 and/or until seating surface 276 abuts seating collar section 246b2. Seating surface 276 abutting one or more of the seating collar sections of guide 140 may substantially block further insertion of guide 140 into housing 170. With seating surface 276 abutting collar section 246a, seating collar section 246b1 and collar section 246b2, guide 140 may be seated in housing 170.

With seating surface 276 abutting one or more of the seating collar sections of guide 140, guide-tab 244a may be locked by guide-tab lock 272a supported by wall section 275a of housing wall 271 and/or guide-tab 244b may be locked by guide-tab lock 272b (indicated in phantom lines) supported by wall section 275b of housing wall 271. The guide-tab lock(s) locking the guide-tab(s) may block guide 140 from proximal movement along axis L (shown in FIG. 1).

With seating surface 276 abutting one or more of the seating collar sections of guide 140, seating collar section 246a may be blocked from rotational movement about axis L by guide-tab lock 272a and guide-tab lock 272b. Seating collar section 246b2 may be blocked from rotational movement about axis L by guide-tab lock 272a. Seating collar section 246b1 may be blocked from rotational movement about axis L by guide-tab lock 272b.

Rod 110 may be inserted into guide 140 with the engagement of boss 242b at pre-operational track 130 until boss 242b interacts with pre-operational trigger 214. The interaction of boss 242b with pre-operational trigger 214 may correspond to an end of the engagement of boss 242b with pre-operational track 130. Rod 110 may be inserted into guide 140 with the engagement of boss 242a at second pre-operational track 131 until boss 242a interacts with second pre-operational trigger 215 (shown in FIG. 2C). The interaction of boss 242a with second pre-operational trigger 215 may correspond to an end of the engagement of boss 242a with second pre-operational track 131. In response to the interaction of the boss(es) with the pre-operational trigger(s), guide 140 may deflect, widening gap 1048, indicating the end of the engagement of the boss(es) with the pre-operational track(s). Further longitudinal insertion of rod 110 into guide 140, may position boss 242b proximal to pre-operational trigger 214 and/or may position boss 242a proximal to second pre-operational trigger 215.

Boss 242b may be positioned proximal to pre-operational trigger 214 against running surface 1126. Running surface 1126 may be disposed adjacent pre-operational trigger 214. Running surface 1126 may be disposed between pre-operational trigger 214 and operation-initiation trigger 416. The insertion of rod 110 positioning boss 242b against running surface 1126 may be the initial displacement.

The initial displacement may position boss 242a against a second running surface (not shown) disposed diametrically opposite running surface 1126. The second running surface may be disposed proximal to second pre-operational trigger 215. The second running surface may be disposed adjacent second pre-operational trigger 215. The second running surface may be adjacent a distal portion of helicoidal tract 223 of second operational track 221.

Adjacent second pre-operational trigger 215, second operational track 221 may support a second operation-initiation trigger (not shown) at a distal end of helicoidal tract 223 of second operational track 221. The second operation-initiation trigger may be disposed diametrically opposite operation-initiation trigger 416. The initial displacement may position boss 242a against the second running surface between second pre-operational trigger 215 and the second operation-initiation trigger.

With rod 110 at the initial displacement, delivery device 100 may be in the pre-operational state. With rod 110 at the initial displacement, delivery device 100 may be at the end of the pre-operational state. With rod 110 at the initial displacement, delivery device 100 may have been prepared for initiation of the operational state.

Running surface 1126 may be adjacent a proximal portion of pre-operational track 130. Running surface 1126 may be adjacent a distal portion of helicoidal tract 122 of operational track 120. Rod 110 may be substantially blocked, by boss 242*b* being positioned proximal to pre-operational trigger 214 and/or by boss 242*a* being positioned proximal to second pre-operational trigger 215, from inadvertent proximal slippage of rod 110 out of guide 140. Rod 110 may be substantially blocked, by boss 242*b* being positioned between pre-operational trigger 214 and operation-initiation trigger 416, from inadvertent further distal displacement. Rod 110 may be substantially blocked, by boss 242*a* being positioned between second pre-operational trigger 215 and the second operation-initiation trigger, from inadvertent further distal displacement. Further distal displacement of rod 110 from the initial displacement may involve intentional manipulation on the part of the operator.

The further distal displacement of rod 110 may be effected by clockwise rotation of rod 110 about axis L. The clockwise rotation of rod 110 about axis L may shift boss 242*b* from being positioned against running surface 1126 to interaction with operation-initiation trigger 416. The clockwise rotation of rod 110 about axis L may shift boss 242*a* from being positioned against the second running surface to interaction with the second operation-initiation trigger. In response to the interaction of the boss(es) with the operation-initiation trigger(s), guide 140 may deflect, widening gap 1048, indicating the initiation of the operational state.

Acoustic and/or tactile indication of guide 140 deflecting may be concomitant of and/or attendant upon widening of gap 1048.

Gap 1048 may be aligned with slot 1179 between wall section 275*a* and wall section 275*b*. Wall section 275*a* and wall section 275*b* may deflect in response to deflection of the guide, widening slot 1179. Acoustic and/or tactile indication of the wall sections deflecting may be concomitant of and/or attendant upon widening of slot 1179.

Finger flange 180 may encompass wall section 275*a* and wall section 275*b*. Finger flange 180 may define hole 1182. A diametrical slot across, and extending radially inward beyond, hole 1182 may be aligned with slot 1179.

Figure 12:
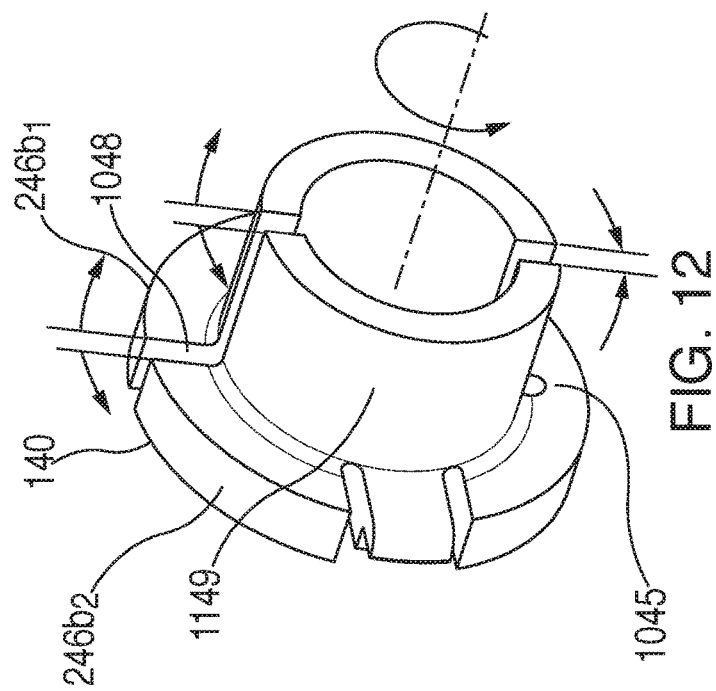
FIG. 12 is another perspective view of apparatus shown in FIG. 11.

FIG. 12 shows a view of a distal face of guide 140, with guide 140 rotated 180° about axis L (shown in FIG. 1) relative to the view shown in FIG. 11. FIG. 12 shows that gap 1048 between seating collar section 246*b*1 and seating collar section 246*b*2 may extend distally along distal guide extension 1149. Gap 1048 may widen, along its longitudinal extension, with deflection of guide 140. Widening of gap 1048 may be associated with a narrowing of a gap in distal guide extension 1149 disposed parallel to and diametrically opposite gap 1048, as guide 140 deflects about hinge 1045.

Figure 13:
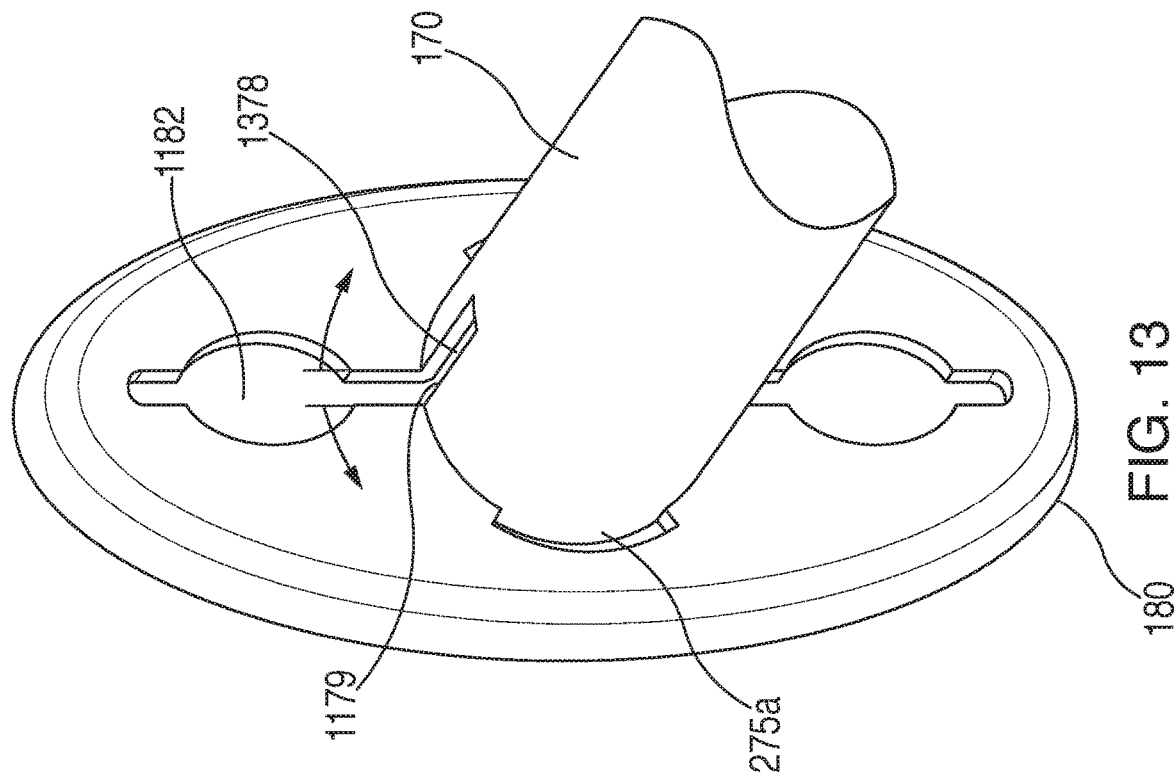
FIG. 13 is another perspective view of apparatus shown in FIG. 11.

FIG. 13 shows a view of a distal face of finger flange 180, with finger flange 180 rotated 180° about axis L (shown in FIG. 1) relative to the view shown in FIG. 11. FIG. 13 shows that the diametrical slot across, and extending radially inward beyond, hole 1182 may be an extension of slot 1179. Slot 1378 in housing 170 may be aligned with slot 1179. Finger flange 180 may deflect in response to wall section 275*a* deflecting in response to deflection of guide 140 (shown in FIG. 12). Acoustic and/or tactile indication of finger flange 180 deflecting may be concomitant of and/or attendant upon widening of slot 1179. The indication produced by finger flange 180 may amplify the indication produced by the wall section(s).

FIGS. 14-27 show details of plunger rod guides that may be components of configurations of the invention.

FIG. 14 shows a front view of a proximal face of plunger rod guide 1440. Guide 1440 may have may have none, some or all of the features and functions of guide 140 (shown in FIGS. 1, 2, 3, 10, 11 and 12). Guide 1440 may include boss 1442*a*. Guide 1440 may include boss 1442*b*. Boss 1442*a* and boss 1442*b* may be disposed diametrically opposite each other relative to a center of guide 1440. Boss 1442*a* and boss 1442*b* may extend toward each other.

Guide 1440 may include radial collar section 1443*a*. Guide 1440 may include radial collar section 1443*b*. Radial collar section 1443*a* and radial collar section 1443*b* may be disposed diametrically opposite each other relative to the center. Radial collar section 1443*a* and radial collar section 1443*b* may extend away from each other.

Guide 1440 may include guide-tab 1444*a*, guide-tab 1444*b*, guide-tab 1444*c* and guide-tab 1444*d*. Guide-tab 1444*a*, guide-tab 1444*b*, guide-tab 1444*c* and guide-tab 1444*d* may be disposed symmetrically relative to the center. Guide-tab 1444*a* and guide-tab 1444*b* may be disposed diametrically opposite each other relative to the center. Guide-tab 1444*a* and guide-tab 1444*b* may extend away from each other. Guide-tab 1444*c* and guide-tab 1444*d* may be disposed diametrically opposite each other relative to the center. Guide-tab 1444*c* and guide-tab 1444*d* may extend away from each other.

Guide 1440 may include seating collar section 1446*a*, seating collar section 1446*b*1 and seating collar section 1446*b*2.

Boss 1442*a* may be supported by arm 1441*a*. Boss 1442*b* may be supported by arm 1441*b*. Arm 1441*a* and arm 1441*b* may be joined at hinge 1445. Hinge 1445 may be resilient. Arm 1441*a* and arm 1441*b* may define gap 1448. Gap 1448 may extend between seating collar section 1446*b*1 and seating collar section 1446*b*2. Gap 1448 may be opposite hinge 1445. Arm 1441*a* may support boss 1442*a* apart from gap 1448. Arm 1041*a* may support boss 1442*a* apart from hinge 1445. Arm 1041*b* may support boss 1442*b* apart from gap 1448. Arm 1441*b* may support boss 1442*b* apart from hinge 1445.

FIG. 15 shows features of illustrative medicament delivery device 1500. Delivery device 1500 may have none, some or all of the features and functions of delivery device 100 (shown in FIG. 11). Delivery device 1500 may define longitudinal axis L1.

Delivery device 1500 may include plunger rod 1510. Rod 1510 may have none, some or all of the features and functions of rod 110 (shown in FIGS. 1, 2, 2A, 2B, 2C, 3, 4A, 4B and 11). Rod 1510 may have none, some or all of features and functions of rod 510 (shown in FIG. 5). Rod 1510 may have none, some or all of the features and functions of rod 610 (shown in FIG. 6). Rod 1510 may be disposed coaxial with axis L1.

Delivery device 1500 may include guide 1440. Guide 1440 may be disposed coaxial with axis L1. Axis L1 may pass through the center of guide 1440. Guide 1440 may include distal guide extension 1549.

Delivery device 1500 may include device housing 1570. Housing 1570 may have none, some or all of the features and functions of housing 170 (shown in FIGS. 1, 2, 3, 11 and 13). Housing 1570 may be disposed coaxial with axis L1.

Delivery device 1500 may include a medicament container (not shown). The medicament container of device 1500 may have none, some or all of the features and functions of medicament container 150 (shown in FIGS. 1, 2 and 3). The medicament container of device 1500 may have none, some or all of the features and functions of medicament container 750 (shown in FIG. 7). The medicament container of device 1500 may have none, some or all of the features and functions of medicament container 850 (shown in FIG. 8). The medicament container of device 1500 may have none, some or all of the features and functions of medicament container 950 (shown in FIG. 9). The medicament container of device 1500 may be disposed coaxial with axis L1.

Delivery device 1500 may include a needle hub (not shown). The needle hub of device 1500 may have none, some or all of the features and functions of needle hub 190 (shown in FIGS. 1, 2 and 3). The needle hub of device 1500 may be disposed coaxial with axis L1.

Rod 1510 may include distal rod end 1511. Rod 1510 may include chamfers 1519 proximal to distal rod end 1511. Rod 1510 may define pre-operational track 1530. Pre-operational track 1530 may extend along a cylindrical surface of rod 1510. Pre-operational track 1530 may support pre-operational trigger 1514. Pre-operational trigger 1514 may be supported at a proximal end of pre-operational track 1530.

Rod 1510 may define a second pre-operational track (not shown). The second pre-operational track may extend along the cylindrical surface of rod 1510 parallel to pre-operational track 1530. The second pre-operational track may extend parallel to pre-operational track 1530 over a full extent of pre-operational track 1530 along the cylindrical surface of rod 1510. The second pre-operational track may be disposed diametrically opposite pre-operational track 1530. The second pre-operational track may support a second pre-operational trigger (not shown). The second pre-operational trigger may be supported at a proximal end of the second pre-operational track. The second pre-operational trigger may be disposed diametrically opposite pre-operational trigger 1514. The second pre-operational trigger may be disposed along rod 1510 at a distance from distal rod end 1511 substantially equal to a distance of pre-operational trigger 1514 from distal rod end 1511.

Rod 1510 may define operational track 1520. Operational track 1520 may extend along the cylindrical surface of rod 1510. Rod 1510 may define second operational track 1521. Operational track 1520 and second operational track 1521 may be disposed parallel to each other along the cylindrical surface.

Operational track 1520 may support operation-initiation trigger 1516. Operation-initiation trigger 1516 may be adjacent to pre-operational trigger 1514. Operational track 1520 may include helicoidal tract 1522. Operation-initiation trigger 1516 may be supported by operational track 1520 at a distal end of helicoidal tract 1522.

Second operational track 1521 may support a second operation-initiation trigger (not shown). The second operation-initiation trigger may be adjacent to the second pre-operational trigger. Second operational track 1521 may include helicoidal tract 1523. The second operation-initiation trigger may be supported by second operational track 1521 at a distal end of helicoidal tract 1523. The second operation-initiation trigger may be disposed diametrically opposite operation-initiation trigger 1516.

Sidewall 1527 may be a sidewall of helicoidal tract 1522. Track 1520 may be defined by sidewall 1527. Running surface 1528 may be a running surface of helicoidal tract 1522. Track 1520 may be defined by running surface 1528.

Distal end 1511 of rod 1510 may be longitudinally inserted through guide 1440. Guide 1440 may define a passageway through which distal rod end 1511 may be inserted.

Rod 1510 may be rounded at distal rod end 1511. Rod 1510 being rounded at distal rod end 1511 may facilitate insertion of distal rod end 1511 through guide 1440. With insertion of distal rod end 1511 through guide 1440, boss 1442*a* (indicated in phantom lines) may engage rod 1510 at pre-operational track 1530. Boss 1442*a* may extend radially inward into pre-operational track 1530. Boss 1442*b* may engage rod 1510 at the second pre-operational track. Boss 1442*b* may extend radially inward into the second pre-operational track. Chamfers 1519 may facilitate engagement of the bosse(s) at the pre-operational track(s) upon insertion of rod 1510 through guide 1440.

Housing 1570 may include housing wall 1571. Housing wall 1571 may include first wall section 1575*a*. Wall section 1575*a* may be arcuate in cross-section transverse to axis L1. Housing wall 1571 may include second wall section 1575*b*. Wall section 1575*b* may be arcuate in cross-section transverse to axis L1. Wall section 1575*a* and wall section 1575*b* may be symmetrically disposed relative to each about axis L1.

Guide 1440 may be inserted into housing 1570, with distal guide extension 1549 extending into an interior of housing wall 1571. Guide 1440 may be disposed in housing 1570 between wall section 1575*a* and wall section 1575*b*.

Housing wall 1571 may support finger flange 1580. Finger flange 1580 may encompass wall section 1575*a* and wall section 1575*b*.

Guide 1440 may be inserted into housing 1570 until seating surface 1576 abuts seating collar section 1446*a* and/or until seating surface 1576 abuts seating collar section 1446*b*1 and/or until seating surface 1576 abuts seating collar section 1446*b*2. A first space between wall section 1575*a* and wall section 1575*b* may accommodate seating collar section 1446*b*1 and seating collar section 1446*b*2. A second space between wall section 1575*a* and wall section 1575*b* may accommodate seating collar section 1446*a*. The first and second spaces may be disposed diametrically opposite each other.

Seating surface 1576 abutting one or more of the seating collar sections of guide 1440 may substantially block further insertion of guide 1440 into housing 1570. With seating surface 1576 abutting collar section 1446*a*, seating collar section 1446*b*1 and collar section 1446*b*2, guide 1440 may be seated in housing 1570.

With seating surface 1576 abutting one or more of the seating collar sections of guide 1440, guide-tab 1444*a* may be locked by guide-tab lock 1572*a* supported by wall section 1575*a* and/or guide-tab 1444*b* may be locked by guide-tab lock 1572*b* supported by wall section 1575*b* and/or guide-tab 1444*d* may be locked by guide-tab lock 1572*d* supported by wall section 1575*b*. Guide-tab 1444*c* may be locked by another guide-tab lock (not shown) supported by wall section 1575*a* and disposed diametrically opposite guide-tab lock 1572*d*.

Each guide-tab lock of housing 1570 may have a proximal surface substantially transverse to axis L1. The proximal surface of each guide-tab lock of housing 1570 may have a radially inner edge facing axis L1. Each guide-tab lock of housing 1570 may have a contoured surface facing axis L1. A radial distance of the contoured surface of each guide-tab lock from axis L1 may increase distally along the contoured surface toward seating surface 1576 from the radially inner edge of the proximal surface of the guide-tab lock.

Each guide-tab of guide 1440 may have a surface contoured substantially complementary to the surface of any of the guide-tab locks of housing 1570. With seating surface 1576 abutting one or more of the seating collar sections of guide 1440, each guide-tab lock of housing 1570 may maintain some, most or all of the contoured surface of the guide-tab of guide 1440 that it locks distal to the proximal surface of the guide-tab lock of housing 1570. Each guide-tab lock of housing 1570 may block the guide-tab of guide 1440 that it locks from proximal movement along axis L1.

The guide-tab lock(s) of housing 1570 locking the guide-tab(s) of guide 1440 may block guide 1440 from proximal movement along axis L1.

Wall section 1575b may include retaining ridge 1574b disposed along a proximal portion of an interior of wall section 1575b. Wall section 1575a may include retaining ridge 1574a (indicated in phantom lines) disposed along a proximal portion of an interior of wall section 1575a. Retaining ridge 1574a may be disposed symmetrical to, and diametrically opposite, retaining ridge 1574b relative to axis L1.

Insertion of guide 1440 into housing 1570 may be carried out as a manufacturing step of device 1500. The insertion of guide 1440 into housing 1570 may begin with distal longitudinal movement of distal guide extension 1549 between retaining ridge 1574a and retaining ridge 1574b. Further distal longitudinal movement of guide 1440 into housing 1570 may bring a distal circumferential edge of radial collar section 1443a into contact with a proximal circumferential aspect of retaining ridge 1574a and/or may bring a distal circumferential edge of radial collar section 1443b into contact with a proximal circumferential aspect of retaining ridge 1574b. With continuing longitudinal insertion of guide 1440 into 1570, interference of each radial collar section with the contacted retaining ridge may force apart wall sections 1575a and 1575b, proximal aspects of the wall sections deflecting radially outward from each other more than distal aspects of the wall sections. Deflection of the wall sections radially outward from each other may allow the radial collar sections to pass distally between the retaining ridges. Deflection of the wall sections radially outward from each other may allow a distal external circumferential edge of each of the guide-tabs of guide 1440 to distally pass the radially inner edge of the proximal surface of the corresponding guide-tab lock of housing 1570. Further insertion of guide 1440 into housing 1570 may dispose a proximal circumferential edge of each radial collar section distal to a distal circumferential aspect of the contacted retaining ridge and/or may dispose some, most or all of the contoured surface of each guide-tab distal to the radially inner edge of the proximal surface of the corresponding guide-tab lock and/or may bring distal aspects of seating collar section 1446a, 1446b1 and 1446b2 into abutment with seating surface 1576.

With seating surface 1576 abutting one or more of the seating collar sections of guide 1440, an exterior circumferential surface of radial collar section 1443b may be disposed along an interior surface of wall section 1575b distal to the distal circumferential aspect of retaining ridge 1574b. Radial collar section 1443b may be blocked from proximal movement along axis L1 by retaining ridge 1574b. Radial collar section 1443b may be blocked from rotational movement about axis L1 by guide-tab lock 1572b and guide-tab lock 1572d. An exterior circumferential surface of radial collar section 1443a may be disposed along an interior surface of wall section 1575a distal to the distal circumferential aspect of retaining ridge 1574a. Radial collar section 1443a may be blocked from proximal movement along axis L1 by retaining ridge 1574a. Radial collar section 1443a may be blocked from rotational movement about axis L1 by guide-tab lock 1572a and by the guide-tab lock supported by wall section 1575a and disposed diametrically opposite guide-tab lock 1572d.

Radial collar section 1443a and/or radial collar section 1443b being blocked from rotational movement about axis L1 may block guide 1440 from rotational movement about axis L1.

Insertion of rod 1510 into guide 1440 may be carried out as a manufacturing step of device 1500. Rod 1510 may be inserted into guide 1440 with the engagement of boss 1442a at pre-operational track 1530 until boss 1442a interacts with pre-operational trigger 1514. Interaction of boss 1442a with pre-operational trigger 1514 may correspond to an end of the engagement of boss 1442a with pre-operational track 1530. Rod 1510 may be inserted into guide 1440 with the engagement of boss 1442b at the second pre-operational track until boss 1442b interacts with the second pre-operational trigger. Interaction of boss 1442b with the second pre-operational trigger may correspond to an end of the engagement of boss 1442b with the second pre-operational track. In response to the interaction of the boss(es) with the pre-operational trigger(s), guide 1440 may deflect, widening gap 1448, indicating the end of the engagement of the boss(es) with the pre-operational track(s).

Upon further longitudinal insertion of rod 1510 into guide 1440, boss 1442a may be positioned proximal to pre-operational trigger 1514, against running surface 1526 between pre-operational trigger 1514 and operation-initiation trigger 1516. The insertion of rod 1510 positioning boss 1442a against running surface 1526 may be the initial displacement.

The initial displacement may position boss 1442b proximal to the second pre-operational trigger. The initial displacement may position boss 1442b against a second running surface (not shown). The second running surface may be disposed, between the second pre-operational trigger and the second operation-initiation trigger, diametrically opposite running surface 1526.

Rod 1510 may be substantially blocked, by boss 1442a being positioned proximal to pre-operational trigger 1514, from inadvertent proximal slippage of rod 1510 out of guide 1440. Rod 1510 may be substantially blocked, by boss 1442b being positioned proximal to the second pre-operational trigger, from inadvertent proximal slippage of rod 1510 out of guide 1440. Rod 1510 may be substantially blocked, by boss 1442a being positioned between pre-operational trigger 1514 and operation-initiation trigger 1516, from inadvertent further distal displacement. Rod 1510 may be substantially blocked, by boss 1442b being positioned between the second pre-operational trigger and the second operation-initiation trigger, from inadvertent further distal displacement. Further distal displacement of rod 1510 from the initial displacement may involve intentional manipulation on the part of an operator of delivery device 1500.

With rod 1510 at the initial displacement, delivery device 1500 may be in the pre-operational state. With rod 1510 at the initial displacement, delivery device 1500 may be at the end of the pre-operational state. With rod 1510 at the initial displacement, delivery device 1500 may have been prepared for initiation of the operational state. The initiation of the operational state may involve the further distal displacement of rod 1510 from the initial displacement.

The further distal displacement of rod 1510 may be effected by clockwise rotation of rod 1510 about axis L1. The clockwise rotation of rod 1510 about axis L1 may shift boss 1442a from being positioned against running surface 1526 to interaction with operation-initiation trigger 1516. The clockwise rotation of rod 1510 about axis L1 may shift boss 1442b from being positioned against the second running surface to interaction with the second operation-initiation trigger. In response to the interaction of the boss(es) with the operation-initiation trigger(s), guide 1440 may deflect, widening gap 1448. Acoustic and/or tactile indication of guide 1440 deflecting may be concomitant of and/or attendant upon widening of gap 1448.

Housing 1570 may define slot 1578. Slot 1578 may be an extension of the first space between wall section 1575*a* and wall section 1575*b*. Slot 1578 may be aligned with gap 1448.

Wall section 1575*a* and/or wall section 1575*b* may deflect in response to deflection of guide 1440, widening the first space between wall section 1575*a* and wall section 1575*b*. Widening the first space between wall section 1575*a* and wall section 1575*b* may widen slot 1578. Slot 1578 may widen more at a proximal end of slot 1578 adjacent finger flange 1580 than at a distal end of slot 1578. Acoustic and/or tactile indication of the wall sections deflecting may be concomitant of and/or attendant upon widening of slot 1578.

Finger flange 1580 may define hole 1582. A diametrical slot across, and extending radially inward beyond, hole 1582 may be a transverse extension of slot 1578. Finger flange 1580 may deflect in response to wall section 1575*a* deflecting in response to deflection of guide 1440 and/or in response to wall section 1575*b* deflecting in response to deflection of guide 1440. Acoustic and/or tactile indication of finger flange 1580 deflecting may be concomitant of and/or attendant upon deflection of the wall section(s). Acoustic and/or tactile indication of finger flange 1580 deflecting may be concomitant of and/or attendant upon widening of slot 1578.

Figure 16:
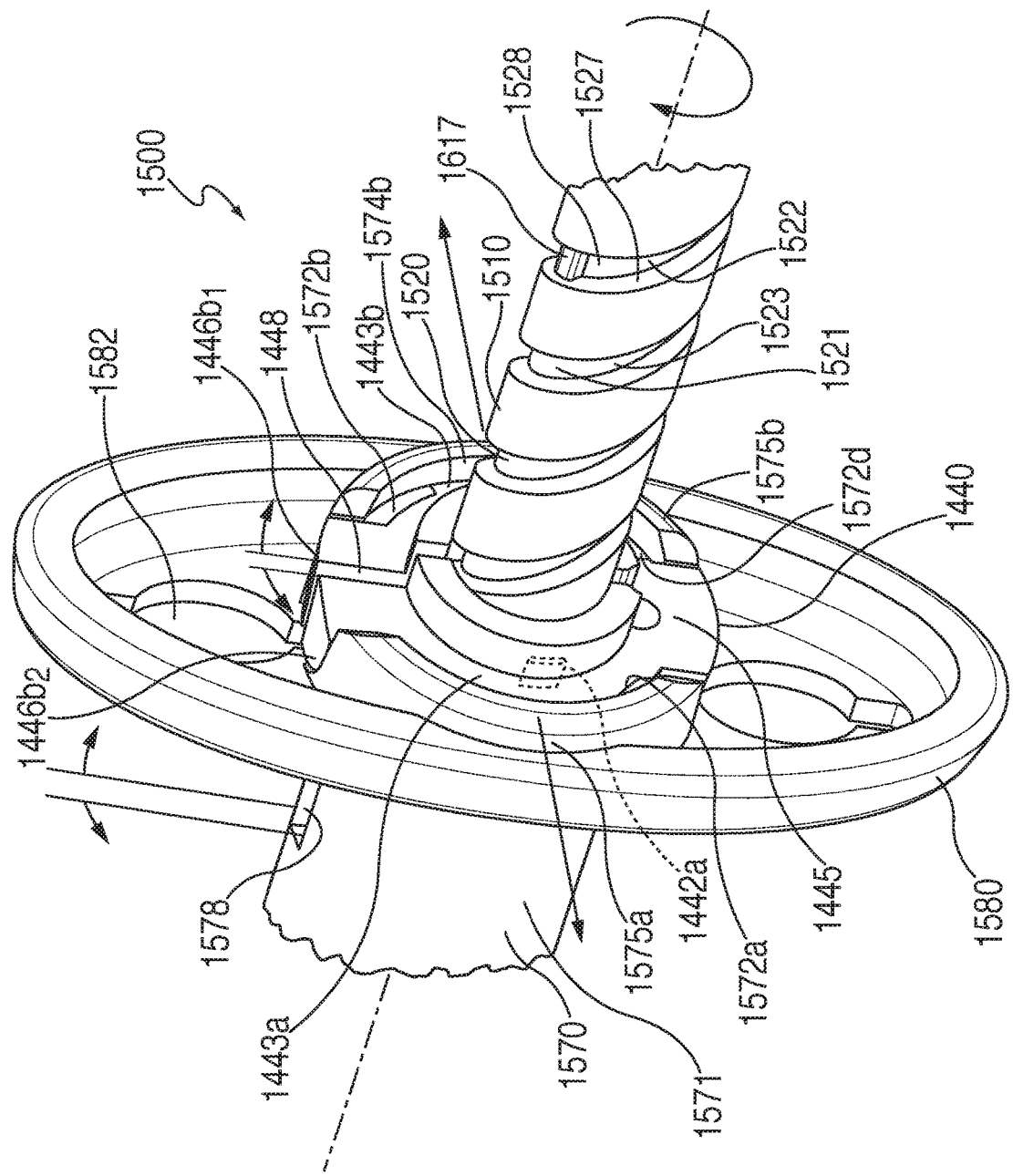
FIG. 16 is another perspective view of the apparatus shown in FIG. 15.

FIG. 16 shows delivery device 1500 with guide 1440 seated in housing 1570 between wall section 1575*a* and wall section 1575*b*. FIG. 16 shows delivery device 1500 with rod 1510 inserted into guide 1440.

With the initiation of the operational state, boss 1442*a* (indicated in phantom lines) may engage rod 1510 at operational track 1520. Boss 1442*a* may extend radially into operational track 1520. Boss 1442*a* may engage with helicoidal tract 1522. Boss 1442*a* may be disposed engaged with helicoidal tract 1522 adjacent operation-initiation trigger 1516 (shown in FIG. 15). Boss 1442*a* may be disposed alongside sidewall 1527 of helicoidal tract 1522. Boss 1442*a* may be disposed against running surface 1528 of helicoidal tract 1522.

With the initiation of the operational state, boss 1442*b* (shown in FIG. 15) may engage rod 1510 at second operational track 1521. Boss 1442*b* may extend radially into second operational track 1521. Boss 1442*b* may engage with helicoidal tract 1523. Boss 1442*b* may be disposed engaged with helicoidal tract 1523 adjacent the second operation-initiation trigger (not shown).

Distal axial movement of guide 1440 relative to housing 1570 may be blocked by seating surface 1576 (shown in FIG. 15).

Proximal axial movement of guide 1440 relative to housing 1570 may be blocked by guide-tab lock 1572*a*. Proximal axial movement of guide 1440 relative to housing 1570 may be blocked by guide-tab lock 1572*b*. Proximal axial movement of guide 1440 relative to housing 1570 may be blocked by guide-tab lock 1572*d*. Proximal axial movement of guide 1440 relative to housing 1570 may be blocked by the guide-tab lock (not shown) supported by wall section 1575*a* and disposed diametrically opposite guide-tab lock 1572*d*.

Proximal axial movement of guide 1440 relative to housing 1570 may be blocked by retaining ridge 1574*b*. Proximal axial movement of guide 1440 relative to housing 1570 may be blocked by retaining ridge 1574*a* (shown in FIG. 15).

Rotational movement of guide 1440 relative to housing 1570 may be blocked by the guide-tab locks of housing 1570. Radial collar section 1443*b* may be blocked from rotational movement relative to housing 1570 by guide-tab lock 1572*d* and guide-tab lock 1572*b*. Radial collar section 1443*a* may be blocked from rotational movement relative to housing 1570 by guide-tab lock 1572*a* and by the guide-tab lock supported by wall section 1575*a* and disposed diametrically opposite guide-tab lock 1572*d*.

Subsequent to the initiation of the operational state, further distal displacement of rod 1510 relative to housing 1570 may be effected by clockwise rotation of rod 1510 about axis L1 (shown in FIG. 15). Helicoidal tract 1522 of operational track 1520 may support priming-initiation trigger 1617. Helicoidal tract 1523 of second operational track 1521 may support a second priming-initiation trigger (not shown) disposed diametrically opposite priming-initiation trigger 1617. The clockwise rotation of rod 1510 about axis L1 may shift boss 1442*a* from being disposed adjacent to operation-initiation trigger 1516 to interaction with priming-initiation trigger 1617. The clockwise rotation of rod 1510 about axis L1 may shift boss 1442*b* from being disposed adjacent to the second operation-initiation trigger to interaction with the second priming-initiation trigger.

In response to the interaction of the boss(es) with the priming-initiation trigger(s), seating collar section 1446*b*1 and seating collar section 1446*b*2 may deflect away from each other about hinge 1445, widening gap 1448. In response to the seating collar sections deflecting, wall sections 1575*a* and 1575*b* may deflect outward. In response to wall sections 1575*a* and 1575*b* deflecting, slot 1578 may widen, with more widening at a proximal end (not shown) of slot 1578 adjacent finger flange 1580 than at a distal end of slot 1578. A diametrical slot across, and extending radially inward beyond, hole 1582 of finger flange 1580 may be a transverse extension of slot 1578. In response to wall sections 1575*a* and 1575*b* deflecting, finger flange 1580 may deflect.

Acoustic and/or tactile indication of the boss(es) interacting with the priming-initiation trigger(s) may be concomitant of and/or attendant upon widening of gap 1448. Acoustic and/or tactile indication of the boss(es) interacting with the priming-initiation trigger(s) may be concomitant of and/or attendant upon deflection of seating collar section 1446*b*1 and seating collar section 1446*b*2 about hinge 1445. Acoustic and/or tactile indication of the boss(es) interacting with the priming-initiation trigger(s) may be concomitant of and/or attendant upon deflection of wall sections 1575*a* and 1575*b*. Acoustic and/or tactile indication of the boss(es) interacting with the priming-initiation trigger(s) may be concomitant of and/or attendant upon widening of slot 1578. Acoustic and/or tactile indication of the boss(es) interacting with the priming-initiation trigger(s) may be concomitant of and/or attendant upon deflection of finger flange 1580.

Some of the acoustic and/or tactile indications may amplify others of the acoustic and/or tactile indications for the operator. For example, the operator may feel the deflection of wall sections 1575*a* and 1575*b* more readily than the operator may feel the deflection of collar section 1446*b*1 and seating collar section 1446*b*2 about hinge 1445.

Acoustic and/or tactile indication of the boss(es) interacting with the priming-initiation trigger(s) may provide a signal to the operator to proceed to priming of device 1500.

FIG. 17 shows a front view of a proximal face of finger flange 1780. Finger flange 1780 may have none, some or all of the features and functions of finger flange 180 (shown in FIGS. 1, 2, 11 and 13). Finger flange 1780 may have none, some or all of the features and functions of finger flange 1580 (shown in FIGS. 15 and 16). Finger flange 1780 may define hole 1782. Finger flange 1780 may define a second hole. The second hole of finger flange 1780 may be symmetrically disposed to hole 1782 relative to a center of finger flange 1780. Finger flange 1780 may define bay 1785. Bay 1785 may be concentric with finger flange 1780.

FIG. 17 shows a front view of a proximal face of plunger rod guide 1740. Guide 1740 may have none, some or all of the features and functions of guide 140 (shown in FIGS. 1, 2, 3, 10, 11 and 12). Guide 1740 may have none, some or all of the features and functions of guide 1440 (shown in FIGS. 14, 15 and 16).

Guide 1740 may include boss 1742a. Boss 1742a may be supported by arm 1741a. Guide 1740 may include boss 1742b. Boss 1742b may be supported by arm 1741b. Arm 1741a and arm 1741b may be symmetrically disposed to each other, relative to a center of guide 1740. Boss 1742a and boss 1742b may be disposed diametrically opposite each other, relative to the center of guide 1740. Boss 1742a and boss 1742b may extend toward each other. Guide 1740 may be concentric with finger flange 1780. Guide 1740 may be suspended across bay 1785.

FIG. 18 shows guide 1740 suspended across bay 1785. Guide 1740 may include distal guide extension 1849a. Distal guide extension 1849a may be arcuate. Distal guide extension 1849a may be associated with arm 1741a. Guide 1740 may include distal guide extension 1849b. Distal guide extension 1849b may be arcuate. Distal guide extension 1849b may be associated with arm 1741b.

Arm 1741a may be suspended across bay 1785. Support member 1886a may suspend arm 1741a across bay 1785. Support member 1886c may suspend arm 1741a across bay 1785.

Arm 1741a may be supported adjacent a first end of arm 1741a by support member 1886a. Support member 1886a may support arm 1741a adjacent a first end of support member 1886a. A second end of support member 1886a may be disposed adjacent hole 1782. Arm 1741a may be supported adjacent a second end of arm 1741a by support member 1886c. Support member 1886c may support arm 1741a adjacent a first end of support member 1886c. A second end of support member 1886c may be disposed adjacent the second hole of finger flange 1780.

Arm 1741b may be suspended across bay 1785. Support member 1886b may suspend arm 1741b across bay 1785. Support member 1886d may suspend arm 1741b across bay 1785.

Arm 1741b may be supported adjacent a first end of arm 1741b by support member 1886b. Support 1886b member may support arm 1741b adjacent a first end of support member 1886b. A second end of support member 1886b may be disposed adjacent hole 1782. Arm 1741b may be supported adjacent a second end of arm 1741b by support member 1886d. Support member 1886d may support arm 1741b adjacent a first end of support member 1886d. A second end of support member 1886d may be disposed adjacent the second hole of finger flange 1780.

Support member 1886a may be disposed proximal to distal guide extension 1849a. Support member 1886c may be disposed proximal to distal guide extension 1849a. Support member 1886a and support member 1886c may be disposed collinearly.

Support member 1886b may be disposed proximal to distal guide extension 1849b. Support member 1886d may be disposed proximal to distal guide extension 1849b. Support member 1886b and support member 1886d may be disposed collinearly.

Support member 1886a and support member 1886b may be disposed parallel to each other. Support member 1886c and support member 1886d may be disposed parallel to each other.

Arm 1741a may support boss 1742a apart from the first end of arm 1741a. Arm 1741a may support boss 1742a apart from the second end of arm 1741a.

Arm 1741b may support boss 1742b apart from the first end of arm 1741b. Arm 1741b may support boss 1742b apart from the second end of arm 1741b.

Figure 19:
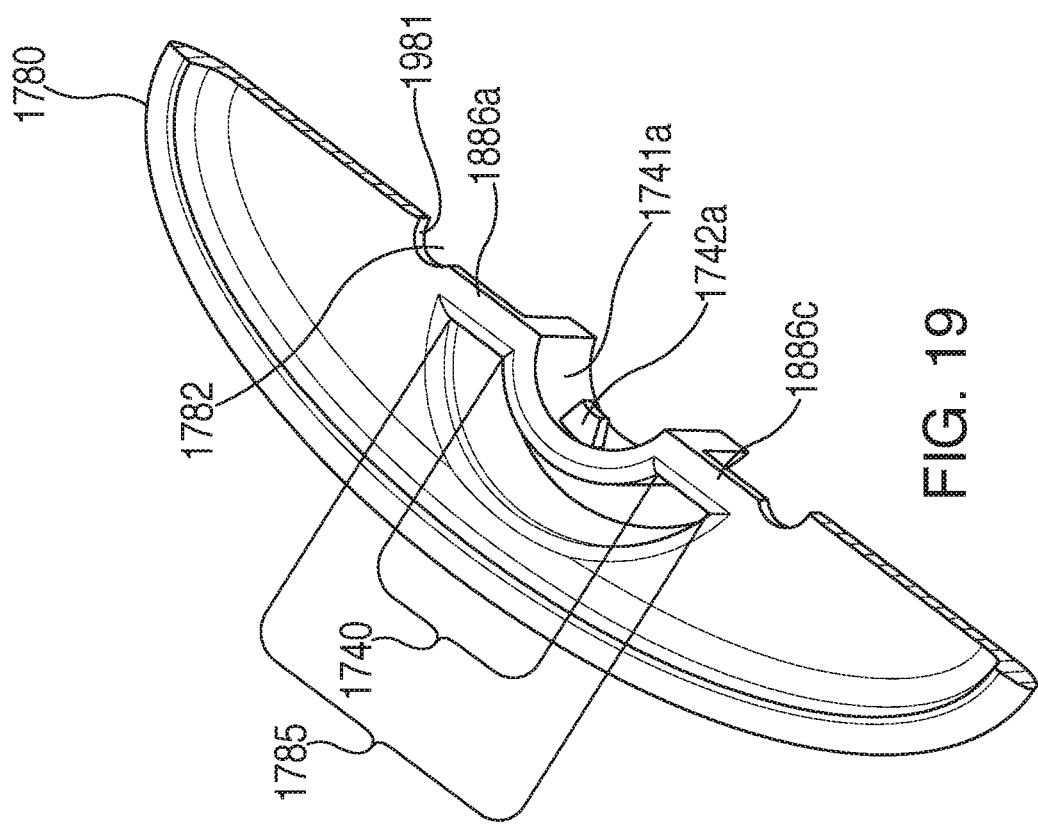
FIG. 19 is a perspective, partial cross-sectional view of the apparatus shown in FIG. 17, the view taken along lines 19-19 (shown in FIG. 17)

FIG. 19 shows guide 1740 suspended across bay 1785 in a cross-sectional view taken along lines 19-19 shown in FIG. 17 (with finger flange 1780 in an orientation similar to that of finger flange 1780 as viewed in FIG. 18). Finger flange 1780 may include annular border 1981. Border 1981 may define hole 1782.

Boss 1742a is shown supported by arm 1741a, the latter supported, adjacent the first end of arm 1741a, by support member 1886a. A lateral side of support member 1886a may be continuous, on the first end of support 1886a, with arm 1741a. The lateral side of support member 1886a may be continuous, on the second end of support member 1886a, with border 1981.

Arm 1741a is shown supported, adjacent the second end of arm 1741a, by support member 1886c. A lateral side of support member 1886c may be continuous, on the first end of support member 1886a, with arm 1741a. The lateral side of support member 1886c may be continuous, on the second end of support member 1886c, with an annular border defining the second hole of finger flange 1780.

Figure 20:
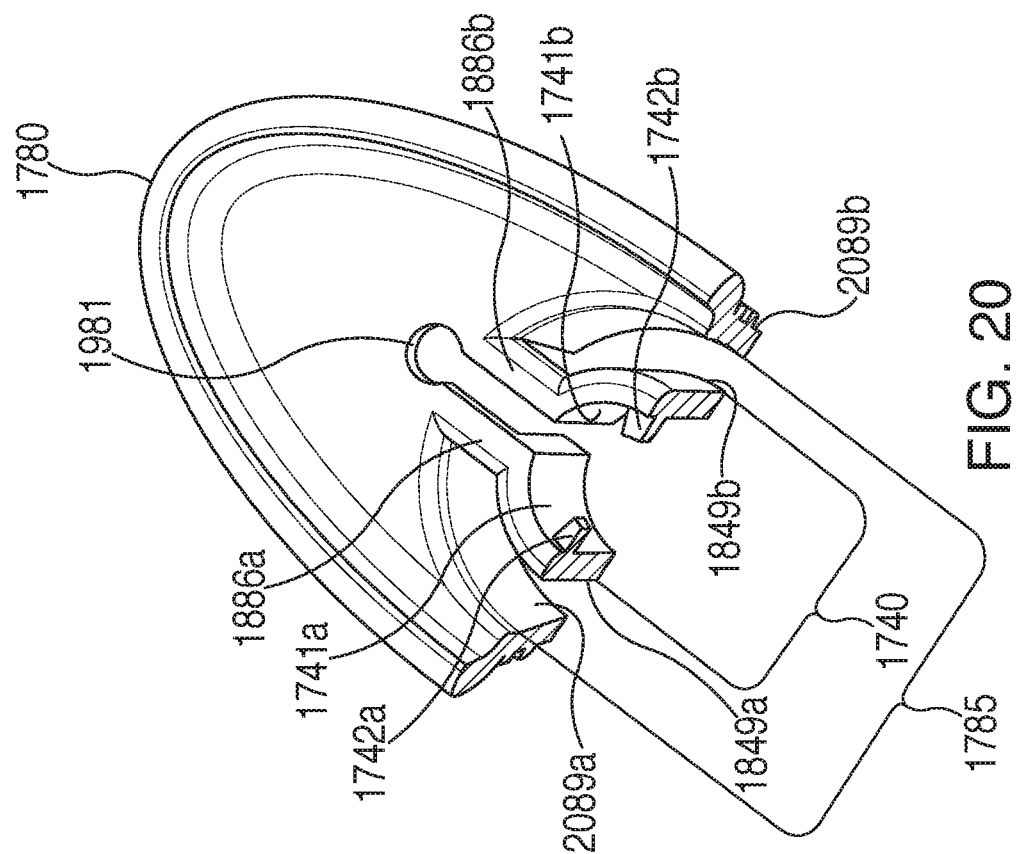
FIG. 20 is another perspective partial cross-sectional view of the apparatus shown in FIG. 17, the view taken along lines 20-20 (shown in FIG. 18)

FIG. 20 shows guide 1740 suspended across bay 1785 in a cross-sectional view taken along lines 20-20 shown in FIG. 18 (with finger flange 1780 in an orientation similar to that of finger flange 1780 as viewed in FIG. 18).

Finger flange 1780 may include distal finger flange extension 2089a. Distal finger flange extension 2089a may be parallel to distal guide extension 1849a. Distal finger flange extension 2089a may be arcuate. Distal finger flange extension 2089a may be concentric with distal guide extension 1849a. Distal finger flange extension 2089a may have a greater radius from the center of finger flange 1780 than distal guide extension 1849a.

Finger flange 1780 may include distal finger flange extension 2089b. Distal finger flange extension 2089b may be parallel to distal guide extension 1849b. Distal finger flange extension 2089b may be arcuate. Distal finger flange extension 2089b may be concentric with distal guide extension 1849b. Distal finger flange extension 2089b may have a greater radius from the center of finger flange 1780 than distal guide extension 1849b.

Deflection of arm 1741a outward from the center of finger flange 1780 may be accommodated by bay 1785. Deflection of arm 1741a outward from the center of finger flange 1780 may be accommodated by a gap between an exterior wall of distal guide extension 1849a and an interior wall of distal finger flange extension 2089a. The gap between the exterior wall of distal guide extension 1849a and the interior wall of distal finger flange extension 2089a may be a portion of bay 1785. Deflection of arm 1741a outward from the center of finger flange 1780 may be larger along a radius passing through boss 1742a than along other radial lines from the center of finger flange 1780. Outward deflection of arm 1741a along a radial line passing through the first end of arm 1741a may be constrained by support member 1886a. Support member 1886a may deform in response to outward deflection of arm 1741a. Support member 1886a may deflect in response to outward deflection of arm 1741a.

Annular border 1981 may deform in response to deformation of support member 1886*a*. Annular border 1981 may deform in response to deflection of support member 1886*a*.

Deflection of arm 1741*b* outward from the center of finger flange 1780 may be accommodated by bay 1785. Deflection of arm 1741*a* outward from the center of finger flange 1780 may be accommodated by a gap between an exterior wall of distal guide extension 1849*b* and an interior wall of distal finger flange extension 2089*b*. The gap between the exterior wall of distal guide extension 1849*b* and the interior wall of distal finger flange extension 2089*b* may be a portion of bay 1785. Deflection of arm 1741*b* outward from the center of finger flange 1780 may be larger along a radius passing through boss 1742*b* than along other radial lines from the center of finger flange 1780. Outward deflection of arm 1741*b* along a radial line passing through the first end of arm 1741*b* may be constrained by support member 1886*b*. Support member 1886*b* may deform in response to outward deflection of arm 1741*b*. Support member 1886*b* may deflect in response to outward deflection of arm 1741*b*. Annular border 1981 may deform in response to deformation of support member 1886*b*. Annular border 1981 may deform in response to deflection of support member 1886*b*.

Figure 21:
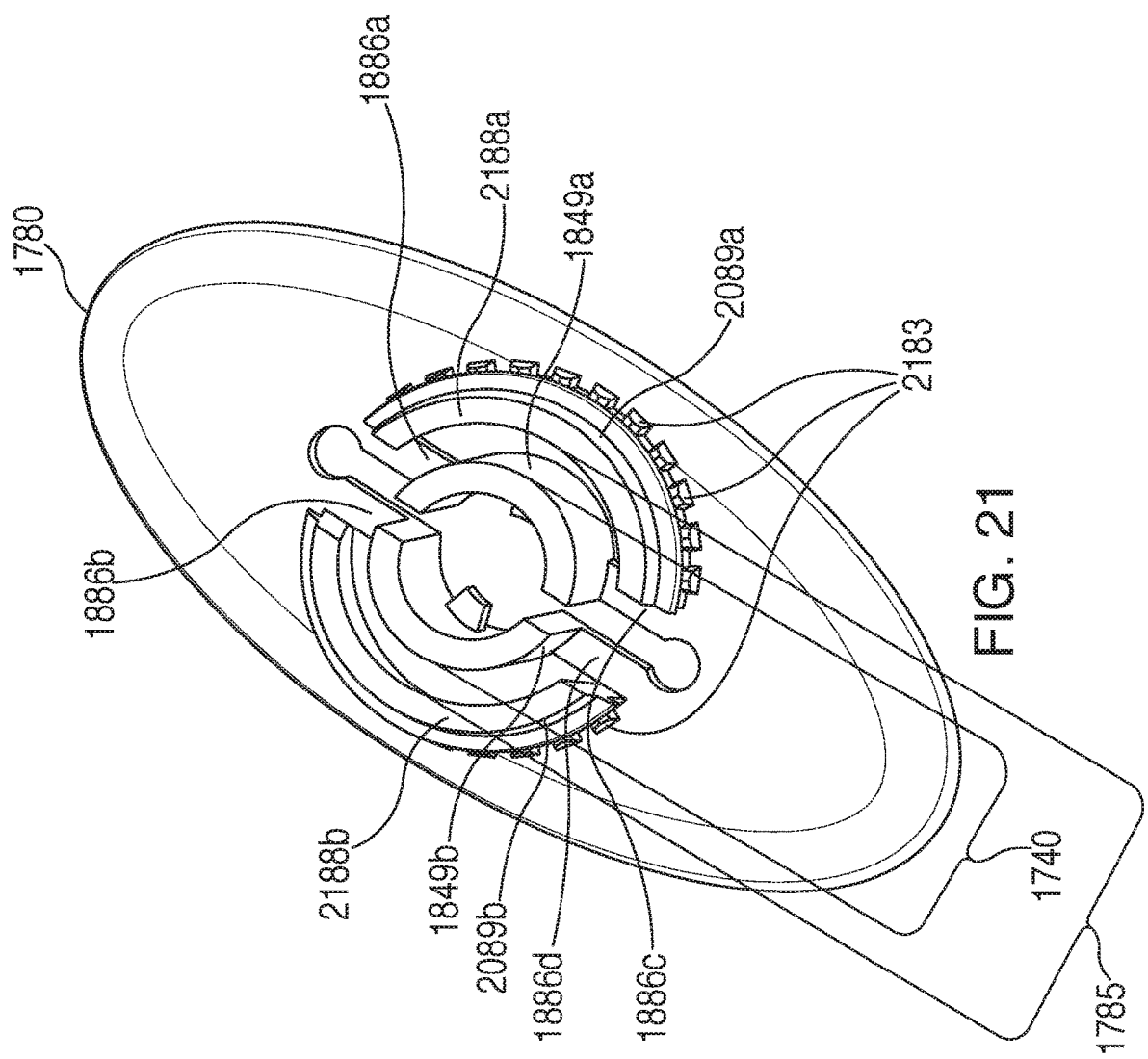
FIG. 21 is another perspective view of the apparatus shown in FIG. 17.

FIG. 21 shows a view of a distal face of finger flange 1780. FIG. 21 shows a view of a distal face of guide 1740, guide 1740 suspended across bay 1785. FIG. 21 shows guide 1740 concentric with finger flange 1780, with distal guide extension 1849*a* concentric with distal finger flange extension 2089*a* and distal guide extension 1849*b* concentric with distal finger flange extension 2089*b*.

Finger flange 1780 may include finger flange-anchoring elements 2183. Finger flange-anchoring elements 2183 may be disposed about an exterior wall of distal finger flange extension 2089*a*. Finger flange-anchoring elements 2183 may be disposed about an exterior wall of distal finger flange extension 2089*b*.

Finger flange 1780 may include distal surface 2188*a*. Distal surface 2188*a* may be disposed transverse to the interior wall of distal finger flange extension 2089*a*. Distal surface 2188*a* may be disposed transverse to the exterior wall of distal finger flange extension 2089*a*.

Finger flange 1780 may include distal surface 2188*b*. Distal surface 2188*b* may be disposed transverse to the interior wall of distal finger flange extension 2089*b*. Distal surface 2188*b* may be disposed transverse to the exterior wall of distal finger flange extension 2089*a*.

Support member 1886*a* may be disposed proximal to distal surface 2188*a*. A distal aspect of support member 1886*a* may be disposed parallel to distal surface 2188*a*. Support member 1886*c* may be disposed proximal to distal surface 2188*a*. A distal aspect of support member 1886*c* may be disposed parallel to distal surface 2188*a*.

Support member 1886*b* may be disposed proximal to distal surface 2188*b*. A distal aspect of support member 1886*b* may be disposed parallel to distal surface 2188*b*. Support member 1886*d* may be disposed proximal to distal surface 2188*b*. A distal aspect of support member 1886*d* may be disposed parallel to distal surface 2188*b*.

Figure 22:
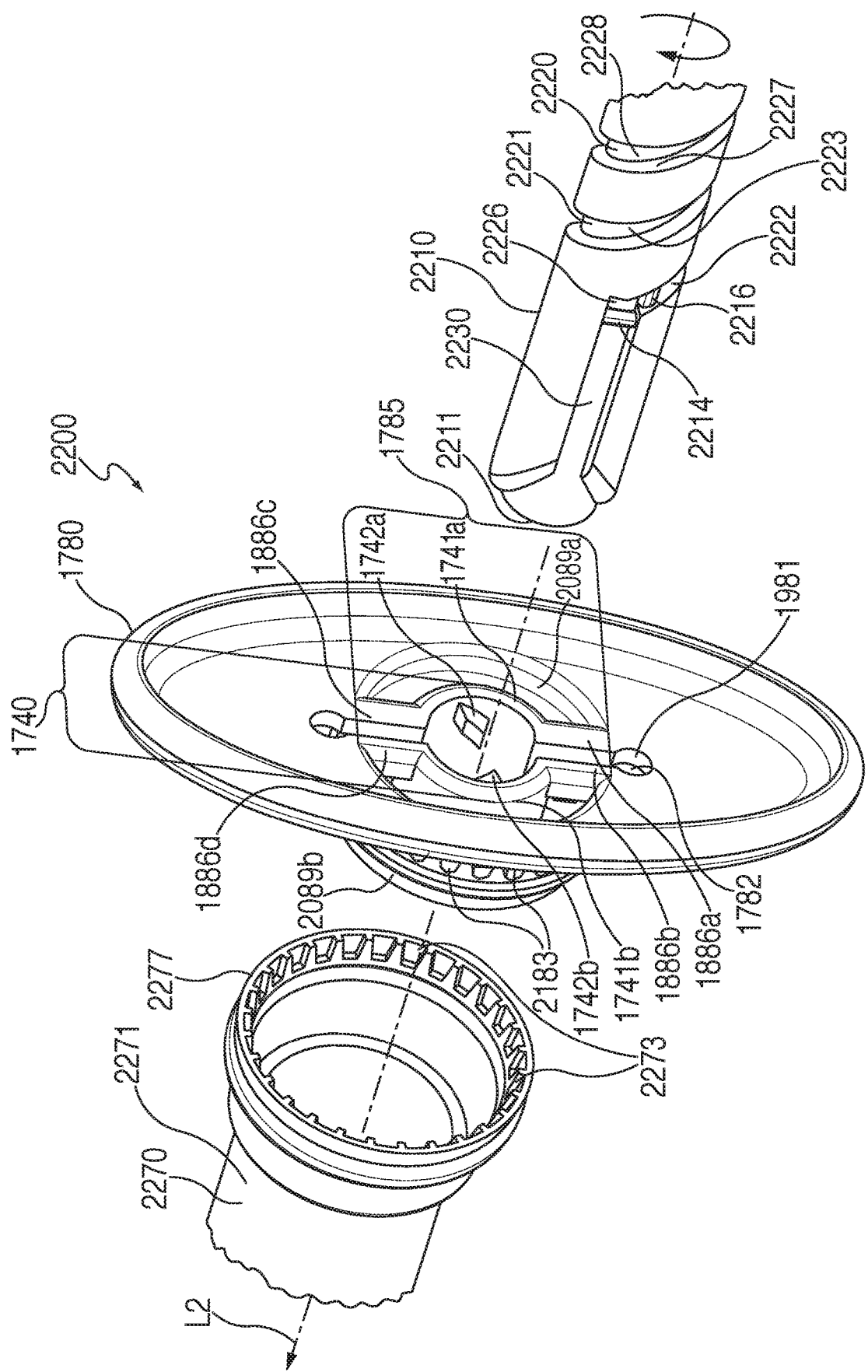
FIG. 22 is an exploded, perspective view of apparatus in accordance with the principles of the invention, including the apparatus shown in FIG. 17.

FIG. 22 shows features of illustrative medicament delivery device 2200. Delivery device 2200 may have none, some or all of the features and functions of delivery device 100 (shown in FIG. 11). Delivery device 2200 may have none, some or all of the features and functions of delivery device 1500 (shown in FIGS. 15 and 16.). Delivery device 2200 may define longitudinal axis L2.

Delivery device 2200 may include plunger rod 2210. Rod 2210 may have none, some or all of the features and functions of rod 110 (shown in FIGS. 1, 2, 2A, 2B, 2C, 3, 4A, 4B and 11). Rod 2210 may have none, some or all of the features and functions of rod 510 (shown in FIG. 5). Rod 2210 may have none, some or all of the features and functions of rod 610 (shown in FIG. 6). Rod 2210 may have none, some or all of the features and functions of rod 1510 (shown in FIGS. 15 and 16). Rod 2210 may be disposed coaxial with axis L2.

Delivery device 2200 may include finger flange 1780. Finger flange 1780 may be disposed coaxial with axis L2. Axis L2 may pass through the center of finger flange 1780. Each of finger flange-anchoring elements 2183 may be structurally equivalent to any other of finger flange-anchoring elements 2183. Each of finger flange-anchoring elements 2183 may be oriented relative to axis L2 equivalently to any other of finger flange-anchoring elements 2183. Finger flange-anchoring elements 2183 may be regularly spaced about the exterior wall of distal finger flange extension 2089*b*. Finger flange-anchoring elements 2183 may be regularly spaced (shown in FIG. 21) about the exterior wall of distal finger flange extension 2089*a*.

Delivery device 2200 may include guide 1740. Guide 1440 may be disposed coaxial with axis L2. Axis L2 may pass through the center of guide 1740. Delivery device 2200 may include support member 1886*a*. Delivery device 2200 may include support member 1886*b*. Delivery device 2200 may include support member 1886*c*. Delivery device 2200 may include support member 1886*d*. The support member(s) may support guide 1740 suspended across bay 1785. The support member(s) may block guide 1740 from rotational motion relative to finger flange 1780.

Delivery device 2200 may include device housing 2270. Housing 2270 may have none, some or all of the features and functions of housing 170 (shown in FIGS. 1, 2, 3, 11 and 13). Housing 2270 may have none, some or all of the features and functions of housing 1570 (shown in FIGS. 15 and 16). Housing 2270 may be disposed coaxial with axis L2.

Delivery device 2200 may include a medicament container (not shown). The medicament container of device 2200 may have none, some or all of the features and functions of medicament container 150 (shown in FIGS. 1, 2 and 3). The medicament container of device 2200 may have none, some or all of the features and functions of medicament container 750 (shown in FIG. 7). The medicament container of device 2200 may have none, some or all of the features and functions of medicament container 850 (shown in FIG. 8). The medicament container of device 2200 may have none, some or all of the features and functions of medicament container 950 (shown in FIG. 9). The medicament container of device 2200 may be disposed coaxial with axis L2.

Delivery device 2200 may include a needle hub (not shown). The needle hub of device 2200 may have none, some or all of the features and functions of needle hub 190 (shown in FIGS. 1, 2 and 3). The needle hub of device 2200 may be disposed coaxial with axis L2.

Rod 2210 may include distal rod end 2211. Rod 2210 may define pre-operational track 2230. Pre-operational track 2230 may extend along a cylindrical surface of rod 2210. Pre-operational track 2230 may support pre-operational trigger 2214. Pre-operational trigger 2214 may be supported at a proximal end of pre-operational track 2230.

Rod 2210 may define a second pre-operational track (not shown). The second pre-operational track may extend along the cylindrical surface of rod 2210 parallel to pre-operational track 2230. The second pre-operational track may extend parallel to pre-operational track 2230 over a full extent of pre-operational track 2230 along the cylindrical surface of rod 2210. The second pre-operational track may be disposed diametrically opposite pre-operational track 2230. The second pre-operational track may support a second pre-operational trigger (not shown). The second pre-operational trigger may be supported at a proximal end of the second pre-operational track. The second pre-operational trigger may be disposed diametrically opposite pre-operational trigger 2214. The second pre-operational trigger may be disposed along rod 2210 at a distance from distal rod end 2211 substantially equal to a distance of pre-operational trigger 2214 from distal rod end 2211.

Rod 2210 may define operational track 2220. Operational track 2220 may extend along the cylindrical surface of rod 2210. Rod 2210 may define second operational track 2221. Operational track 2220 and second operational track 2221 may be disposed parallel to each other along the cylindrical surface.

Operational track 2220 may support operation-initiation trigger 2216. Operation-initiation trigger 2216 may be adjacent to pre-operational trigger 2214. Operational track 2220 may include helicoidal tract 2222. Operation-initiation trigger 2216 may be supported by operational track 2220 at a distal end of helicoidal tract 2222.

Second operational track 2221 may support a second operation-initiation trigger (not shown). The second operation-initiation trigger may be adjacent to the second pre-operational trigger. Second operational track 2221 may include helicoidal tract 2223. The second operation-initiation trigger may be supported by second operational track 2221 at a distal end of helicoidal tract 2223. The second operation-initiation trigger may be disposed diametrically opposite operation-initiation trigger 2216.

Sidewall 2227 may be a sidewall of helicoidal tract 2222. Track 2220 may be defined by sidewall 2227. Running surface 2228 may be a running surface of helicoidal tract 2222. Track 2220 may be defined by running surface 2228.

Distal end 2211 of rod 2210 may be longitudinally inserted through guide 1740. Guide 1740 may define a passageway through which distal rod end 2211 may be inserted.

Rod 2210 may be rounded at distal rod end 2111. Rod 2210 being rounded at distal rod end 2211 may facilitate insertion of distal rod end 2211 through guide 1740. With insertion of distal rod end 2211 through guide 1740, boss 1742*b* may engage rod 2210 at pre-operational track 2230. Boss 1742*b* may extend radially inward into pre-operational track 2230. Boss 1742*a* may engage rod 2210 at the second pre-operational track. Boss 1742*a* may extend radially inward into the second pre-operational track.

Housing 2270 may include housing wall 2271. Housing wall 2271 may include proximal housing end-wall 2277. Proximal housing end-wall 2277 may border a proximal opening in housing 2270. The proximal opening in housing 2270 may be disposed coaxial with axis L2. Distal to proximal housing end-wall 2277, housing 2270 may include finger flange-anchoring accepting elements 2273. Finger flange-anchoring accepting elements 2273 may be structurally complementary to finger flange-anchoring elements 2183. Each of finger flange-anchoring accepting elements 2273 may be structurally complementary to any of finger flange-anchoring elements 2183.

Each of finger flange-anchoring accepting elements 2273 may be structurally equivalent to any other of finger flange-anchoring accepting elements 2273. Each of finger flange-anchoring accepting elements 2273 may be oriented relative to axis L2 equivalently to any other of finger flange-anchoring accepting elements 2273. Finger flange-anchoring accepting elements 2273 may be disposed about an interior surface of housing wall 2271. Finger flange-anchoring accepting elements 2273 may be regularly spaced about the interior surface of housing wall 2271. Regular spacing of finger flange-anchoring accepting elements 2273 may correspond to regular spacing of finger flange-anchoring elements 2183.

Finger flange 1780 may be inserted into the proximal opening of housing 2270. Inserting finger flange 1780 into the proximal opening of housing 2270 may bring one or more of finger flange-anchoring elements 2183 into contact with one or more of finger flange-anchoring accepting elements 2273. Inserting finger flange 1780 into the proximal opening of housing 2270 may mate finger flange-anchoring elements 2183 with finger flange-anchoring accepting elements 2273.

Mating finger flange-anchoring elements 2183 with finger flange-anchoring accepting elements 2273 may dispose finger flange 1780 coaxial with housing 2270. Disposing finger flange 1780 coaxial with housing may dispose guide 1740 coaxial with housing 2270. Mating finger flange-anchoring elements 2183 with finger flange-anchoring accepting elements 2273 may affix finger flange 1780 to housing 2270.

Affixing finger flange 1780 to housing 2270 by mating finger flange-anchoring elements 2183 with finger flange-anchoring accepting elements 2273 may block finger flange 1780 from further insertion into housing 2270. Affixing finger flange 1780 to housing 2270 by mating finger flange-anchoring elements 2183 with finger flange-anchoring accepting elements 2273 may block finger flange 1780 from axial movement along axis L2. Blocking finger flange 1780 from axial movement along axis L2 may block guide 1740 from axial movement along axis L2. Affixing finger flange 1780 to housing 2270 by mating finger flange-anchoring elements 2183 with finger flange-anchoring accepting elements 2273 may block finger flange 1780 from rotational movement about axis L2. Blocking finger flange 1780 from rotational movement about axis L2 may block guide 1740 from rotational movement about axis L2.

Affixing finger flange 1780 to housing 2270 may be facilitated by a plurality of coaxial circumferential orientations of finger flange 1780 relative to housing 2270 that may bring finger flange-anchoring elements 2183 into mating-compatible contact with finger flange-anchoring accepting elements 2273. The plurality of coaxial circumferential orientations of finger flange 1780 relative to housing 2270 that may bring finger flange-anchoring elements 2183 into mating-compatible contact with finger flange-anchoring accepting elements 2273 may be numbered at a total number of finger flange-anchoring accepting elements 2273. Affixing finger flange 1780 to housing 2270 may be carried out as a manufacturing step of device 2200.

Insertion of rod 2210 into guide 1740 may be carried out as a manufacturing step of device 2200.

Rod 2210 may be inserted into guide 1740 with the engagement of boss 1742*b* at pre-operational track 2230 until boss 1442*b* interacts with pre-operational trigger 2214. Interaction of boss 1742*b* with pre-operational trigger 2214 may correspond to an end of the engagement of boss 1742*b* with pre-operational track 2230. In response to interaction of boss 1742*b* with pre-operational trigger 2214, arm 1741*b* may deflect radially outward, along the radius passing through boss 1742*b*, toward the interior wall of distal finger flange extension 2089*b*. Deflection of arm 1741*b* may indicate the end of the engagement of boss 1742*b* at pre-operational track 2230.

Rod 2210 may be inserted into guide 1740 with the engagement of boss 1742*a* at the second pre-operational track until boss 1742*a* interacts with the second pre-operational trigger. Interaction of boss 1742*a* with the second pre-operational trigger may correspond to an end of the engagement of boss 1742*a* with the second pre-operational track. In response to interaction of boss 1742*a* with the second pre-operational trigger, arm 1741*a* may deflect radially outward, along the radius passing through boss 1742*a*, toward the interior wall of distal finger flange extension 2089*a*. Deflection of arm 1741*a* may indicate an end of engagement of boss 1742*a* at the second pre-operational track.

Upon further longitudinal insertion of rod 2210 into guide 1740, boss 1742*b* may be positioned proximal to pre-operational trigger 2214, against running surface 2226 between pre-operational trigger 2214 and operation-initiation trigger 2216. The insertion of rod 2210 positioning boss 1742*b* against running surface 2226 may be the initial displacement.

The initial displacement may position boss 1742*a* proximal to the second pre-operational trigger. The initial displacement may position boss 1742*a* against a second running surface (not shown). The second running surface may be disposed, between the second pre-operational trigger and the second operation-initiation trigger, diametrically opposite running surface 2226.

Rod 2210 may be substantially blocked, by boss 1742*b* being positioned proximal to pre-operational trigger 2214, from inadvertent proximal slippage of rod 2210 out of guide 1740. Rod 2210 may be substantially blocked, by boss 1742*a* being positioned proximal to the second pre-operational trigger, from inadvertent proximal slippage of rod 2210 out of guide 1740. Rod 2210 may be substantially blocked, by boss 1742*b* being positioned between pre-operational trigger 2214 and operation-initiation trigger 2216, from inadvertent further distal displacement. Rod 2210 may be substantially blocked, by boss 1742*a* being positioned between the second pre-operational trigger and the second operation-initiation trigger, from inadvertent further distal displacement. Further distal displacement of rod 2210 from the initial displacement may involve intentional manipulation on the part of an operator of delivery device 2200.

With rod 2210 at the initial displacement, delivery device 2200 may be in the pre-operational state. With rod 2210 at the initial displacement, delivery device 2200 may be at the end of the pre-operational state. With rod 2210 at the initial displacement, delivery device 2200 may have been prepared for initiation of the operational state. The initiation of the operational state may involve the further distal displacement of rod 2210 from the initial displacement.

The further distal displacement of rod 2210 may be effected by clockwise rotation of rod 2210 about axis L2. The clockwise rotation of rod 2210 about axis L2 may shift boss 1742*b* from being positioned against running surface 2226 to interaction with operation-initiation trigger 2216. The clockwise rotation of rod 2210 about axis L2 may shift boss 1742*a* from being positioned against the second running surface to interaction with the second operation-initiation trigger.

In response to the interaction of boss 1742*b* with operation-initiation trigger 2216, arm 1741*b* may deflect radially outward, along the radius passing through boss 1742*b*, toward the interior wall of distal finger flange extension 2089*b*. Arm 1741*b* deflecting outward may deform support member 1886*b*. Arm 1741*b* deflecting outward may deform support member 1886*d*. Deformation of support member 1886*b* may deform annular border 1981. Deformation of support member 1886*d* may deform an annular border of the second hole of finger flange 1780 disposed symmetrical to hole 1782 relative to the center of guide 1740.

In response to the interaction of boss 1742*a* with the second operation-initiation trigger, arm 1741*a* may deflect radially outward, along the radius passing through boss 1742*a*, toward the interior wall of distal finger flange extension 2089*a*. Arm 1741*a* deflecting outward may deform support member 1886*a*. Arm 1741*a* deflecting outward may deform support member 1886*c*. Deformation of support member 1886*a* may deform annular border 1981. Deformation of support member 1886*c* may deform the annular border of the second hole.

Acoustic and/or tactile indication of the interaction of the boss(es) with the operation-initiation trigger(s) may be concomitant of and/or attendant upon deflection of arm 1741*a* and/or of arm 1741*b*.

Acoustic and/or tactile indication of the interaction of the boss(es) with the operation-initiation trigger(s) may be concomitant of and/or attendant upon deformation of the support member(s).

Figure 23:
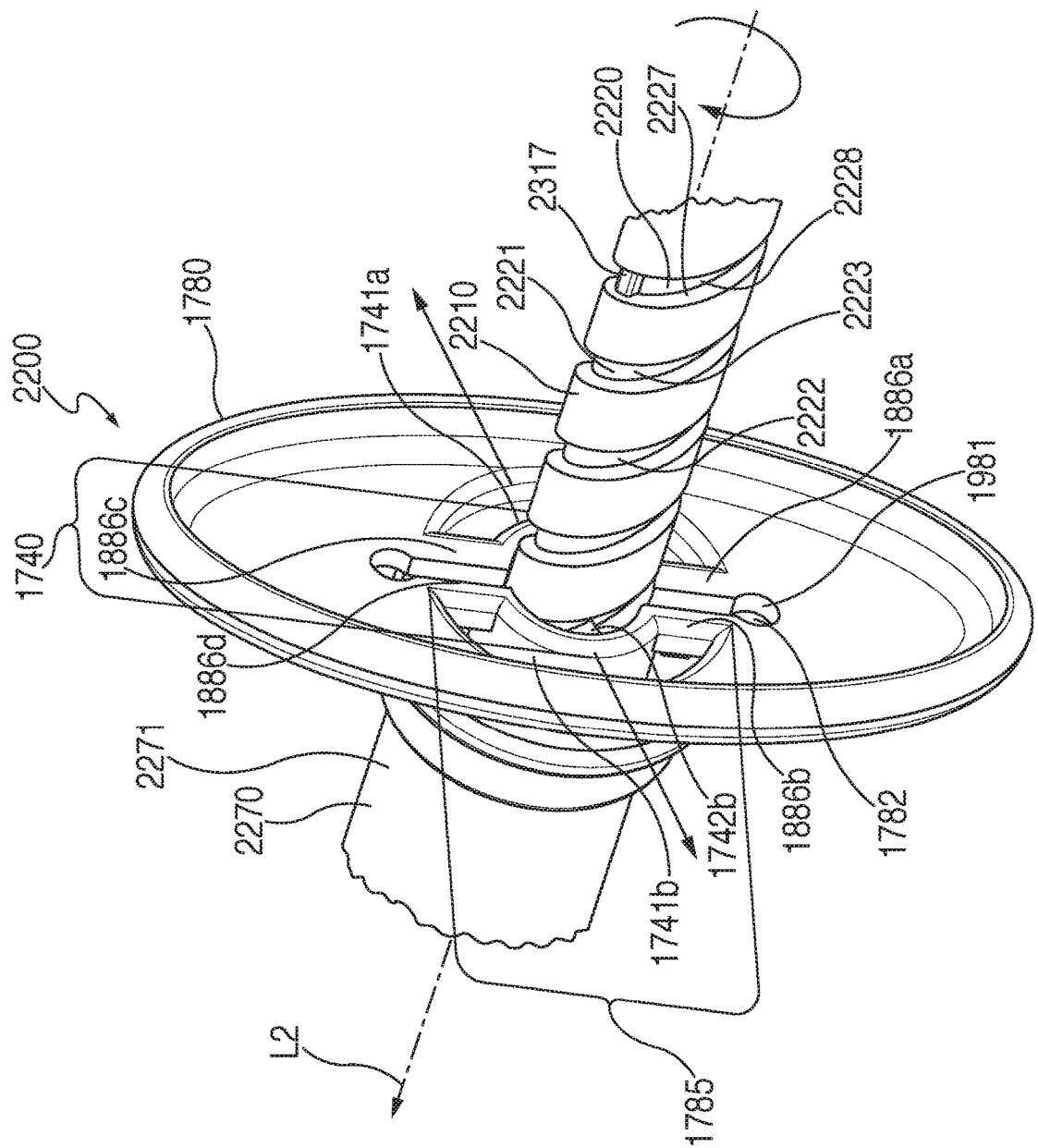
FIG. 23 is another perspective view of the apparatus shown in FIG. 22.

FIG. 23 shows delivery device 2200 with finger flange 1780 affixed, coaxial with axis L2, to housing 2270 and with guide 1740 suspended, coaxial with axis L2, across bay 1785. FIG. 23 shows delivery device 2200 with rod 2210 inserted into guide 1740.

With the initiation of the operational state, boss 1742*b* may engage rod 2210 at operational track 2220. Boss 1742*b* may extend radially into operational track 2220. Boss 1742*b* may engage with helicoidal tract 2222. Boss 1742*b* may be disposed engaged with helicoidal tract 2222 adjacent operation-initiation trigger 2216 (shown in FIG. 22). Boss 1742*b* may be disposed alongside sidewall 2227 of helicoidal tract 2222. Boss 1742*b* may be disposed against running surface 2228 of helicoidal tract 2222.

With the initiation of the operational state, boss 1742*a* (shown in FIG. 22) may engage rod 2210 at second operational track 2221. Boss 1742*a* may extend radially into second operational track 2221. Boss 1742*a* may engage with helicoidal tract 2223. Boss 1742*a* may be disposed engaged with helicoidal tract 2223 adjacent the second operation-initiation trigger (not shown).

Subsequent to the initiation of the operational state, further distal displacement of rod 2210 relative to housing 2270 may be effected by clockwise rotation of rod 2210 about axis L2. Helicoidal tract 2222 of operational track 2220 may support priming-initiation trigger 2317. Helicoidal tract 2223 of second operational track 2221 may support a second priming-initiation trigger (not shown) disposed diametrically opposite priming-initiation trigger 2317. The clockwise rotation of rod 2210 about axis L2 may shift boss 1742*b* from being disposed adjacent to operation-initiation trigger 2216 to interaction with priming-initiation trigger 2317. The clockwise rotation of rod 2210 about axis L2 may shift boss 1742*a* from being disposed adjacent to the second operation-initiation trigger to interaction with the second priming-initiation trigger.

In response to the interaction of boss 1742*b* with priming-initiation trigger 2317, arm 1741*b* may deflect radially outward. Arm 1741*b* deflecting outward may deform support member 1886*b*, with attendant deformation of annular border 1981. Arm 1741*b* deflecting outward may deform support member 1886*d*, with attendant deformation of the annular border of the second hole symmetrically disposed to hole 1782.

In response to the interaction of boss 1742a with the second priming-initiation trigger, arm 1741a may deflect radially outward. Arm 1741a deflecting outward may deform support member 1886a, with attendant deformation of annular border 1981. Arm 1741a deflecting outward may deform support member 1886c, with attendant deformation of the annular border of the second hole.

Acoustic and/or tactile indication of the interaction of the boss(es) with the priming-initiation trigger(s) may be concomitant of and/or attendant upon deflection of arm 1741a and/or of arm 1741b.

Acoustic and/or tactile indication of boss 1742b interacting with priming-initiation trigger 2317 and/or of boss 1742a interacting with the second priming-initiation trigger may provide a signal to the operator to proceed to priming of device 2200.

FIG. 24 shows a front view of a proximal face of plunger rod guide 2440. Guide 2440 may have may have none, some or all of the features and functions of guide 140 (shown in FIGS. 1, 2, 3, 10, 11 and 12). Guide 2440 may have may have none, some or all of the features and functions of guide 1440 (shown in FIGS. 14, 15 and 16). Guide 2440 may have may have none, some or all of the features and functions of guide 1740 (shown in FIGS. 17, 18, 19, 20, 21, 22 and 23). Guide 2440 may include boss 2442a. Guide 2440 may include boss 2442b. Boss 2442a and boss 2442b may be disposed diametrically opposite each other, relative to a center of guide 2440. Boss 2442a and boss 2442b may extend toward each other. Guide 2440 may be C-shaped. Guide 2440 may include a C-shaped clip.

Boss 2442a may be supported by arm 2441a. Boss 2442a may be indirectly supported by arm 2441a. Arm-supported spacer 2447a may be disposed between boss 2442a and arm 2441a. Arm-supported spacer 2447a may be directly supported by arm 2441a. Boss 2442a may be directly supported by arm-supported spacer 2447a.

Boss 2442b may be supported by arm 2441b. Boss 2442b may be indirectly supported by arm 2441b. Arm-supported spacer 2447b may be disposed between boss 2442b and arm 2441b. Arm-supported spacer 2447b may be directly supported by arm 2441b. Boss 2442b may be directly supported by arm-supported spacer 2447b.

Arm-supported spacer 2447a and arm-supported spacer 2447b may be disposed diametrically opposite each other, relative to the center. Arm-supported spacer 2447a and arm-supported spacer 2447b may extend toward each other.

Arm 2441a and arm 2441b may be joined at hinge 2445. Hinge 2445 may be resilient. Arm 2441a and arm 2441b may define gap 2448. Gap 2448 may extend between an end of arm 2441a and an end of arm 2441b. Gap 2448 may be opposite hinge 2445. Arm 2441a may support boss 2442a apart from gap 2448. Arm 2441a may support boss 2442a apart from hinge 2445. Arm 2441b may support boss 2442b apart from gap 2448. Arm 2441b may support boss 2442b apart from hinge 2445. A width of gap 2448 may change during a deflection of guide 2440. Gap 2448 may widen during the deflection of guide 2440. Gap 2448 may narrow during the deflection of guide 2440.

FIG. 25 shows features of illustrative medicament delivery device 2500. Delivery device 2500 may have none, some or all of the features and functions of delivery device 100 (shown in FIG. 11). Delivery device 2500 may have none, some or all of the features and functions of delivery device 1500 (shown in FIGS. 15 and 16.). Delivery device 2500 may have none, some or all of the features and functions of delivery device 2200 (shown in FIGS. 22 and 23.). Delivery device 2500 may define longitudinal axis L3.

Delivery device 2500 may include plunger rod 2510. Rod 2510 may have none, some or all of the features and functions of rod 110 (shown in FIGS. 1, 2, 2A, 2B, 2C, 3, 4A, 4B and 11). Rod 2510 may have none, some or all of the features and functions of rod 510 (shown in FIG. 5). Rod 2510 may have none, some or all of the features and functions of rod 610 (shown in FIG. 6). Rod 2510 may have none, some or all of the features and functions of rod 1510 (shown in FIGS. 15 and 16). Rod 2510 may have none, some or all of the features and functions of rod 2210 (shown in FIGS. 22 and 23). Rod 2510 may be disposed coaxial with axis L3.

Delivery device 2500 may include device housing 2570. Housing 2570 may have none, some or all of the features and functions of housing 170 (shown in FIGS. 1, 2, 3, 11 and 13). Housing 2570 may have none, some or all of the features and functions of housing 1570 (shown in FIGS. 15 and 16). Housing 2570 may have none, some or all of the features and functions of housing 2270 (shown in FIGS. 22 and 23). Housing 2570 may be disposed coaxial with axis L3.

Delivery device 2500 may include a medicament container (not shown). The medicament container of device 2500 may have none, some or all of the features and functions of medicament container 150 (shown in FIGS. 1, 2 and 3). The medicament container of device 2500 may have none, some or all of the features and functions of medicament container 750 (shown in FIG. 7). The medicament container of device 2500 may have none, some or all of the features and functions of medicament container 850 (shown in FIG. 8). The medicament container of device 2500 may have none, some or all of the features and functions of medicament container 950 (shown in FIG. 9). The medicament container of device 2500 may be disposed coaxial with axis L3.

Delivery device 2500 may include a needle hub (not shown). The needle hub of device 2500 may have none, some or all of the features and functions of needle hub 190 (shown in FIGS. 1, 2 and 3). The needle hub of device 2500 may be disposed coaxial with axis L3.

Rod 2510 may include distal rod end 2511. Rod 2510 may define pre-operational track 2530. Pre-operational track 2530 may extend along a cylindrical surface of rod 2510. Pre-operational track 2530 may support pre-operational trigger 2514. Pre-operational trigger 2514 may be supported at a proximal end of pre-operational track 2530.

Rod 2510 may define a second pre-operational track (not shown). The second pre-operational track may extend along the cylindrical surface of rod 2510 parallel to pre-operational track 2530. The second pre-operational track may extend parallel to pre-operational track 2530 over a full extent of pre-operational track 2530 along the cylindrical surface of rod 2510. The second pre-operational track may be disposed diametrically opposite pre-operational track 2530. The second pre-operational track may support a second pre-operational trigger (not shown). The second pre-operational trigger may be supported at a proximal end of the second pre-operational track. The second pre-operational trigger may be disposed diametrically opposite pre-operational trigger 2514. The second pre-operational trigger may be disposed along rod 2510 at a distance from distal rod end 2511 substantially equal to a distance of pre-operational trigger 2514 from distal rod end 2511.

Rod 2510 may define operational track 2520. Operational track 2520 may extend along the cylindrical surface of rod 2510. Rod 2510 may define second operational track 2521.

Operational track 2520 and second operational track 2521 may be disposed parallel to each other along the cylindrical surface.

Operational track 2520 may support operation-initiation trigger 2516. Operation-initiation trigger 2516 may be adjacent to pre-operational trigger 2514. Operational track 2520 may include helicoidal tract 2522. Operation-initiation trigger 2516 may be supported by operational track 2520 at a distal end of helicoidal tract 2522.

Second operational track 2521 may support a second operation-initiation trigger (not shown). The second operation-initiation trigger may be adjacent to the second pre-operational trigger. Second operational track 2521 may include helicoidal tract 2523. The second operation-initiation trigger may be supported by second operational track 2521 at a distal end of helicoidal tract 2523. The second operation-initiation trigger may be disposed diametrically opposite operation-initiation trigger 2516.

Sidewall 2527 may be a sidewall of helicoidal tract 2522. Track 2520 may be defined by sidewall 2527. Running surface 2528 may be a running surface of helicoidal tract 2522. Track 2520 may be defined by running surface 2528.

Housing 2570 may include finger flange 2580. Housing 2570 may include housing wall 2571. Finger flange 2580 may be supported by housing wall 2571.

Housing 2570 may include frame 2532. Frame 2532 may be configured to accommodate guide 2440. Frame 2532 may be configured for structural complementarity of frame 2532 to guide 2440.

Frame 2532 may be continuous with housing wall 2571. Frame 2532 may be integral to housing wall 2571. Frame 2532 may be disposed adjacent to finger flange 2580. Frame 2532 may be disposed distal to finger flange 2580. Frame 2532 may be disposed circumferentially about axis L3. Frame 2532 may be disposed coaxial with axis L3. Frame 2532 may define opening 2536a. Frame 2532 may define opening 2536b. Frame 2532 may define opening 2536c. Frame 2532 may define opening 2536d. Structural elements of frame 2532 may border opening 2536a and/or opening 2536b and/or opening 2536c and/or opening 2536d. Opening 2536a and/or opening 2536b and/or opening 2536c and/or opening 2536d may be disposed circumferentially about axis L3.

Frame 2532 may include distal circumferential ridge 2533. Circumferential ridge 2533 may be disposed circumferentially about axis L3. Circumferential ridge 2533 may be disposed coaxial with axis L3. Circumferential ridge 2533 may have an outer circumference transverse to axis L3 greater than an outer circumference transverse to axis L3 of housing wall 2571 distal to circumferential ridge 2533. Circumferential ridge 2533 may be configured as a radial outward extension of housing wall 2571. Circumferential ridge 2533 may be configured as a radial protuberance of housing wall 2571. An interior circumferential surface of circumferential ridge 2533 may be an interior surface of housing wall 2571.

Frame 2532 may include circumferential ledge 2538. Circumferential ridge 2533 may include circumferential ledge 2538. Circumferential ledge 2538 may be disposed circumferentially about axis L3. Circumferential ledge 2538 may be disposed coaxial with axis L3. A proximal surface of circumferential ledge 2538 may be disposed transverse to axis L3.

Frame 2532 may include longitudinal frame element 2534. Longitudinal frame element 2534 may be disposed parallel to axis L3. Longitudinal frame element 2534 may be supported, at a distal end of longitudinal frame element 2534, by circumferential ridge 2533. Longitudinal frame element 2534 may be integral, at the distal end of longitudinal frame element 2534, to circumferential ridge 2533. Longitudinal frame element 2534 may be integral, at the distal end of longitudinal frame element 2534, to circumferential ledge 2538. Longitudinal frame element 2534 may be continuous, at the distal end of longitudinal frame element 2534, with a portion of housing wall 2571 distal to circumferential ledge 2538. Longitudinal frame element 2534 may be integral, at the distal end of longitudinal frame element 2534, to the portion of housing wall 2571 distal to circumferential ledge 2538. Longitudinal frame element 2534 may be a portion of housing wall 2571. An interior surface of longitudinal frame element 2534 may be an interior surface of housing wall 2571.

Longitudinal frame element 2534 may be supported, at a proximal end (not shown) of longitudinal frame element 2534, by finger flange 2580. Longitudinal frame element 2534 may be supported, at the proximal end of longitudinal frame element 2534, by a proximal circumferential ridge (not shown) parallel to circumferential ridge 2533 and adjacent finger flange 1580. The proximal circumferential ridge may have none, some or all of the features and functions of circumferential ridge 2533.

Frame 2532 may include circumferential frame element 2535a. Frame 2532 may include circumferential frame element 2535b. Circumferential frame element 2535a and/or circumferential frame element 2535b may be disposed circumferentially about axis L3. Circumferential frame element 2535a and/or circumferential frame element 2535b may be disposed coaxial with axis L3. Circumferential frame element 2535a and/or circumferential frame element 2535b may be supported by longitudinal frame element 2534. Circumferential frame element 2535a and/or circumferential frame element 2535b may be integral to longitudinal frame element 2534. Circumferential frame element 2535a and/or circumferential frame element 2535b may be supported, at an end away from longitudinal frame element 2534, by housing wall 2571. Circumferential frame element 2535a and/or circumferential frame element 2535b may be continuous, at the end away from longitudinal frame element 2534, with housing wall 2571. Circumferential frame element 2535a and/or circumferential frame element 2535b may be a portion of housing wall 2571. An interior surface of circumferential frame element 2535a and/or circumferential frame element 2535b may be an interior surface of housing wall 2571.

Circumferential frame element 2535a and longitudinal frame element 2534 may border opening 2536a. Circumferential frame element 2535a and longitudinal frame element 2534 may border opening 2536c. Circumferential frame element 2535b and longitudinal frame element 2534 may border opening 2536b. Circumferential frame element 2535b and longitudinal frame element 2534 may border opening 2536d.

Frame 2532 may include lateral longitudinal ledge 2537. Lateral longitudinal ledge 2537 may be disposed parallel to axis L3. Lateral longitudinal ledge 2537 may be disposed transverse to circumferential ledge 2538. Lateral longitudinal ledge 2537 may be disposed athwart the end away from longitudinal frame element 2534 of circumferential frame element 2535b. Frame 2532 may include a second lateral longitudinal ledge (not shown). The second lateral longitudinal ledge may be disposed athwart the end away from longitudinal frame element 2534 of circumferential frame element 2535a. Lateral longitudinal ledge 2537 and/or the second lateral longitudinal ledge may extend along a radius transverse to axis L3 beyond a radius transverse to axis L3 of an outer surface of circumferential frame element 2535a and/or circumferential frame element 2535b.

Delivery device 2500 may include guide 2440. Guide 2440 may include distal guide extension 2549. Guide 2440 may define central axis C. Axis C may pass through the center of guide 2440. Hinge 2445 may extend parallel to axis C along distal guide extension 2549. Gap 2448 (shown in FIG. 24) may have a longitudinal extension, parallel to axis C, opposite hinge 2445.

Guide 2440 may include distal arm-supported spacer 2547c. An interior wall of distal guide extension 2549 may support arm-supported spacer 2547c. The interior wall of distal guide extension 2549 supporting arm-supported spacer 2547c may be an interior wall of a distal extension of arm 2441a.

Guide 2440 may include distal arm-supported spacer 2547d. An interior wall of distal guide extension 2549 may support arm-supported spacer 2547d. The interior wall of distal guide extension 2549 supporting arm-supported spacer 2547d may be an interior wall of a distal extension of arm 2441b.

Arm-supported spacer 2547c and arm-supported spacer 2547d may be disposed diametrically opposite each other. Arm-supported spacer 2447c and arm-supported spacer 2447d may extend toward each other.

Arm-supported spacer 2447a and arm-supported spacer 2547c may be disposed parallel to each other. Between arm-supported spacer 2447a and arm-supported spacer 2547c, guide 2440 may define opening A transverse to axis C. Arm-supported spacer 2447b and arm-supported spacer 2547d may be disposed parallel to each other. Between arm-supported spacer 2447b and arm-supported spacer 2547d, guide 2440 may define opening B transverse to axis C.

Guide 2440 may be affixed to housing 2570. Guide 2440 may be clipped onto housing 2570. Guide 2440 may be clipped onto frame 2532 in a direction transverse to axis L3. Guide 2440 may be clipped onto frame 2532 such that axis C is disposed collinearly with axis L3.

Guide 2440 may be clipped onto housing 2570 such that guide 2440 is blocked from distal movement along axis L3 relative to housing 2570. Guide 2440 may be clipped onto housing 2570 such that guide 2440 is blocked from rotational movement about axis L3 relative to housing 2570. Clipping guide 2440 onto frame 2532 may be carried out as a manufacturing step of device 2500.

Clipping guide 2440 onto frame 2532 may proceed in several stages. All the stages may involve substantially maintaining an orientation of guide 2440 relative to frame 2532. The orientation may include alignment of axis C parallel to axis L3. The orientation may include alignment of the longitudinal extension of gap 2448 parallel to longitudinal frame element 2534. The orientation may include alignment of a distal face of guide 2440 coplanar with circumferential ledge 2538. The orientation may include alignment of arm-supported spacer 2447a with opening 2536a and/or alignment of arm-supported spacer 2447b with opening 2536b and/or alignment of arm-supported spacer 2547c with opening 2536c and/or alignment of arm-supported spacer 2547d with opening 2536d.

In a preparatory stage of clipping guide 2440 onto frame 2532 and at a completed stage of clipping guide 2440 onto frame 2532, guide 2440 may be undeflected. With guide 2440 undeflected, the width of gap 2448 may have a reference value. The reference value may be less than a diameter passing through axis L3 between an outer surface of circumferential frame element 2535a and an outer surface of circumferential frame element 2535b. With guide 2440 deflected, the width of gap 2448 may increase from the reference value. In a transition stage of clipping guide 2440 onto frame 2532, between the preparatory stage and the completed stage, guide 2440 may be deflected.

The preparatory stage may involve decreasing distance between axis C and axis L3 until guide 2440 is brought into initial contact with frame 2532. The initial contact of guide 2440 with frame 2532 may bring the end of arm 2441a into contact with circumferential frame element 2535a and may bring the end of arm 2441b into contact with circumferential frame element 2535b. The preparatory stage may bring a portion of the distal face of guide 2440 against circumferential ledge 2538. The preparatory stage may bring a portion of each arm-supported spacer of guide 2440 into the opening in frame 2532 with which the arm-supported spacer is aligned.

The transition stage may involve further decreasing the distance between axis C and axis L3, forcing a deflection of guide 2440 about hinge 2445, with the ends of arm 2441a and arm 2441b moving apart to accommodate the outer surface of circumferential frame element 2535a and the outer surface of circumferential frame element 2535b. During the transition stage, the width of gap 2448 may increase to at least a value of the diameter between the outer surface of circumferential frame element 2535a and the outer surface of circumferential frame element 2535b. During the transition stage, each arm-supported spacer of guide 2440 may move further into the opening in frame 2532 with which the arm-supported spacer is aligned.

After the width of gap 2448 reaches the value of the diameter during the transition stage, the width of gap 2448 may decrease toward the reference value with further decreasing of the distance between axis C and axis L3. The distance between axis C and axis L3 may be decreased until axis C and axis L3 are collinear at the completed stage. At the completed stage, the width of gap 2448 may be the reference value.

At the completed stage, guide 2440 may be disposed coaxial with housing 2570. An interior surface of guide 2440 along hinge 2445 may be disposed against longitudinal frame element 2534. Other interior surfaces of guide 2440 may be disposed against the outer surface of circumferential frame element 2535a or the outer surface of circumferential frame element 2535b. The distal face of guide 2440 may be disposed against circumferential ledge 2538. The proximal face of guide 2440 may be disposed against a distal surface of finger flange 2580. A longitudinal extension of the end of arm 2441b may be disposed against lateral longitudinal ledge 2537. A longitudinal extension of the end of arm 2441a may be disposed against the second lateral longitudinal ledge.

At the completed stage, with the width of gap 2448 being smaller than the diameter between the outer surface of circumferential frame element 2535a and the outer surface of circumferential frame element 2535b, guide 2440 may be substantially blocked from inadvertent transverse slippage of guide 2440 from frame 2532. Stabilization of guide 2440 maintaining guide 2440 coaxial with housing 2570 may be provided by the structural complementarity of frame 2532 to guide 2440.

At the completed stage, the distal face of guide 2440 being disposed against circumferential ledge 2538 may block guide 2440 from distal axial movement relative to housing 2570. The proximal face of guide 2440 being disposed against the distal surface of finger flange 2580 may block guide 2440 from proximal axial movement relative to housing 2570. The longitudinal extension of the end of arm 2441a and the longitudinal extension of the end of arm 2441b being disposed against the lateral longitudinal ledges of frame 2532 may block guide 2440 from rotational movement relative to housing 2570.

At the completed stage, the arm-supported spacers may be disposed extending radially inward toward axis L3. Boss 2442a and boss 2442b may be disposed extending radially inward toward axis L3. A distance across axis L3 between boss 2442a and boss 244b may be less than a diameter of the cylindrical surface of rod 2510.

At the completed stage, rod 2510 may be inserted into housing 2570 and through guide 2440. Insertion of rod 2510 into housing 2570 and through guide 2440 may be carried out as a manufacturing step of device 2500. Distal end 2511 of rod 2510 may be longitudinally inserted into housing 2570 and through guide 2440. Guide 2440 may define a passageway through which distal rod end 2511 may be inserted.

With insertion of distal rod end 2511 through guide 2440, boss 2442b may engage rod 2510 at pre-operational track 2530. Boss 2442b may extend radially inward into pre-operational track 2530. Boss 2442a may engage rod 2510 at the second pre-operational track. Boss 2442a may extend radially inward into the second pre-operational track.

A radially inward facing surface of arm-supported spacer 2447a and/or of arm-supported spacer 2447b and/or of arm-supported spacer 2447c and/or of arm-supported spacer 2447d may be disposed alongside the cylindrical surface of rod 2510.

Rod 2510 may be inserted into guide 2440 with engagement of boss 2442b at pre-operational track 2530 until boss 2442b interacts with pre-operational trigger 2514. Interaction of boss 2442b with pre-operational trigger 2514 may correspond to an end of the engagement of boss 2442b with pre-operational track 2530. In response to the interaction of boss 2442b with pre-operational trigger 2514, guide 2440 may deflect. In response to the interaction of boss 2442b with pre-operational trigger 2514, arm 2441b may deflect. Deflection of arm 2441b may indicate the end of the engagement of boss 2442b at pre-operational track 2530.

Rod 2510 may be inserted into guide 2440 with engagement of boss 2442a at the second pre-operational track until boss 2442a interacts with the second pre-operational trigger. Interaction of boss 2442a with the second pre-operational trigger may correspond to an end of the engagement of boss 2442a with the second pre-operational track. In response to the interaction of boss 2442a with the second pre-operational trigger, guide 2440 may deflect. In response to the interaction of boss 2442a with the second pre-operational trigger, arm 2441a may deflect. Deflection of arm 2441a may indicate an end of engagement of boss 2442a at the second pre-operational track. Arm 2441a and arm 2441b may deflect about hinge 2445.

Guide 2440 may deflect within openings 2536. Guide 2440 may deflect relative to housing 2570. An exterior surface of guide 2440 may deflect relative to housing 2570. An interior surface of guide 2440 may deflect relative to housing 2570.

Upon further longitudinal insertion of rod 2510 into guide 2240, boss 2242b may be positioned proximal to pre-operational trigger 2514, against running surface 2526 between pre-operational trigger 2514 and operation-initiation trigger 2516. The insertion of rod 2510 positioning boss 2242b against running surface 2526 may be the initial displacement.

The initial displacement may position boss 2242a proximal to the second pre-operational trigger. The initial displacement may position boss 2242a against a second running surface (not shown). The second running surface may be disposed, between the second pre-operational trigger and the second operation-initiation trigger, diametrically opposite running surface 2526.

Rod 2510 may be substantially blocked, by boss 2442b being positioned proximal to pre-operational trigger 2514, from inadvertent proximal slippage of rod 2510 out of guide 2440. Rod 2510 may be substantially blocked, by boss 2442a being positioned proximal to the second pre-operational trigger, from inadvertent proximal slippage of rod 2510 out of guide 2440. Rod 2510 may be substantially blocked, by boss 2442b being positioned between pre-operational trigger 2514 and operation-initiation trigger 2516, from inadvertent further distal displacement. Rod 2510 may be substantially blocked, by boss 2442a being positioned between the second pre-operational trigger and the second operation-initiation trigger, from inadvertent further distal displacement. Further distal displacement of rod 2510 from the initial displacement may involve intentional manipulation on the part of an operator of delivery device 2500.

With rod 2510 at the initial displacement, delivery device 2500 may be in the pre-operational state. With rod 2510 at the initial displacement, delivery device 2500 may be at the end of the pre-operational state. With rod 2510 at the initial displacement, delivery device 2500 may have been prepared for initiation of the operational state. The initiation of the operational state may involve the further distal displacement of rod 2510 from the initial displacement.

The further distal displacement of rod 2510 may be effected by clockwise rotation of rod 2510 about axis L3. The clockwise rotation of rod 2510 about axis L3 may shift boss 2242b from being positioned against running surface 2526 to interaction with operation-initiation trigger 2516. The clockwise rotation of rod 2510 about axis L3 may shift boss 2242a from being positioned against the second running surface to interaction with the second operation-initiation trigger. In response to the interaction of the boss(es) with the operation-initiation trigger(s), guide 2440 may deflect, widening gap 2448.

Acoustic and/or tactile indication of guide 2440 deflecting may be concomitant of and/or attendant upon widening of gap 2448. The operator may feel the exterior surface of guide 2440 deflecting. The interior surface of guide 2440 returning to a non-deflected position against the exterior surface of frame 2532 may produce an audible sound.

FIG. 26 shows a view of the distal surface of finger flange 2580. The distal surface of finger flange 2580 may include distal surface 2688. Finger flange 2580 may support longitudinal frame element 2534. Distal surface 2688 may support longitudinal frame element 2534. Distal surface 2688 may abut the proximal end of longitudinal frame element 2534. Longitudinal frame element 2534 may be continuous with finger flange 2580.

FIG. 26 shows a distal view of frame 2532. Frame 2532 may include a portion of distal surface 2688. The portion of distal surface 2688 may border opening 2536a, also bordered by longitudinal frame element 2534 and circumferential frame element 2535a.

Distal surface 2688 may proximally limit frame 2532. Circumferential ridge 2533 may distally limit frame 2532. A portion of circumferential ridge 2533 may border opening 2536c, also bordered by longitudinal frame element 2534 and circumferential frame element 2535a.

FIG. 27 shows delivery device 2500 with guide 2440 clipped onto housing 2570, with a view of circumferential frame element 2535b through opening B. Distal guide extension 2549 is shown distally limited by circumferential ridge 2533. FIG. 27 shows delivery device 2500 with rod 2510 inserted into housing 2570 and through guide 2440.

With the initiation of the operational state, boss 2442b (indicated in phantom lines) may engage rod 2510 at operational track 2520. Boss 2442b may extend radially into operational track 2520. Boss 2442b may engage with helicoidal tract 2522. Boss 2442b may be disposed engaged with helicoidal tract 2522 adjacent operation-initiation trigger 2516 (shown in FIG. 25). Boss 2442b may be disposed alongside sidewall 2527 of helicoidal tract 2522. Boss 2442b may be disposed against running surface 2528 of helicoidal tract 2522.

With the initiation of the operational state, boss 2442a (shown in FIG. 25) may engage rod 2510 at second operational track 2521. Boss 2442a may extend radially into second operational track 2521. Boss 2442a may engage with helicoidal tract 2523. Boss 2442a may be disposed engaged with helicoidal tract 2523 adjacent the second operation-initiation trigger (not shown).

Subsequent to the initiation of the operational state, further distal displacement of rod 2510 relative to housing 2570 and guide 2440 may be effected by clockwise rotation of rod 2510 about axis L3. Helicoidal tract 2522 of operational track 2520 may support priming-initiation trigger 2717. Helicoidal tract 2523 of second operational track 2521 may support a second priming-initiation trigger (not shown) disposed diametrically opposite priming-initiation trigger 2717. The clockwise rotation of rod 2510 about axis L3 may shift boss 2442b from being disposed adjacent to operation-initiation trigger 2516 to interaction with priming-initiation trigger 2717. The clockwise rotation of rod 2510 about axis L3 may shift boss 2442a from being disposed adjacent to the second operation-initiation trigger to interaction with the second priming-initiation trigger.

In response to the interaction of the boss(es) with the priming-initiation trigger(s), guide 2440 may deflect. In response to the interaction of the boss(es) with the priming-initiation trigger(s), arm 2441a and arm 2441b may deflect outward about hinge 2445, with concomitant and/or attendant acoustic and/or tactile indication of the boss(es) interacting with the priming-initiation trigger(s).

Acoustic and/or tactile indication of the boss(es) interacting with the priming-initiation trigger(s) may provide a signal to the operator to proceed to priming of device 2500.

During operation of delivery device 2500, portions of the operator's fingers may be disposed distal to finger flange 2580 alongside guide 2440. Portions of the operator's fingers being disposed alongside guide 2440 may provide the operator with tactile indication of deflection of guide 2440.

Operation of delivery device 2500 may dispose portions of the operator's fingers alongside hinge 2445. Portions of the operator's fingers being disposed alongside hinge 2445 may provide the operator with tactile indication of deflection of guide 2440.

Delivery device 2500 as shown in FIG. 27 features finger flange 2580 with a long elliptical axis (not shown) of finger flange 2580 oriented substantially perpendicular to the direction of deflection of guide 2440.

In some embodiments (not shown), the finger flange may have a long elliptical axis aligned with the direction of deflection of the guide. Portions of the operator's fingers may be positioned alongside a portion of the guide that is in line with the deflection of the guide. This may provide the operator with tactile indication of deflection of the guide.

Figure 28:
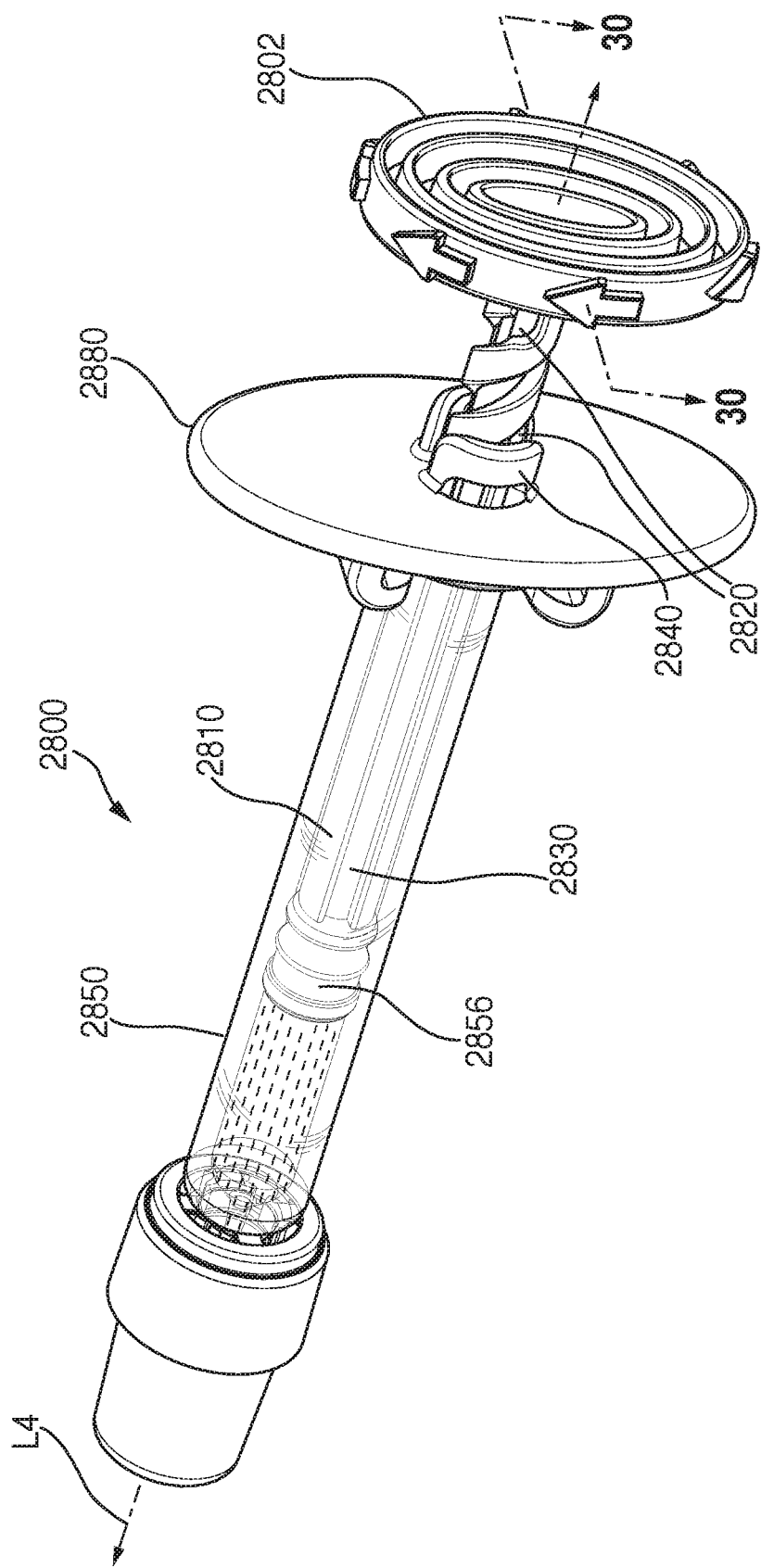
FIG. 28 is a perspective view of apparatus in accordance with the principles of the invention.

FIG. 28 shows illustrative delivery device 2800. Delivery device 2800 may have one or more features in common with one or more of devices 100 (shown in FIG. 1), 1500 (shown in FIG. 15) and 2500 (shown in FIG. 25). Delivery device 2800 may include knob 2802, finger flange 2880, medicament container 2850, medicament 2860, plunger rod 2810, plunger 2856, pre-operational track 2830, guide 2840 and operational track 2820.

Figure 29:
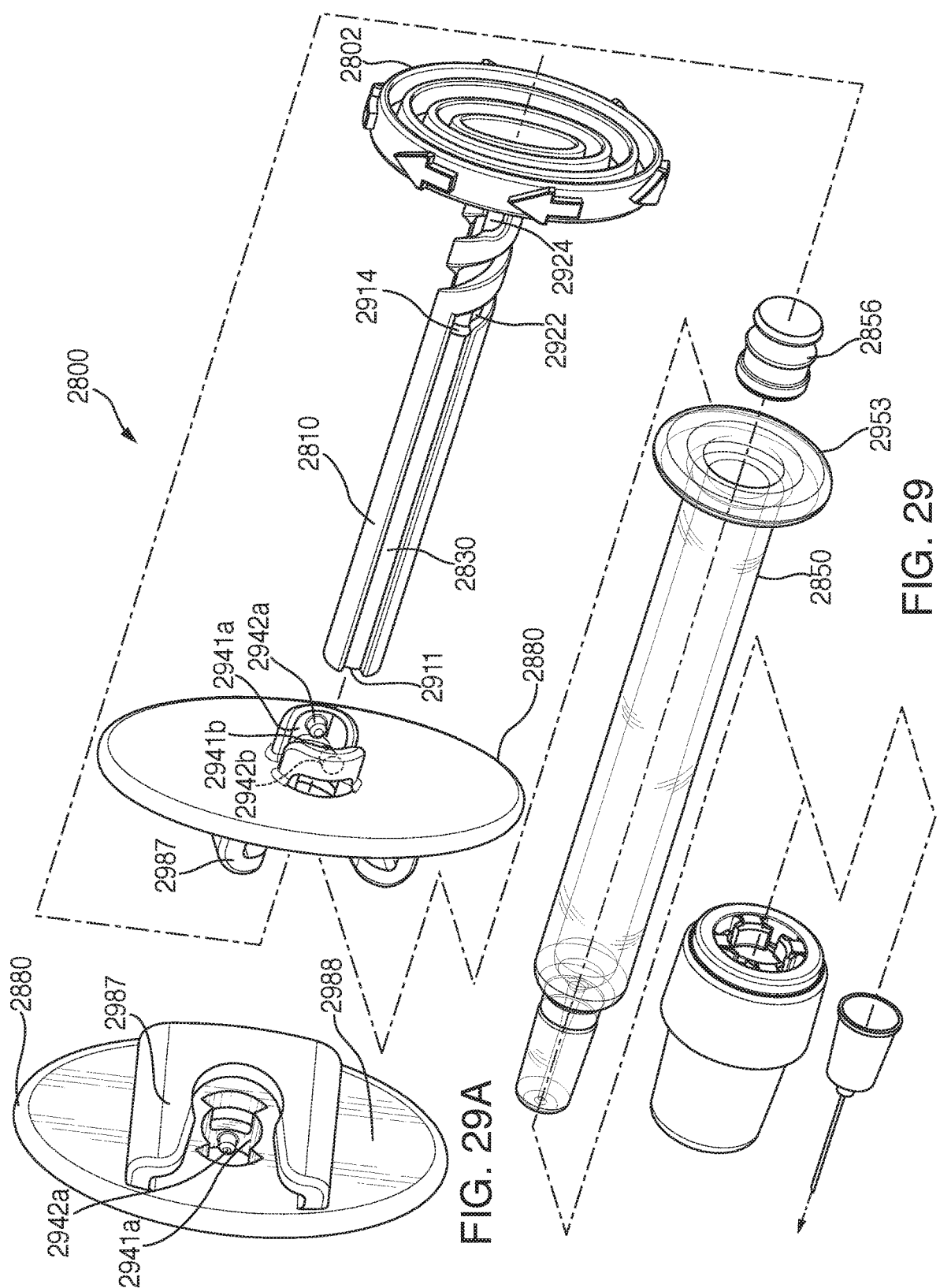
FIG. 29 is an exploded, perspective view of the apparatus shown in FIG. 28.

FIG. 29 shows that delivery device 2800 may include proximal rim 2953, bracket 2987, guide arm 2941A, guide arm 2941B, boss 2942A, boss 1942B, pre-operational protrusion 2914, helical tract 2922, longitudinal tract 2924. FIG. 29A shows distal surface 2988 of finger flange 2880.

Figure 30:
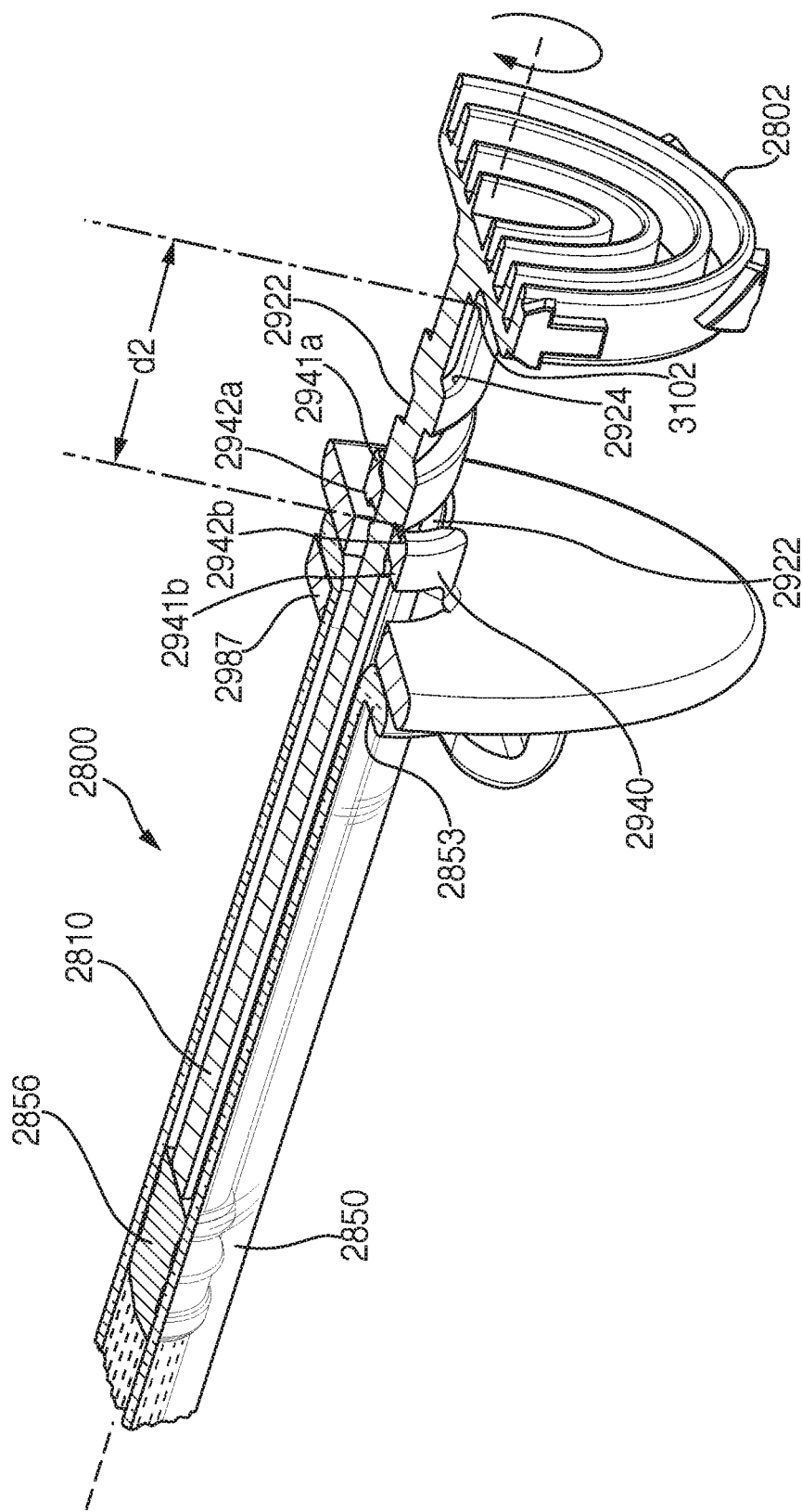
FIG. 30 is a partial cross-sectional view of the apparatus shown in FIG. 28, the view taken along lines 30-30 (shown in FIG. 28)

FIG. 30 is a cross-section view taken along view lines 30-30 (shown in FIG. 28). Distance d2 between boss 2942b and terminal surface 3012 of longitudinal track 2924. In operation, rotation of knob 2802 decreases d2.

Figure 31A:
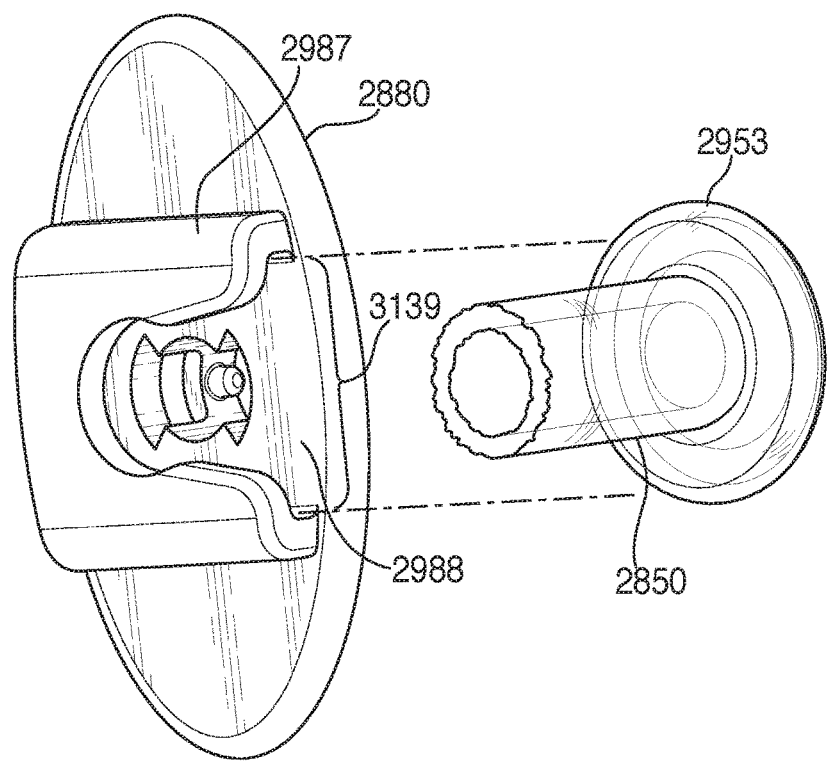
FIG. 31A is an enlarged detail of the apparatus shown in FIG. 29.

FIG. 31A shows recess 3139 of bracket 2987. Bracket 2987 may be supported by distal surface 2988. Recess 3139 may receive rim 2953.

Figure 31B:
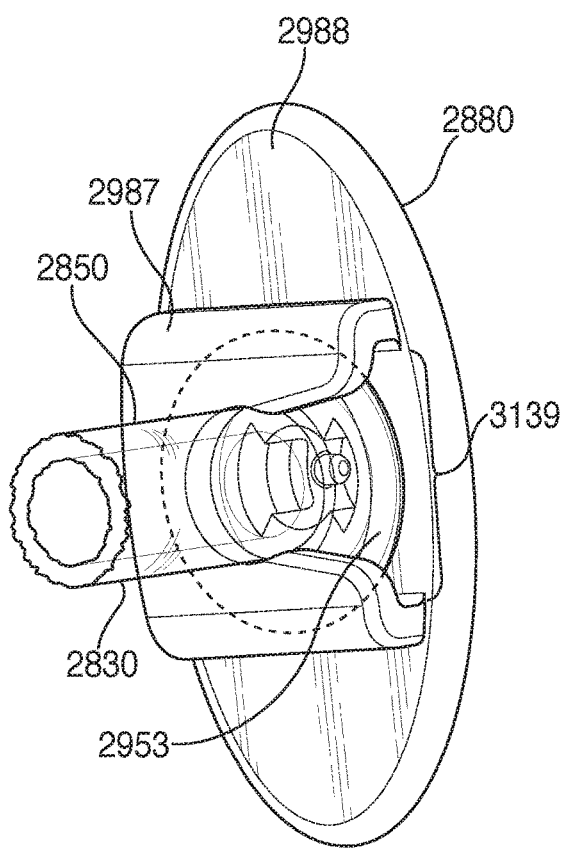
FIG. 31B is an enlarged detail of the apparatus shown in FIG. 29.

FIG. 31B shows rim 3953 having been received in recess 3139.

Figure 32:
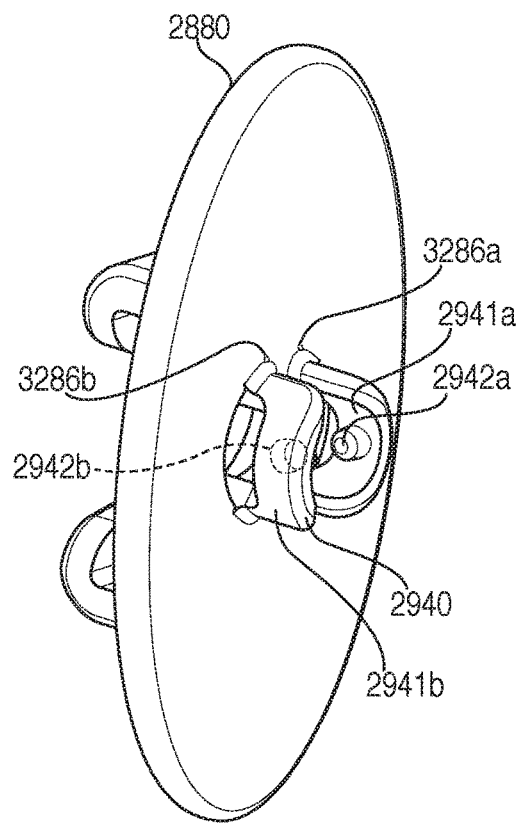
FIG. 32 is a perspective view of apparatus in accordance with the principles of the invention.

FIG. 32 shows support 3286a supporting arm 2941a. Support 3286b supports arm 2941b. Supports 3286a and 3286b may be oriented vertically relative to finger flange 2880.

Figure 33:
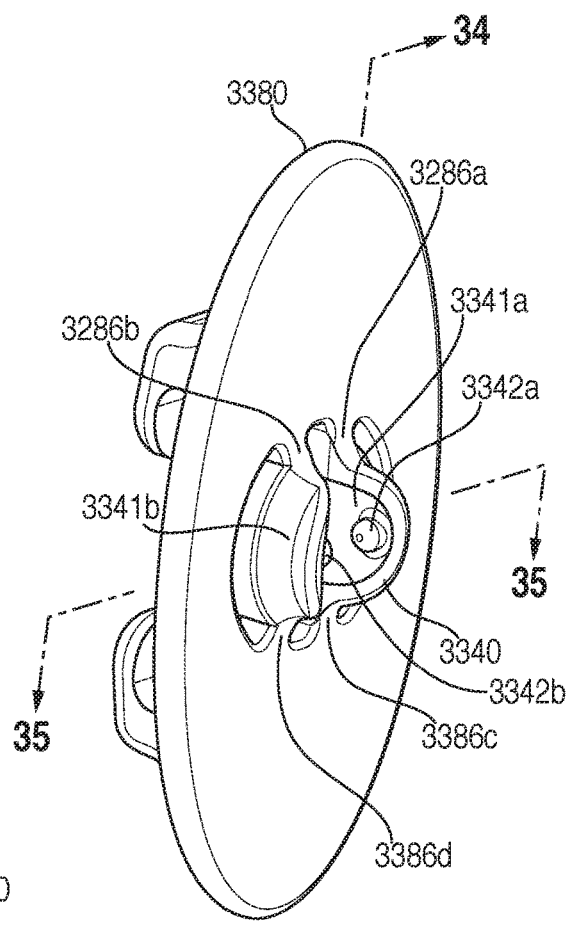
FIG. 33 is a perspective view of apparatus in accordance with the principles of the invention.

FIG. 33 shows finger flange 3380. Finger flange 3380 may include guide 3340. Guide 3340 may include arm 3341a, which may support boss 3342a. Guide 3340 may include arm 3341b, which may support boss 3342b. Support 3286a may support arm 3341a. Support 3286b may support arm 3341b.

Figure 33A:
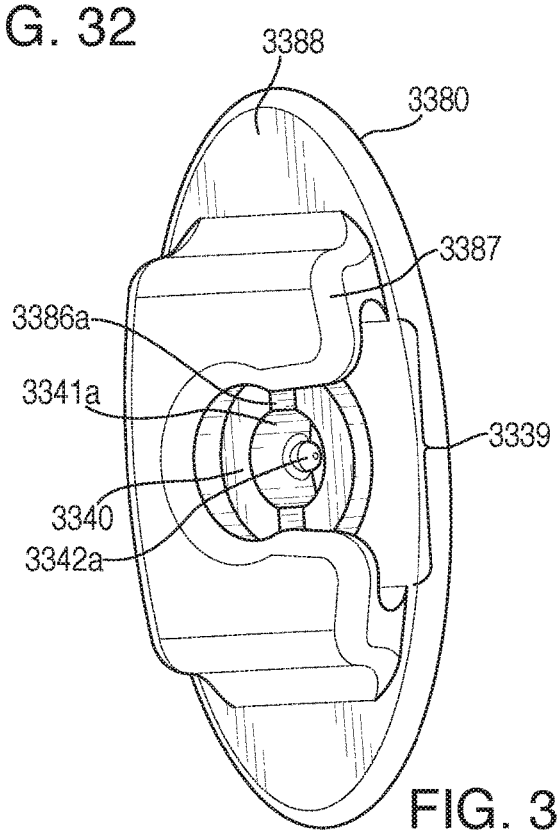
FIG. 33A is a perspective view of apparatus in accordance with the principles of the invention.

FIG. 33A shows recess 3339 of bracket 3387, which may be supported by distal surface 3388.

Figure 34:
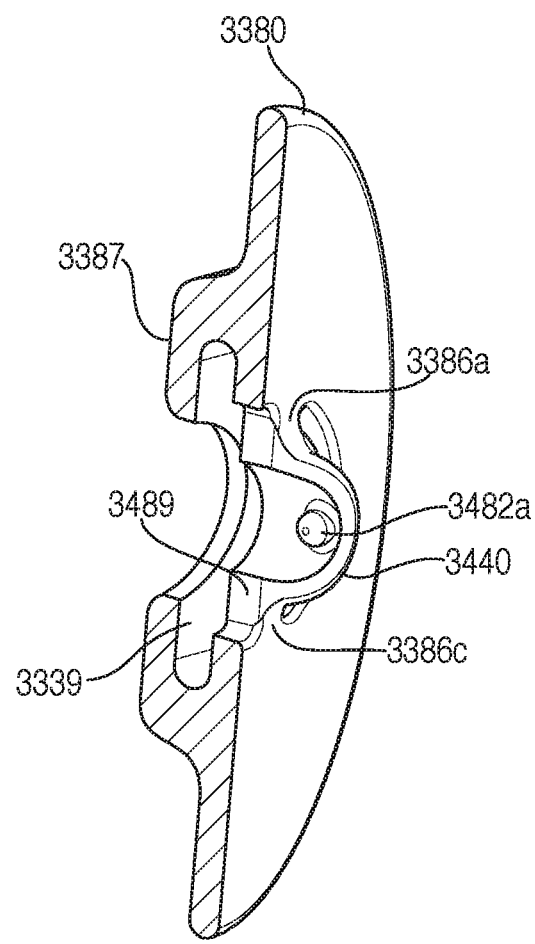
FIG. 34 is a partial cross-sectional view of the apparatus shown in FIG. 33, the view taken along lines 34-34 (shown in FIG. 33)

FIG. 34 is a partial [global] cross-sectional view taken along view lines 34-34 (shown in FIG. 30). Supports 3386a and support 3386c may support part of guide 3440. Supports 3386a and 3386c may be oriented horizontally relative to finger flange 3380. Distal extension 3489 of guide 3440 may border recess 3339.

Figure 35:
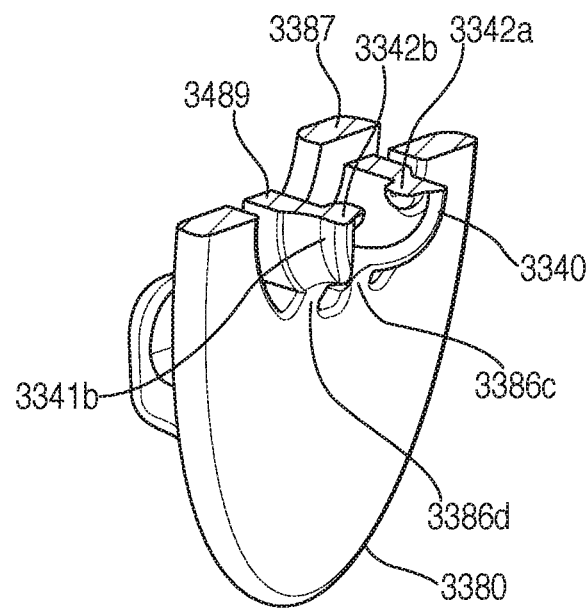
FIG. 35 is a partial cross-sectional view of the apparatus shown in FIG. 33, the view taken along lines 35-35 (shown in FIG. 33)

FIG. 35 is a partial cross-sectional view taken along view lines 35-35 (shown in FIG. 33). Support 3386c may support arm 3341a. Support 3486d may support arm 3341b. Distal extension 3489 may lie within the plane of finger flange 3380.

Figure 36:
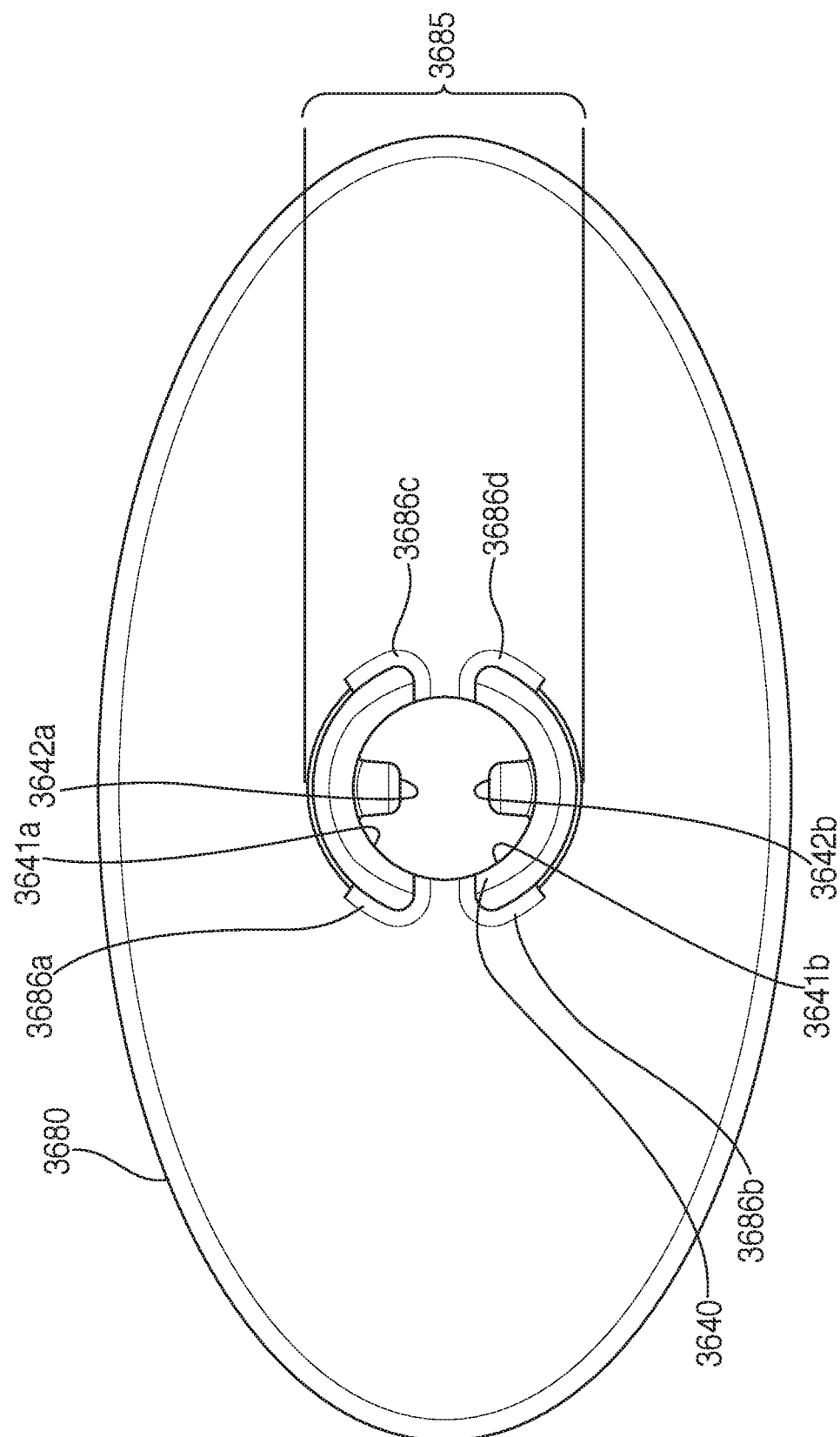
FIG. 36 is an end-view of apparatus in accordance with the principles of the invention.

FIG. 36 shows finger flange 3680. Finger flange 3680 may include guide 3640. Guide 3640 may include arm 3641a. Arm 3641a may support boss 3642a. Support 3686a may support arm 3641a. Support 3686c may support arm 3641a. Guide 3640 may include arm 3641b. Arm 3641b may support boss 3642b. Support 3686b may support arm 3641b. Support 3686d may support arm 3641b. Supports 3686a and 3686c may support arm 3641a within bay 3685. Supports 3686b and 3686d may support arm 3641b within bay 3685. In operation, guide 3640 may deflect radially outwardly within bay 3685.

Figure 37A:
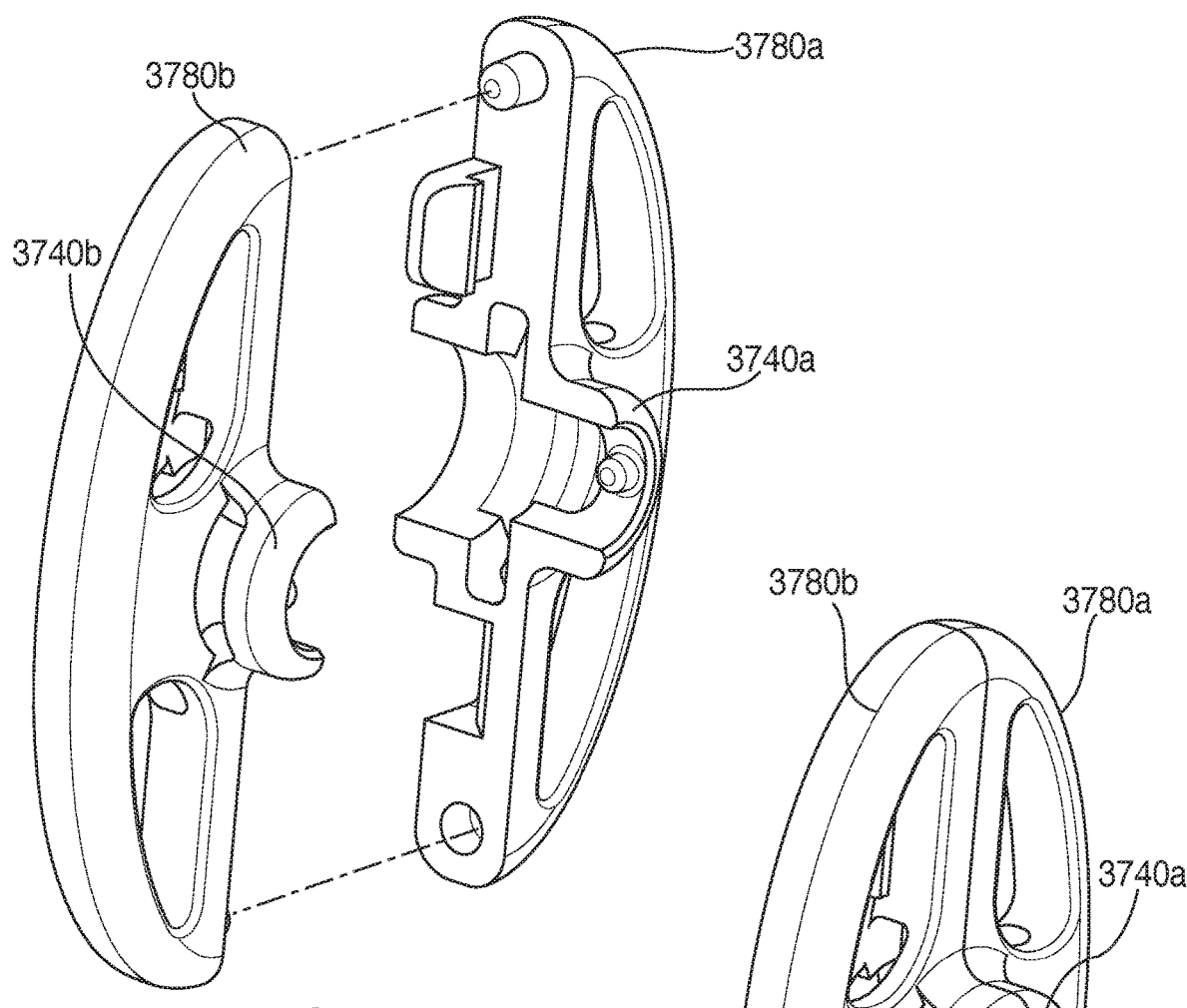
FIG. 37A is a perspective view of apparatus in accordance with the principles of the invention.

FIG. 37A shows finger flange components 3780a and 3780b in an unassembled state. Component 3780a may support guide component 3740a. Component 3780b may support guide component 3740b.

Figure 37B:
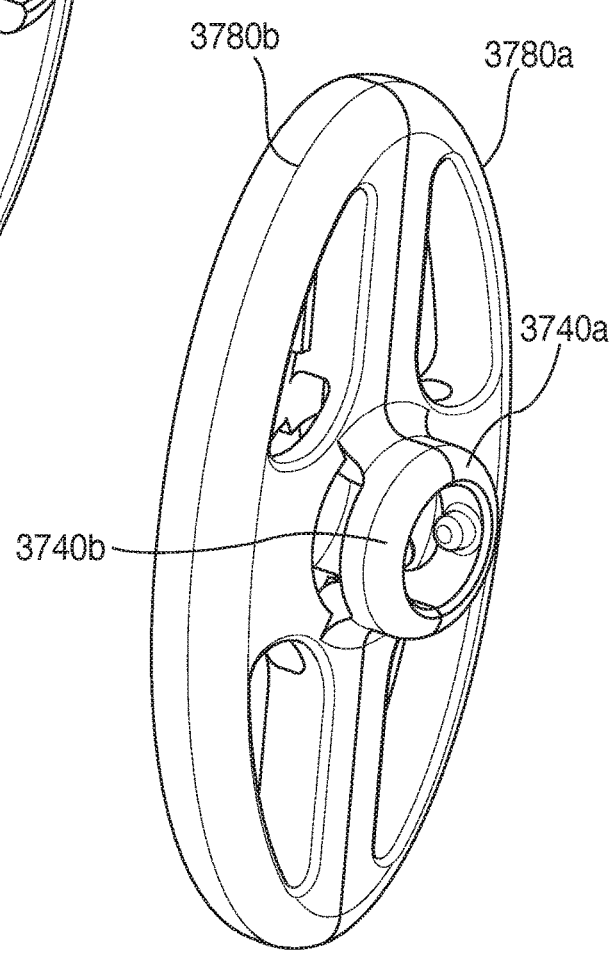
FIG. 37B is a perspective view of apparatus in accordance with the principles of the invention.

FIG. 37B shows components 3780a and 3780b in an assembled state.

FIG. 38A shows components 3780a and 3780b in the unassembled state. Distal surface 3888a may support bracket component 3887a. Distal surface 3888b may support bracket component 3887b. Bracket component 3887a may define recess component 3839a. Bracket component 3887b may define recess component 3839b.

FIG. 38B shows that recesses 3839a and 3839b form opening 3839 when finger flange components 3780a and 3780b are assembled.

Figure 38C:
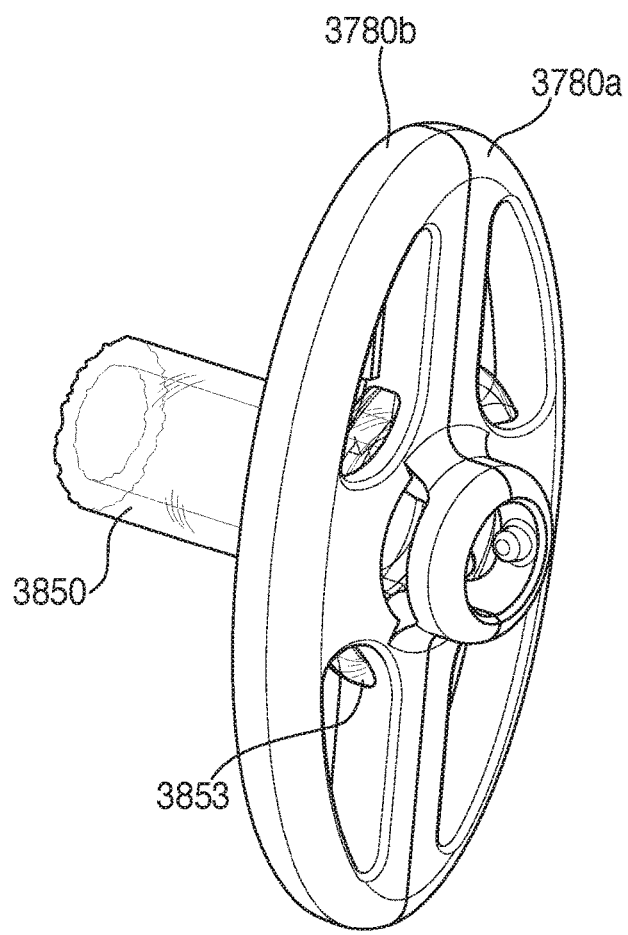
FIG. 38C is a perspective view of apparatus in accordance with the principles of the invention.

FIG. 38C shows rim 3853 of container 3850 assembled with finger flange components 3780a and 3780b. Finger flange components 3780a and 3780b may be drawn together transversely to medicament container 3850 during assembly.

Figure 39:
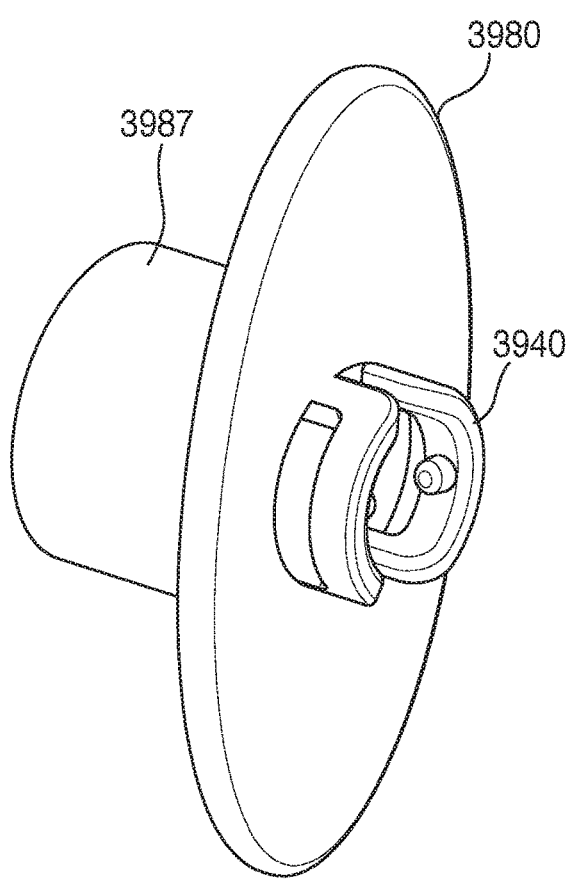
FIG. 39 is a perspective view of apparatus in accordance with the principles of the invention.

FIG. 39 shows illustrative finger flange 3980. Finger flange 3980 may support guide 3940. Finger flange 3980 may include bracket 3987.

Figure 40:
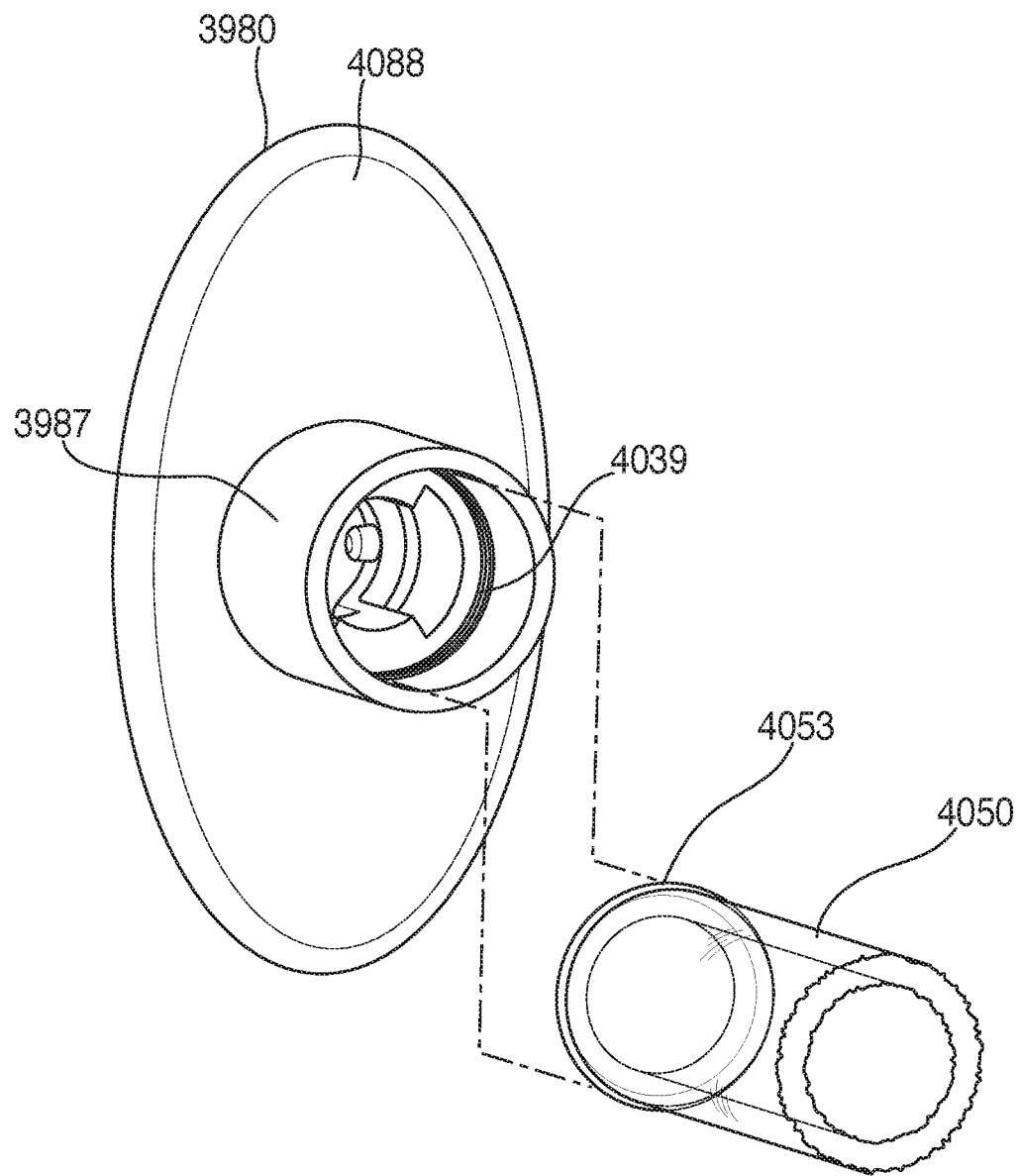
FIG. 40 is an exploded, perspective view of apparatus in accordance with the principles of the invention.

FIG. 40 shows recess 4039 of bracket 3987. Bracket 3987 may be supported by distal surface 4088. Recess 4039 may receive rim 4053 of medicament container 4050.

Figure 41:
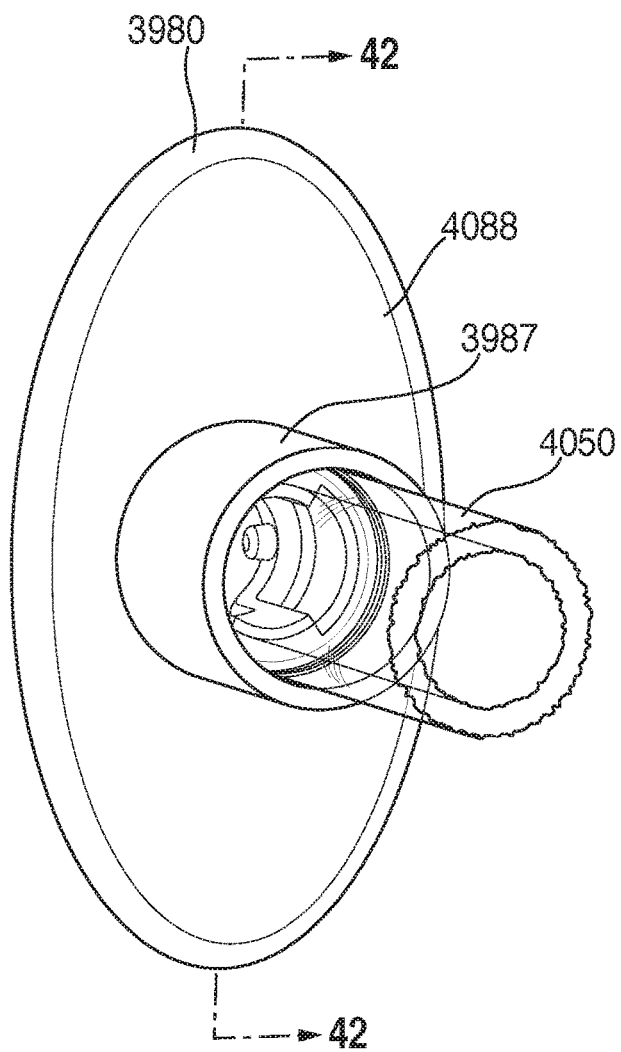
FIG. 41 is a perspective view of the apparatus shown in FIG. 40.

FIG. 41 shows medicament container 4050 assembled with finger flange components 3980. Medicament container 4050 may be inserted longitudinally into bracket 3987 during assembly.

Figure 42:
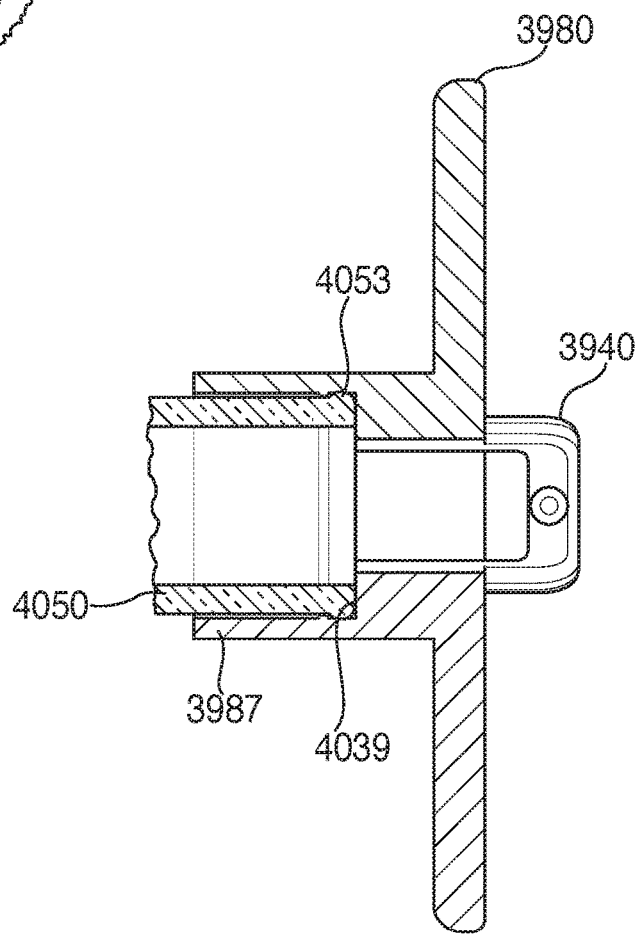
FIG. 42 is a partial cross-sectional view of the apparatus shown in FIG. 41, the view taken along lines 42-42 (shown in FIG. 41)

FIG. 42 shows partial cross-sectional view taken along lines 42-42 (shown FIG. 41). FIG. 42 shows bracket 3987. Bracket 3987 may receive medicament container 4050. Recess 4039 may retain rim 4053.

Figure 43A:
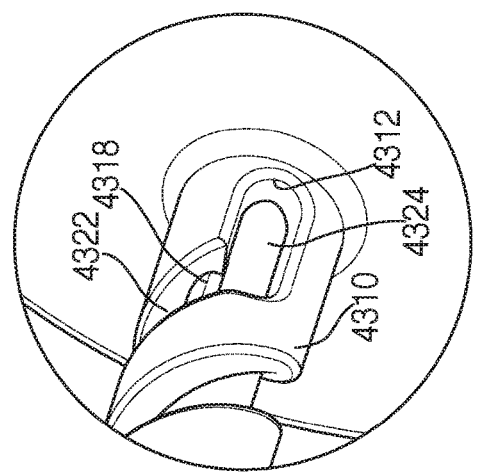
FIG. 43A is a perspective view of apparatus in accordance with the principles of the invention.
Figure 43:
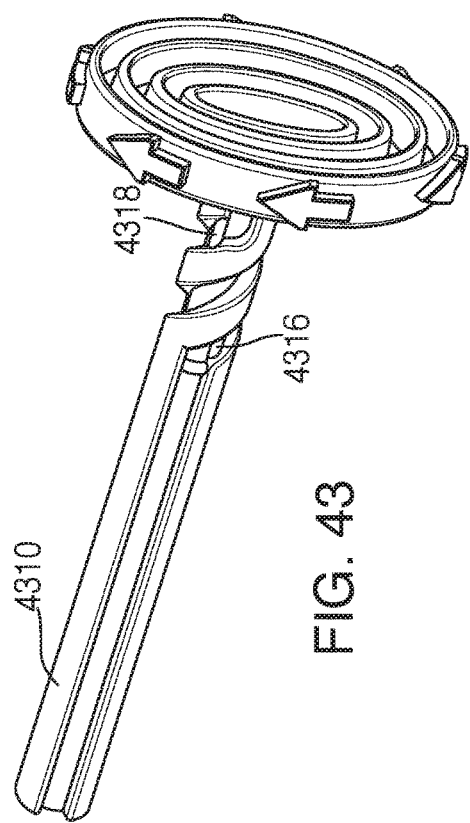
FIG. 43 is a perspective view of apparatus in accordance with the principles of the invention.

FIG. 43 shows illustrative plunger rod 4310. Rod 4310 may include first operational trigger 4316. Rod 4310 may show final stage delivery trigger 4318.

FIG. 43A shows illustrative helical tract 4322 and longitudinal tract 4324. Helical tract 4322 may support final stage delivery trigger 4318 adjacent to longitudinal tract 4324. Longitudinal tract 4324 may terminate proximally at terminal surface 4312.

Figure 44:
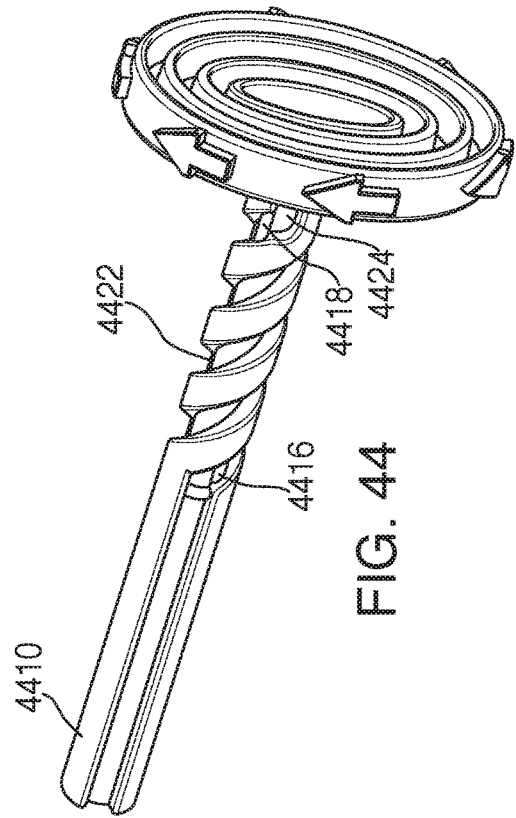
FIG. 44 is a perspective view of apparatus in accordance with the principles of the invention.

FIG. 44 shows illustrative rod 4410. Rod 4410 may include first operational trigger 4416 and final stage delivery trigger 4418. Helical tract 4422 may support final stage delivery trigger 4418 adjacent to longitudinal tract 4444. Helical tract 4422 may have a longitudinal span that is longer than that of helical tract 4322 (shown in FIG. 43A). A longer longitudinal span may provide for more expansive pre-delivery functionality, such as priming, mixing or both priming and mixing.

Figure 45:
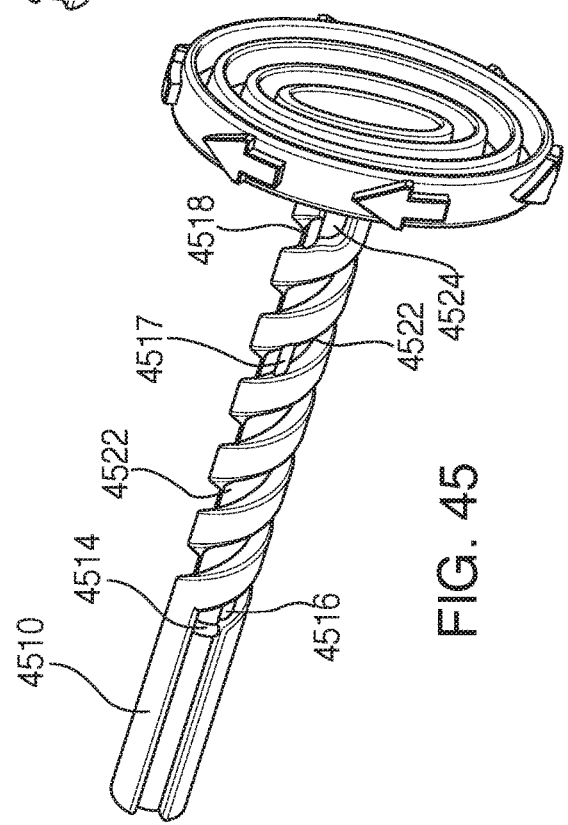
FIG. 45 is a perspective view of apparatus in accordance with the principles of the invention.

FIG. 45 shows illustrative plunger rod 4510. Plunger rod 4510 may include first operational trigger 4516 and final stage delivery trigger 4518. Plunger rod 4510 may include helical tract 4522. Helical tract 4522 may support final stage delivery trigger 4518 adjacent to longitudinal tract 4524. Helical tract 4522 may support intermediate trigger 4517. In operation, trigger 4517 may provide indication of the end of a pre-delivery function, such as mixing, and the beginning of a later pre-delivery function, such as priming.

FIG. 46 shows illustrative plunger rod 4610. Rod 4610 may include first operational trigger 4616. Rod 4610 may include final stage delivery trigger 4618. Rod 4610 may include helical tract 4622 and longitudinal tract 4624. Helical tract 4622 may support final stage delivery trigger 4618 adjacent to longitudinal tract 4624.

FIG. 47 shows illustrative plunger rod 4710. Rod 4710 may include first operational trigger 4716. Rod 4710 may include final stage delivery trigger 4718. Rod 4710 may include helical tract 4722. Helical tract 4722 may support final stage delivery trigger 4718 adjacent to longitudinal tract 4724. Helical tract 4722 may have a longitudinal span that is shorter than that of helical tract 4622 (shown in FIG. 46). A short span may provide for delivery of medicaments that do not require mixing or extensive priming.

FIG. 48 shows illustrative plunger rod 4810. Rod 4810 may include first operational trigger 4816. Rod 4810 may include final stage delivery trigger 4818. Rod 4810 may include helical tract 4822. Helical tract 4822 may support final stage delivery trigger 4818 adjacent to longitudinal tract 4824. Helical tract 4822 may have a higher pitch (each revolution corresponding to a greater longitudinal translation) than that of helical tract 4622 (shown in FIG. 46).

FIG. 49 shows illustrative plunger rod 4910. Rod 4910 may include first operational trigger 4916. Rod 4910 may include final stage delivery trigger 4918. Rod 4910 may include helical tract 4922. Helical tract 4922 may support final stage delivery trigger 4918 adjacent to longitudinal tract 4924. Helical tract 4922 may include a distal portion that has a higher pitch than that of a proximal portion (closer than is the distal portion to final stage delivery trigger 4918).

FIG. 50 shows illustrative plunger rod 5010. Rod 5010 may include first operational trigger 5016. Rod 5010 may include final stage delivery trigger 5018. Rod 5010 may include longitudinal tract 50101. Rod 5010 may include longitudinal tract 5024. Longitudinal tract 50101 may be circumferentially displaced relative to longitudinal tract 5024. Circumferential tract 5007 may bridge circumferentially between longitudinal tract 50101 and longitudinal tract 5024. Longitudinal tract 50101 may support intermediate trigger 5017 adjacent to circumferential tract 5007. Circumferential tract 5007 may support final stage delivery trigger 5018 adjacent to longitudinal tract 5024. Tract 50101 may be used to provide one or more pre-delivery functions. Circumferential tract 5007 may provide for transition from pre-delivery functions to delivery functions provided by longitudinal tract 5024.

FIG. 51 shows illustrative plunger rod 5110. Rod 5110 may include first operational trigger 5116. Rod 5110 may include final stage delivery trigger 5118. Rod 5110 may include longitudinal tract 51101. Rod 5110 may include longitudinal tract 5124. Longitudinal tract 51101 may be circumferentially displaced relative to longitudinal tract 5124. Circumferential tract 5107 may bridge circumferentially between longitudinal tract 51101 and longitudinal tract 5124. Longitudinal tract 51101 may support intermediate trigger 5117 adjacent to circumferential tract 5107. Circumferential tract 5107 may support final stage delivery trigger 5118 adjacent to longitudinal tract 5124. Tract 51101 may be used to provide one or more pre-delivery functions. Circumferential tract 5107 may provide for transition from pre-delivery functions to delivery functions provided by longitudinal tract 5124. Longitudinal tract 51101 may have a longitudinal span that is shorter than that of longitudinal tract 50101 (shown in FIG. 50). A short span may provide for delivery of medicaments that do not require mixing or extensive priming.

FIG. 52 shows illustrative plunger rod 5210. Rod 5210 may include first operational trigger 5216. Rod 5210 may include final stage delivery trigger 5218. Rod 5210 may include longitudinal tract 52101. Rod 5210 may include longitudinal tract 5224. Longitudinal tract 52101 may be circumferentially displaced relative to longitudinal tract 5224. Circumferential tract 5207 may bridge circumferentially between longitudinal tract 52101 and longitudinal tract 5224. Longitudinal tract 52101 may support first intermediate trigger 5217a. Longitudinal tract 52101 may support first intermediate trigger 5217b. Longitudinal tract 52101 may support second intermediate trigger 5217b adjacent to circumferential tract 5207. Longitudinal tract 52101 may support first intermediate trigger 5217a proximal to second intermediate trigger 5217b.

Circumferential tract 5207 may support final stage delivery trigger 5218 adjacent to longitudinal tract 5224. Tract 52101 may be used to provide one or more pre-delivery functions. Circumferential tract 5207 may provide for transition from pre-delivery functions to delivery functions provided by longitudinal tract 5224.

In operation, first intermediate trigger 5217a may provide indication of the end of a pre-delivery function, such as mixing, and the beginning of a later pre-delivery function, such as priming. In operation, second intermediate trigger 5217b may provide indication of the end of the later pre-delivery function.

FIG. 53 shows illustrative plunger rod 5310. Rod 5310 may include first operational trigger 5316. Rod 5310 may include final stage delivery trigger 5318. Rod 5310 may include longitudinal tract 53101. Rod 5310 may include longitudinal tract 5324. Longitudinal tract 53101 may be circumferentially displaced relative to longitudinal tract 5324. Circumferential tract 5307 may bridge circumferentially between longitudinal tract 53101 and longitudinal tract 5324. Longitudinal tract 53101 may support intermediate trigger 5317 adjacent to circumferential tract 5307. Circumferential tract 5307 may support final stage delivery trigger 5318 adjacent to longitudinal tract 5324. Longitudinal tract 5324 may have a longitudinal span that is greater than that of longitudinal tract 5124 (shown in FIG. 51). Longer longitudinal span of a longitudinal tract proximal to a final stage delivery trigger may provide longer delivery stroke. Longer longitudinal span of a longitudinal tract proximal to a final stage delivery trigger may provide delivery of a larger target amount of medicament.

Figure 54:
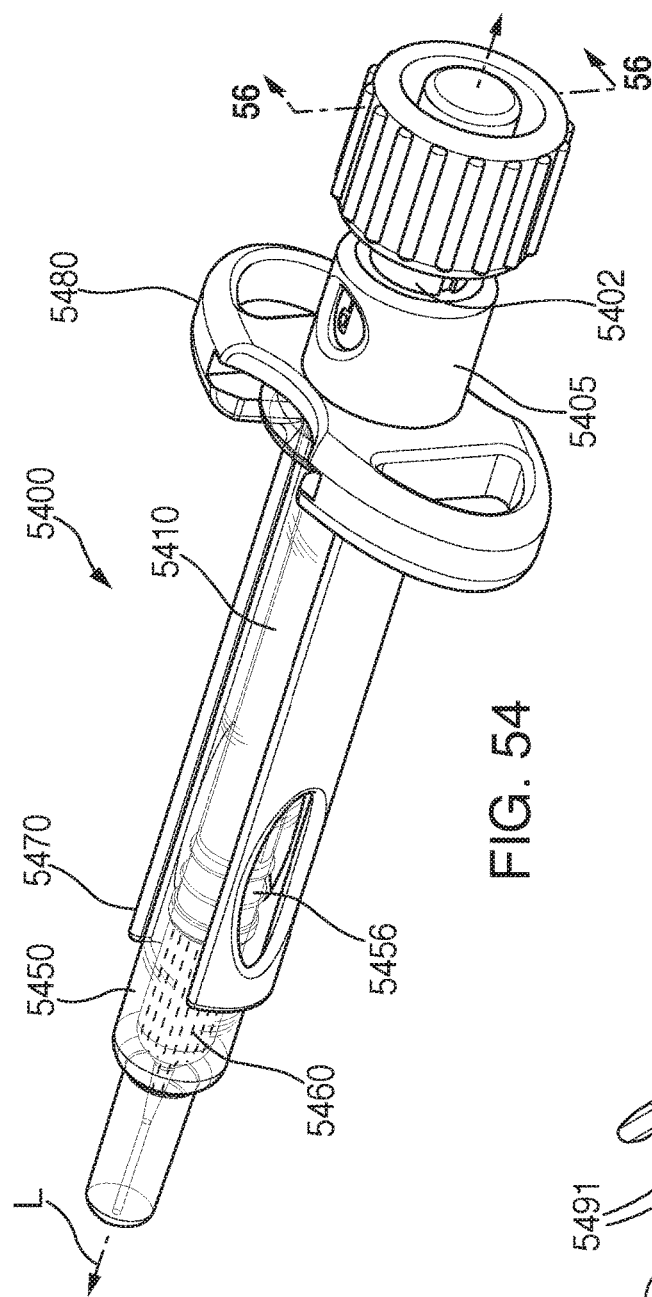
FIG. 54 is a perspective view of apparatus in accordance with the principles of the invention.

FIG. 54 shows illustrative delivery device 5400. Delivery device 5400 may have one or more features in common with one or more of devices 100 (shown in FIG. 1), 1500 (shown in FIG. 15), 2500 (shown in FIG. 25) and 2800 (shown in FIG. 28). Delivery device 5400 may include knob 5402, collar 5405, finger flange 5480, housing 5470, medicament container 5450, medicament 5460, plunger rod 5410 and plunger 5456.

Delivery device 5400 may define longitudinal axis L. Delivery device 5400 is shown in a state that may be a pre-operational state. In the pre-operational state, delivery device 5400 may be fully assembled. In the pre-operational state, delivery device 5400 may be prepared for priming. In the pre-operational state, delivery device 5400 may be prepared for preparation of medicament for discharge. In the pre-operational state, delivery device 5400 may be prepared for discharge of medicament. In the pre-operational state, discharge of medicament from delivery device 5400 may not have begun.

Knob 5402 may be disposed coaxially with axis L.

Rod 5410 may be disposed coaxially with axis L. Rod 5410 may be a component of a mixing configuration (not shown). Knob 5402 may be threadingly attached to rod 5410.

Container 5450 may be a component of a mixing configuration (not shown). Container 5450 may be disposed coaxially with axis L. Container 5450 may be cylindrical, partially cylindrical or have any other suitable form. A distal portion of rod 5410 may be disposed within container 5450.

Container 5450 may contain medicament component 5460. Container 5450 may be engaged with plunger 5456. A distal end of rod 5410 may abut a proximal surface of plunger 5456.

Housing 5470 may be disposed coaxially with axis L. Housing 5470 may be cylindrical, partially cylindrical or have any other suitable form.

Finger flange 5480 may be separate from housing 5470. Finger flange 5480 may be attached to housing 5470. Finger flange 5480 may be integral to housing 5470.

Collar 5405 may be disposed coaxially with axis L. Collar 5405 may be cylindrical, partially cylindrical or have any other suitable form. Collar 5405 may be attached to finger flange 5480. Collar 5405 may be integral to finger flange 5480. Collar 5405 may be attached to housing 5470. Collar 5405 may be integral to housing 5470.

Figure 54A:
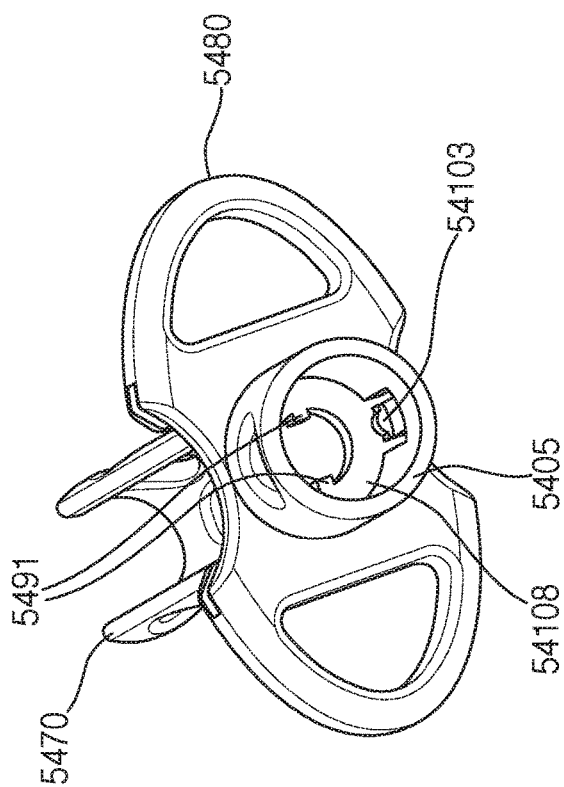
FIG. 54A is a perspective view of apparatus in accordance with the principles of the invention.

FIG. 54A shows a view of part of the interior of collar 5405. Collar 5405 may include anti-rotation projections 5491, which may include one, two or more anti-rotation projections. Collar 5405 may include bearing surface 54108. Knob 5405 may include one or more tangs such as tang 54103.

Figure 55:
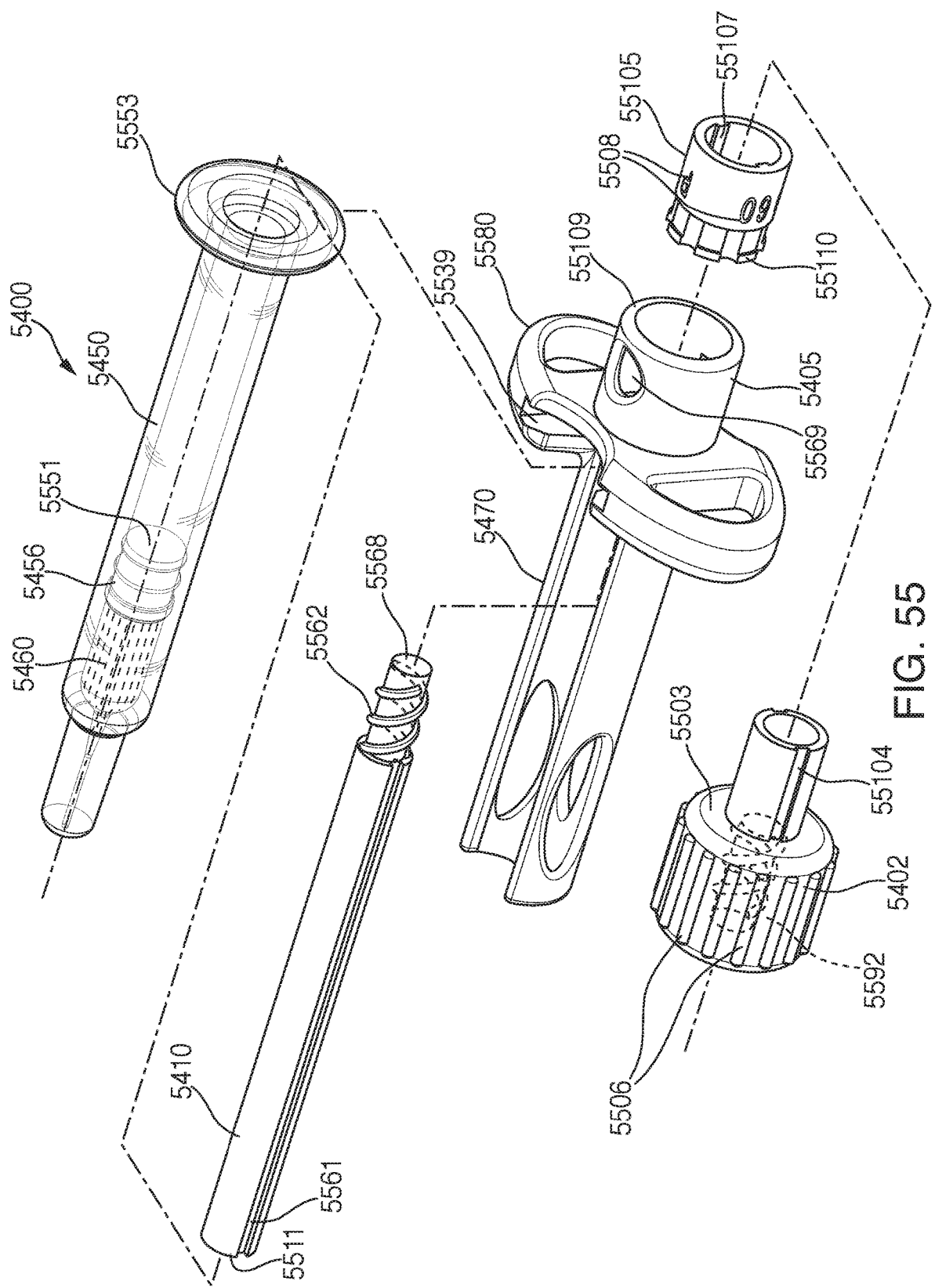
FIG. 55 is an exploded, perspective view of the apparatus shown in FIG. 54.

FIG. 55 shows features of delivery device 5400. FIG. 55 shows knob 5402. Knob 5402 may contain threads 5592 (shown in phantom) internal to knob 5402. Knob 5402 may support abutment surface 5503. Knob 4502 may a include keyway, such keyway 55104, which may be one of numerous keyways. Keyway 55104 may include a slot.

Knob 5402 may include turn ridges 5506. Turn ridges 5506 may be utilized by the operator to effect rotation of knob 5402 about axis L.

Turn ridges 5506 may be spaced circumferentially around knob 5402. Turn ridges 5506 being spaced regularly about the circumference of knob 5402 may provide the operator a measure of an extent of rotation performed.

Distal rod end 5511 may define a distal end of anti-rotation slot 5561. Anti-rotation slot 5561 may be parallel to axis L. Distal rod end 5511 may include one or more additional anti-rotation slots or features (not shown) distributed about the circumference of rod 5410 in a regular or irregular manner. Anti-rotation slot 5561 may extend all or some of the way proximally to threads 5562. Threads 5562 may extend proximally some or all of the way to proximal rod end 5568. Threads 5562 may engage threads 5592 of knob 5402.

Container 5450 may be disposed in device 5400 distal to finger flange 5480. Container 5450 may be disposed in housing 5470 distal to finger flange 5480. Proximal rim 5553 of container 5450 surrounding a proximal opening of container 5450 may be recessed in device 5400 distal to finger flange 5480. Proximal rim 5553 of container 5450 may be recessed in device 5400. Device 5400 may include recess 5539. Recess 5539 may receive rim 5553.

Knob 5402 may be disposed coaxially within collar 5405. Collar 5405 may include viewing window 5569. Collar 5405 may support index surface 55109.

Device 5400 may include indicator sleeve 55105. Sleeve 55105 may be disposed coaxially within collar 5405. Knob 5402 may be disposed coaxially within sleeve 55105. Sleeve 55105 may include signage 5508. Signage 5508 may be visible through window 5569.

Sleeve 55105 may include one or more keys such as key 55107. Key 55107 may be a rail. Key 55107 may engage keyway 55104. Engagement of key 55107 and keyway 55104 may rotationally engage sleeve 55105 with knob 5402. Sleeve 55105 may support one or more teeth such as tooth 55110. Tooth 55110 may engage tang 54103 (shown in FIG. 54A) to retain sleeve 55105 within collar 5405. Engagement of tang 54103 and tooth 55110 may retain tooth 55105 against bearing surface 55108 (shown in FIG. 54A).

Rod 5410 may be contained in container 5450 with distal end 5511 abutting plunger proximal face 5551. Proximal rod end 5568 may extend proximally into collar 5405. Proximal rod end 5568 may extend proximally into sleeve 55105.

Knob 5402 may extend distally into sleeve 55105 to threadingly engage rod 5410. Knob 5402 may extend distally into collar 5405 to threadingly engage rod 5410.

FIG. 56 shows a cross-sectional view along view lines 56-56 (shown in FIG. 54). FIG. 56 shows device 5400 in a pre-operational state. In the pre-operational state, device 5400 may be ready for priming. X shows the distance away from index surface 55109. Abutment surface 5503 may be at a position $x_0$ from index surface 55109. Rod 5410 may abut plunger 5456 within container 5450. Distal plunger face 5457 may seal medicament 5460 within container 5450.

Y shows the distance away from container inflection point 5693. Distal face 5657 may be disposed at a distance $y_0$ from inflection point 5693 near a distal end of container 5450. Inflection point 5693 is at a distal termination of a constant diameter of container 5450 and illustrates an arbitrary reference point along an inner sidewall of container 5450 to show how medicament discharge is proportional to movement of other elements of the device. Distal to inflection point 5630, the sidewall of container 5430 may include shoulder 56100.

When knob 5402 is displaced longitudinally along direction B into collar 5405, abutment surface 5503 will move to position $x_1$ and will abut index surface 55109, thus priming device 5400.

FIG. 57 shows abutment surface 5503 abutting index surface 55109. The device is now in a post-priming, pre-delivery state. Distal face 5657 has been displaced from position $y_0$ to position $y_1$ and has advanced medicament 5460 out of the distal end of device 5400. Knob 5402 may now be rotated in direction C. Projection 5491 may rotationally retain rod 5410. Projection 5491 may rotationally retain rod 5410 by interference with slot 5561. As such, rotation of knob 5402 causes knob 5403 to back away from index surface 55109.

FIG. 58 shows knob 5402 backed-off from index surface 55109 so that abutment surface 5503 is positioned at $x_2$. Distal face 5657 remains at position $y_1$ (indicated also as $y_2$ to show that $y_2$ corresponds to the state of the device when abutment surface 5503 is at $x_2$). Sleeve 55105 may rotate in tandem with knob 5402, thus moving signage 5508 to show a different portion of signage 5508 (shown in FIG. 55) through window 5569 (shown in FIG. 55). The portion of signage 5508 that is visible through window 5569 may indicate a target amount of medicament to be delivered by longitudinal movement of knob 5402 in direction B.

When knob 5402 is displaced longitudinally along direction B into collar 5405, abutment surface 5503 will move to position $x_1$ and will abut index surface 55109, thus priming device 5400.

FIG. 59 shows device 5400 in a post-delivery state. Abutment surface 5503 may abut index surface 55109 at position $x_3$ (which coincides with the position of abutment surface 5503 at the end of priming). Distal face 5657 has been displaced to position $y_3$ and has advanced the target amount of medicament 5460 out of the distal end of device 5400.

Figure 60:
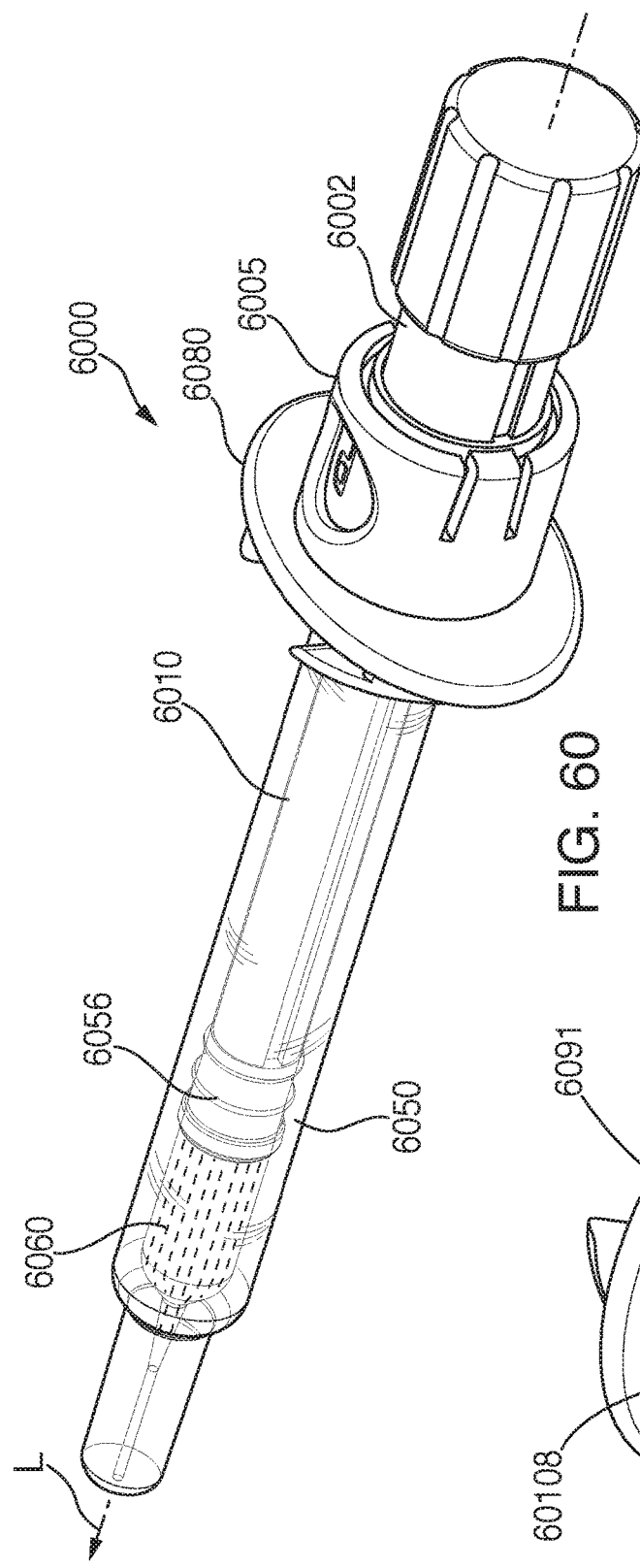
FIG. 60 is a perspective view of apparatus in accordance with the principles of the invention.

FIG. 60 shows illustrative delivery device 6000. Delivery device 6000 may have one or more features in common with one or more of devices 100 (shown in FIG. 1), 1500 (shown in FIG. 15), 2500 (shown in FIG. 25), 2800 (shown in FIG. 28) and 5400 (shown in FIG. 54). Delivery device 6000 may include knob 6002, collar 6005, finger flange 6080, medicament container 6050, medicament 6060, plunger rod 6010 and plunger 6056.

Delivery device 6000 may define longitudinal axis L. Delivery device 6000 is shown in a state that may be a pre-operational state. In the pre-operational state, delivery device 6000 may be fully assembled. In the pre-operational state, delivery device 6000 may be prepared for pre-delivery functions that may include priming. In the pre-operational state, delivery device 6000 may be prepared for preparation of medicament for discharge. In the pre-operational state, delivery device 6000 may be prepared for discharge of medicament. In the pre-operational state, discharge of medicament from delivery device 6000 may not have begun.

Knob 6002 may be disposed coaxially with axis L.

Rod 6010 may be disposed coaxially with axis L. Rod 6010 may be a component of a mixing configuration (not shown). Knob 6002 may be threadingly attached to rod 6010.

Container 6050 may be a component of a mixing configuration (not shown). Container 6050 may be disposed coaxially with axis L. Container 6050 may be cylindrical, partially cylindrical or have any other suitable form. A distal portion of rod 6010 may be disposed within container 6050.

Container 6050 may contain medicament component 6060. Container 6050 may be engaged with plunger 6056. A distal end of rod 6010 may abut a proximal surface of plunger 6056.

Collar 6005 may be disposed coaxially with axis L. Collar 6005 may be cylindrical, partially cylindrical or have any other suitable form. Collar 6005 may be attached to finger flange 6080. Collar 6005 may be integral to finger flange 6080.

Figure 60A:
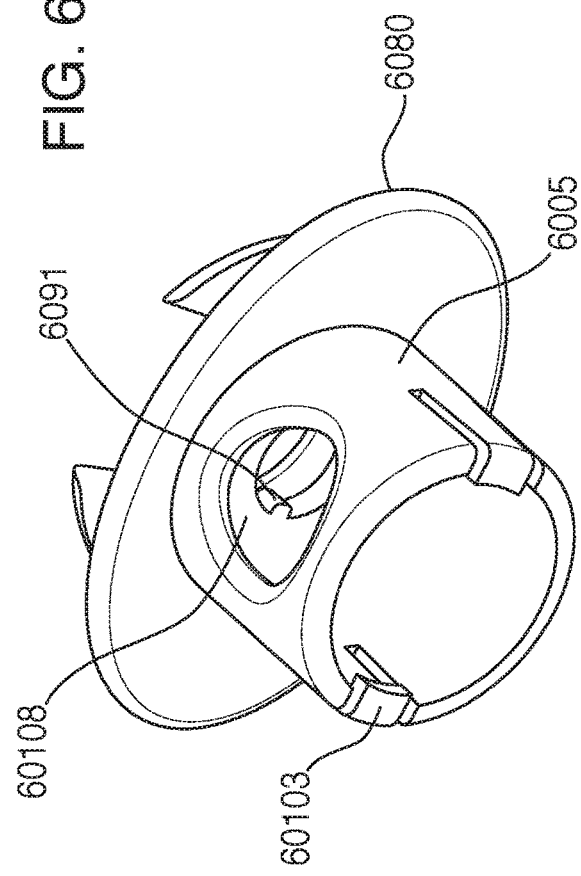
FIG. 60A is a perspective view of apparatus in accordance with the principles of the invention.

FIG. 60A shows a view of part of the interior of collar 6005. Collar 6005 may include one or more anti-rotation projections such as anti-rotation projection 6091. Collar 6005 may include bearing surface 60108. Knob 6005 may include one or more tangs such as tang 60103.

Figure 61:
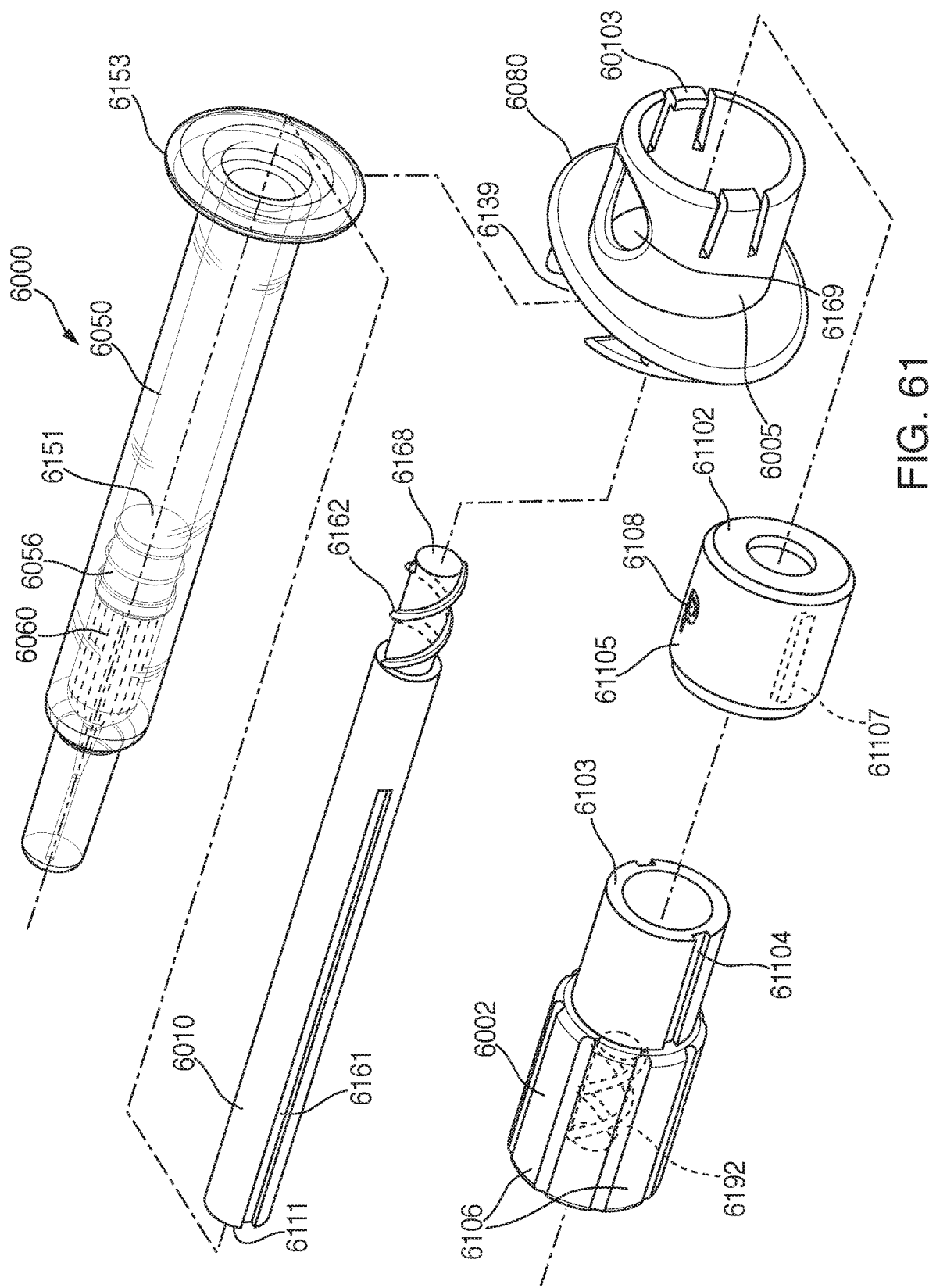
FIG. 61 is an exploded, perspective view of apparatus in accordance with the principles of the invention.

FIG. 61 shows features of delivery device 6000. FIG. 61 shows knob 6002. Knob 6002 may contain threads 6192 (shown in phantom) internal to knob 6002. Knob 6002 may support abutment surface 6103. Knob 4502 may a include keyway, such keyway 61104, which may be one of numerous keyways. Keyway 61104 may include a slot.

Knob 6002 may include turn ridges 6106. Turn ridges 6106 may be utilized by the operator to effect rotation of knob 6002 about axis L.

Turn ridges 6106 may be spaced circumferentially around knob 6002. Turn ridges 6106 being spaced regularly about the circumference of knob 6002 may provide the operator a measure of an extent of rotation performed.

Distal rod end 6111 may define a distal end of anti-rotation slot 6161. Anti-rotation slot 6161 may be parallel to axis L. Distal rod 6110 may include one or more additional anti-rotation slots or features (not shown) distributed about the circumference of rod 6010 in a regular or irregular manner. Anti-rotation slot 6161 may extend all or some of the way proximally to threads 6162. Threads 6162 may extend proximally some or all of the way to proximal rod end 6168. Threads 6162 may engage threads 6192 of knob 6002.

Container 6050 may be disposed in device 6000 distal to finger flange 6080. Proximal rim 6153 of container 6050 surrounding a proximal opening of container 6050 may be recessed in device 6000 distal to finger flange 6080. Proximal rim 6153 of container 6050 may be recessed in device 6000. Device 6000 may include recess 6139. Recess 6139 may receive rim 6153.

Knob 6002 may be disposed coaxially within collar 6005. Collar 6005 may include viewing window 6169.

Device 6000 may include indicator sleeve 61105. Sleeve 61105 may be disposed coaxially within collar 6005. Knob 6002 may be disposed coaxially within sleeve 61105. Sleeve 61105 may include signage 6108. Signage 6108 may be visible through window 6169.

Sleeve 61105 may include key 61107 (shown in phantom line). Key 61107 may be a rail. Key 61107 may engage keyway 61104. Engagement of key 61107 and keyway 61104 may rotationally engage sleeve 61105 with knob 6002. Sleeve 61105 may support sleeve distal surface 61102. Sleeve distal surface 61102 may lie against bearing surface 60108 (shown in FIG. 60A). Tang 60103 may retain sleeve 61105 within collar 6005. Engagement of tang 60103 sleeve 61105 may retain sleeve distal surface 61102 against bearing surface 61108.

Rod 6010 may be contained in container 6050 with distal end 6111 abutting plunger proximal face 6151. Proximal rod end 6168 may extend proximally into collar 6005. Proximal rod end 6168 may extend proximally into sleeve 61105. Knob 6002 may extend distally into sleeve 61105 to threadingly engage rod 6010. Knob 6002 may extend distally into collar 6005 to threadingly engage rod 6010.

Figures 62, 63:
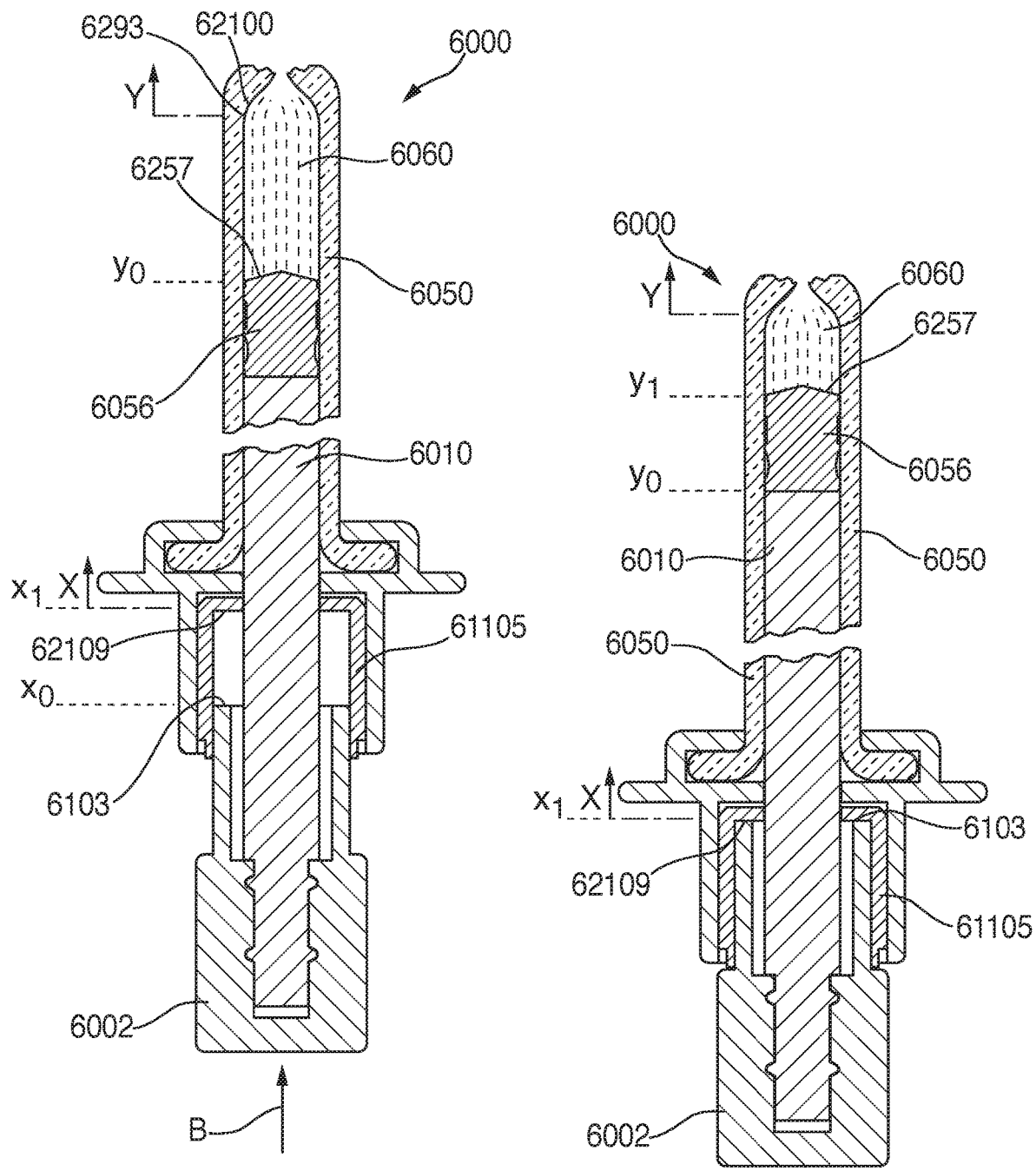
FIG. 62 is a partial cross-sectional view of apparatus in accordance with the principles of the invention.
FIG. 63 is a partial cross-sectional view of apparatus in accordance with the principles of the invention.

FIG. 62 shows a cross-sectional view along view lines 62-62 (shown in FIG. 60). FIG. 62 shows sleeve 61105. Sleeve 61105 may include index surface 62109. Device 6000 may be in a pre-operational state. In the pre-operational state, device 6000 may be ready for pre-delivery functions, which may include priming. X shows the distance away from index surface 62109. Abutment surface 6103 may be at a position $x_0$ from index surface 62109. Rod 6010 may abut plunger 6056 within container 6050. Distal plunger face 6257 may seal medicament 6060 within container 6050.

Y shows the distance away from container inflection point 6293. Distal face 6257 may be disposed at a distance $y_0$ from inflection point 6293 near a distal end of container 6050. Inflection point 6293 is at a distal termination of a constant diameter of container 6050 and illustrates an arbitrary reference point along an inner sidewall of container 6050 to show how medicament discharge is proportional to movement of other elements of device 6000. Distal to inflection point 6230, the sidewall of container 6030 may include shoulder 62100.

When knob 6002 is displaced longitudinally along direction B into collar 6005, abutment surface 6103 will move to position $x_1$ and will abut index surface 62109, thus priming device 6000.

FIG. 63 shows abutment surface 6103 abutting index surface 62109. The device is now in a post-priming, pre-delivery state. Distal face 6257 has been displaced from position $y_0$ to position $y_1$ and has advanced medicament 6060 out of the distal end of device 6000. Knob 6002 may now be rotated in direction C. Projection 6091 may rotationally retain rod 6010. Projection 6091 (shown in FIG. 60A) may rotationally retain rod 6010 by interference with slot 6161 (shown in FIG. 61). As such, the rotation of knob 6002 may cause knob 6002 to back away from index surface 62109.

FIG. 64 shows knob 6002 backed-off from index surface 62109 so that abutment surface 6103 is positioned at $x_2$. Distal face 6257 remains at position $y_1$ (indicated also as $y_2$ to show that $y_2$ corresponds to the state of the device when abutment surface 6103 is at $x_2$). Sleeve 61105 may rotate in tandem with knob 6002, thus moving signage 6108 to show a different portion of signage 6108 (shown in FIG. 61) through window 6169 (shown in FIG. 61). The portion of signage 6108 that is visible through window 6169 may indicate a target amount of medicament to be delivered by longitudinal movement of knob 6002 in direction B.

When knob 6002 is displaced longitudinally along direction B into collar 6005, abutment surface 6103 will move to position $x_1$ and will abut index surface 62109, thus completing pre-delivery functions, such as priming, of device 6000.

FIG. 65 shows device 6000 in a post-delivery state. Abutment surface 6103 may abut index surface 62109 at position $x_3$ (which coincides with the position of abutment surface 6103 at the end of a pre-delivery function, such priming). Distal face 6257 has been displaced to position $y_3$ and has advanced the target amount of medicament 6060 out of the distal end of device 6000.

Figure 66:
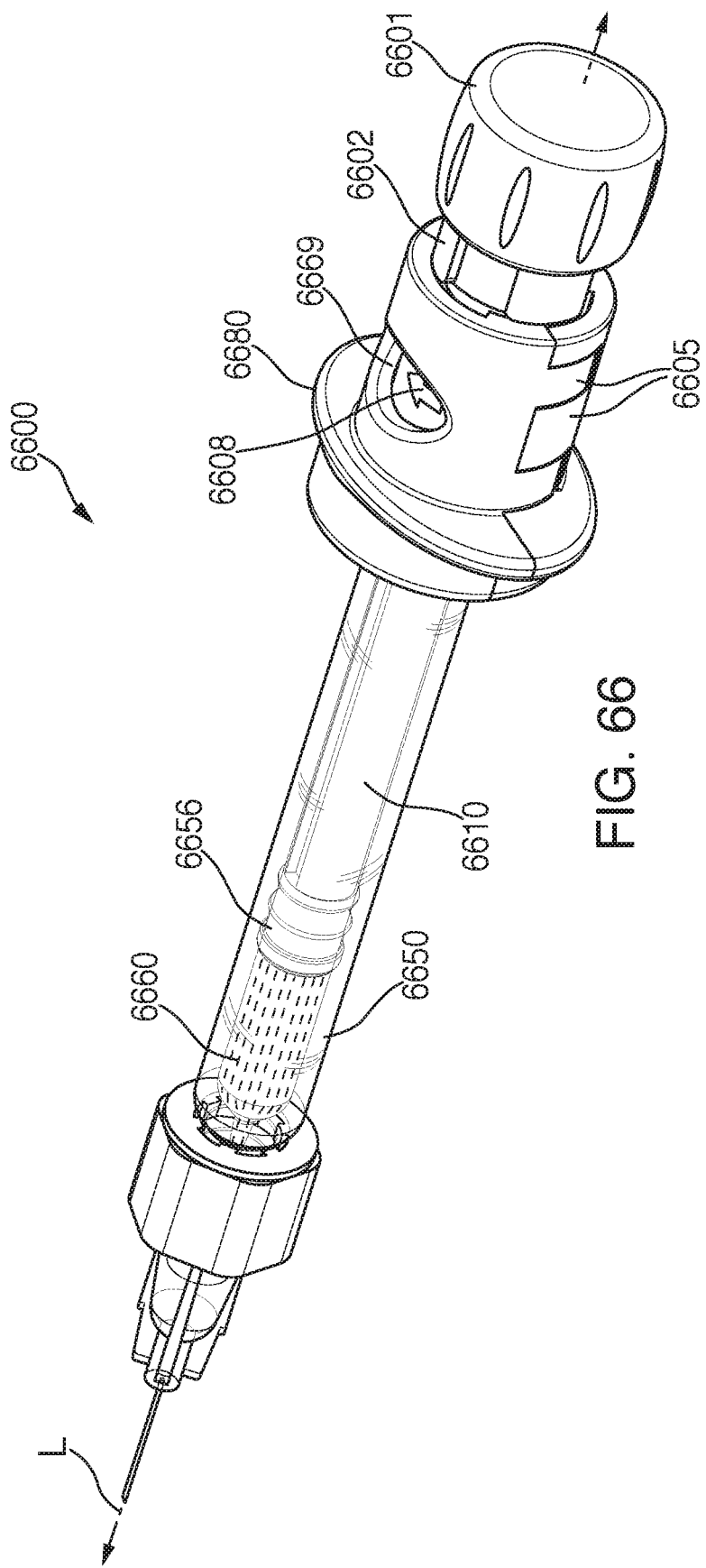
FIG. 66 is a perspective view of apparatus in accordance with the principles of the invention.

FIG. 66 shows illustrative medicament delivery device 6600. Delivery device 6600 may have one or more features in common with one or more of devices 100 (shown in FIG. 1), 1500 (shown in FIG. 15), 2500 (shown in FIG. 25), 2800 (shown in FIG. 28), 5400 (shown in FIG. 54) and 6000 (shown in FIG. 60).

Delivery device 6600 may define longitudinal axis L. Delivery device 6600 is shown in a state that may be a pre-operational state. In the pre-operational state, delivery device 6600 may be fully assembled. In the pre-operational state, delivery device 6600 may be prepared for priming. In the pre-operational state, delivery device 6600 may be prepared for preparation of medicament for discharge. In the pre-operational state, delivery device 6600 may be prepared for discharge of medicament. In the pre-operational state, discharge of medicament from delivery device 6600 may not have begun.

Delivery device 6600 may include proximal knob 6602. Knob 6602 may be disposed coaxial with axis L. Grip 6601 may be provided on knob 6602.

Delivery device 6600 may include plunger rod 6610. Rod 6610 may be a component of a mixing configuration (not shown). Knob 6602 may be threadingly attached to rod 6610.

Delivery device 6600 may include medicament container 6650. Container 6650 may be a component of a mixing configuration (not shown). Container 6650 may be disposed coaxial with axis L. Container 6650 may be cylindrical, partially cylindrical or have any other suitable form. A distal portion of rod 6610 may be disposed within container 6650.

Container 6650 may contain medicament component 6660. Container 6650 may be engaged with plunger 6656. A distal end of rod 6610 may abut a proximal surface of plunger 6656.

Delivery device 6600 may include finger flange 6680.

Delivery device 6600 may include collar 6605. Collar 6605 may be disposed coaxial with axis L. Collar 6605 may be cylindrical, partially cylindrical or have any other suitable form. Collar 6605 may be attached to finger flange 6680. Collar 6605 may be integral to finger flange 6680. Collar 6605 may include window 6669. Knob 6602 may be concentrically disposed within collar 6605. Knob 6602 may include signage 6608. Signage 6608 may be visible through window 6669.

Figure 67:
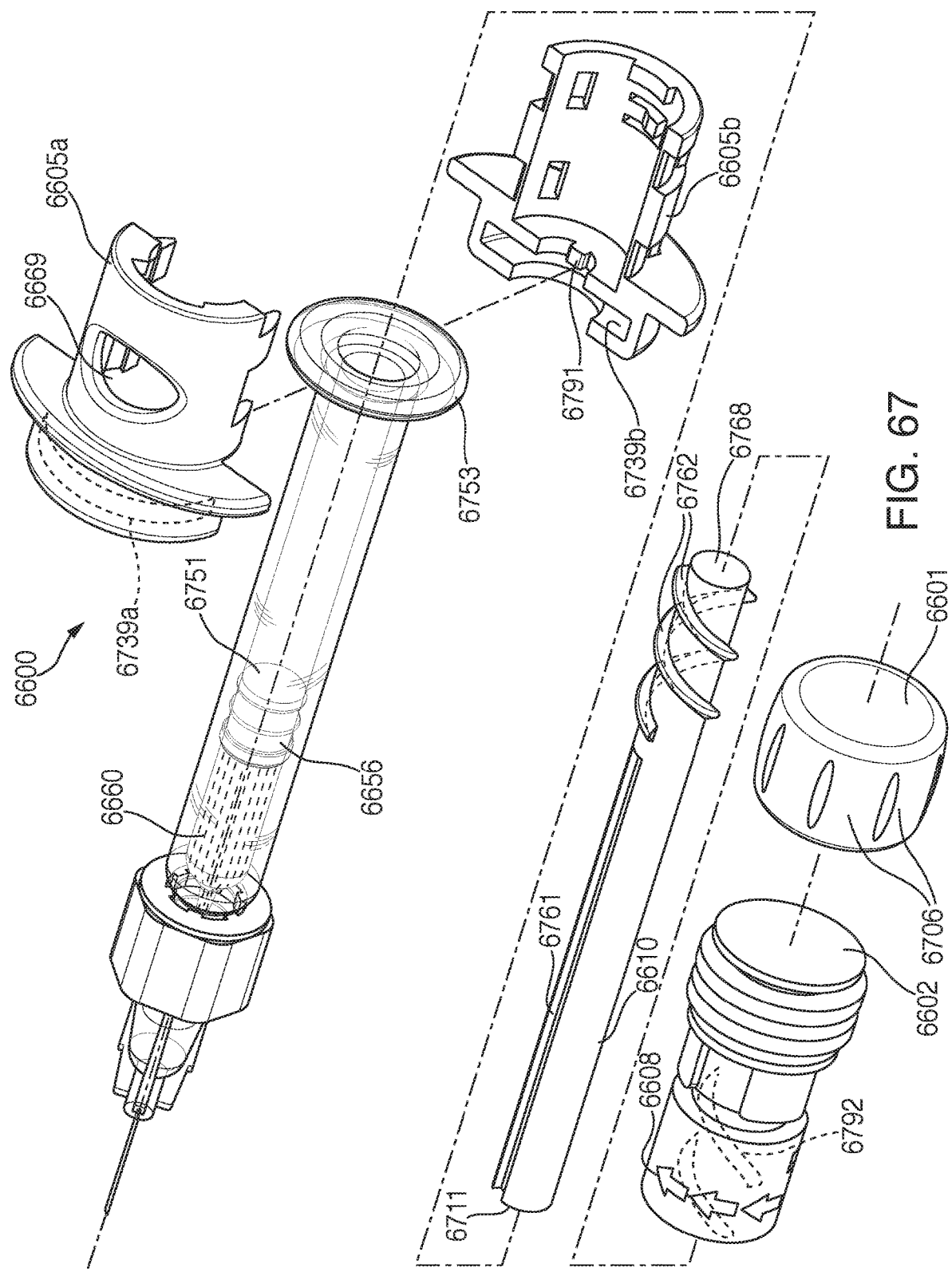
FIG. 67 is an exploded, perspective view of apparatus in accordance with the principles of the invention.

FIG. 67 shows features of delivery device 6600. FIG. 67 shows knob 6602. Knob 6602 may contain threads 6792 (shown in phantom) internal to knob 6602.

Grip 6601 may contribute to traction on knob 6602 for effecting longitudinal translation of rod 6610. Grip 6601 may contribute to ergonomic finger contact of the operator with knob 6602 for effecting longitudinal translation of rod 6610. The finger contact with knob 6602 through grip 6601 may conduct tactile feedback to the operator of an extent of distal longitudinal translation of rod 6610 along axis L.

Grip 6601 may include turn ridges 6706. Turn ridges 6706 may be utilized by the operator to effect rotation of knob 6602 about axis L. Turn ridges 6706 may contribute to traction on knob 6602 for effecting translation of rod 6610. Turn ridges 6706 may contribute to ergonomic finger contact of the operator with knob 6602 for effecting translation of rod 6610 through rotation of knob 6602. The finger contact with turn ridges 6706 may conduct tactile feedback to the operator of an extent of translation of rod 6610 along axis L.

Turn ridges 6706 may be spaced circumferentially around knob 6602. Turn ridges 6706 may be spaced regularly around a circumference of grip 6601. Turn ridges 6706 being spaced regularly about the circumference of grip 6601 may provide the operator a measure of an extent of rotation performed.

Signage 6608 may include turn-direction signage. Knob 6602 may include turn direction signage. In the operational state, delivery device 6600 may effect distal displacement of rod 6610 within container 6650 in response to rotation of knob 6602 about axis L in only one of two rotational directions. Signage 6708 may provide the operator with cues as to an effective rotational direction. The cues may serve as reminders before and/or during the operational state. The cues may be visual. The cues may be tactile.

As depicted, the effective rotational direction for distal displacement of rod 6610 within container 6650 in response to rotation of knob 6602 about axis L may be clockwise for delivery device 6600. (For some embodiments, not shown, counter-clockwise rotation may the effective rotational direction. For some embodiments, turn direction signage may provide cues for counter-clockwise rotation.)

Distal rod end 6711 may define a distal end of anti-rotation slot 6761. Anti-rotation slot 6761 may be parallel to axis L. Distal rod end 6711 may include one or more additional anti-rotation slots or features (not shown) distributed about the circumference of rod 6610 in a regular or irregular manner. Anti-rotation slot 6761 may extend all or some of the way proximally to threads 6762. Threads 6762 may extend proximally some or all of the way to proximal rod end 6768. Threads 6762 may engage threads 6792 of knob 6602.

Container 6650 may be disposed in device 6600. Proximal rim 6753 of container 6650 surrounding a proximal opening of container 6650 may be recessed in device 6600. Container 6650 may include container component 6650a and container component 6650b. Container components 6650a and 6650b may be displaced toward each other transversely relative to axis L to enclose rim 6753 within recesses 6739a and 6739b (shown in phantom).

Rod 6610 may be contained in container 6650 with distal end 6711 abutting plunger proximal face 6751. Proximal rod end 6768 may extend proximally into collar 6605. Knob 6602 may extend distally into collar 6605 to threadingly engage rod 6610.

Collar 6605 may include one or more anti-rotation projections such anti-rotation projection 6791. Anti-rotation projection 6791 may extend into anti-rotation slot 6761. A corresponding anti-rotation slot and anti-rotation projection may be engaged on the opposite side of rod 6610. Engagement of one or more of the projections in one or more of the slots may operationally prevent rotation of rod 6610.

With rotation of rod 6610 prevented by interaction of rod 6610 and projection 6791 and with knob 6602 being threadingly engaged with rod 6610, rotation of knob 6602 may displace rod 6610 axially.

Figure 68:
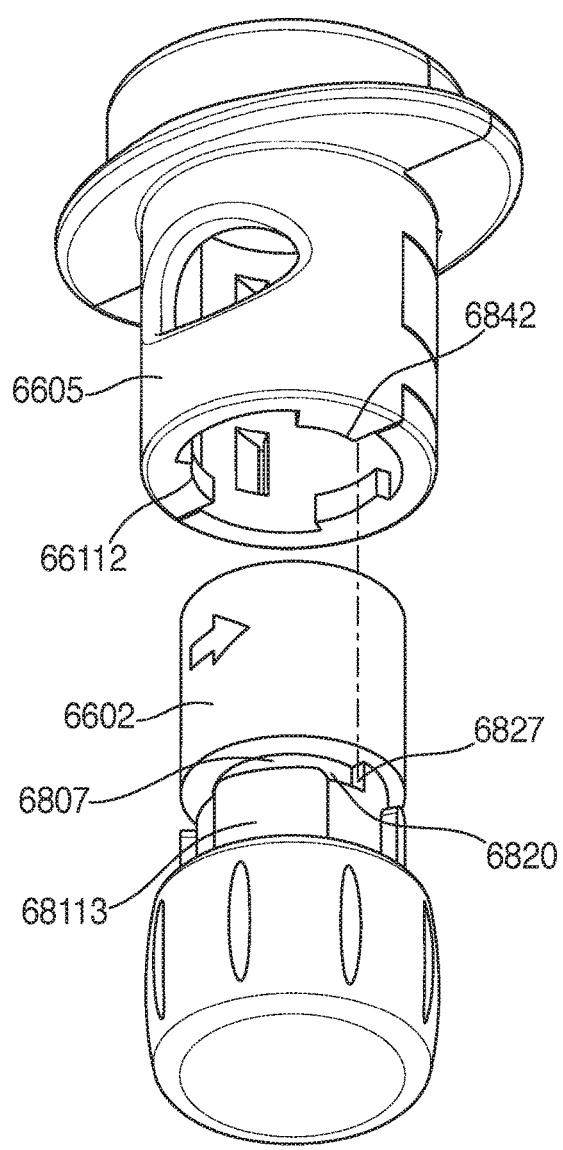
FIG. 68 is an exploded, perspective view of apparatus in accordance with the principles of the invention.

FIG. 68 shows collar 6605. Collar 6605 may include boss 6842. Boss 6842 may be disposed on an interior portion of collar 6605. Boss 6842 may include a tab that extends radially inward. Collar 6605 may include one or more auxiliary tabs such as auxiliary tab 68112. Auxiliary tab 68112 may be disposed interior collar 6605. Auxiliary tab 68112 may extend radially inward. Boss 6842 may extend radially inward farther than does auxiliary tab 68112.

Knob 6602 may include operational track 6820. Operational track 6820 may begin at lateral surface 6827. Operational track 6820 may include annular tract 6807. Knob 6602 may include one or more circumferential plateaus such as circumferential plateau 68113. Circumferential plateau 68113 may extend radially outward.

When assembled, lateral surface 6827 may be circumferentially aligned with boss 6842 (as shown by a broken line). Boss 6842 may be engaged with annular tract 6807. Engagement of boss 6842 with annular tract 6807 may operationally prevent longitudinal motion of knob 6602 relative to collar 6605. Circumferential plateau 68113 may be engaged with boss 6842. Circumferential plateau 68113 may be engaged with auxiliary tab 68112. Engagement of circumferential plateau 68113 with annular tract 6807 may operationally prevent longitudinal motion of knob 6602 relative to collar 6605. Engagement of circumferential plateau 68113 with auxiliary tab 68112 may operationally prevent longitudinal motion of knob 6602 relative to collar 6605.

Figure 69:
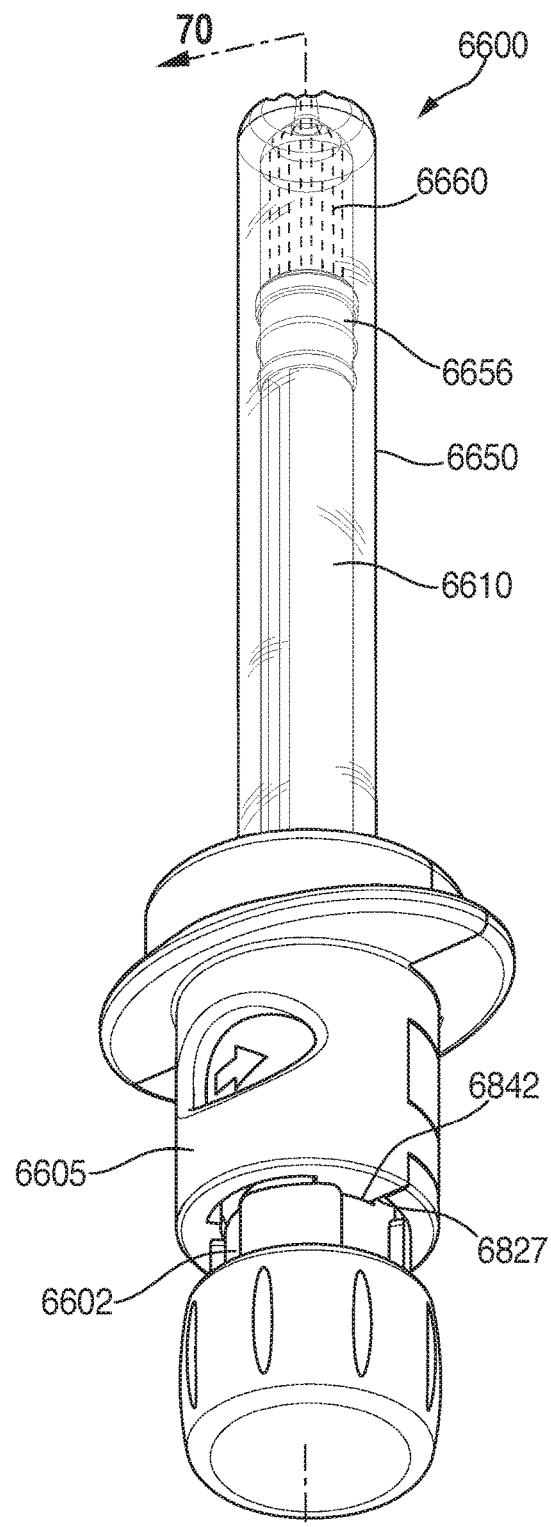
FIG. 69 is a perspective view of apparatus in accordance with the principles of the invention.

FIG. 69 shows device 6600 assembled in a pre-operational state, in an orientation corresponding to that shown in FIG. 68, with lateral surface 6827 circumferentially aligned with boss 6842.

Figures 70, 70A:
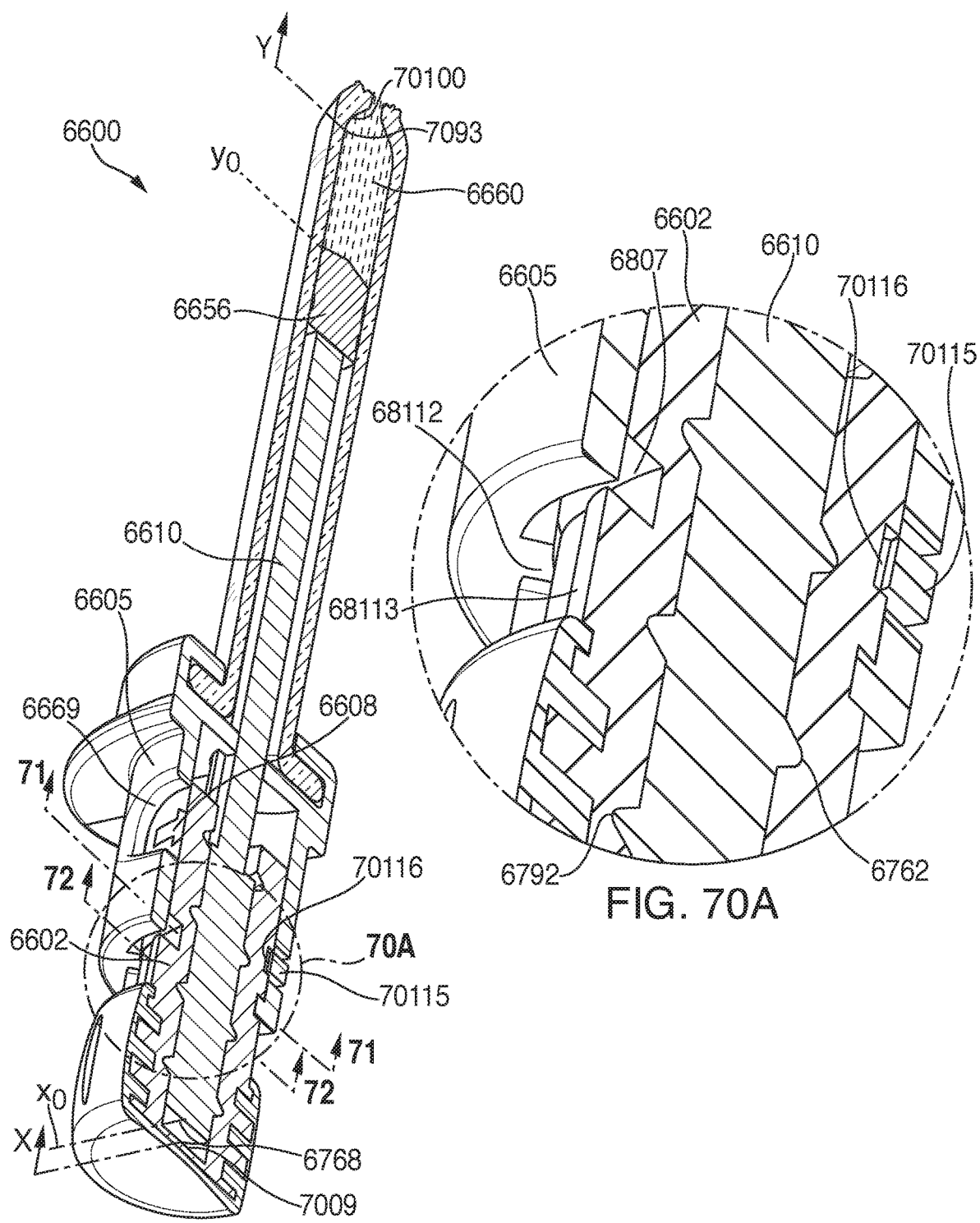
FIG. 70 is a partial cross-sectional, perspective view of the apparatus shown in FIG. 69, the view taken along lines 70-70 (shown in FIG. 69)
FIG. 70A is an enlarged detail of the apparatus shown in FIG. 70.

FIG. 70 is a cross-sectional view taken along view lines 70-70 (shown in FIG. 69). FIG. 70 shows rod 6610 coaxially disposed within knob 6602. Knob 6602 is concentric to collar 6605. Knob 6602 may extend into collar 6605. X shows the distance away from interior knob surface 7009 of proximal rod end 6768. Proximal rod end 6768 may be at a position $x_0$ from interior surface 9009. Rod 6610 may abut plunger 6656 within container 6650. Distal plunger face 7057 may seal medicament 8360 within container 6650.

Y shows the distance away from container inflection point 7093 of distal plunger face 7057. Distal face 7057 may be disposed at a distance $y_0$ from inflection point 7093 near a distal end of container 6650. Inflection point 7093 is at a distal termination of a constant diameter of container 6650 and illustrates an arbitrary reference point along an inner sidewall of container 6605 to show how medicament discharge is proportional to movement of other elements of the device. Distal to inflection point 7093, the sidewall of container 6650 may include shoulder 70100. Window 6669 may reveal a portion of signage 6608. The portion may indicate that medicament preparation functions such as priming has not yet begun.

Collar 6605 may include retaining clip 70115. Knob 6602 may include clip dock 70116. In the pre-operational state, retaining clip 70115 may be circumferentially aligned with clip dock 70116. Retaining clip 70115 may be engaged with clip dock 70116. Engagement of retaining clip 70115 with clip dock 70116 may block knob 6602 from inadvertent rotation relative to collar 6605 prior to operation.

FIG. 70A shows details of the view of device 6600 shown in FIG. 70. FIG. 70A shows rod 6610 within knob 6602, which is within collar 6605. Rod thread 6762 may be engaged with knob thread 6792. Annular tract 6807 may be disposed radially inward from collar 6605. Circumferential plateau 68113 may be disposed proximal to annular tract 6807 in the view provided by FIG. 70. Auxiliary tab 68112 may be disposed circumferentially away from plateau 68113 at the pre-operational state depicted. Retaining clip 70115 is shown engaged with clip dock 70116.

Figure 71:
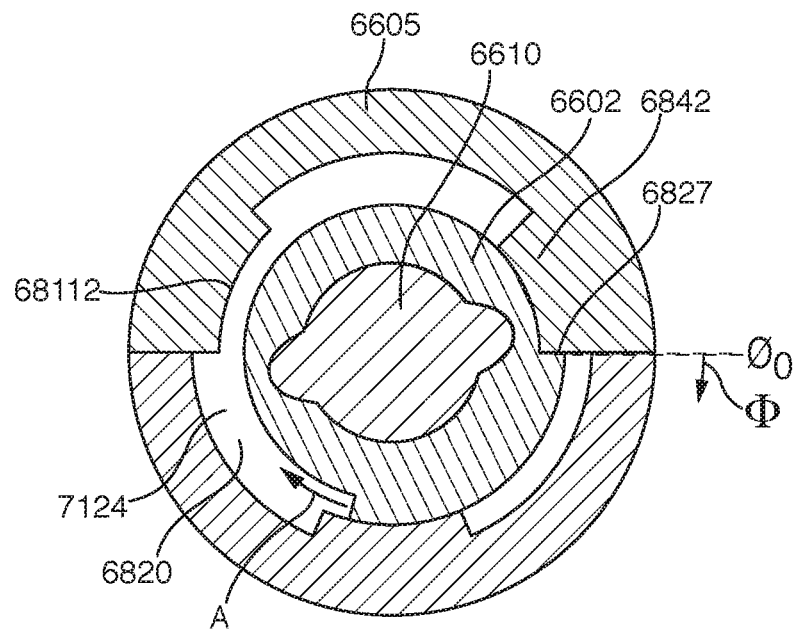
FIG. 71 is a cross-sectional view of the apparatus shown in FIG. 70, the view taken along lines 71-71 (shown in FIG. 70)

FIG. 71 is a cross-sectional view taken along view lines 71-71 (shown in FIG. 70). FIG. 71 shows rod 6610 disposed concentric to and within knob 6602. Knob 6602 may be concentric to and within collar 6605. Boss 6842 is shown disposed alongside lateral surface 6827 of track 6820. Track 6820 may include longitudinal tract 7124. Arrow A indicates rotation of knob 6602 that may shift longitudinal tract 7124 toward auxiliary tab 68112.

Angle Φ gives the rotational displacement between knob 6602 and collar 6605. In the pre-operational state of rotation, Φ is $\phi_0$. Rotation of knob 6602 in the direction of arrow A past auxiliary tab 68112 may bring longitudinal tract 7124 into alignment with boss 6842.

Figure 72:
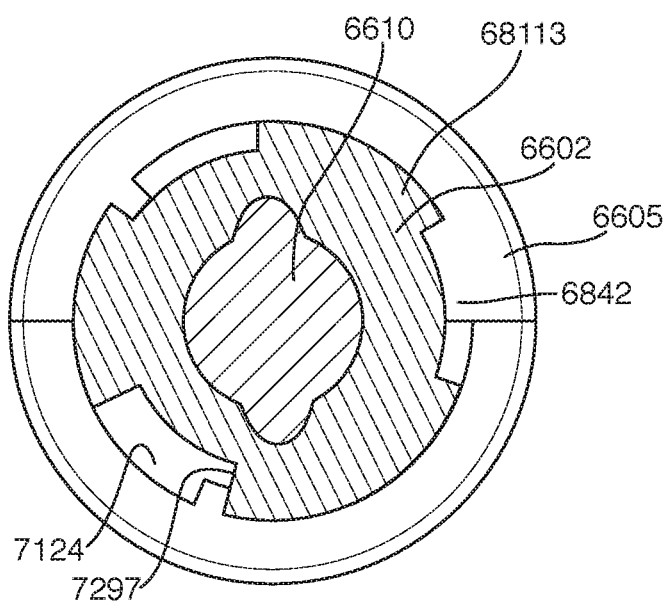
FIG. 72 is a partial cross-sectional view of the apparatus shown in FIG. 70, the view taken along lines 72-72 (shown in FIG. 70)

FIG. 72 is a partial cross-sectional view taken along view lines 72-72 (shown in FIG. 70) proximal to collar 6605. In this view through rod 6610 and knob 6602, a proximal surface of collar 6605 lying below the plane of the cross-section can be seen in the same orientation as is shown in FIG. 71. In this orientation, circumferential plateau 68113 may be partly proximally covering boss 6842. Longitudinal tract 7124 may terminate circumferentially at lateral surface 7297.

FIG. 73 shows device 6600 in a state different from that shown in FIG. 70. Knob 6602 is shown rotated relative to its position vis-à-vis collar 6605 as shown in FIG. 70. The rotation of knob 6602 is illustrated to have caused a longitudinal translation of rod 6610. Proximal rod end 6768 has been shifted longitudinally from position $x_0$ to position $x_1$. The distal shift of rod 6610 within container 6650 has distally displaced plunger 6656 so that distal face 7057 is disposed at position $y_1$, thus driving medicament 6660 out of the distal end of the device. The medicament may be driven out in proportion to the rotation of knob 6602 within collar 6605. Signage 6608 viewed through window 6669 may indicate that the rotation has begun to occur.

FIG. 74 is a cross-sectional view taken along view lines 74-74 (shown in FIG. 73). FIG. 74 shows knob 6602 rotated relative to collar 6605 to angle $\phi_1$. Further rotation in Φ may abut lateral surface 7297 against a lateral surface of boss 6842 circumferentially facing lateral surface 7297. The further rotation in Φ may bring longitudinal tract 7124 into alignment with boss 6842.

FIG. 75 is a partial cross-sectional view taken along view lines 75-75 (shown in FIG. 73) proximal to collar 6605. In this view through rod 6610 and knob 6602, the proximal surface of collar 6605 lying below the plane of the cross-section can be seen in the same orientation as is shown in FIG. 74.

Figure 76:
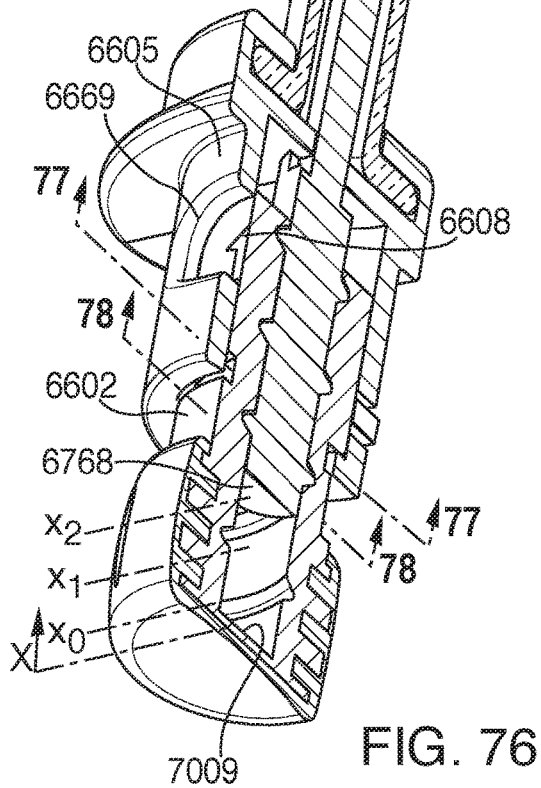
FIG. 76 is a partial cross-sectional, perspective view of apparatus in accordance with the principles of the invention.

FIG. 76 shows delivery device 6600 in a state different from that shown in FIG. 73. The state shown in FIG. 76 may correspond to termination of rotation of knob 6602 within collar 6605. The rotation of knob 6602 is illustrated to have caused a longitudinal translation of rod 6610. Proximal rod end 6768 has been shifted longitudinally to position $x_2$. The distal shift of rod 6610 within container 6650 has distally displaced plunger 6656 so that distal face 7057 is disposed at position $y_2$ relative to inflection point 7093, thus driving medicament 6660 out of the distal end of the device. The medicament may be driven out in proportion to the rotation of knob 6602 within collar 6605. Signage 6608 may indicate through window 6769 that the rotation has terminated and the device is ready for medicament delivery by longitudinal distal displacement of knob 6602 relative to collar 6605.

Figure 77:
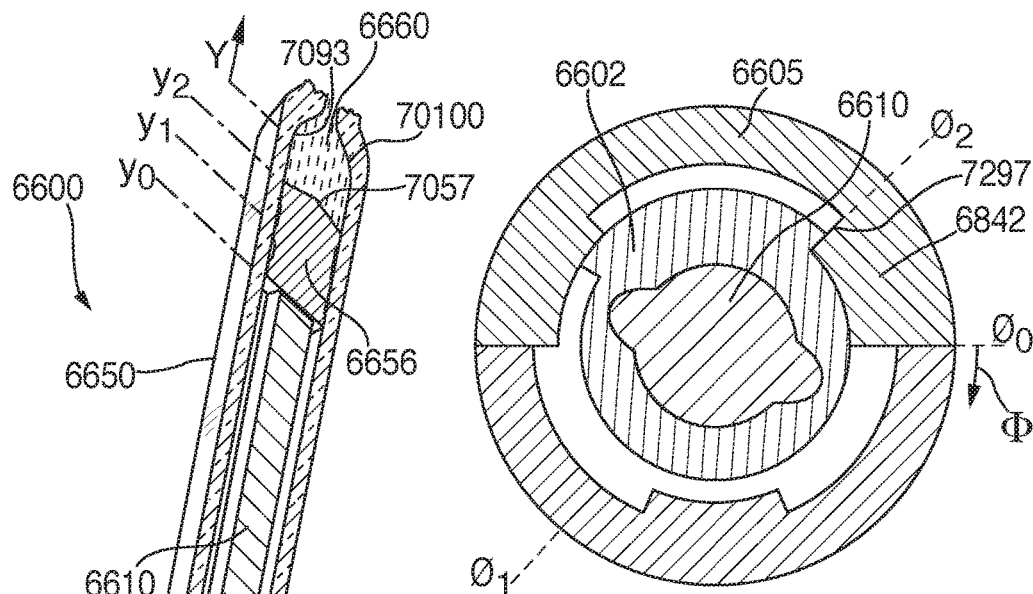
FIG. 77 is a cross-sectional view of the apparatus shown in FIG. 76, the view taken along lines 77-77 (shown in FIG. 76)

FIG. 77 is a cross-sectional view taken along view lines 77-77 (shown in FIG. 76). FIG. 77 shows knob 6602 rotated relative to collar 6605 to angle $\phi_2$. Lateral surface 7297 may abut against the lateral surface of boss 6842 circumferentially facing lateral surface 7297. Boss 6842 may be aligned with longitudinal tract 7124 (blocked from view by boss 6842).

Figure 78:
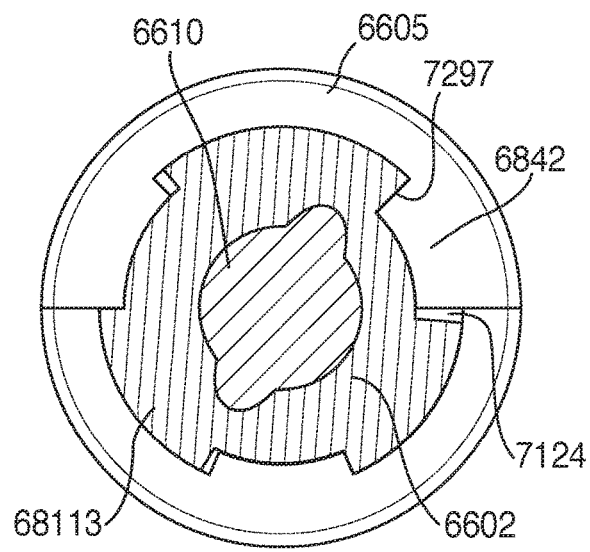
FIG. 78 is a partial cross-sectional view of the apparatus shown in FIG. 76, the view taken along lines 78-78 (shown in FIG. 76)

FIG. 78 is a partial cross-sectional view taken along view lines 78-78 (shown in FIG. 76) proximal to collar 6605. In this view through rod 6610 and knob 6602, the proximal surface of collar 6605 lying below the plane of the cross-section can be seen in the same orientation as is shown in FIG. 77.

FIG. 79 shows device 6600, in the same state as that shown in FIG. 76, at termination of rotation. Lateral surface 7297 may circumferentially abut boss 6842. Longitudinal tract 7124 may be in alignment with boss 6842. Boss 6842 may circumferentially lie entirely within longitudinal tract 7124. Longitudinal tract 7124 may include terminal surface 7912. Z gives the distance of boss 6842 from terminal surface 7912. In the view shown, Z is $z_0$. When Z is $z_0$, device 6600 is ready for, but has not yet begun, delivery of medicament 6660. When knob 6602 will be displaced longitudinally along into collar 6605, medicament 6660 is discharged. Medicament discharge may be terminated by abutment of boss 6482 against terminal surface 7912.

FIG. 80 is a view of knob 6602 showing terminal surface 7912. FIG. 80 provides a view of terminal surface 7912 in relation to longitudinal tract 7124 and lateral surface 7297. This view shows an intersection of annular tract 6807 and longitudinal tract 7124 adjacent lateral surface 7297. Lateral surface 7297 may circumferentially terminate track 6820 in the direction of rotation. Terminal surface 7912 may lie at the proximal terminus of longitudinal tract 7124.

FIG. 81 is a partial cross-sectional view taken along lines 81-81 (shown in FIG. 80). FIG. 81 provides another view of terminal surface 7912 in relation to longitudinal tract 7124 and lateral surface 7297.

Figure 82:
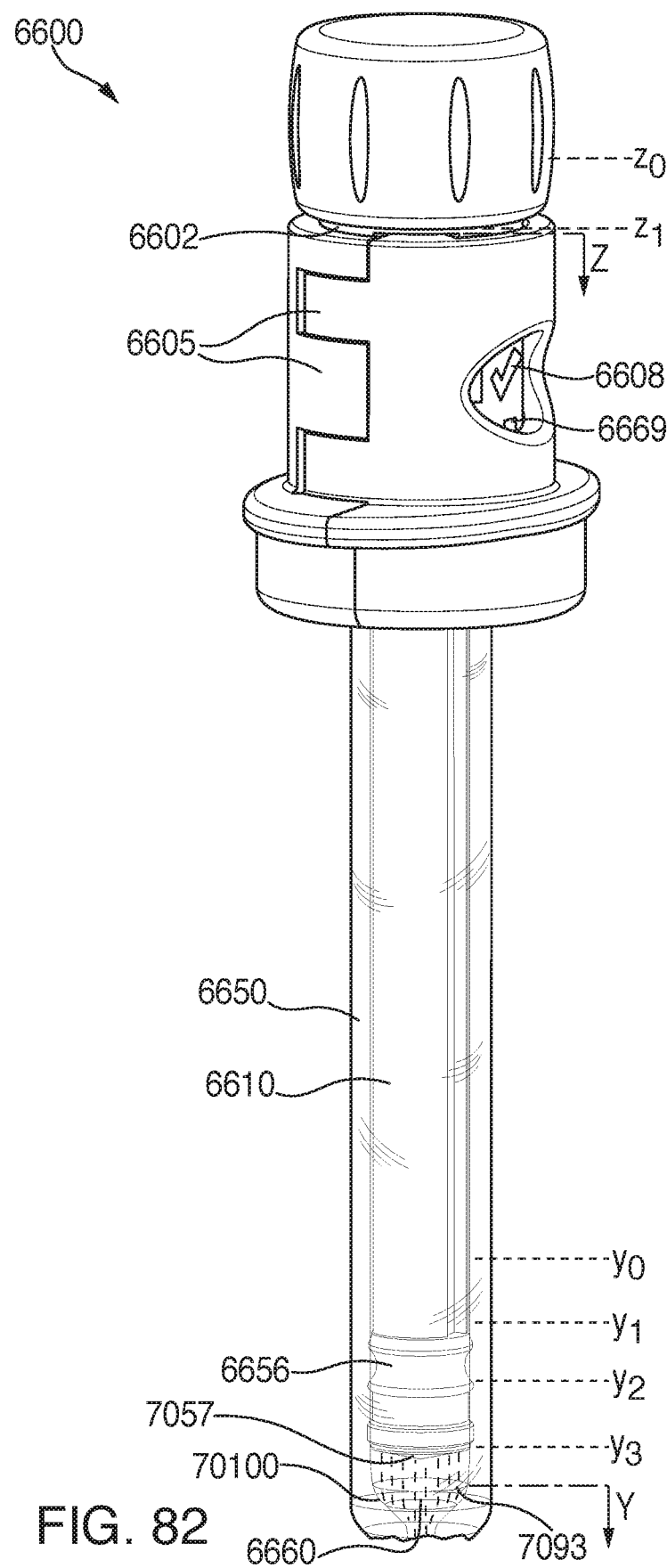
FIG. 82 is a perspective view of apparatus in accordance with the principles of the invention.

FIG. 82 shows device 6600, inverted to illustrate a medicament delivery orientation, upon completion of medicament delivery. Longitudinal displacement of knob 6602 relative to collar 6605 brings boss 6842 into abutment with terminal surface 7912, thus terminating longitudinal displacement of rod 6610 and plunger 6656. Z is now $z_1$, which is about zero. The difference $z_0 - z_1$ may correspond to a target amount of medicament to be delivered. Distal face 7057 may be displaced to $y_3$. The distance between $y_2$ and $y_3$ is proportional, through the diameter of the container, to the target amount. Position $y_3$ may be proximal to inflection point 7093. Position $y_3$ may be longitudinally even with inflection point 7093. When distal face 7057 is at $y_3$, a residuum of medicament 6660 may remain between distal face 7057 and distal end of container 6650. When distal face 7057 is at $y_3$, a residuum of medicament 6660 may remain between distal face 7057 and shoulder 70100. The residuum may be a bulk liquid. The bulk liquid may have a volume that is greater than the volume of a film or a drop that would be expected to adhere to container 6650.

Distal face 7057 is thus detained prior to crossing inflection point 7093. This may avoid deformation of distal face 7057 against shoulder 70100. The deformation may cause a discrepancy between the target amount and the actual amount discharged through the distal end of device 6600.

Figure 83:
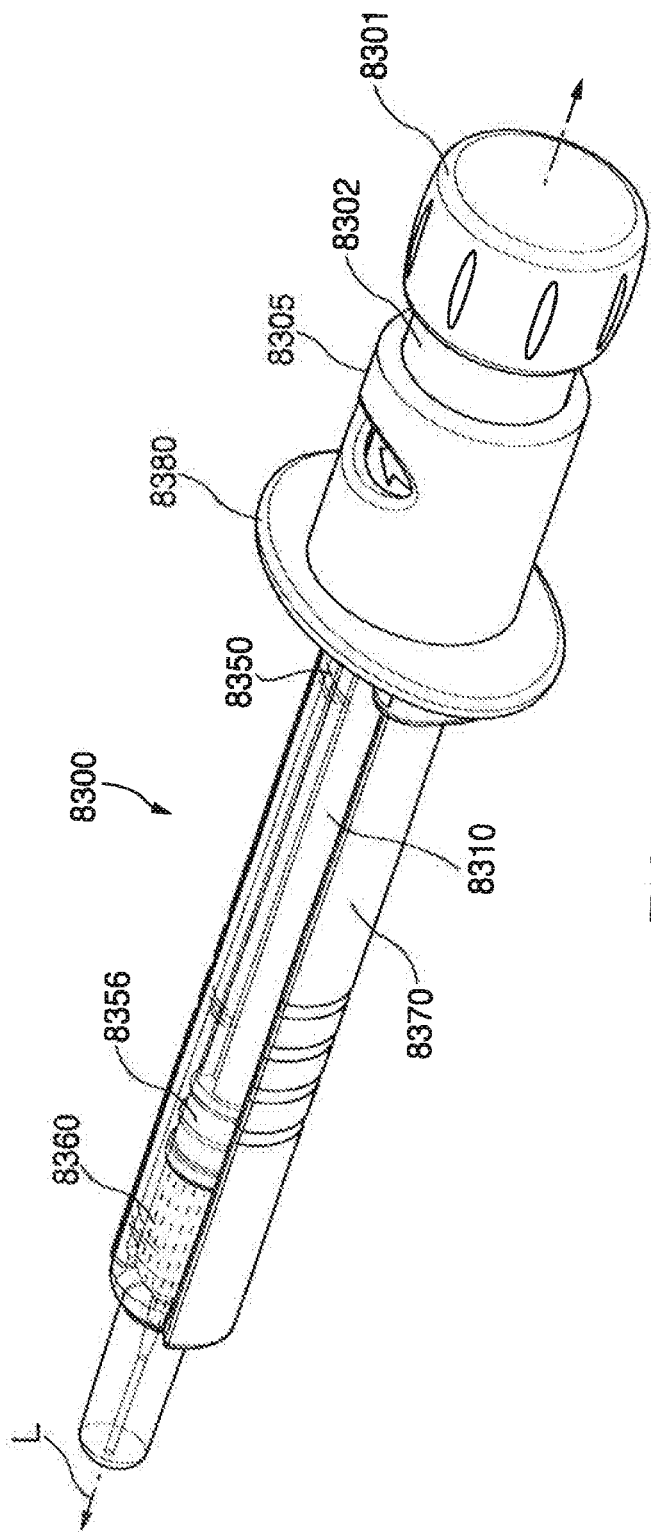
FIG. 83 is a perspective view of apparatus in accordance with the principles of the invention.

FIG. 83 shows illustrative medicament delivery device 8300. Delivery device 8300 may have one or more features in common with one or more of devices 100 (shown in FIG. 1), 1500 (shown in FIG. 15), 2500 (shown in FIG. 25), 2800 (shown in FIG. 28), 5400 (shown in FIG. 54), 6000 (shown in FIG. 60) and 6600 (shown in FIG. 66).

Delivery device 8300 may define longitudinal axis L. Delivery device 8300 is shown in a state that may be a pre-operational state. In the pre-operational state, delivery device 8300 may be fully assembled. In the pre-operational state, delivery device 8300 may be prepared for priming. In the pre-operational state, delivery device 8300 may be prepared for preparation of medicament for discharge. In the pre-operational state, delivery device 8300 may be prepared for discharge of medicament. In the pre-operational state, discharge of medicament from delivery device 8300 may not have begun.

Delivery device 8300 may include proximal knob 8302. Knob 8302 may be disposed coaxial with axis L. Grip 8301 may be provided on knob 8302.

Delivery device 8300 may include plunger rod 8310. Rod 8310 may be a component of a mixing configuration (not shown). Knob 8302 may be threadingly attached to rod 8310.

Delivery device 8300 may include medicament container 8350. Container 8350 may be a component of a mixing configuration (not shown). Container 8350 may be disposed coaxial with axis L. Container 8350 may be cylindrical, partially cylindrical or have any other suitable form. A distal portion of rod 8310 may be disposed within container 8350.

Container 8350 may contain medicament component 8360. Container 8350 may be engaged with plunger 8356. A distal end of rod 8310 may abut a proximal surface of plunger 8356.

Delivery device 8300 may include device housing 8370. Housing 8370 may be disposed coaxial with axis L. Housing 8370 may be cylindrical, partially cylindrical or have any other suitable form.

Delivery device 8300 may include finger flange 8380. Finger flange 8380 may be separate from housing 8370. Finger flange 8380 may be attached to housing 8370. Finger flange 8380 may be integral to housing 8370.

Delivery device 8300 may include collar 8305. Collar 8305 may be disposed coaxial with axis L. Collar 8305 may be cylindrical, partially cylindrical or have any other suitable form. Collar 8305 may be attached to finger flange 8380. Collar 8305 may be integral to finger flange 8380. Collar 8305 may be attached to housing 8370. Collar 8305 may be integral to housing 8370.

Figure 84:
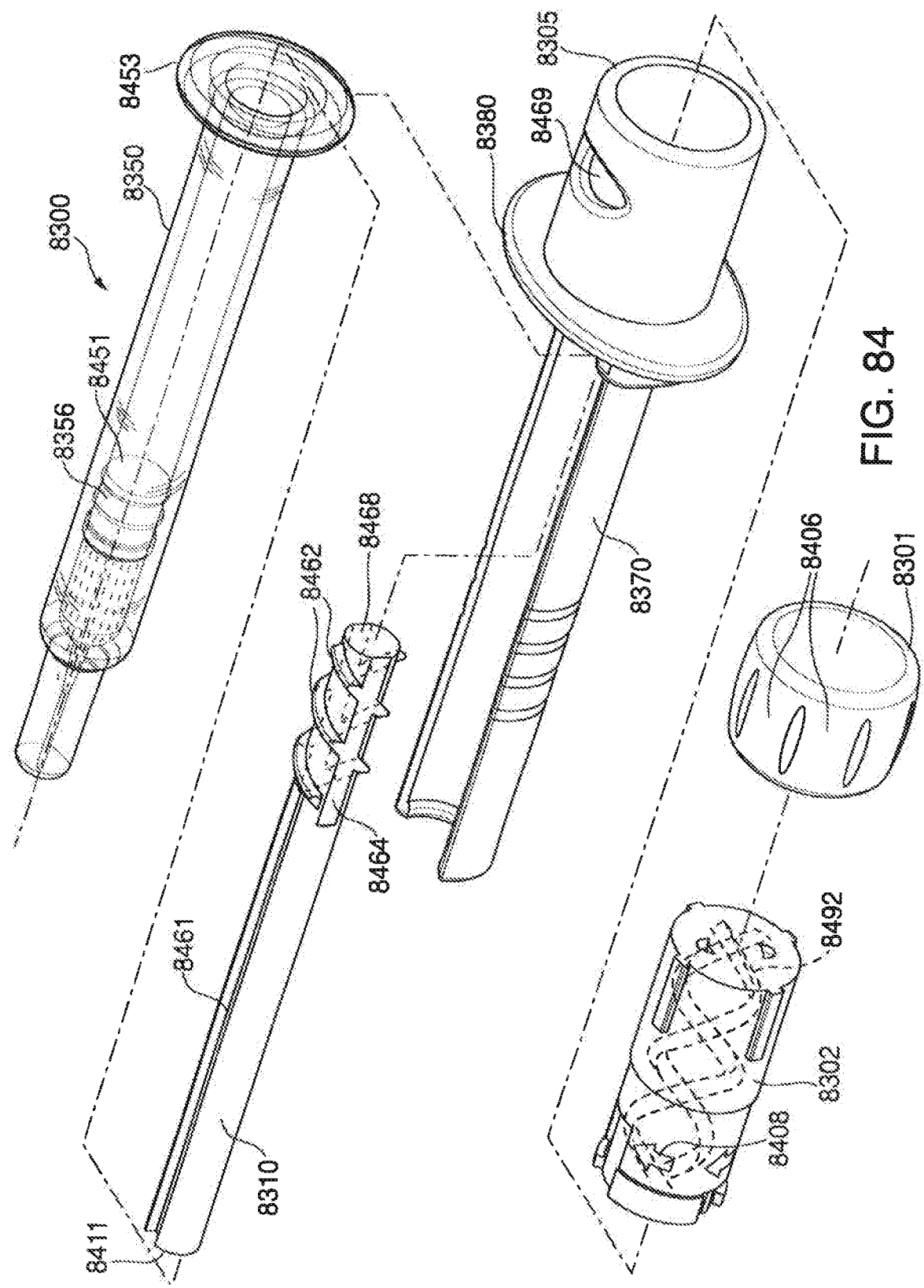
FIG. 84 is an exploded, perspective view of the apparatus shown in FIG. 83.

FIG. 84 shows features of delivery device 8300. FIG. 84 shows knob 8302. Knob 8302 may contain threads 8492 (shown in phantom) internal to knob 8302.

Grip 8301 may contribute to traction on knob 8302 for effecting longitudinal translation of rod 8310. Grip 8301 may contribute to ergonomic finger contact of the operator with knob 8302 for effecting longitudinal translation of rod 8310. The finger contact with knob 8302 through grip 8301 may conduct tactile feedback to the operator of an extent of distal longitudinal translation of rod 8310 along axis L.

Knob 8302 may include turn ridges 8406. Turn ridges 8406 may be utilized by the operator to effect rotation of knob 8302 about axis L. Turn ridges 8406 may contribute to traction on knob 8302 for effecting translation of rod 8310. Turn ridges 8406 may contribute to ergonomic finger contact of the operator with knob 8302 for effecting translation of rod 8310 through rotation of knob 8302. The finger contact with turn ridges 8406 may conduct tactile feedback to the operator of an extent of translation of rod 8310 along axis L.

Turn ridges 8406 may be spaced circumferentially around knob 8302. Turn ridges 8406 may be spaced regularly around a circumference of grip 8301. Turn ridges 8406 being spaced regularly about the circumference of grip 8301 may provide the operator a measure of an extent of rotation performed.

Knob 8302 may include turn direction signage 8408. In the operational state, delivery device 8300 may effect distal displacement of rod 8310 within container 8350 in response to rotation of knob 8302 about axis L in only one of two rotational directions. Turn direction signage 8408 may provide the operator with cues as to an effective rotational direction. The cues may serve as reminders before and/or during the operational state. The cues may be visual. The cues may be tactile.

As depicted, the effective rotational direction for distal displacement of rod 8310 within container 8350 in response to rotation of knob 8302 about axis L may be clockwise for delivery device 8300. (For some embodiments, not shown, counter-clockwise rotation may the effective rotational direction. For some embodiments, turn direction signage may provide cues for counter-clockwise rotation.)

Distal rod end 8411 may define a distal end of anti-rotation slot 8461. Anti-rotation slot 8461 may be parallel to axis L. Distal rod end 8411 may include one or more additional anti-rotation slots or features (not shown) distributed about the circumference of rod 8310 in a regular or irregular manner. Anti-rotation slot 8461 may extend all or some of the way proximally to threads 8462. Threads 8462 may extend proximally some or all of the way to proximal rod end 8468. Threads 8462 may engage threads 8492 of knob 8302.

Rod 8310 may include flat face 8464. Flat face 8464 may be parallel to axis L. Rod 8310 may include one or more additional flat faces (not shown) distributed about the circumference of rod 8310 in a regular or irregular manner. Flat face 8464 may extend all or some of the way from near anti-rotation slot 8461 to proximal end 8468. Flat face 8464 may be longitudinally coextensive with threads 8462. Flat face 8464 may be circumferentially displaced from slot 8461. The circumferential displacement may be 90° of arc from slot 8461.

Container 8350 may be disposed in device 8300 distal to finger flange 8380. Container 8350 may be disposed in housing 8370 distal to finger flange 8380. Proximal rim 8453 of container 8350 surrounding a proximal opening of container 8350 may be recessed in device 8300 distal to finger flange 8380. Proximal rim 8453 of container 8350 may be recessed in housing 8370.

Knob 8302 may be disposed coaxially within collar 8305. Collar 8305 may include viewing window 8469. A portion of signage 8408 may be visible through window 8469.

Rod 8310 may be contained in container 8350 with distal end 8411 abutting plunger proximal face 8451. Proximal rod end 8468 may extend proximally into collar 8305. Knob 8302 may extend distally into collar 8305 to threadingly engage rod 8310.

FIG. 85 shows collar 8305. Collar 8305 may include boss 8542. Collar 8305 may include flexible panel 8566. Flexible panel 8566 may be included in boss 8542. Boss 8542 may be disposed on an interior portion of collar 8305. Flexible panel 8566 may be disposed on an interior portion of collar 8305.

Knob 8302 may include operational track 8520. Operational track 8520 may begin at lateral surface 8527. Adjacent lateral face 8527, track 8520 may include protrusion 8514. Boss 8542 may slidingly engage track 8520. Flexible panel 8566 may interact with protrusion 8514.

FIG. 86 is a cross-sectional view taken along viewlines 86-86 (shown in FIG. 85). FIG. 86 shows track 8520 and lateral surface 8527 disposed on a periphery of knob 8302. Track 8520 may include annular tract 8607. Annular tract 8607 may support protrusion 8514. Annular tract 8607 may support protrusion 8618. Track 8520 may include longitudinal tract 8624. Track 8520 may include running surface 8628.

FIG. 87 shows knob 8302 extending into collar 8305 such that flexible panel 8566 of collar 8305 is adjacent protrusion 8514 of knob 8302.

Figure 88:
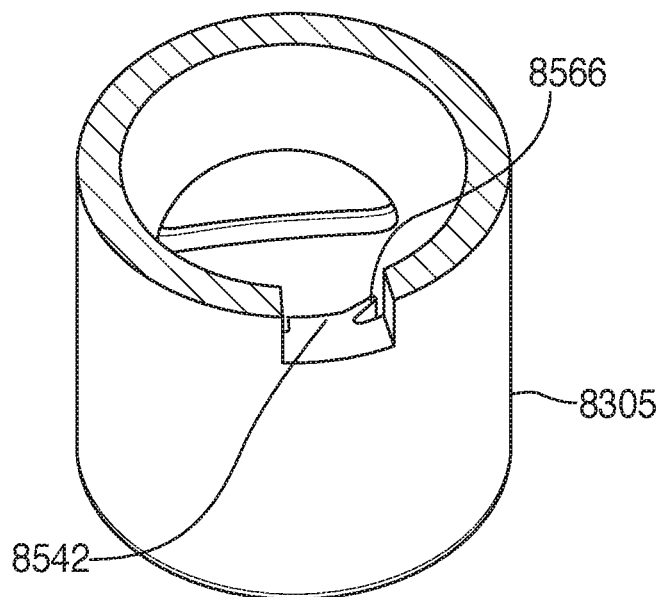
FIG. 88 is a partial cross-sectional, perspective view of the apparatus shown in FIG. 85, the view taken along lines 88-88 (shown in FIG. 85)

FIG. 88 is a cross-sectional view taken along view lines 88-88 (shown in FIG. 85). FIG. 88 shows collar 8305, boss 8542 and flexible panel 8566.

Figure 89:
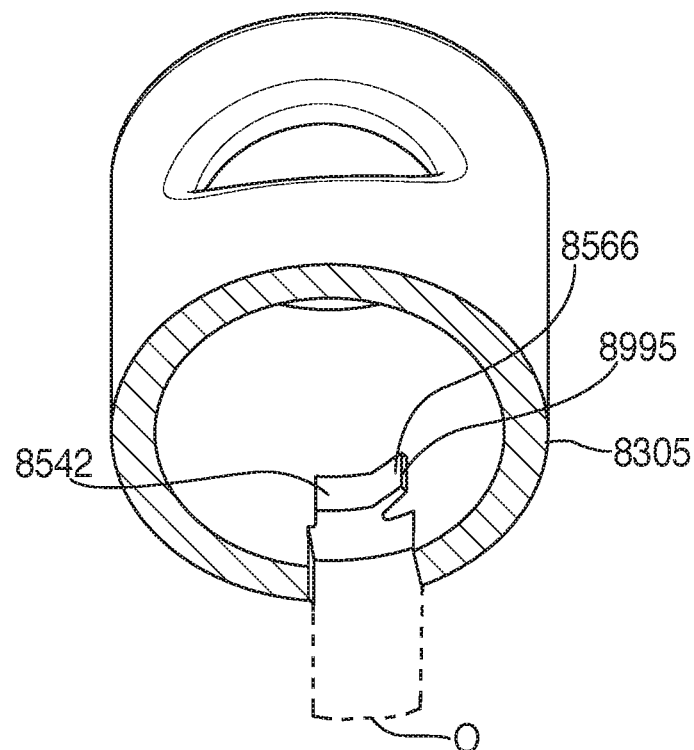
FIG. 89 is another view of the apparatus shown in FIG. 88.

FIG. 89 shows a view of collar 8305 that is different from the view shown in FIG. 88. FIG. 89 shows boss 8542 and flexible panel 8566. Flexible panel 8566 may include free end 8995. Opening O in collar 8305 may be adjacent to flexible panel 8566.

FIG. 90 shows delivery device 8300 assembled in a pre-operational state. Knob 8302 may extend into collar 8305. Flexible panel 8566 may be adjacent to protrusion 8514. X shows a direction of a distance away from interior knob surface 9009 of proximal rod end 8468. Proximal rod end 8468 may be at a position $x_0$ from interior surface 9009. Rod 8310 may abut plunger 8356 within container 8350. Distal plunger face 9057 may seal medicament 8360 within container 8350. Y shows a direction of a distance away from container inflection point 9093 of distal plunger face 9057. Distal face 9057 may be disposed at a distance $y_0$ from inflection point 9093 near a distal end of container 8350. Inflection point 9093 is at a distal termination of a constant diameter of container 8350 and illustrates an arbitrary reference point along an inner sidewall of container 8350 to show how medicament discharge is proportional to movement of other elements of the device. Distal to inflection point 9093, the sidewall of container 8350 may include shoulder 90100. Window 8469, shown in detail in inset, distal proximal to finger flange 8380, reveals signage 8408.

FIG. 91 is a cross-sectional view taken along view lines 91-91 (shown in FIG. 90) and rotated about 180° from the view shown in FIG. 90. FIG. 91 shows signage 408 through window 8469. The cross-section through finger flange 8380 shows rod 8310 and slot 8461. Anti-rotation projection 9191 may extend into anti-rotation slot 8461. A corresponding anti-rotation slot and anti-rotation projection (shown, but not numbered) may be present on the opposite side of rod 8310. Engagement of one or more of the projections in one or more of the slots may operationally prevent rotation of rod 8310.

FIG. 92 is a cross-sectional view taken along view lines 92-92 (shown in FIG. 90). FIG. 92 shows rod 8310 concentric within knob 8302. Knob 8302 is within and concentric to collar 8305. Boss 8542 is shown with an inner radial surface disposed alongside annular tract 8607. Protrusion 8514 lies between free end 8995 of flexible panel 8566 and the rest of boss 8542. Arrow A indicates rotation of knob 8302 that may shift longitudinal tract 8624 alongside boss 8542.

Angle φ gives the rotational displacement between knob 8302 and collar 8305. In the pre-operational state of rotation, Φ is $\phi_0$. Rotation of knob 8302 in the direction of arrow A may bring free end 8995 of panel 8566 into interaction with protrusion 8514. The interaction may cause a deflection of free end 8995. The interaction may cause a deflection of panel 8566. The interaction may produce a sensible indication. The indication may be tactile, acoustic or both. Opening O (shown in FIG. 89) may contribute to sensibility of acoustic indication.

With rotation of rod 8310 prevented by interaction of rod 8310 and projection 9191 (shown in FIG. 91) and with knob 8302 being threadingly engaged with rod 8310, rotation of knob 8302 may displace rod 8310 axially.

After free end 8995 passes over protrusion 8514 in direction A, protrusion 8514 interferes with free end 8995, thus preventing back-rotation of knob 8302.

FIG. 93 shows device 8300 in a state different from that shown in FIG. 90. Knob 8302 is shown rotated relative to its position vis-à-vis collar 8305 as shown in FIG. 90. (The rotational position of knob 8302 in FIG. 85 corresponds to the rotational position of knob 8302 in FIG. 90. The rotational position of knob 8302 in FIG. 93A corresponds the rotational position of knob 8302 in FIG. 93.)

FIG. 93A shows knob 8302 by itself in the same orientation in which it is shown in FIG. 93. FIG. 93A shows annular tract 8607 and longitudinal tract 8624 of track 8520. Running surface 8628 is visible. Longitudinal tract 8624 of track 8520 is visible. Annular tract 8607 is visible.

FIG. 93 shows free end 8995 of flexible panel 8566 alongside running surface 8628. The rotation of knob 8302 is illustrated to have caused a longitudinal translation of rod 8310. Proximal rod end 8468 has been shifted longitudinally from position $x_0$ (shown in FIG. 90) to position $x_1$. The distal shift of rod 8310 within container 8350 has distally displaced plunger 8356 so that distal face 9057 is disposed at position $y_1$, thus driving medicament 8360 out of the distal end of the device. The medicament may be driven out in proportion to the rotation of knob 8302 within collar 8305. Signage 8408 may indicate through window 8469 that the rotation has begun to occur.

FIG. 94 is a cross-sectional view taken along view lines 94-94 (shown in FIG. 93). FIG. 94 shows knob 8302 rotated relative to collar 8305 to angle $\phi_1$. Further rotation in Φ may bring boss 8542 into longitudinal tract 8624.

FIG. 95 shows delivery device 8300 in a state different from that shown in FIG. 93. The state shown in FIG. 95 may correspond to termination of rotation of knob 8302 within collar 8305.

FIG. 95A shows knob 8302 by itself in the same orientation in which it is shown in FIG. 95. FIG. 95A shows annular tract 8607 intersecting longitudinal tact 8624. Projection 8618 may be contiguous or near contiguous with intersection of annular tract 8607 and longitudinal tact 8624.

FIG. 95 shows free end 8995 of flexible panel 8566 alongside protrusion 8618. The rotation of knob 8302 is illustrated to have caused a longitudinal translation of rod 8310. Proximal rod end 8468 has been shifted longitudinally to position $x_2$. The distal shift of rod 8310 within container 8350 has distally displaced plunger 8356 so that distal face 9057 is disposed at position $y_2$ relative to inflection point 9093, thus driving medicament 8360 out of the distal end of the device. The medicament may be driven out in proportion to the rotation of knob 8302 within collar 8305. Signage 8408 may indicate through window 8469 that the rotation has terminated and the device is ready for medicament delivery by longitudinal distal displacement of knob 8302 relative to collar 8305.

FIG. 96 is a cross-sectional view taken along view lines 96-96 (shown in FIG. 95). FIG. 96 shows knob 8302 rotated relative to collar 8305 to angle $\phi_2$. The rotation now has brought boss 8542 into longitudinal tract 8624. The rotation has brought free end 8995 into interaction with protrusion 8618 as panel 8566 passed over protrusion 8618. The interaction may cause a deflection of free end 8995. The interaction may cause a deflection of panel 8566. The interaction may produce a sensible indication. The indication may be tactile, acoustic or both. After free end 8995 passes over protrusion 8618 and enters longitudinal tract 8624, protrusion 8618 interferes with free end 8995, thus preventing back-rotation of knob 8302. Lateral surface 9697 interferes with boss 8542, thus preventing further rotation of knob 8302. Boss 8542 is now confined to longitudinal tract 8624 and the device is prepared for delivery of medicament as a result of distal longitudinal displacement of knob 8302 relative to collar 8305.

Figure 97:
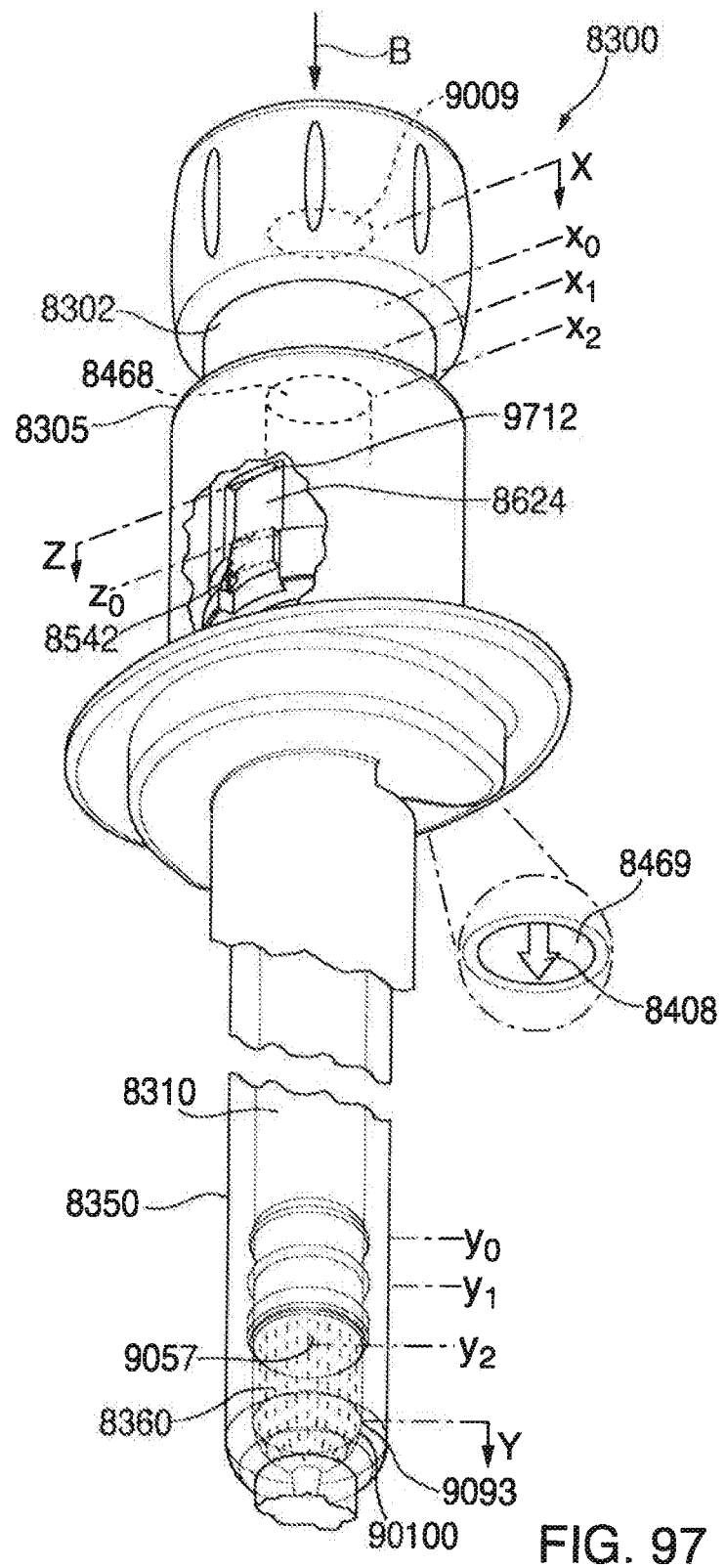
FIG. 97 is a perspective view of apparatus in accordance with the principles of the invention, including a cutaway of external features providing a view of internal features of the apparatus.

FIG. 97 shows device 8300 inverted to illustrate a medicament delivery orientation. Longitudinal tract 8624 includes terminal surface 9712 (shown in break-away view). Z gives a direction of a distance of boss 8542 from terminal surface 9712. In the view shown, the distance is $z_0$. When the distance is $z_0$, device 8300 is ready for, but has not yet begun, delivery of medicament 8360. When knob 8302 is displaced longitudinally along direction B into collar 8305, medicament 8360 is discharged.

Figure 98:
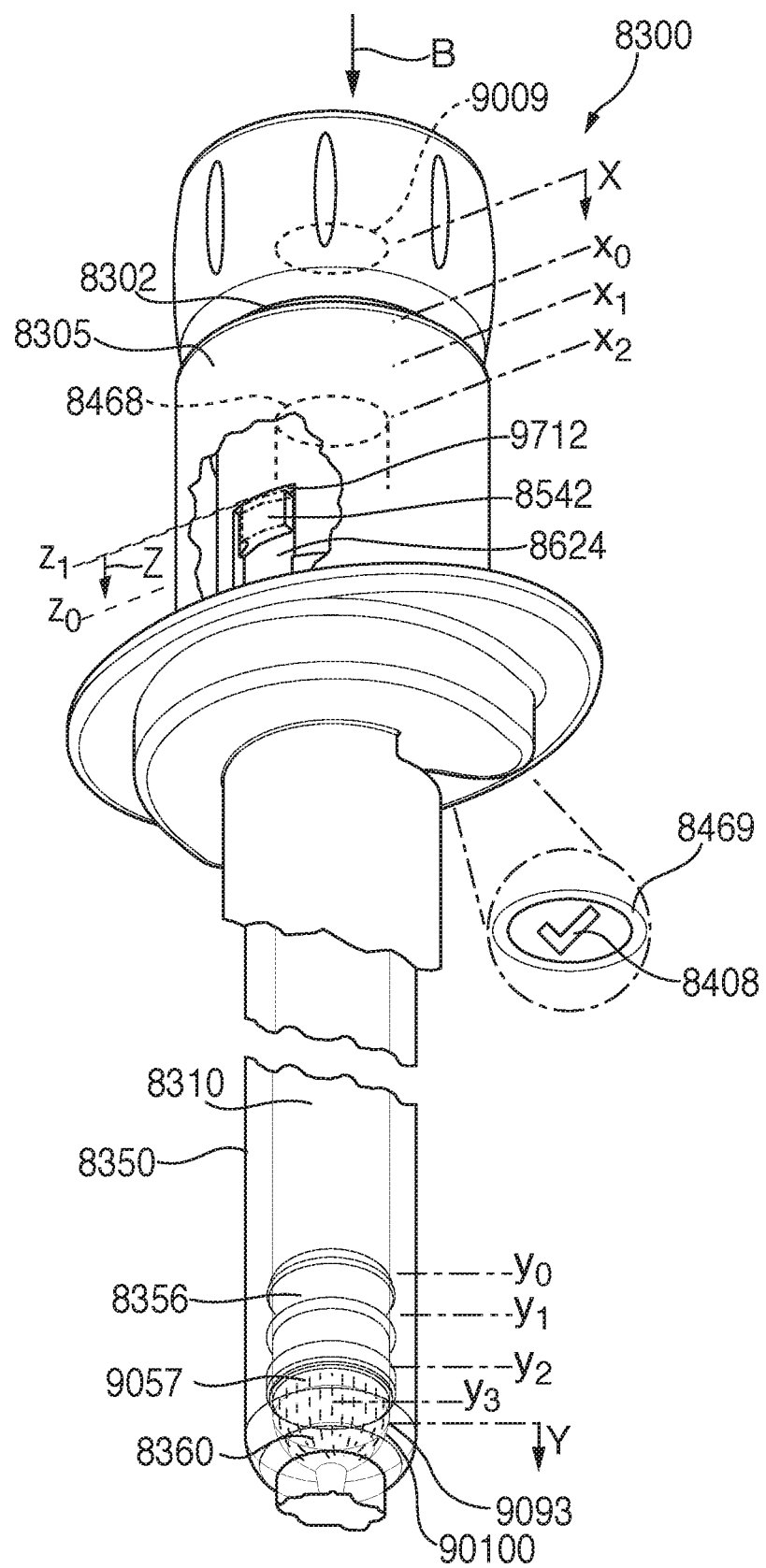
FIG. 98 is a perspective view of apparatus in accordance with the principles of the invention, including a cutaway of external features providing a view of internal features of the apparatus.

FIG. 98 shows device 8300 upon completion of medicament delivery. Longitudinal displacement of knob 8302 relative to collar 8305 brings boss 8542 into abutment with terminal surface 9712, thus terminating longitudinal displacement of rod 8310 and plunger 8356. The distance of boss 8542 from terminal surface 9712 is now $z_1$, which is about zero. Distal face 9057 is displaced to $y_3$. The distance between $y_2$ and $y_3$ is proportional, through the diameter of the container, to the target amount. Position $y_3$ may be proximal to inflection point 9093. Position $y_3$ may be longitudinally even with inflection point 9093. When distal face 9057 is at $y_3$, a residuum of medicament 8360 may remain between distal face 9057 and distal end of container 8350. When distal face 9057 is at $y_3$, a residuum of medicament 8360 may remain between distal face 9057 and shoulder 90100. The residuum may be a bulk liquid. The bulk liquid may have a volume that is greater than the volume of a film or a drop that would be expected to adhere to container 8350.

Distal face 9057 is thus detained prior to crossing inflection point 9093. This may avoid deformation of distal face 9057 against shoulder 90100. The deformation may cause a discrepancy between the target amount and the actual amount discharged through the distal end of device 8300.

Figure 99:
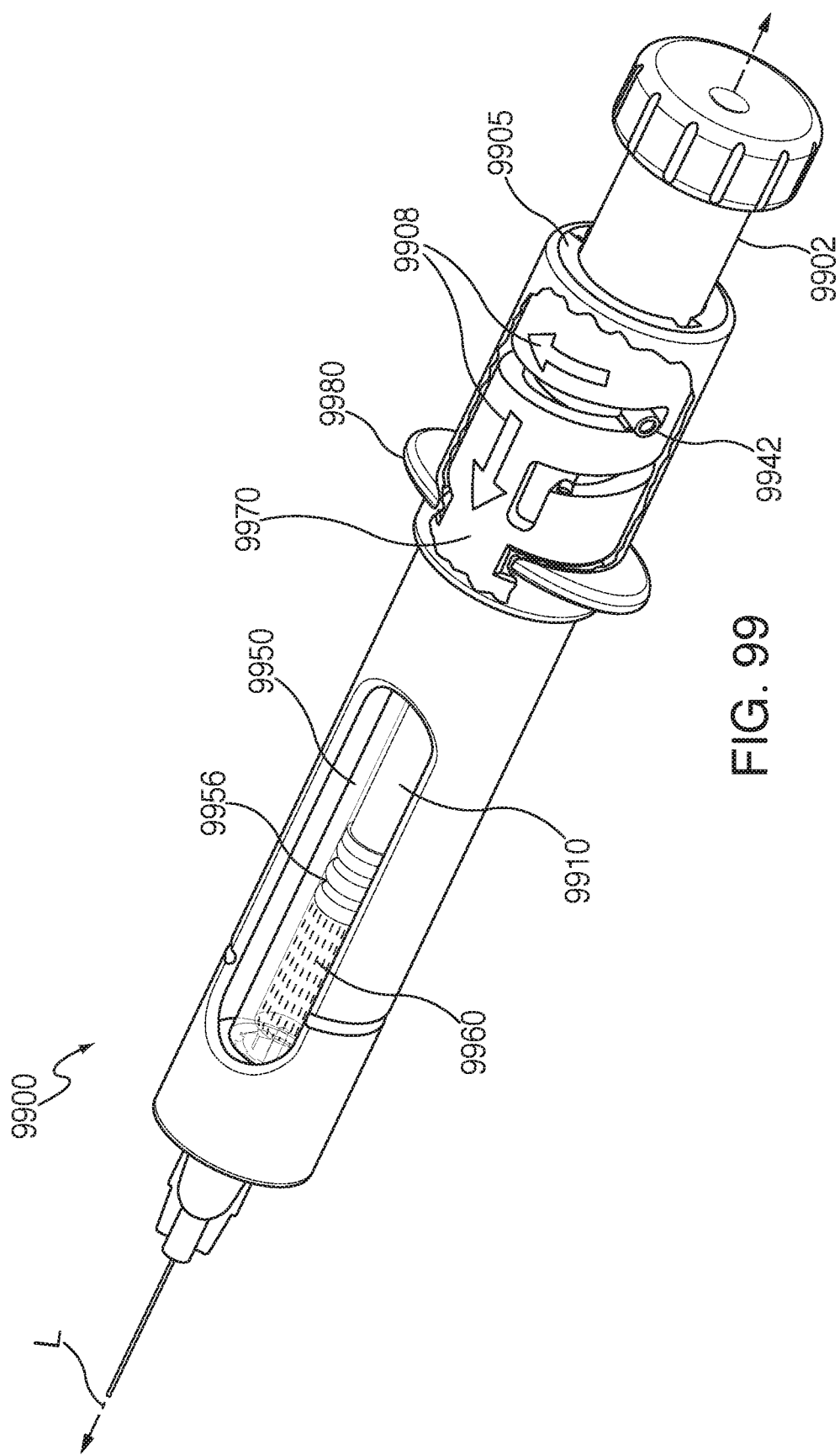
FIG. 99 is a perspective view of apparatus in accordance with the principles of the invention, including a cutaway of external features providing a view of internal features of the apparatus.

FIG. 99 shows illustrative delivery device 9900. Device 9900 may have one or more features in common with one or more of devices 100 (shown in FIG. 1), 1500 (shown in FIG. 15), 2500 (shown in FIG. 25), 2800 (shown in FIG. 28), 5400 (shown in FIG. 54), 6000 (shown in FIG. 60), 6600 (shown in FIG. 66) and 8300 (shown in FIG. 99).

Delivery device 9900 may define longitudinal axis L. Device 9900 may include knob 9902, collar 9905, finger flange 9980, housing 9970, medicament container 9950, medicament 9960, plunger rod 9910 and plunger 9956. Knob 9902 may include boss 9942. Collar 9905 may include signage 9908. Signage 9908 may be visible through housing 9970. Boss 9942 may be visible through housing 9970.

Boss 9942 may project radially outward from axis L. Knob 9902 may be disposed concentrically within collar 95. Boss 9942 may project radially inward. Collar 9905 may be disposed concentrically within knob 9902.

Figure 100:
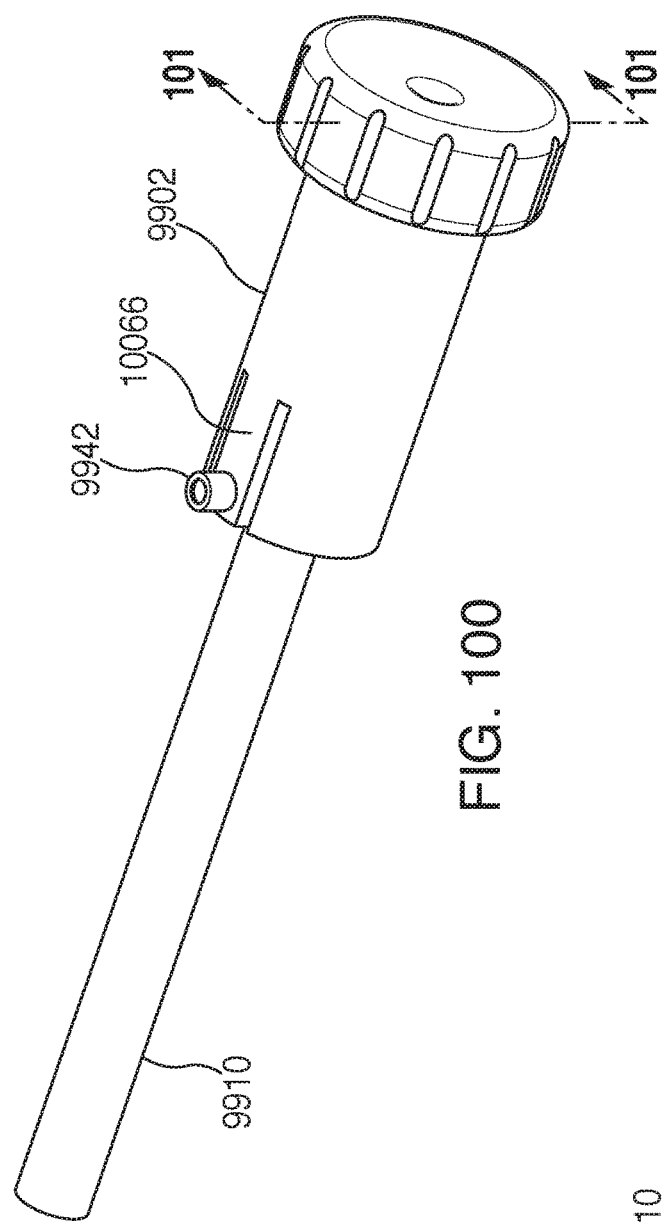
FIG. 100 is a perspective view of apparatus in accordance with the principles of the invention.

FIG. 100 shows knob 9902. Knob 9902 may include flexible panel 10066. Flexible panel 10066 may support boss 9942. Knob 9902 may be affixed to rod 9910. Rod 9910 may be of monolithic manufacture with rod 9910.

Figure 101:
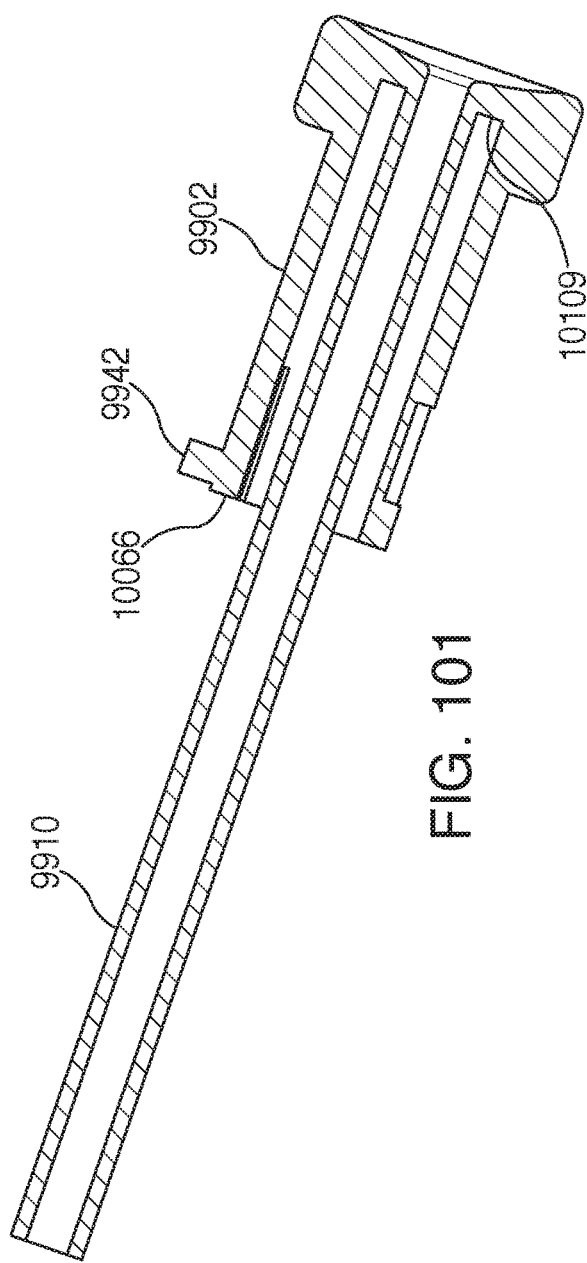
FIG. 101 is a partial cross-sectional, perspective view of the apparatus shown in FIG. 100, the view taken along lines 101-101 (shown in FIG. 100)

FIG. 101 is a cross-sectional view taken along view lines 101-101 (shown in FIG. 100). FIG. 101 shows knob 9902. Knob 9902 may include proximal interior surface 10109. Proximal interior surface 10109 may support rod 9910. Proximal interior surface 10109 and rod 9910 may be threadingly engaged. Rod 9910 and knob 9902 may rotate together. Rotation of knob 9902 may cause rotation of rod 9910.

FIG. 102 shows collar 9905. Collar 9905 may include track 10220. Track 10220 may include helical tract 10222. Track 10220 may include longitudinal tract 10224. Helical tract 10222 may intersect longitudinal tract 10224. Track 10220 may radially, with respect to axis L, traverse the thickness of a wall of collar 9905. Longitudinal tract 10224 may terminate at distal terminal surface 10212. Track 10220 may support pre-operational trigger 10214. Pre-operational trigger 10214 may releasably retain boss 9942 (shown in FIG. 99). Track 10222 may support final stage delivery trigger 10218 adjacent to longitudinal tract 10224. Rotation of knob 9902 within collar 9905 may axially displace rod 9910 (shown in FIG. 99). Rotation of knob 9902 within collar 9905 may move boss 9942 along track 10220 and along signage 9908.

Boss 9942 may interfere with pre-operational trigger 10214. Boss 9942 may interfere with pre-delivery trigger 10218. Interference between boss 9942 and pre-operational trigger 10214 may deflect flexible panel 10066 (shown in FIG. 99). Interference between boss 9942 and pre-delivery trigger 10214 may deflect flexible panel 10066. Deflection of flexible panel 10066 may provide indication of progress of medicament discharge. The position of boss 9942 relative to signage 9908 during the rotation may provide an indication of the relative amount of medicament 9960 (shown in FIG. 99) that has been discharged from device 9900.

After boss 9942 passes final stage delivery trigger 10218 during the rotation, boss 9942 may abut lateral surface 10297 of longitudinal tract 10224, terminating the rotation. Distal longitudinal motion of knob 9902 may cause abutment of boss 9942 against terminal surface 10212. Abutment of boss 9942 against terminal surface 10212 may terminate medicament delivery from device 9900. Travel of boss 9942 distally along the full extent of longitudinal tract 10224 may effect delivery of the target amount.

Rotation of knob 9902 may effect pre-operational functions, such as priming, of device 9900. Longitudinal distal motion of knob 9902 after the rotation may effect delivery of medicament 9960 from device 9900.

Thus, apparatus and methods for medicament delivery have been provided. Persons skilled in the art will appreciate that the present invention can be practiced by other than the described embodiments, which are presented for purposes of illustration rather than of limitation. The present invention is limited only by the claims that follow.

What is claimed is:

1. A medicament delivery device defining a longitudinal axis and having a distal end, the device comprising:
   a collar disposed coaxial with the longitudinal axis and supporting a flexible panel and a projection; and
   a plunger rod that is threadingly engaged, coaxially within the collar, with a proximal knob having a track that supports a trigger;
wherein:
   the flexible panel:
      is configured, responsive to interaction with the trigger, to move in deflection relative to the longitudinal axis; and
      slidingly engages the track to longitudinally retain the knob during a rotation of the knob about the longitudinal axis;
   the projection slidingly engages a longitudinally extending structure of the plunger rod to rotationally retain the plunger rod during the rotation, the rotation driving the plunger rod toward the distal end;

the longitudinally extending structure:
  extends along a length that is disposed between a proximal thread of the plunger rod and a distal end of the plunger rod; and
  supports a surface feature configured to interfere with the projection to longitudinally retain the plunger rod from proximal movement; and the projection:
  projects radially inward;
  has a distal stop surface that provides blockage against distal movement of the projection relative to the surface feature; and
  proximal to the distal stop surface, provides passage for proximal movement of the projection relative to the surface feature.

2. The device of claim 1 wherein:
the track includes an annular tract and a longitudinal tract, the annular tract intersecting the longitudinal tract, the flexible panel slidingly engaging:
  the annular tract during the rotation; and
  the longitudinal tract during a longitudinal translation of the knob;
the longitudinal tract retains the knob rotationally during the translation and corresponds, in longitudinal extent from the intersecting, to a target amount of medicament;
the translation is delimited by interference between the flexible panel and a proximal terminal surface of the longitudinal tract; and
the interference:
  limits motion of the flexible panel, relative to the knob, to motion that is directed away from the terminal surface and parallel to the longitudinal axis; and
  terminates advancement of medicament out of the distal end.

3. The device of claim 2 wherein:
the collar further supports a bracket configured to retain, coaxially with the knob, a medicament container;
the container defines a bore bound by an interior sidewall that defines, along a segment of the sidewall, a uniform diameter,
a distal end of the plunger rod abuts a plunger within the container, the plunger being slidingly engaged with the sidewall;
before the translation, the plunger seals a pre-delivery amount of the medicament between an inner distal shoulder of the container and the plunger; and,
after the translation, a distal portion of the segment contacts a bulk liquid residuum contained between the inner distal shoulder and the plunger.

4. The device of claim 3 wherein an amount of the medicament in the residuum is no greater than the pre-delivery amount less the target amount.

5. The device of claim 3 wherein the distal portion of the segment directly contacts the residuum.

6. The device of claim 3 wherein the rotation sets the pre-delivery amount between the inner distal shoulder of the container and the plunger, the rotation preparing the medicament for delivery.

7. The device of claim 6 wherein the preparing comprises mixing components of the medicament within the container.

8. The device of claim 6 wherein the preparing comprises priming the container.

9. The device of claim 8 wherein the priming comprises distal discharge of air from the container.

10. The device of claim 2 wherein the knob further has signage providing indication of a stage of device operation and the collar defines a window exposing a portion of the signage, the portion indicating:
  prior to the rotation, a medicament preparation stage of the device operation; and
  after the rotation, a medicament delivery stage of the device operation.

11. The device of claim 10 wherein the portion indicates, during the rotation, continuation of the preparation stage.

12. The device of claim 10 wherein the portion indicates:
  after the rotation and prior to the translation, commencement of the delivery stage; and
  after the translation, completion of the delivery stage.

13. The device of claim 1 wherein:
the surface feature has a proximal stop surface that provides blockage against distal movement of the projection relative to the surface feature; and,
distal to the proximal stop surface, the surface feature provides passage for proximal movement of the projection relative to the surface feature.

14. The device of claim 1 wherein the longitudinally extending structure:
is a slot that extends radially inward; and
the surface feature extends, in a plane transverse to the longitudinal axis, into the slot.

15. The device of claim 1 wherein the longitudinally extending structure:
is a rail that extends radially outward; and
the surface feature extends, in a plane transverse to the longitudinal axis, out from the rail.

16. A medicament delivery device defining a longitudinal axis and having a distal end, the device comprising:
a collar disposed coaxial with the longitudinal axis and supporting a flexible panel and a projection; and
a plunger rod that is threadingly engaged, coaxially within the collar, with a proximal knob having a track that supports a trigger;
wherein:
the flexible panel:
  is configured, responsive to interaction with the trigger, to move in deflection relative to the longitudinal axis; and
  slidingly engages the track to longitudinally retain the knob during a rotation of the knob about the longitudinal axis;
the projection slidingly engages a longitudinally extending structure of the plunger rod to rotationally retain the plunger rod during the rotation, the rotation driving the plunger rod toward the distal end;
the track includes an annular tract and a longitudinal tract, the annular tract intersecting the longitudinal tract, the flexible panel slidingly engaging:
  the annular tract during the rotation; and
  the longitudinal tract during a longitudinal translation of the knob;
the longitudinal tract retains the knob rotationally during the translation and corresponds, in longitudinal extent from the intersecting, to a target amount of medicament;
the translation is delimited by interference between the flexible panel and a proximal terminal surface of the longitudinal tract; and
the interference:
  limits motion of the flexible panel, relative to the knob, to motion that is directed away from the terminal surface and parallel to the longitudinal axis; and terminates advancement of medicament out of the distal end;
the flexible panel is supported by a boss that is supported by the collar; and,
in the rotation:
the boss is in sliding engagement with the annular tract; and
the flexible panel trails all other surfaces of the boss.

17. The device of claim 16 wherein the flexible panel includes a free end that is disposed more radially inward than any other surface of the flexible panel.

18. The device of claim 17 wherein, in the rotation, the free end trails all other surfaces of the flexible panel.

19. The device of claim 17 wherein a running surface of the track supports the trigger, the free end interacting with the trigger, to produce the deflection, when the flexible panel passes by the trigger.

20. The device of claim 19 wherein the interaction occurs upon initiation of the rotation.

21. The device of claim 20 wherein, prior to the interaction:
the boss is disposed adjacent a portion of the annular tract that is circumferentially most distant, in the direction of the rotation, from the longitudinal tract; and
the trigger limits motion of the free end along the track.

22. The device of claim 19 wherein the interaction occurs upon completion of the rotation.

23. The device of claim 22 wherein the trigger:
is disposed on the annular tract at a juncture of the annular tract and the longitudinal tract; and
following the interaction, limits rotary motion of the knob in a direction opposite the rotation.

24. The device of claim 23 wherein, following the interaction, the flexible panel is circumferentially aligned with the longitudinal tract.

25. The device of claim 19 wherein the deflection provides indication of the interaction.

26. The device of claim 25 wherein the indication is tactile.

27. The device of claim 25 wherein the indication is acoustic.

28. The device of claim 17 wherein the trigger has a stop surface configured to block passage of the free end in a direction opposite to the rotation.

29. The device of claim 28 wherein:
the trigger is a protrusion;
the interaction is an interference between the free end and the trigger; and,
during the rotation, the flexible panel passes by the stop surface after passing by all other surfaces of the trigger.

30. The device of claim 28 wherein:
the trigger is a recess;
the interaction is an urging of the free end against the recess; and,
during the rotation, the flexible panel passes by the stop surface before passing by any other surface of the trigger.

31. The device of claim 16 wherein:
the rotation is delimited by abutment of the boss against a lateral surface of the longitudinal tract; and
the abutment circumferentially aligns the boss with the longitudinal tract.

32. The device of claim 31 wherein the abutment provides tactile indication of completion of a medicament preparation stage of device operation.

33. The device of claim 31 wherein the abutment provides acoustic indication of completion of a medicament preparation stage of device operation.

34. The device of claim 16 wherein the interference provides indication of completion of a medicament delivery stage of device operation.

35. A medicament delivery device for delivering a target amount of medicament from a distal end of the device, the device defining a longitudinal axis and comprising:
a collar disposed coaxial with the longitudinal axis and having a boss and a projection; and
a plunger rod that is threadingly engaged, coaxially within the collar, with a proximal knob having a track, the track including an annular tract and a longitudinal tract;
wherein:
the boss slidingly engages:
the annular tract to longitudinally retain the knob during a rotation of the knob about the longitudinal axis; and,
after the rotation of the knob, the longitudinal tract during a longitudinal translation of the knob;
the projection slidingly engages a longitudinally extending structure of the plunger rod to rotationally retain the plunger rod during the rotation, the rotation driving the plunger rod toward the distal end; and
the translation advances the target amount out of the distal end.

36. The device of claim 35 wherein:
the longitudinal tract intersects the annular tract;
the rotation is delimited by abutment of the boss against a lateral surface of the longitudinal tract;
the translation is delimited by interference between the boss and a proximal terminal surface of the longitudinal tract;
the longitudinal tract retains the knob rotationally during the translation and corresponds, in longitudinal extent from a location of the abutment, to the target amount; and
the interference:
limits motion of the boss, relative to the knob, to motion that is directed away from the terminal surface and parallel to the longitudinal axis; and
terminates advancement of medicament out of the distal end.

37. The device of claim 36 wherein the abutment provides tactile indication of completion of a medicament preparation stage of device operation.

38. The device of claim 36 wherein the abutment provides acoustic indication of completion of a medicament preparation stage of device operation.

39. The device of claim 36 wherein the interference provides indication of completion of a medicament delivery stage of device operation.

40. The device of claim 35 wherein:
the collar further has a bracket configured to retain, coaxially with the knob, a medicament container;
the container defines a bore bound by an interior sidewall that defines, along a segment of the sidewall, a uniform diameter,
a distal end of the plunger rod abuts a plunger within the container, the plunger being slidingly engaged with the sidewall;
before the translation, the plunger seals a pre-delivery amount of the medicament between an inner distal shoulder of the container and the plunger; and,
after the translation, a distal portion of the segment contacts a bulk liquid residuum contained between the inner distal shoulder and the plunger, an amount of the medicament in the residuum being no greater than the pre-delivery amount less the target amount.

41. The device of claim 40 wherein the rotation sets the pre-delivery amount between the inner distal shoulder of the container and the plunger, the rotation preparing the medicament for delivery.

42. The device of claim 41 wherein the preparing comprises mixing components of the medicament within the container.

43. The device of claim 41 wherein the preparing comprises priming the container.

44. The device of claim 43 wherein the priming comprises distal discharge of air from the container.

45. The device of claim 35 wherein the knob further has signage providing indication of a stage of device operation and the collar defines a window exposing a portion of the signage, the portion indicating:
prior to the rotation, a medicament preparation stage of the device operation;
during the rotation, continuation of the preparation stage; and,
after the rotation, a medicament delivery stage of the device operation.

46. The device of claim 45 wherein the portion indicates:
after the rotation and prior to the translation, commencement of the delivery stage; and
after the translation, completion of the delivery stage.

47. The device of claim 35 wherein the longitudinally extending structure:
extends along a length that is disposed between a proximal thread of the plunger rod and a distal end of the plunger rod; and
supports a surface feature configured to interfere with the projection to longitudinally retain the plunger rod from proximal movement.

48. The device of claim 47, wherein:
the surface feature has a proximal stop surface that provides blockage against distal movement of the projection relative to the surface feature; and,
distal to the proximal stop surface, the surface feature provides passage for proximal movement of the projection relative to the surface feature.

49. The device of claim 47 wherein the projection:
projects radially inward; and
has a distal stop surface that provides blockage against distal movement of the projection relative to the surface feature;
wherein, proximal to the distal stop surface, the projection provides passage for proximal movement of the projection relative to the surface feature.

50. The device of claim 47 wherein the longitudinally extending structure:
is a slot that extends radially inward; and
the surface feature extends, in a plane transverse to the longitudinal axis, into the slot.

51. The device of claim 47 wherein the longitudinally extending structure:
is a rail that extends radially outward; and
the surface feature extends, in a plane transverse to the longitudinal axis, out from the rail.

52. The device of claim 35 wherein the boss includes a flexible panel that has a free end that is disposed more radially inward than any other surface of the boss.

53. The device of claim 52 wherein a running surface of the track supports a trigger, the free end being configured, responsive to interaction between the free end and the trigger, to move in deflection relative to the longitudinal axis when the flexible panel passes by the trigger.

54. The device of claim 53 wherein the interaction occurs upon initiation of the rotation.

55. The device of claim 54 wherein, prior to the interaction:
the boss is disposed adjacent a portion of the annular tract that is circumferentially most distant, in the direction of the rotation, from the longitudinal tract; and
the trigger limits motion of the free end along the track.

56. The device of claim 53 wherein the interaction occurs upon completion of the rotation.

57. The device of claim 56 wherein the trigger:
is disposed on the annular tract at a juncture of the annular tract and the longitudinal tract; and
following the interaction, limits rotary motion of the knob in a direction opposite the rotation.

58. The device of claim 53 wherein the deflection provides indication of the interaction.

59. The device of claim 58 wherein the indication is tactile.

60. The device of claim 58 wherein the indication is acoustic.

61. The device of claim 52 wherein the trigger has a trigger stop surface configured to block passage of the free end in a direction opposite to the rotation.

62. The device of claim 61 wherein:
the trigger is a protrusion;
the interaction is an interference between the free end and the trigger; and,
during the rotation, the flexible panel passes by the trigger stop surface after passing by all other surfaces of the trigger.

63. The device of claim 61 wherein:
the trigger is a recess;
the interaction is an urging of the free end against the recess; and,
during the rotation, the flexible panel passes by the trigger stop surface before passing by any other surface of the trigger.

64. A method of manufacturing a medicament delivery device, the method comprising:
providing a knob having an annular recess that includes a surface from which extends a protrusion;
providing a collar that supports a flexible panel that extends into an interior of the collar;
positioning the knob coaxially within the collar so that a free end of the flexible panel extends radially inward beyond the protrusion and is deflectable by the protrusion when the knob rotates relative to the collar;
threadingly engaging a plunger rod with the knob; and
securing the plunger rod against rotation relative to the knob.

65. The method of claim 64 wherein the providing a knob comprises providing a knob that has a longitudinal recess that:
intersects the annular recess; and
supports a terminal surface configured to abut the flexible panel.

66. The method of claim 64 wherein:
the providing a collar comprises providing a collar that includes a projection; and
the securing includes engaging the projection with a longitudinally extending structure of the plunger rod.

67. The method of claim 66 wherein:
the longitudinally extending structure includes a slot; and the engaging includes insertion of the projection into the slot.

68. The method of claim 66 wherein:
the longitudinally extending structure includes a rail; and
the engaging includes positioning the projection alongside the rail.

69. The method of claim 64 further comprising providing the plunger rod, wherein the plunger rod includes an end supporting a thread engageable with the knob.

70. A medicament delivery device for delivering a target amount of medicament from a distal end of the device, the device defining a longitudinal axis and comprising:
a collar disposed coaxial with the longitudinal axis and having a boss and a projection; and
a plunger rod that is threadingly engaged, coaxially within the collar, with a proximal knob having a track, the track including an annular tract and a longitudinal tract;
wherein:
the boss slidingly engages:
the annular tract to longitudinally retain the knob during a rotation of the knob about the longitudinal axis; and
the longitudinal tract during a longitudinal translation of the knob;
the projection slidingly engages a longitudinally extending structure of the plunger rod to rotationally retain the plunger rod during the rotation, the rotation driving the plunger rod toward the distal end;
the translation:
is delimited by interference between the boss and a proximal terminal surface of the longitudinal tract; and
advances the target amount out of the distal end;
the longitudinally extending structure:
extends along a length that is disposed between a proximal thread of the plunger rod and a distal end of the plunger rod; and
supports a surface feature configured to interfere with the projection to longitudinally retain the plunger rod from proximal movement; and
the projection:
projects radially inward;
has a distal stop surface that provides blockage against distal movement of the projection relative to the surface feature; and
proximal to the distal stop surface, provides passage for proximal movement of the projection relative to the surface feature.

71. The device of claim 70 wherein:
the longitudinal tract intersects the annular tract;
the rotation is delimited by abutment of the boss against a lateral surface of the longitudinal tract;
the longitudinal tract retains the knob rotationally during the translation and corresponds, in longitudinal extent from a location of the abutment, to the target amount; and
the interference:
limits motion of the boss, relative to the knob, to motion that is directed away from the terminal surface and parallel to the longitudinal axis; and
terminates advancement of medicament out of the distal end.

72. The device of claim 71 wherein the abutment provides tactile indication of completion of a medicament preparation stage of device operation.

73. The device of claim 71 wherein the abutment provides acoustic indication of completion of a medicament preparation stage of device operation.

74. The device of claim 71 wherein the interference provides indication of completion of a medicament delivery stage of device operation.

75. The device of claim 70 wherein:
the collar further has a bracket configured to retain, coaxially with the knob, a medicament container;
the container defines a bore bound by an interior sidewall that defines, along a segment of the sidewall, a uniform diameter,
a distal end of the plunger rod abuts a plunger within the container, the plunger being slidingly engaged with the sidewall;
before the translation, the plunger seals a pre-delivery amount of the medicament between an inner distal shoulder of the container and the plunger; and,
after the translation, a distal portion of the segment contacts a bulk liquid residuum contained between the inner distal shoulder and the plunger, an amount of the medicament in the residuum being no greater than the pre-delivery amount less the target amount.

76. The device of claim 75 wherein the rotation sets the pre-delivery amount between the inner distal shoulder of the container and the plunger, the rotation preparing the medicament for delivery.

77. The device of claim 76 wherein the preparing comprises mixing components of the medicament within the container.

78. The device of claim 76 wherein the preparing comprises priming the container.

79. The device of claim 78 wherein the priming comprises distal discharge of air from the container.

80. The device of claim 70 wherein the knob further has signage providing indication of a stage of device operation and the collar defines a window exposing a portion of the signage, the portion indicating:
prior to the rotation, a medicament preparation stage of the device operation;
during the rotation, continuation of the preparation stage; and,
after the rotation, a medicament delivery stage of the device operation.

81. The device of claim 80 wherein the portion indicates:
after the rotation and prior to the translation, commencement of the delivery stage; and
after the translation, completion of the delivery stage.

82. The device of claim 70 wherein:
the surface feature has a proximal stop surface that provides blockage against distal movement of the projection relative to the surface feature; and,
distal to the proximal stop surface, the surface feature provides passage for proximal movement of the projection relative to the surface feature.

83. The device of claim 70 wherein the longitudinally extending structure:
is a slot that extends radially inward; and
the surface feature extends, in a plane transverse to the longitudinal axis, into the slot.

84. The device of claim 70 wherein the longitudinally extending structure:
is a rail that extends radially outward; and
the surface feature extends, in a plane transverse to the longitudinal axis, out from the rail.

85. The device of claim 70 wherein the boss includes a flexible panel that has a free end that is disposed more radially inward than any other surface of the boss.

86. The device of claim 85 wherein a running surface of the track supports a trigger, the free end being configured, responsive to interaction between the free end and the trigger, to move in deflection relative to the longitudinal axis when the flexible panel passes by the trigger.

87. The device of claim 86 wherein the interaction occurs upon initiation of the rotation.

88. The device of claim 87 wherein, prior to the interaction:
- the boss is disposed adjacent a portion of the annular tract that is circumferentially most distant, in the direction of the rotation, from the longitudinal tract; and
- the trigger limits motion of the free end along the track.

89. The device of claim 86 wherein the interaction occurs upon completion of the rotation.

90. The device of claim 89 wherein the trigger:
- is disposed on the annular tract at a juncture of the annular tract and the longitudinal tract; and
- following the interaction, limits rotary motion of the knob in a direction opposite the rotation.

91. The device of claim 86 wherein the deflection provides indication of the interaction.

92. The device of claim 91 wherein the indication is tactile.

93. The device of claim 91 wherein the indication is acoustic.

94. The device of claim 85 wherein the trigger has a trigger stop surface configured to block passage of the free end in a direction opposite to the rotation.

95. The device of claim 94 wherein:
- the trigger is a protrusion;
- the interaction is an interference between the free end and the trigger; and,
- during the rotation, the flexible panel passes by the trigger stop surface after passing by all other surfaces of the trigger.

96. The device of claim 94 wherein:
- the trigger is a recess;
- the interaction is an urging of the free end against the recess; and,
- during the rotation, the flexible panel passes by the trigger stop surface before passing by any other surface of the trigger.

97. A medicament delivery device for delivering a target amount of medicament from a distal end of the device, the device defining a longitudinal axis and comprising:
- a collar disposed coaxial with the longitudinal axis and having a boss and a projection; and
- a plunger rod that is threadingly engaged, coaxially within the collar, with a proximal knob having a track, the track including an annular tract and a longitudinal tract;

wherein:
- the boss slidingly engages:
  - the annular tract to longitudinally retain the knob during a rotation of the knob about the longitudinal axis; and
  - the longitudinal tract during a longitudinal translation of the knob;
- the projection slidingly engages a longitudinally extending structure of the plunger rod to rotationally retain the plunger rod during the rotation, the rotation driving the plunger rod toward the distal end; and,
- in the translation, the knob carries the threadingly engaged plunger rod distally forward.

98. The device of claim 97 wherein the plunger rod moving distally forward advances the target amount out of the distal end.

* * * * *